(12) United States Patent
Hancox et al.

(10) Patent No.: US 8,293,735 B2
(45) Date of Patent: Oct. 23, 2012

(54) THIENOPYRIMIDINE DERIVATIVES AS PI3K INHIBITORS

(75) Inventors: Timothy Colin Hancox, Slough (GB); Neil Anthony Pegg, Slough (GB); Alan John Nadin, Harlow (GB); Stephen Price, Harlow (GB)

(73) Assignee: F. Hoffmann-La Roche AG, Basel (CH)

( * ) Notice: Subject to any disclaimer, the term of this patent is extended or adjusted under 35 U.S.C. 154(b) by 130 days.

(21) Appl. No.: 12/739,435

(22) PCT Filed: Oct. 27, 2008

(86) PCT No.: PCT/GB2008/003621
§ 371 (c)(1),
(2), (4) Date: Oct. 12, 2010

(87) PCT Pub. No.: WO2009/053715
PCT Pub. Date: Apr. 30, 2009

(65) Prior Publication Data
US 2011/0021496 A1    Jan. 27, 2011

(30) Foreign Application Priority Data
Oct. 26, 2007    (GB) .................................. 0721059.8

(51) Int. Cl.
*A61K 31/535* (2006.01)
*C07D 413/14* (2006.01)
(52) U.S. Cl. ..................... 514/234.2; 544/117
(58) Field of Classification Search ............... 544/117; 514/234.2
See application file for complete search history.

(56) References Cited

U.S. PATENT DOCUMENTS

| | | | |
|---|---|---|---|
| 3,475,429 A | 10/1969 | Woitun et al. |
| 3,661,908 A | 5/1972 | Woitun et al. |
| 3,763,156 A | 10/1973 | Woitun et al. |
| 3,838,121 A | 9/1974 | Woitun et al. |
| 4,007,187 A | 2/1977 | Fauran et al. |
| 4,146,716 A | 3/1979 | Cox et al. |
| 4,196,207 A | 4/1980 | Webber et al. |
| 6,423,716 B1 | 7/2002 | Matsuno et al. |
| 6,608,053 B2 | 8/2003 | Hayakawa et al. |
| 6,838,457 B2 | 1/2005 | Hayakawa et al. |
| 7,037,915 B2 | 5/2006 | Hayakawa et al. |
| 7,173,029 B2 | 2/2007 | Hayakawa et al. |
| 7,750,002 B2 | 7/2010 | Shuttleworth et al. |
| 7,776,856 B2 | 8/2010 | Shuttleworth et al. |
| 7,781,433 B2 | 8/2010 | Chuckowree et al. |
| 7,846,929 B2 | 12/2010 | Folkes et al. |
| 7,872,003 B2 | 1/2011 | Shuttleworth et al. |
| 7,888,352 B2 | 2/2011 | Bayliss et al. |
| 7,893,059 B2 | 2/2011 | Castanedo et al. |
| 2003/0220365 A1 | 11/2003 | Stewart et al. |
| 2008/0076758 A1 | 3/2008 | Folkes et al. |
| 2008/0269210 A1 | 10/2008 | Castanedo et al. |
| 2009/0098135 A1 | 4/2009 | Belvin et al. |
| 2009/0156601 A1 | 6/2009 | McDonald et al. |
| 2009/0209559 A1 | 8/2009 | Chuckowree et al. |
| 2009/0318411 A1 | 12/2009 | Castanedo et al. |
| 2010/0016306 A1 | 1/2010 | Baker et al. |
| 2010/0292468 A1 | 11/2010 | Babu et al. |
| 2010/0305084 A1 | 12/2010 | Castanedo et al. |
| 2010/0305096 A1 | 12/2010 | Castanedo et al. |

FOREIGN PATENT DOCUMENTS

| | | |
|---|---|---|
| EP | 1 277 738 A1 | 1/2003 |
| GB | 1393161 | 5/1975 |
| WO | 2004/017950 A2 | 3/2004 |
| WO | 2004/065391 A1 | 8/2004 |
| WO | 2009/053716 A1 | 4/2009 |

OTHER PUBLICATIONS

Cancer and Metastasis Reviews (1998), 17(1), 91-106.*
Science (1999), vol. 286, 531-537.*
Cecil Textbook of Medicine, 20$^{th}$ edition (1996), vol. 2, pp. 2050-2057.*
Cecil Testbook of Medicine, 20$^{th}$ edition (1996), vol. 2, pp. 1992-1996.*
FDA mulls drug to slow late-stage Alzheimer's [Online], [retrieved on Sep. 23, 2009]. Retrieved from the Internet, URL;hyyp://www.cnn.com/2003/HEALTH/conditions/09/24/alzheimers.drug.ap/index.html>.*
Huff, Joel R., Journal of Medicinal Chemistry, vol. 34, No. 8, Aug. 1991, pp. 2305-2314.* Bachman et al. et al., "The PIK3CA gene is mutated with high frequency in human breast cancers" Cancer Biol Ther 3(8):772-775 (Aug. 2004).
Briel, D. et al., "Selective Nucleophilic Replacement of the (Continued)

*Primary Examiner* — Rebecca Anderson
(74) *Attorney, Agent, or Firm* — Alex Andrus; Genentech, Inc

(57) ABSTRACT

Thienopyrimidines of formula (I) wherein W and $R^1$ to $R^4$ are as defined in the claims, and the pharmaceutically acceptable salts thereof are inhibitors of PI3K and are selective for the p110δ isoform, which is a class Ia PI3 kinase, over both other class Ia and class Ib kinases. The compounds may be used to treat diseases and disorders arising from abnormal cell growth, function or behavior associated with PI3 kinase such as cancer, immune disorders, cardiovascular disease, viral infection, inflammation, metabolism/endocrine function disorders and neurological disorders.

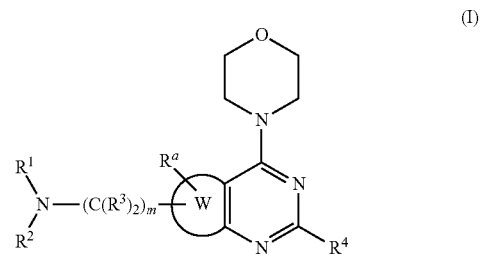

(I)

16 Claims, No Drawings

OTHER PUBLICATIONS

Benzylsulfanyl Group in 2,4-Disulfanyl-substituted Thieno[2,3-d]pyrimidin-6-carboxylic Acid Derivatives by Secondary Amines"J. Heterocyclic Chem 42(5):841-846 (Jul. 2005).

International Search Report for PCT/GB2005/004137 (Mar. 21, 2006).

Garcia-Echeverria et al. et al., "Drug discovery approaches targeting the PI3/Akt pathway in cancer" Oncogene 27:5511-5526 (2008).

Kang et al. et al., "Phophatidylinositol 3-kinase mutations identified in human cancer are oncogenic" P Natl Acad Sci USA 102(3):802-807 (Jan. 18, 2005).

Manhas, M.S. et al., "Heterocyclic Compounds. V. 2,4-Disubstituted Thienopyrimidones (1)" J. Heterocyclic Chem. 13:633-638 (Jun. 1976).

Raynaud et al. et al., "Biological properties of potent inhibitors of class I phophatidylinositide 3-kinases: from PI-103 through PI-540, PI-620 to the oral agent GDC-0941" Mol Cancer Ther 8(7):1725-1738 (Jul. 2009).

Samuels et al., "High frequency of mutations of the PIK3CA gene in human cancers" Science 304:554 (Apr. 23, 2004).

Shayesteh et al. et al., "PIK3CA is implicated as an ongogene in ovarian cancer" Nat Genet 21:99-102 (Jan. 1999).

Workman et al. et al., "Drugging the PI3 kinome" Nature Biotech 24(7):794-796 (Jul. 2006).

Yap et al. et al., "Targeting the PI3K-AKT-mTOR pathway: progress, pitfalls, and promises" Current Opin Pharm 8:393-412 (2008).

\* cited by examiner

THIENOPYRIMIDINE DERIVATIVES AS PI3K INHIBITORS

RELATED APPLICATIONS

This application is a National Stage Application under 35 U.S.C. §371 and claims the benefit of priority to International Application No. PCT/GB2008/003621 having an International Filing Date of 27 Oct. 2008 which claims the benefit of priority of United Kingdom Application Serial Number 0721059.8 filed on 26 Oct. 2007, which are herein incorporated by reference in their entireties.

FIELD OF THE INVENTION

The present invention relates to indolyl thienopyrimidine compounds and to their use as inhibitors of phosphatidylinositol 3-kinase (PI3K).

BACKGROUND TO THE INVENTION

Phosphatidylinositol (hereinafter abbreviated as "PI") is one of a number of phospholipids found in cell membranes. In recent years it has become clear that PI plays an important role in intracellular signal transduction. In the late 1980s, a PI3 kinase (PI3K) was found to be an enzyme which phosphorylates the 3-position of the inositol ring of phosphatidylinositol (M. Whitman et al., 1988, Nature, 332, 644-646).

PI3K was originally considered to be a single enzyme, but it has now been clarified that a plurality of subtypes are present in PI3K. Each subtype has its own mechanism for regulating activity. Three major classes of PI3Ks have been identified on the basis of their in vitro substrate specificity (B. Vanhaesebroeck et al, 1997, Trends in Biochemical Sciences, 22, 267-272). Substrates for class I PI3Ks are PI, PI 4-phosphate (PI4P) and PI 4,5-biphosphate (PI (4,5)P2). Class I PI3Ks are further divided into two groups, class Ia and class Ib, in terms of their activation mechanism. Class Ia PI3Ks include PI3K p110α, p110β and p110δ subtypes, which transmit signals from tyrosine kinase-coupled receptors. Class Ib PI3K includes a p110γ subtype activated by a G protein-coupled receptor. PI and PI(4)P are known as substrates for class II PI3Ks. Class II PI3Ks include PI3K C2α, C21β and C2γ subtypes, which are characterized by containing C2 domains at the C terminus. The substrate for class III PI3Ks is PI only.

In the PI3K subtypes, the class Ia subtype has been most extensively investigated to date. The three subtypes of class Ia are heterodimers of a catalytic 110 kDa subunit and regulatory subunits of 85 kDa or 55 kDa. The regulatory subunits contain SH2 domains and bind to tyrosine residues phosphorylated by growth factor receptors with a tyrosine kinase activity or oncogene products, thereby inducing the PI3K activity of the p110 catalytic subunit which phosphorylates its lipid substrate. Thus, the class Ia subtypes are considered to be associated with cell proliferation and carcinogenesis, immune disorders and conditions involving inflammation.

WO 01/083456 describes a series of condensed heteroaryl derivatives which have activity as inhibitors of PI3 K and which suppress cancer cell growth.

SUMMARY OF THE INVENTION

It has now been found that a series of novel thienopyrimidine compounds have activity as inhibitors of PI3K. The compounds exhibit selectivity for the p110δ subtype of PI3 kinase, over both other class Ia and class Ib PI3Ks. Accordingly, the present invention provides a compound which is a thienopyrimidine of formula (I):

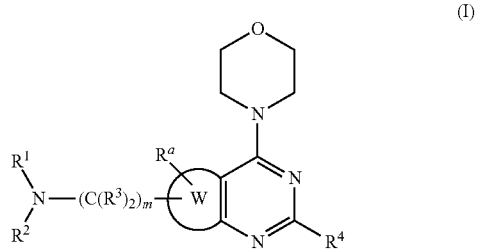

wherein
W represents a thiophene ring;
$R^1$ and $R^2$ form, together with the N atom to which they are attached, a group of the following formula (IIa):

in which A is selected from:

(a) a group selected from homopiperazine, piperazine, piperidine, pyrrolidine and azetidine, which group is substituted by one or more substituents selected from $C_3$-$C_{10}$ cycloalkyl which is unsubstituted or substituted, an O-containing ring which is tetrahydrofuran, tetrahydropyran or oxetane and which is unsubstituted or substituted, —NR'—(CR'$_2$)$_r$—X wherein each R' is independently H or $C_1$-$C_6$ alkyl, r is 0 or 1 and X is selected from $C_3$-$C_{10}$ cycloalkyl which is unsubstituted or substituted, an O-containing ring which is tetrahydrofuran, tetrahydropyran or oxetane and which is unsubstituted or substituted, and a 4-membered saturated N-containing heterocyclic ring which is unsubstituted or substituted, and which group is optionally substituted by one or more further substituents;

(b) a 4- to 7-membered saturated N-containing heterocyclic ring which includes 0 or 1 additional heteroatoms selected from N, S and O, the ring being fused to a second ring selected from a 4- to 7-membered saturated N-containing heterocyclic ring as defined above, a 5- to 12-membered unsaturated heterocyclic ring, a 5- to 7-membered saturated O-containing heterocyclic ring, a 3- to 12-membered saturated carbocyclic ring and an unsaturated 5- to 12-membered carbocyclic ring to form a heteropolycyclic ring system, the heteropolycyclic ring system being unsubstituted or substituted;

(c) a 4- to 7-membered saturated N-containing heterocyclic ring which includes 0 or 1 additional heteroatoms selected from N, S and O and which further comprises, linking two constituent atoms of the ring, a bridgehead group selected from —(CR'$_2$)$_n$— and —(CR'$_2$)$_r$—O—(CR'$_2$)$_s$— wherein each R' is as defined above, n is 1, 2 or 3, r is as defined above and s is 0 or 1, the remaining ring positions being unsubstituted or substituted; and (d) a group of formula (IIb):

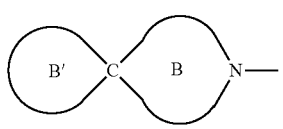

(IIb)

wherein ring B is a 4- to 7-membered saturated N-containing heterocyclic ring which includes 0 or 1 additional heteroatoms selected from N, S and O and ring B' is a 3- to 12-membered saturated carbocyclic ring, a 5- to 7-membered saturated O-containing heterocyclic ring or a 4- to 7-membered saturated N-containing heterocyclic ring as defined above, each of B and B' being unsubstituted or substituted;

m is 0, 1 or 2;

$R^3$ is H or $C_1$-$C_6$ alkyl; $R^a$ is selected from R', halo, CN, C(O)NR'$_2$, halo($C_1$-$C_6$)alkyl, SO$_2$R', SO$_2$NR'$_2$, NR'SO$_2$R', NR'C(O)R', NR'C(O)OR', NR'C(O)NR'$_2$, OR' and NR'$_2$, wherein each R' is independently as defined above; and $R^4$ is an indole group which is unsubstituted or substituted; or a pharmaceutically acceptable salt thereof.

DETAILED DESCRIPTION OF THE INVENTION

As used herein, the term "fused" indicates that two rings are joined together by a common bond between two adjacent ring atoms. The term "spiro-fused" indicates that two rings are linked through a single common carbon atom, The term "bridgehead" denotes a linking group, of one or more atoms in length, which connects two non-adjacent ring atoms. In each of these three cases a polycyclic (typically a bicyclic) structure is the result.

When any group, ring, group, ring, substituent or moiety defined herein is substituted, it is typically substituted by Z or $R^5$ as defined below.

A $C_1$-$C_6$ alkyl group is linear or branched. A $C_1$-$C_6$ alkyl group is typically a $C_1$-$C_4$ alkyl group, for example a methyl, ethyl, n-propyl, i-propyl, n-butyl, sec-butyl or tert-butyl group. A $C_1$-$C_6$ alkyl group is unsubstituted or substituted, typically by one or more groups Z or $R^5$ as defined below. Typically it is $C_1$-$C_4$ alkyl, for example methyl, ethyl, i-propyl, n-propyl, t-butyl, s-butyl or n-butyl.

Z is selected from H, unsubstituted $C_1$-$C_6$ alkyl, halo, —OR, —SR, —$(C(R^6)_2)_q$R, —CH$_2$OR, —CF$_3$, -(halo)-$C_1$-$C_6$ alkyl, —$(C(R^6)_2)_q$O-(halo)-$C_1$-$C_6$ alkyl, —CO$_2$R, —$(C(R^6)_2)_q$CO$_2$R, —$(C(R^6)_2)_q$COR, CF$_2$OH, CH(CF$_3$)OH, C(CF$_3$)$_2$OH, —(CH$_2$)$_q$OR, —$(C(R^6)_2)_q$OR, —(CH$_2$)$_q$NR$_2$, —$(C(R^6)_2)_q$NR$_2$, —C(O)N(R)$_2$, —$(C(R^6)_2)_q$CONR$_2$, —NR$_2$, —$(C(R^6)_2)_q$NR$_2$, —$(C(R^6)_2)_q$NRC(O)R, —$(C(R^6)_2)_q$NRC(O)OR, —S(O)$_p$R, —S(O)$_p$N(R)$_2$, —$(C(R^6)_2)_q$S(O)$_p$N(R)$_2$, —OC(O)R, —$(C(R^6)_2)_q$OC(O)R, —OC(O)N(R)$_2$, —$(C(R^6)_2)_q$OC(O)N(R)$_2$, —NRS(O)$_p$R, —$(C(R^6)_2)_q$NRS(O)$_p$R, —NRC(O)N(R)$_2$, —$(C(R^6)_2)_q$NRC(O)N(R)$_2$, CN, —NO$_2$, =O, a 5- to 12-membered aryl or heteroaryl group, which group is unsubstituted or substituted and a 4- to 7-membered saturated N-containing heterocyclic ring, wherein each R is independently selected from H, $C_1$-$C_6$ alkyl, $C_3$-$C_{10}$ cycloalkyl and a 5- to 12-membered aryl or heteroaryl group, the group being unsubstituted or substituted, or when two groups R are attached to an N atom they form, together with the N atom, a 4- to 7-membered saturated N-containing heterocyclic ring; p is 1 or 2 and q is 0, 1 or 2.

$R^5$ is selected from $C_1$-$C_6$ alkoxy, OR$^6$, SR$^6$, S(O)$_p$R$^6$, nitro, CN, halogen, —C(O)R$^6$, —CO$_2$R$^6$, —C(O)N(R$^6$)$_2$ and —N(R$^6$)$_2$. $R^6$, each of which is the same or different when more than one is present in a given substituent, is selected from H, $C_1$-$C_6$ alkyl and $C_3$-$C_{10}$ cycloalkyl, and p is 1 or 2.

A halogen or halo group is F, Cl, Br or I. Preferably it is F, Cl or Br. A $C_1$-$C_6$ alkyl group substituted by halogen may be denoted by the term "halo-$C_1$-$C_6$ alkyl", which means an alkyl group in which one or more hydrogens is replaced by halo. A halo-$C_1$-$C_6$ alkyl group preferably contains one, two or three halo groups. A preferred example of such a group is trifluoromethyl.

A $C_1$-$C_6$ alkoxy group is linear or branched. It is typically a $C_1$-$C_4$ alkoxy group, for example a methoxy, ethoxy, propoxy, i-propoxy, n-propoxy, n-butoxy, sec-butoxy or tert-butoxy group. A $C_1$-$C_6$ alkoxy group is unsubstituted or substituted, typically by one or more groups Z or $R^5$ as defined above.

A $C_3$-$C_{10}$ cycloalkyl group may be, for instance, $C_3$-$C_8$ cycloalkyl such as cyclopropyl, cyclobutyl, cyclopentyl, cyclohexyl, or cycloheptyl. Typically it is $C_3$-$C_6$ cycloalkyl, for example cyclopropyl, cyclobutyl or cyclopentyl. In one embodiment it is cyclopropyl. A $C_3$-$C_{10}$ cycloalkyl group is unsubstituted or substituted, typically by one or more groups Z or $R^5$ as defined above.

A saturated 4- to 7-membered N-containing heterocyclic ring typically contains one nitrogen atom and either an additional N atom or an O or S atom, or no additional heteroatoms. It may be, for example, azetidine, pyrrolidine, piperidine, piperazine, morpholine, thiomorpholine or homopiperazine. A 4-membered saturated N-containing heterocyclic ring is typically azetidine.

A 4- to 7-membered, or a 4-membered, saturated N-containing heterocyclic ring as defined above is unsubstituted or substituted on one or more ring carbon atoms and/or on any additional N atom present in the ring. Examples of suitable substituents include one or more groups Z or $R^5$ as defined above, and a $C_1$-$C_6$ alkyl group which is unsubstituted or substituted by a group Z or $R^5$ as defined above.

When A is a group selected from piperazine, piperidine and pyrrolidine which is substituted by —NR'—(CR'$_2$)$_r$—X as defined under (a) above, parameter r is typically 1. A is typically substituted by a group selected from cyclopropyl, cyclobutyl, —NH—CH$_2$-cyclopropyl, —NH-cyclopropyl, —NH—CH$_2$-tetrahydrofuranyl, —NH-tetrahydrofuranyl, —NH—CH$_2$-tetrahydropyranyl, —NH-tetrahydropyranyl and azetidinyl. Specific examples of such a group A include the following structures:

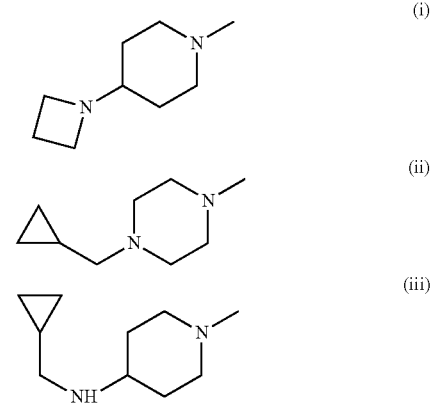

-continued

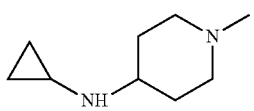
(iv)

The group A is optionally substituted by one or more further substituents. Such further substituents are typically selected from groups Z and $R^5$ as defined above.

A 5- to 7-membered saturated O-containing heterocyclic ring contains at least one O atom and 0, 1 or 2, typically 0 or 1, additional heteroatoms selected from O, N and S. It is, for instance, tetrahydropyran, tetrahydropyran or morpholine.

A 3- to 12-membered saturated carbocyclic ring is a 3-, 4-, 5-, 6-, 7-, 8-, 9-, 10, 11- or 12-membered carbocyclic ring containing only saturated bonds. It is a monocyclic or fused bicyclic ring system. It is, for instance, a 3- to 7-membered saturated carbocyclic ring. Examples include cyclopropane, cyclobutane, cyclopentane, cyclohexane and cycloheptane, and bicyclic ring systems in which two such rings are fused together.

An unsaturated 5- to 12-membered carbocyclic group is a 5-, 6-, 7-, 8-, 9-, 10, 11- or 12-membered carbocyclic ring containing at least one unsaturated bond. It is a monocyclic or fused bicyclic ring system. The group is non-aromatic or aromatic, for instance a 5- to 12-membered aryl group. Examples include benzene, naphthalene, indane, indene and tetrahydronaphthalene rings, or phenyl, naphthyl, indanyl, indenyl and tetrahydronaphthyl groups. The group is unsubstituted or substituted, typically by one or more groups Z or $R^5$ as defined above.

An aryl group is a 5- to 12-membered aromatic carbocyclic group. It is monocyclic or bicyclic. Examples include phenyl and naphthyl groups. The group is unsubstituted or substituted, for instance by a group Z or $R^5$ as defined above.

An unsaturated 5- to 12-membered heterocyclic group is a 5-, 6-, 7-, 8-, 9-, 10, 11- or 12-membered heterocyclic ring containing at least one unsaturated bond and at least one heteroatom selected from O, N and S. It is a monocyclic or fused bicyclic ring system. The group is non-aromatic or aromatic, for instance heteroaryl. The group may be, for example, furan, thiophene, pyrrole, pyrrolopyrazine, pyrrolopyrimidine, pyrrolopyridine, pyrrolopyridazine, indole, isoindole, pyrazole, pyrazolopyrazine, pyrazolopyrimidine, pyrazolopyridine, pyrazolopyridazine, imidazole, imidazopyrazine, imidazopyrimidine, imidazopyridine, imidazopyridazine, benzimidazole, benzodioxole, benzodioxine, benzoxazole, benzothiophene, benzothiazole, benzofuran, indolizinyl, isoxazole, oxazole, oxadiazole, thiazole, isothiazole, thiadiazole, dihydroimidazole, dihydrobenzofuran, dihydrodioxinopyridine, dihydropyrrolopyridine, dihydrofuranopyridine, dioxolopyridine, pyridine, quinoline, isoquinoline, thienopyrimidine, quinoxaline, tetrahydrobenzofuran, tetrahydroquinoline, tetrahydroisoquinoline, 5,6,7,8-tetrahydro-imidazo[1,5-a]pyrazine, 5,6,7,8-tetrahydro-imidazo[1,2-a]pyrazine, thienopyrazine, pyrimidine, pyridazine, pyrazine, triazine, triazole or tetrazole. The group is unsubstituted or substituted, typically by one or more groups Z or $R^5$ as defined above.

Heteroaryl is a 5- to 12-membered aromatic heterocyclic group which contains 1, 2, 3, or 4 heteroatoms selected from O, N and S. It is monocyclic or bicyclic. Typically it contains one N atom and 0, 1, 2 or 3 additional heteroatoms selected from O, S and N. It may be, for example, a 5- to 7-membered heteroaryl group. Typically it is selected from the heteroaryl groups included in the above list of options for a 5- to 12-membered unsaturated heterocyclic group.

Examples of a 4- to 7-membered saturated N-containing heterocyclic ring which is fused to a second ring as defined above to form a heteropolycyclic ring system include a group selected from azetidine, pyrrolidine, piperidine, piperazine, morpholine, thiomorpholine and homopiperazine, said group being fused to a second ring as defined above. The second ring is typically a 4- to 7-membered saturated N-containing heterocyclic ring as defined above or a 5- to 12-membered unsaturated heterocyclic group. More typically the second ring is a 5-, 6- or 7-membered saturated N-containing heterocyclic ring or a 5- to 7-membered unsaturated heterocyclic ring. Typical examples of the second ring include azetidine, pyrrolidine, piperidine, piperazine, morpholine, thiomorpholine, homopiperazine, pyrrole, imidazole, pyridine, pyridazine, pyrimidine, pyrazine, tetrahydrofuran and tetrahydropyran. Examples of the resulting heteropolycyclic system include octahydro-pyrrolo[1,2-a]pyrazine and octahydro-pyrrolo[3,4-c]pyrrole. Specific examples of the heteropolycyclic system include the following structures:

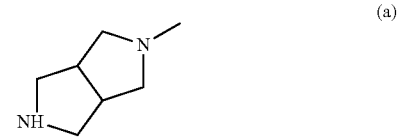
(a)

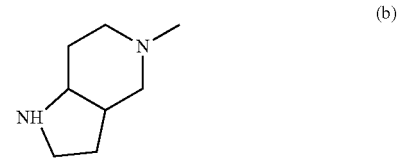
(b)

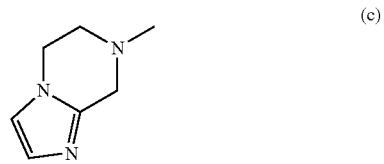
(c)

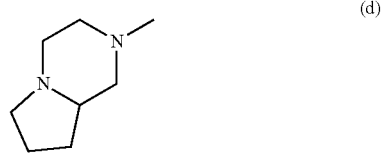
(d)

(e)

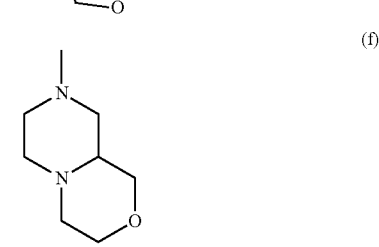
(f)

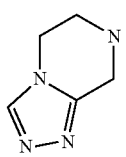
(g)

Examples of a 4- to 7-membered saturated N-containing heterocyclic group as defined above which includes a bridgehead group —(CR'$_2$)$_n$— or —(CR'$_2$)$_r$—O—(CR'$_2$)$_s$— as defined above include 3,8-diaza-bicyclo[3.2.1]octane, 2,5-diaza-bicyclo[2.2.1]heptane, 8-aza-bicyclo[3.2.1]octane, 2-aza-bicyclo[2.2.1]heptane, 3,6-diaza-bicyclo[3.1.1]heptane, 6-aza-bicyclo[3.1.1]heptane, 3,9-diaza-bicyclo[4.2.1]nonane and 3-oxa-7,9-diazabicyclo[3.3.1]nonane.

Specific examples of this group include the following structures:

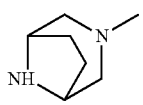
(a')

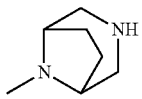
(b')

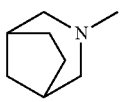
(c')

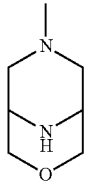
(d')

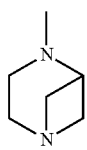
(e')

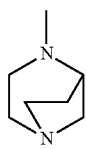
(f')

Examples of a group of formula (IIb) as defined above include groups derived from a 4- to 7-membered saturated N-containing heterocyclic group as defined above which is spiro-fused at any available ring carbon atom to a 3 to 12-membered saturated carbocyclic ring, typically to a 3- to 6-membered saturated carbocyclic ring, or to a 4- to 7-membered saturated N-containing heterocyclic group. Examples include a group selected from azetidine, pyrrolidine, piperidine and piperazine which is spiro-fused at a ring carbon atom to a group selected from cyclopropane, cyclobutane, cyclopentane, cyclohexane, azetidine, pyrrolidine, piperidine, piperazine and tetrahydropyran.

The group of formula (IIb) may, for instance, be a group derived from 3,9-diazaspiro[5.5]undecane, 2,7-diazaspiro[3.5]nonane, 2,8-diazaspiro[4.5]decane or 2,7-diazaspiro[4.4]nonane. Specific examples of a group of formula (IIb) include the following structures:

(i')

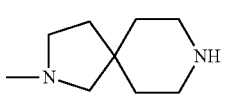
(ii')

(iii')

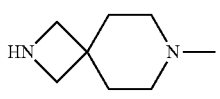
(iv')

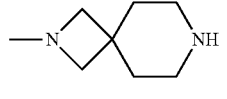
(v')

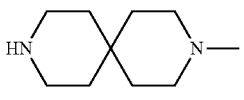
(vi')

(vii')

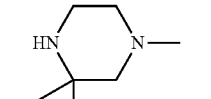
(viii')

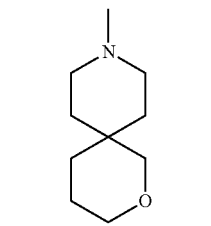
(ix')

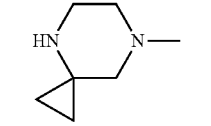
(x')

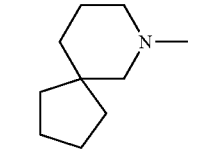
(xi')

-continued

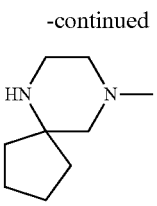
(xii')

R[4] is an indolyl group which is unsubstituted or substituted. The indolyl group may be linked to the thienopyrimidine core via any available ring position. It may, for instance, be an indol-4-yl, indol-5-yl, indol-6-yl or indol-7-yl group. Typically it is indol-4-yl or indol-6-yl, more typically an indol-4-yl group.

When substituted, the indolyl may be substituted at one or more available ring positions. Typically it bears a substituent on the benzene moiety of the indole group. For instance, an indol-4-yl group is typically substituted at the 5-, 6- or 7-position, more typically at the 5- or 6-position. An indol-5-yl group is typically substituted at the 4-, 6- or 7-position, more typically at the 4- or 6-position. An indol-6-yl group is typically substituted at the 4-, 5- or 7-position, more typically at the 4- or 5-position. An indol-7-yl group is typically substituted at the 4-, 5- or 6-position, more typically at the 5- or 6-position.

When the indolyl group is substituted it may be substituted by a group Z or R[5] as defined above. In a typical embodiment the indolyl group is substituted by a group selected from R, —OR, —SR, —S(O)$_p$R, CH$_2$OR, —C(O)R, —CO$_2$R, CF$_3$, CF$_2$OH, CH(CF$_3$)OH, C(CF$_3$)$_2$OH, —(CH$_2$)$_q$OR, —(CH$_2$)$_q$NR$_2$, —C(O)N(R)$_2$, —NR$_2$, —N(R)C(O)R, —S(O)$_p$N(R)$_2$, —OC(O)R, OC(O)N(R)$_2$, —N(R)S(O)$_p$R, —NRC(O)N(R)$_2$, CN, halo, —NO$_2$ and a 5-membered heteroaryl group containing 1, 2, 3 or 4 heteroatoms selected from O, N and S, wherein R, p and q are as defined above in the definition of Z. In another typical embodiment the indolyl group is substituted by a group selected from C$_1$-C$_6$ alkyl, CN, halo, —C(O)NR$_2$, halo(C$_1$-C$_6$)alkyl such as CF$_3$, NO$_2$, OR, SR, NR$_2$, C(O)R, SOR, SO$_2$R, SO$_2$NR$_2$, NRC(O)R, CO$_2$R and a 5-membered heteroaryl group as defined above. In another more typical embodiment the indolyl group is substituted by a group selected from CN, halo, —C(O)NR$_2$, halo(C$_1$-C$_6$) alkyl such as CF$_3$, —SO$_2$R, —SO$_2$NR$_2$, and a 5-membered heteroaryl group containing 1, 2, 3 or 4 heteroatoms selected from O, N and S. In the above embodiments R is typically H or C$_1$-C$_6$ alkyl.

Typically the substituent on the indolyl group is an electron-withdrawing group. When the substituent is a 5-membered heteroaryl group it may be, for example, furan, thiophene, pyrrole, imidazole, pyrazole, triazole, tetrazole, oxazole, isoxazole, oxadiazole, thiazole, isothiazole, or thiadiazole.

In one embodiment a substituted indolyl group is an indol-4-yl group substituted at the 5- or 6-position, in particular the 5-position, by CN, halo, —C(O)NH$_2$, —CF$_3$, —SO$_2$Me, —SO$_2$NMe$_2$ or a 5-membered heteroaryl group as defined above. Typically the indol-4-yl group is substituted at the 5- or 6-position by halo, in particular by F. More typically the indol-4-yl group is substituted at the 5-position by halo, in particular by F.

The parameter m in formula (I) is 0, 1 or 2. Typically m is 1 or 2. More typically m is 1.

When, in above definition (a) of A, the homopiperazine, piperazine, piperidine, pyrrolidine, morpholine or azetidine group is optionally substituted by one or more substituents, it is substituted on a ring carbon atom or a ring heteroatom by one or more groups Z or R[5] as defined above. Typical examples of the substituent include halo, oxo (=O), —C(O)—N(R[10])$_2$ and —C(R[10])$_2$—OR[10] wherein R[10] is H or unsubstituted C$_1$-C$_6$ alkyl. Examples of —C(O)—N(R[10])$_2$ include —C(O)—N(CH$_3$)$_2$ and —C(O)—NH$_2$. Examples of —C(R[10])$_2$—OR[10] include —CH$_2$—OH and —CH$_2$—OCH$_3$.

When, in above definition (b) of A, the heteropolycyclic ring system is substituted, it is substituted on a ring carbon atom or a ring heteroatom by one or more groups Z or R[5] as defined above. Typical examples of the substituent include oxo —C(O)—N(R[10])$_2$, —C(O)OR[10] and —S(O)$_2$R[10] wherein R[10] is as defined above. Examples of the substituent —C(O)—N(R[10])$_2$ include —C(O)—NH$_2$, —C(O)NH(CH$_3$) and —C(O)N(CH$_3$)$_2$. Examples of —C(O)R[10] include —C(O)CH$_3$. Examples of —C(R[10])$_2$—OR[10] include —CH$_2$—OH and —CH$_2$—OCH$_3$. Examples of the substituent —C(O)OR[10] include —C(O)OH and —C(O)OCH$_3$. A typical example of —S(O)$_2$R[10] is —S(O)$_2$CH$_3$.

When, in above definition (d) of A, the ring B or B' is substituted, it is substituted on a ring carbon atom or a ring heteroatom by one or more groups Z or R[5] as defined above. Typical examples of the substituent include halo, C$_1$-C$_6$ alkyl, —C(O)—N(R[10])$_2$, —C(O)R[10], —C(O)OR[10] and —S(O)$_2$R[10] wherein R[10] is as defined above. Examples of the substituent —C(O)—N(R[10])$_2$ include —C(O)—NH$_2$, —C(O)NH(CH$_3$) and —C(O)N(CH$_3$)$_2$. Examples of —C(O)R[10] include —C(O)CH$_3$. yde-C(R[10])$_2$—OR[10] include —CH$_2$—OH and —CH$_2$—OCH$_3$. Examples of the substituent —C(O)OR[10] include —C(O)OH and —C(O)OCH$_3$. A typical example of —S(O)$_2$R[10] is —S(O)$_2$CH$_3$.

The thiophene ring W in formula (I) adopts either of the two available regiochemical orientations. Thus, in one embodiment the thienopyrimidine is of the following formula (Ia):

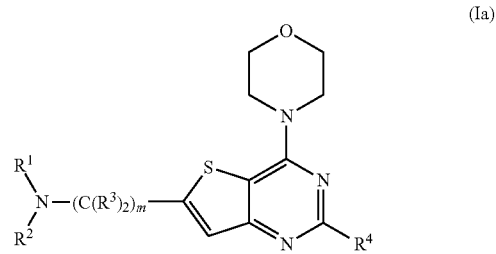
(Ia)

wherein R[1], R[2], R[3], R[4] and m are as defined above for formula (I).

In a second embodiment the thienopyrimidine is of the following formula (Ib):

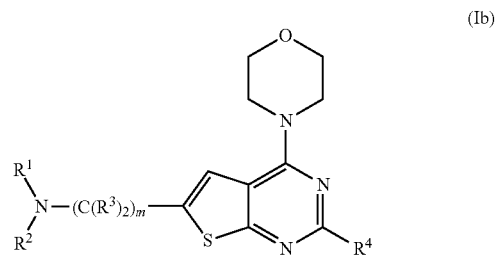
(Ib)

wherein R[1], R[2], R[3], R[4] and m are as defined above for formula (I).

Specific examples of compounds of the invention include the compound listed in the following Table 1:

TABLE 1

| Compound No. | Structure | Name |
|---|---|---|
| 1 | 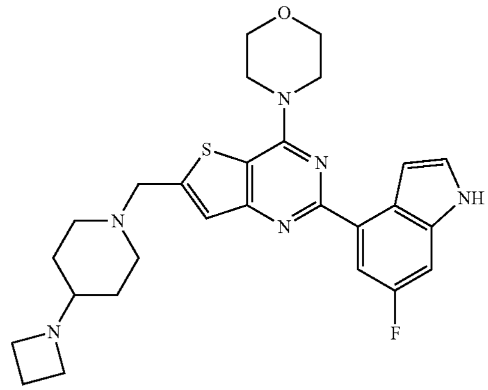 | 6-(4-Azetidin-1-yl-piperidin-1-ylmethyl)-2-(6-fluoro-1H-indol-4-yl)-4-morpholin-4-yl-thieno[3,2-d]pyrimidine |
| 2 | 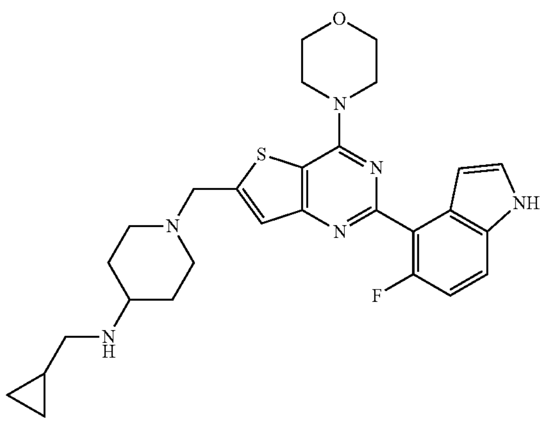 | Cyclopropylmethyl-{1-[2-(5-fluoro-1H-indol-4-yl)-4-morpholin-4-yl-thieno[3,2-d]pyrimidin-6-ylmethyl]-piperidin-4-yl}-amine |
| 3 | 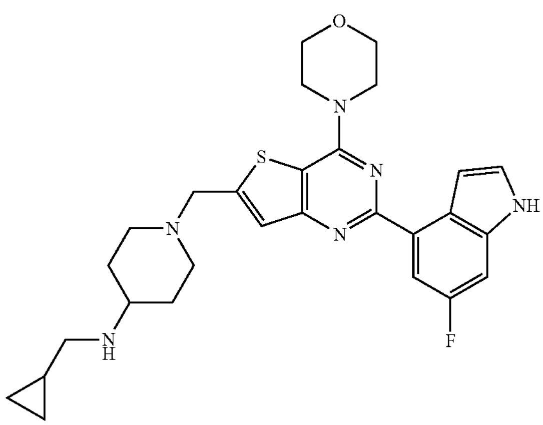 | Cyclopropylmethyl-{1-[2-(6-fluoro-1H-indol-4-yl)-4-morpholin-4-yl-thieno[3,2-d]pyrimidin-6-ylmethyl]-piperidin-4-yl}-amine |
| 4 | 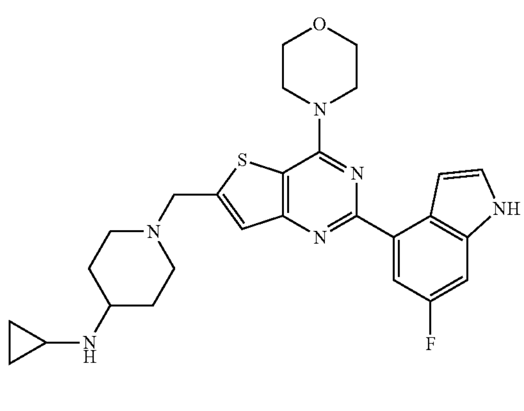 | Cyclopropyl-{1-[2-(6-fluoro-1H-indol-4-yl)-4-morpholin-4-yl-thieno[3,2-d]pyrimidin-6-ylmethyl]-piperidin-4-yl}-amine |

TABLE 1-continued

| Compound No. | Structure | Name |
|---|---|---|
| 5 | 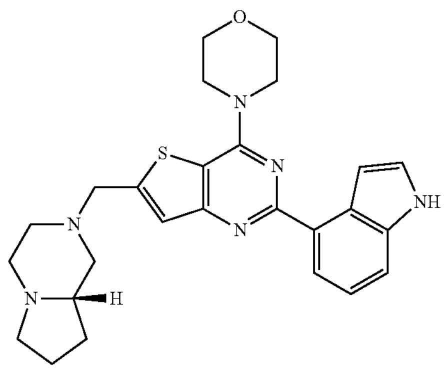 | 6-[(S)-1-(Hexahydro-pyrrolo[1,2-a]pyrazin-2-yl)methyl]-2-(1H-indol-4-yl)-4-morpholin-4-yl-thieno[3,2-d]pyrimidine |
| 6 | 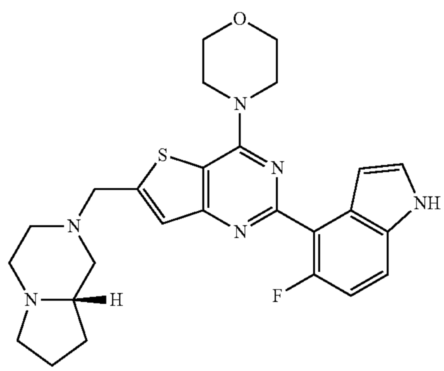 | 2-(5-Fluoro-1H-indol-4-yl)-6-[(S)-1-(hexahydro-pyrrolo[1,2-a]pyrazin-2-yl)methyl]-4-morpholin-4-yl-thieno[3,2-d]pyrimidine |
| 7 | 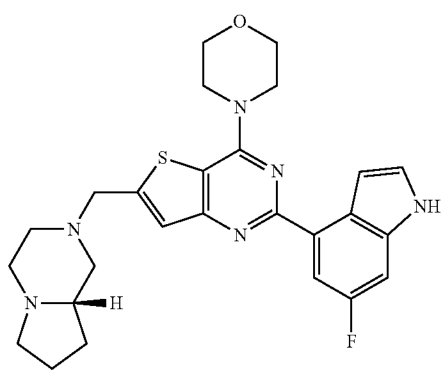 | 2-(6-Fluoro-1H-indol-4-yl)-6-[(S)-1-(hexahydro-pyrrolo[1,2-a]pyrazin-2-yl)methyl]-4-morpholin-4-yl-thieno[3,2-d]pyrimidine |
| 8 | 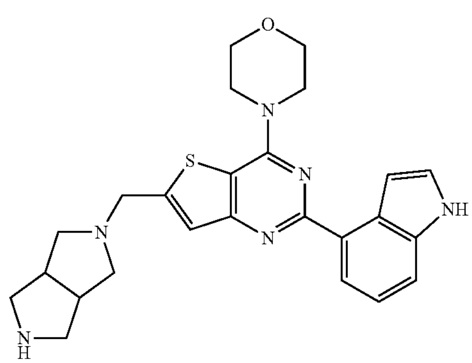 | 6-(Hexahydro-pyrrolo[3,4-c]pyrrol-2-ylmethyl)-2-(1H-indol-4-yl)-4-morpholin-4-yl-thieno[3,2-d]pyrimidine |

TABLE 1-continued

| Compound No. | Structure | Name |
|---|---|---|
| 9 | 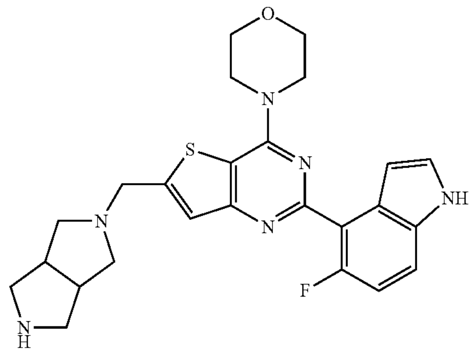 | 2-(5-Fluoro-1H-indol-4-yl)-6-(hexahydro-pyrrolo[3,4-c]pyrrol-2-ylmethyl)-4-morpholin-4-yl-thieno[3,2-d]pyrimidine |
| 10 | 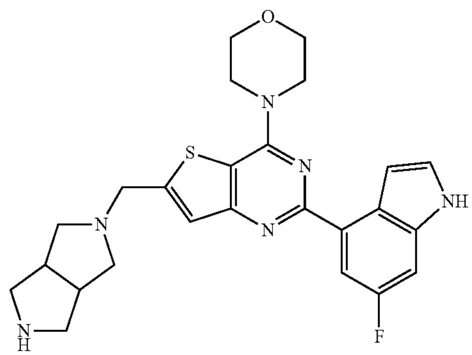 | 2-(6-Fluoro-1H-indol-4-yl)-6-(hexahydro-pyrrolo[3,4-c]pyrrol-2-ylmethyl)-4-morpholin-4-yl-thieno[3,2-d]pyrimidine |
| 11 | 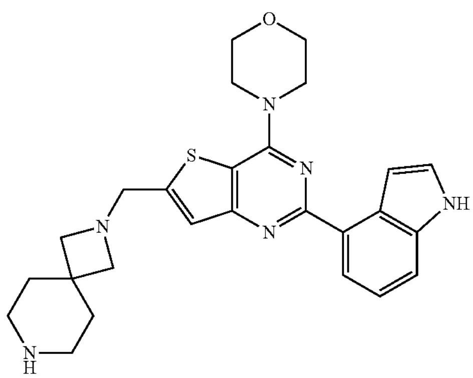 | 6-(2,7-Diaza-spiro[3.5]non-2-ylmethyl)-2-(1H-indol-4-yl)-4-morpholin-4-yl-thieno[3,2-d]pyrimidine |
| 12 | 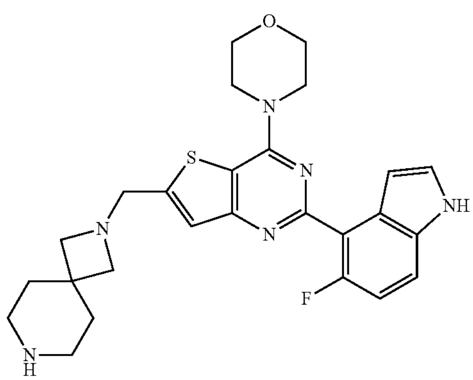 | 6-(2,7-Diaza-spiro[3.5]non-2-ylmethyl)-2-(5-fluoro-1H-indol-4-yl)-4-morpholin-4-yl-thieno[3,2-d]pyrimidine |

TABLE 1-continued

| Compound No. | Structure | Name |
|---|---|---|
| 13 | 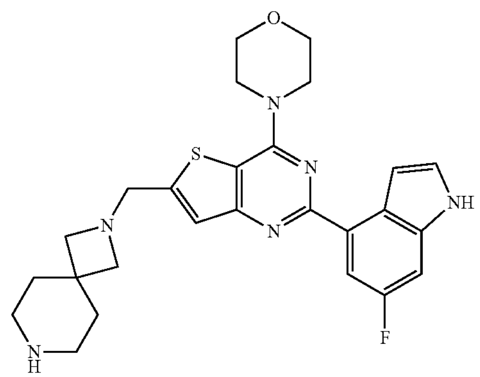 | 6-(2,7-Diaza-spiro[3.5]non-2-ylmethyl)-2-(6-fluoro-1H-indol-4-yl)-4-morpholin-4-yl-thieno[3,2-d]pyrimidine |
| 14 | 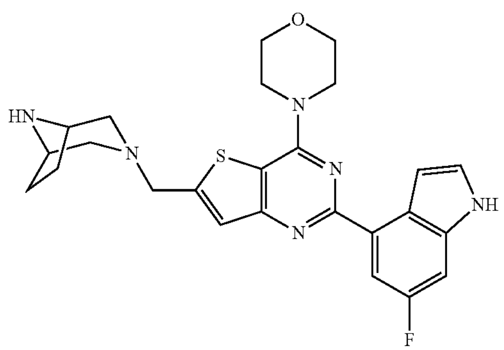 | 6-(3,8-Diaza-bicyclo[3.2.1]oct-3-ylmethyl)-2-(6-fluoro-1H-indol-4-yl)-4-morpholin-4-yl-thieno[3,2-d]pyrimidine |
| 16 | 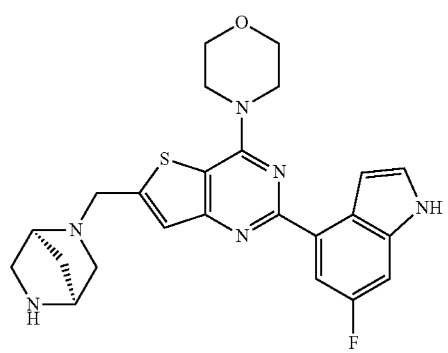 | 6-[(1S,5S)-1-(3,6-Diaza-bicyclo[3.1.1]hept-6-yl)methyl]-2-(6-fluoro-1H-indol-4-yl)-4-morpholin-4-yl-thieno[3,2-d]pyrimidine |
| 18 | 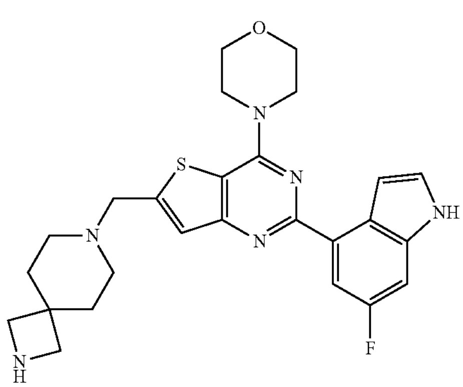 | 6-(2,7-Diaza-spiro[3.5]non-7-ylmethyl)-2-(6-fluoro-1H-indol-4-yl)-4-morpholin-4-yl-thieno[3,2-d]pyrimidine |

TABLE 1-continued

| Compound No. | Structure | Name |
|---|---|---|
| 19 | 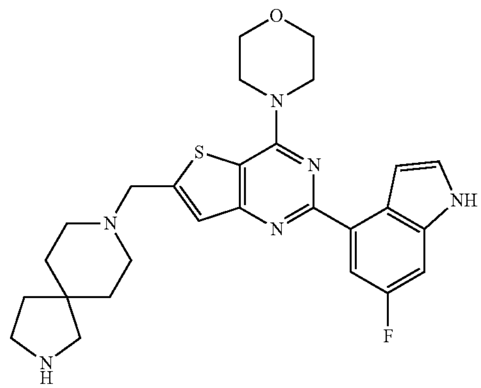 | 6-(2,8-Diaza-spiro[4.5]dec-8-ylmethyl)-2-(6-fluoro-1H-indol-4-yl)-4-morpholin-4-yl-thieno[3,2-d]pyrimidine |
| 20 | 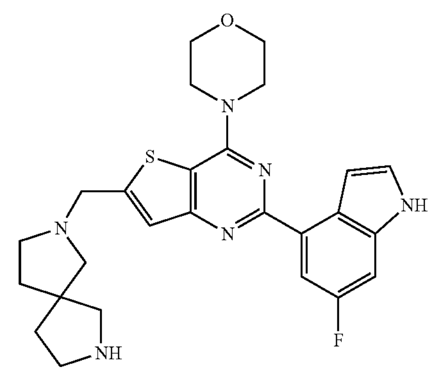 | 6-(2,7-Diaza-spiro[4.4]non-2-ylmethyl)-2-(6-fluoro-1H-indol-4-yl)-4-morpholin-4-yl-thieno[3,2-d]pyrimidine |
| 21 | 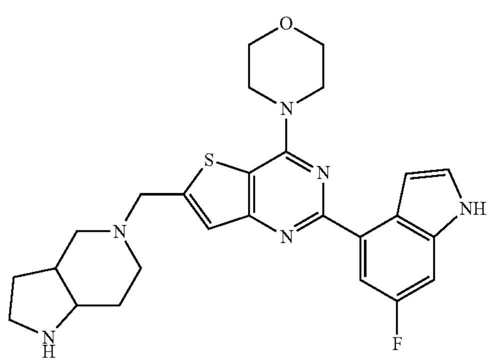 | 2-(6-Fluoro-1H-indol-4-yl)-4-molpholin-4-yl-6-(octahydro-pyrrolo[3,2-c]pyridin-5-ylmethyl)-thieno[3,2-d]pyrimidine |
| 22 | 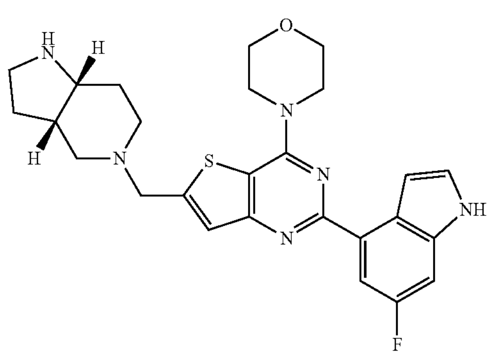 | 2-(6-Fluoro-1H-indol-4-yl)-4-morpholin-4-yl-6-[(3aS,7aR)-1-(octahydro-pyrrolo[3,2-c]pyridin-5-yl)methyl]-thieno[3,2-d]pyrimidine |

TABLE 1-continued

| Compound No. | Structure | Name |
|---|---|---|
| 23 | 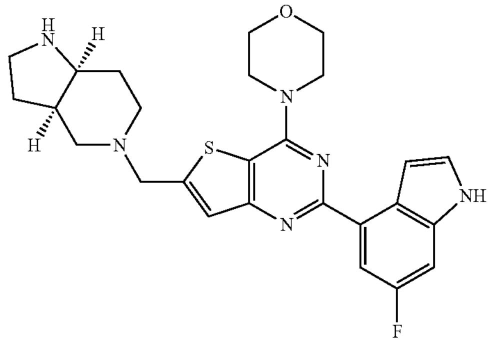 | 2-(6-Fluoro-1H-indol-4-yl)-4-morpholin-4-yl-6-[(3aR,7aS)-1-(octahydro-pyrrolo[3,2-c]pyridin-5-yl)methyl]-thieno[3,2-d]pyrimidine |
| 24 | 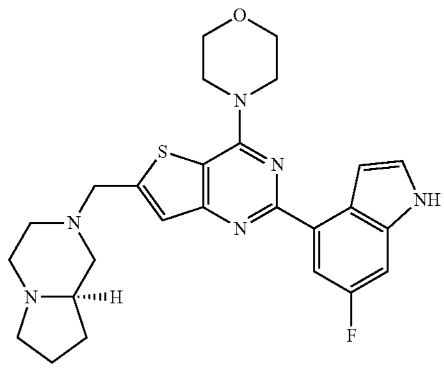 | 2-(6-Fluoro-1H-indol-4-yl)-6-[(R)-1-(hexahydro-pyrrolo[1,2-a]pyrazin-2-yl)methyl]-4-morpholin-4-yl-thieno[3,2-d]pyrimidine |
| 27 | 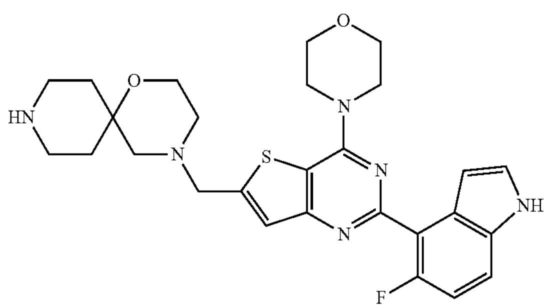 | 4-[2-(5-Fluoro-1H-indol-4-yl)-4-morpholin-4-yl-thieno[3,2-d]pyrimidin-6-ylmethyl]-1-oxa-4,9-diaza-spiro[5.5]undecane |
| 28 | 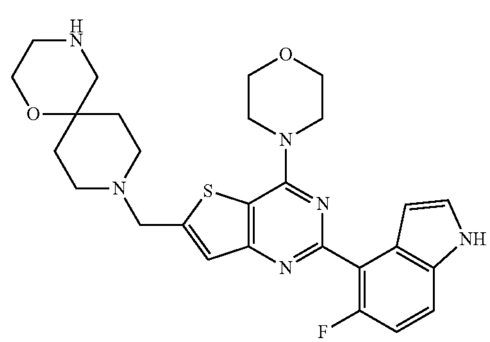 | 9-[2-(5-Fluoro-1H-indol-4-yl)-4-morpholin-4-yl-thieno[3,2-d]pyrimidin-6-ylmethyl]-1-oxa-4,9-diaza-spiro[5.5]undecane |

TABLE 1-continued

| Compound No. | Structure | Name |
|---|---|---|
| 29 | 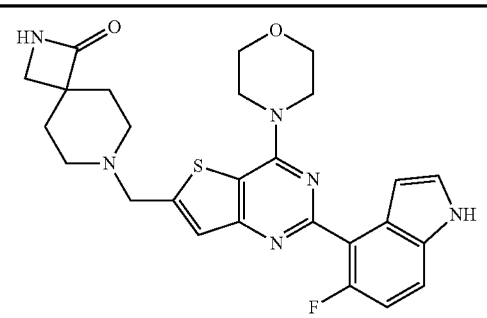 | 7-[2-(5-Fluoro-1H-indol-4-yl)-4-morpholin-4-yl-thieno[3,2-c]pyrimidin-6-ylmethyl]-2,7-diaza-spiro[3.5]nonan-1-one |
| 31 | 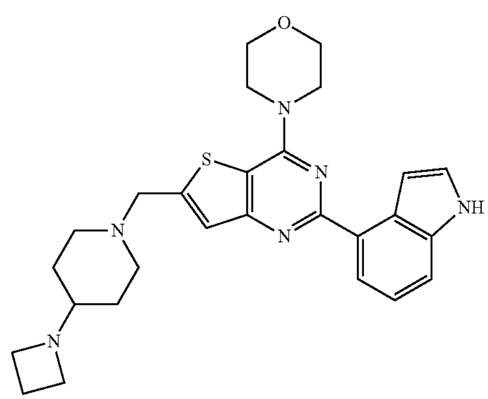 | 6-(4-Azetidin-1-yl-piperidin-1-ylmethyl)-2-(1H-indol-4-yl)-4-morpholin-4-yl-thieno[3,2-d]pyrimidine |
| 32 | 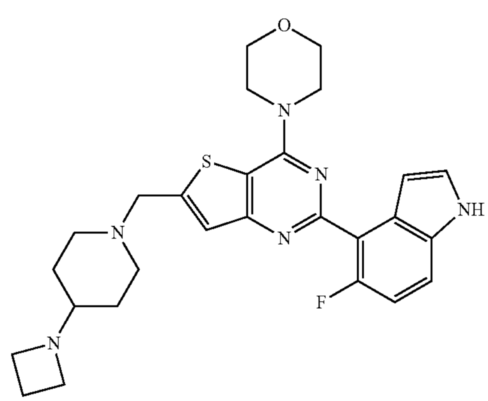 | 6-(4-Azetidin-1-yl-piperidin-1-ylmethyl)-2-(5-fluoro-1H-indol-4-yl)-4-morpholin-4-yl-thieno[3,2-d]pyrimidine |
| 33 | 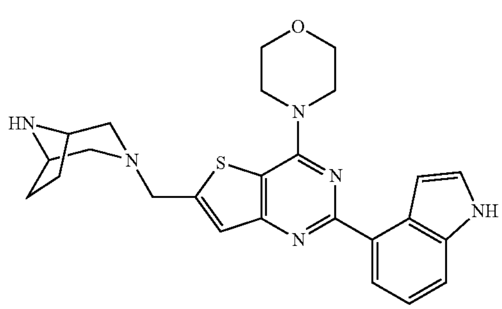 | 6-(3,8-Diaza-bicyclo[3.2.1]oct-3-ylmethyl)-2-(1H-indol-4-yl)-4-morpholin-4-yl-thieno[3,2-d]pyrimidine |

TABLE 1-continued

| Compound No. | Structure | Name |
|---|---|---|
| 34 | 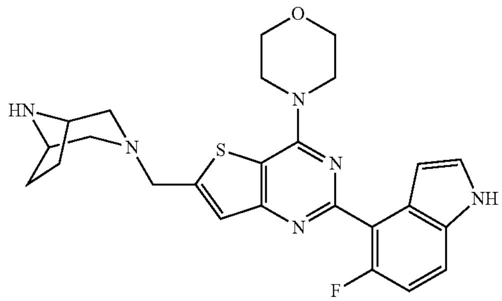 | 6-(3,8-Diaza-bicyclo[3.2.1]oct-3-ylmethyl)-2-(5-fluoro-1H-indol-4-yl)-4-morpholin-4-yl-thieno[3,2-d]pyrimidine |
| 35 | 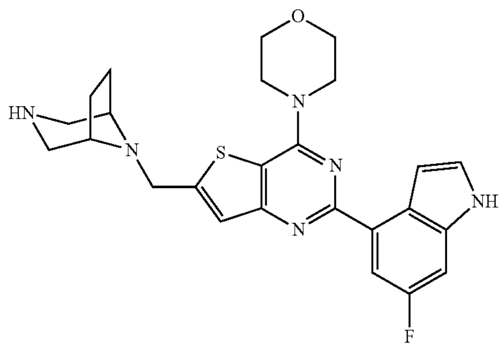 | 6-(3,8-Diaza-bicyclo[3.2.1]oct-8-ylmethyl)-2-(6-fluoro-1H-indol-4-yl)-4-morpholin-4-yl-thieno[3,2-d]pyrimidine |
| 36 | 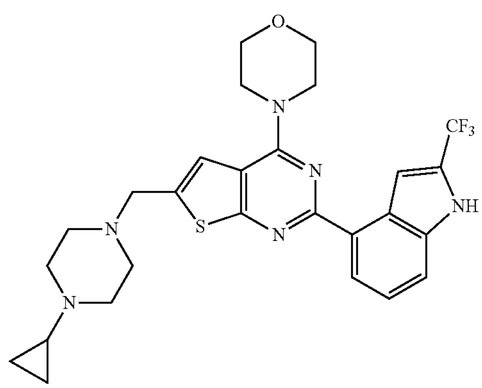 | 6-(4-Cyclopropyl-piperazin-1-ylmethyl)-4-morpholin-4-yl-2-(2-trifluoromethyl-1H-indol-4-yl)-thieno[2,3-d]pyrimidine |
| 37 | 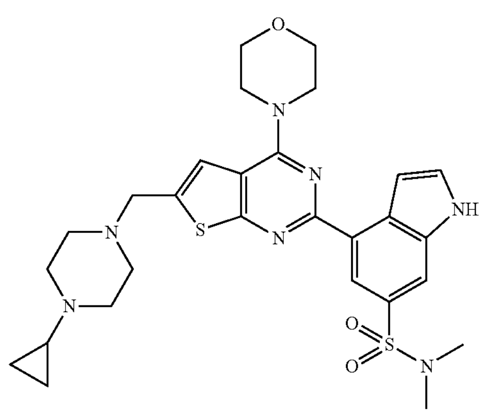 | 4-[6-(4-Cyclopropyl-piperazin-1-ylmethyl)-4-morpholin-4-yl-thieno[2,3-d]pyrimidin-2-yl]-1H-indole-6-sulfonic acid dimethylamide |

TABLE 1-continued

| Compound No. | Structure | Name |
|---|---|---|
| 38 | 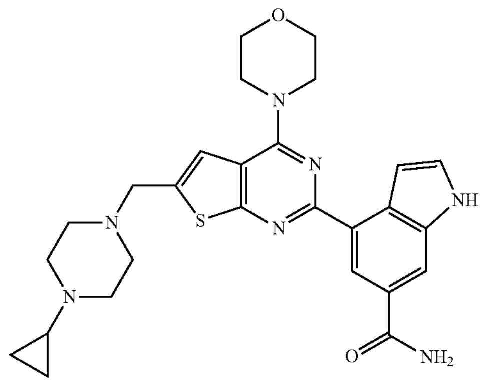 | 4-[6-(4-Cyclopropyl-piperazin-1-ylmethyl)-4-morpholin-4-yl-thieno[2,3-d]pyrimidin-2-yl]-1H-indole-6-carboxylic acid amide |
| 39 | 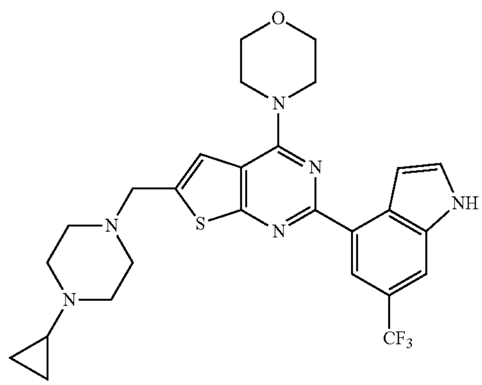 | 6-(4-Cyclopropyl-piperazin-1-ylmethyl)-4-morpholin-4-yl-2-(6-trifluoromethyl-1H-indol-4-yl)-thieno[2,3-d]pyrimidine |
| 40 | 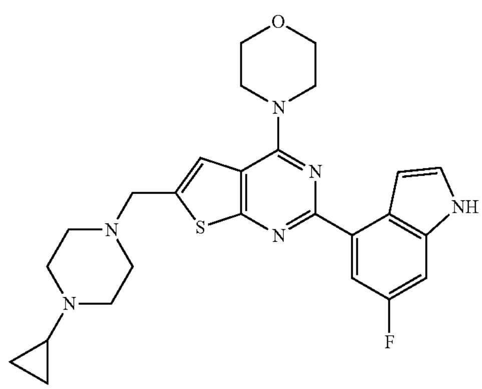 | 6-(4-Cyclopropyl-piperazin-1-ylmethyl)-2-(6-fluoro-1H-indol-4-yl)-4-morpholin-4-yl-thieno[2,3-d]pyrimidine |
| 41 | 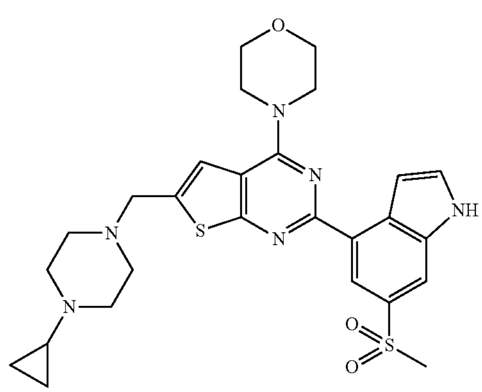 | 6-(4-Cyclopropyl-piperazin-1-ylmethyl)-2-(6-methanesulfonyl-1H-indol-4-yl)-4-morpholin-4-yl-thieno[2,3-d]pyrimidine |

TABLE 1-continued

| Compound No. | Structure | Name |
|---|---|---|
| 42 | 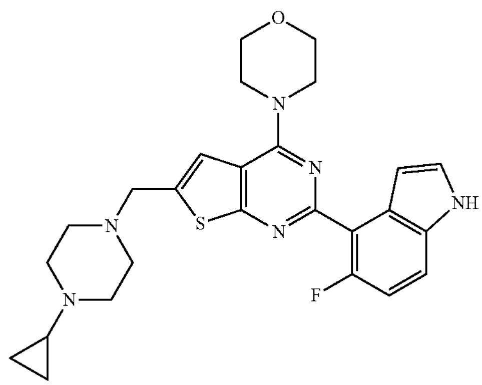 | 6-(4-Cyclopropyl-piperazin-1-ylmethyl)-2-(5-fluoro-1H-indol-4-yl)-4-morpholin-4-yl-thieno[2,3-d]pyrimidine |
| 43 | 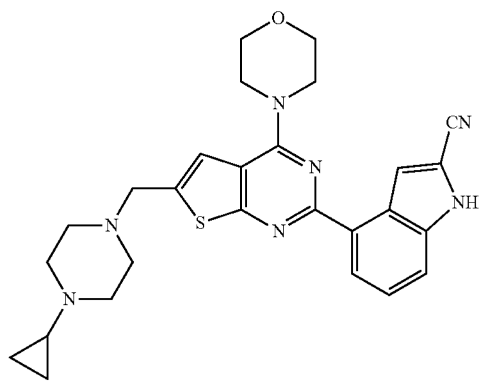 | 4-[6-(4-Cyclopropyl-piperazin-1-ylmethyl)-4-morpholin-4-yl-thieno[2,3-d]pyrimidin-2-yl]-1H-indole-2-carbonitrile |
| 44 | 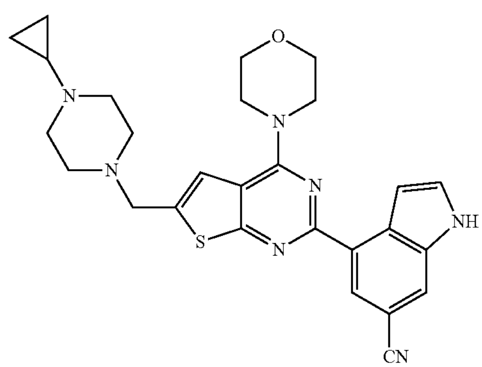 | 4-[6-(4-Cyclopropyl-piperazin-1-ylmethyl)-4-morpholin-4-yl-thieno[2,3-d]pyrimidin-2-yl]-1H-indole-6-carbonitrile |
| 45 | 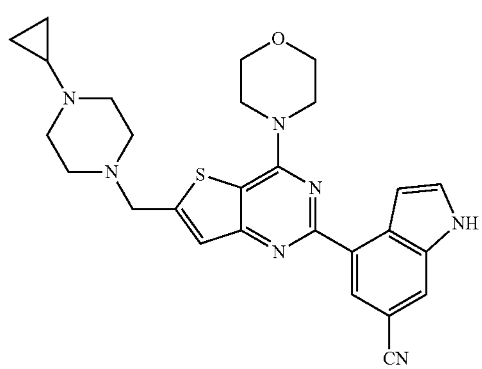 | 4-[6-(4-Cyclopropyl-piperazin-1-ylmethyl)-4-mmpholin-4-yl-thieno[3,2-d]pyrimidine-2-yl]-1H-indole-6-carbonitrile |

TABLE 1-continued

| Compound No. | Structure | Name |
|---|---|---|
| 46 | 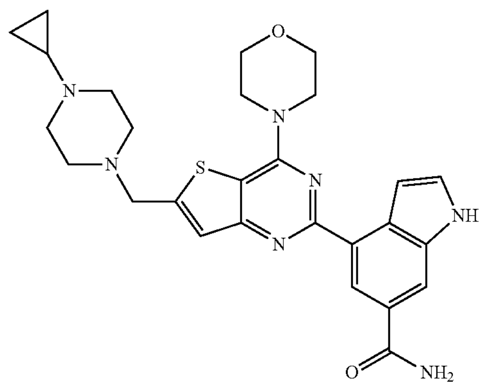 | 4-[6-(4-Cyclopropyl-piperazin-1-ylmethyl)-4-morpholin-4-yl-thieno[3,2-d]pyrimidine-2-yl]-1H-indole-6-carboxylic acid amide |
| 47 | 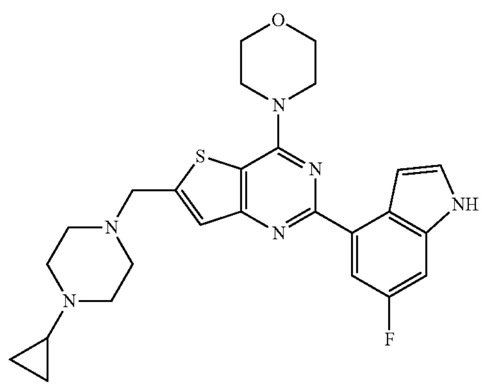 | 6-(4-Cyclopropyl-piperazin-1-ylmethyl)-2-(6-fluoro-1H-indol-4-yl)-4-morpholin-4-yl-thieno[3,2-d]pyrimidine |
| 48 | 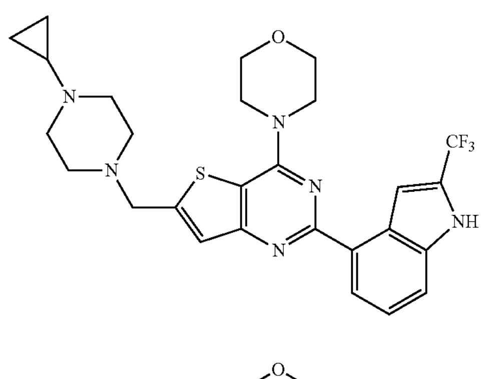 | 6-(4-Cyclopropyl-piperazin-1-ylmethyl)-4-morpholin-4-yl-2-(2-trifluoromethyl-1H-indol-4-yl)-thieno[3,2-d]pyrimidine |
| 49 | 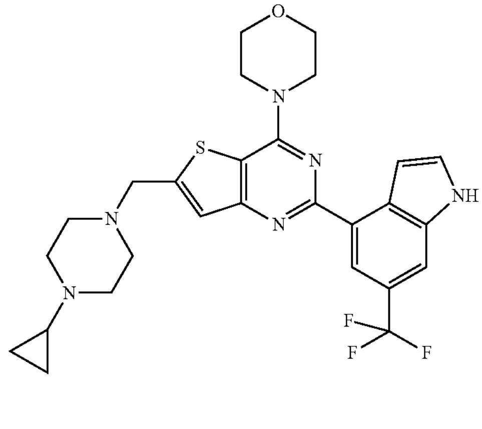 | 6-(4-Cyclopropyl-piperazin-1-ylmethyl)-4-morpholin-4-yl-2-(6-trifluoromethyl-1H-indol-4-yl)-thieno[3,2-d]pyrimidine |

TABLE 1-continued

| Compound No. | Structure | Name |
|---|---|---|
| 50 | 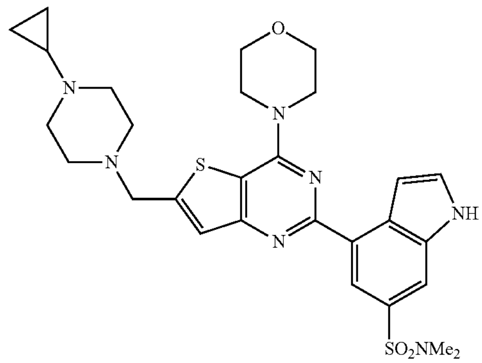 | 6-(4-Cyclopropyl-piperazin-1-ylmethyl)-2-(6-methyl-1H-indol-4-yl)-4-morpholin-4-yl-thieno[3,2-d]pyrimidine |
| 51 | 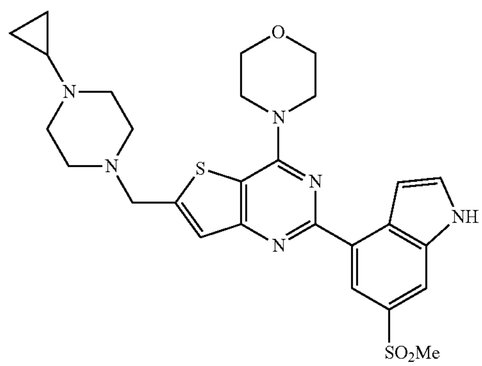 | 6-(4-Cyclopropyl-piperazin-1-ylmethyl)-2-(6-methanesulfonyl-1H-indol-4-yl)-4-morpholin-4-yl-thieno[3,2-d]pyrimidine |
| 52 | 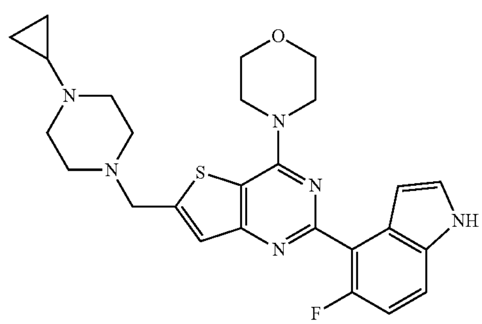 | 6-(4-Cyclopropyl-piperazin-1-ylmethyl)-2-(5-fluoro-1H-indol-4-yl)-4-morpholin-4-yl-thieno[3,2-d]pyrimidine |
| 53 | 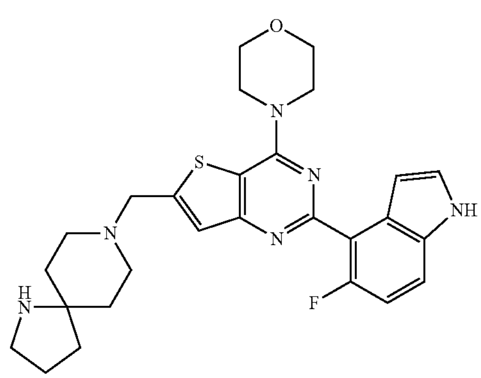 | 6-(1,8-Diaza-spiro[4.5]dec-8-ylmethyl)-2-(5-fluoro-1H-indol-4-yl)-4-morpholin-4-yl-thieno[3,2-d]pyrimidine |

TABLE 1-continued

| Compound No. | Structure | Name |
|---|---|---|
| 54 | 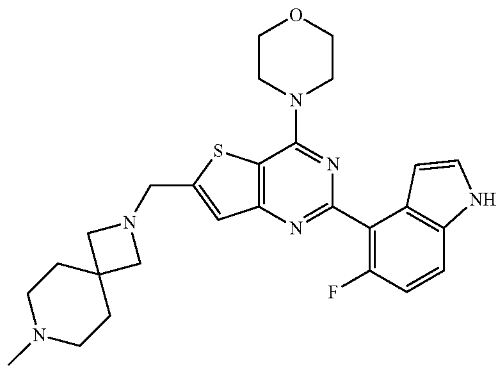 | 2-(5-Fluoro-1H-indol-4-yl)-6-(7-methyl-2,7-diaza-spiro[3.5]non-2-ylmethyl)-4-molpholin-4-yl-thieno[3,2-d]pyrimidine |
| 55 | 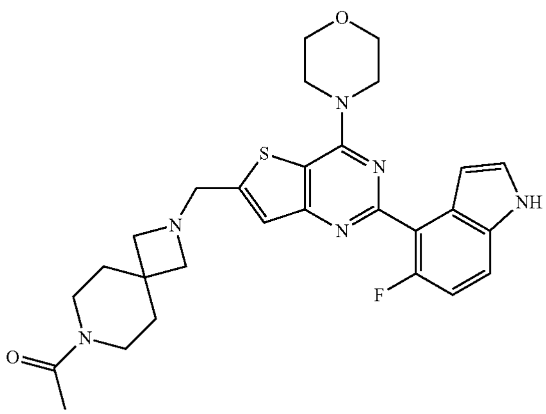 | 1-{2-[2-(5-Fluoro-1H-indol-4-yl)-4-morpholin-4-yl-thieno[3,2-d]pyrimidin-6-ylmethyl]-2,7-diaza-spiro[3.5]non-7-yl}-ethanone |
| 56 | 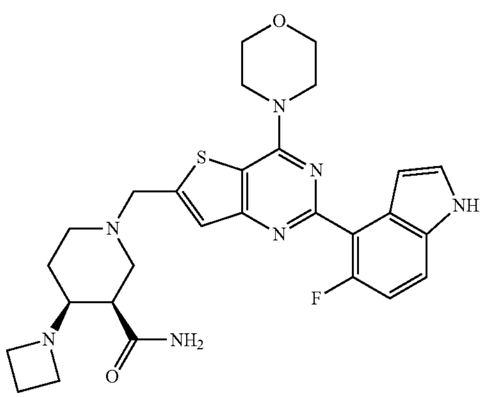 | (3R*,4S*)-4-Azetidin-1-yl-1-[2-(5-fluoro-1H-indol-4-yl)-4-morpholin-4-yl-thieno[3,2-d]pyrimidin-6-ylmethyl]-piperidine-3-carboxylic acid amide |
| 57 | 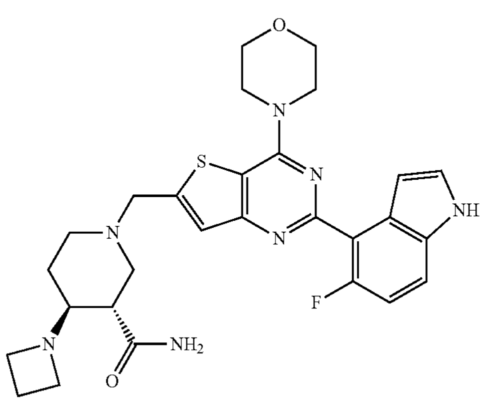 | (3R*,4R*)-4-Azetidin-1-yl-1-[2-(5-fluoro-1H-indol-4-yl)-4-morpholin-4-yl-thieno[3,2-d]pyrimidin-6-ylmethyl]-piperidine-3-carboxylic acid amide |

TABLE 1-continued

| Compound No. | Structure | Name |
|---|---|---|
| 58 | 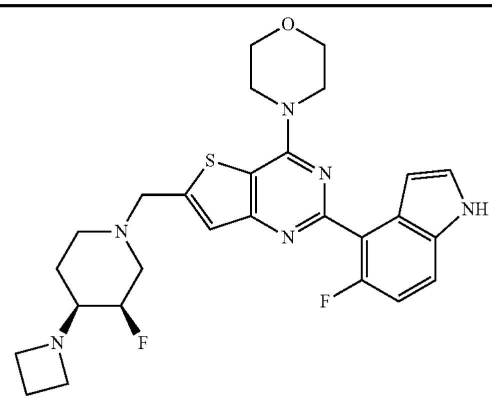 | (±)-6-((Cis)-4-Azetidin-1-yl-3-fluoro-piperidin-1-ylmethyl)-2-(5-fluoro-1H-indol-4-yl)-4-morpholin-4-yl-thieno[3,2-d]pyrimidine |
| 59 | 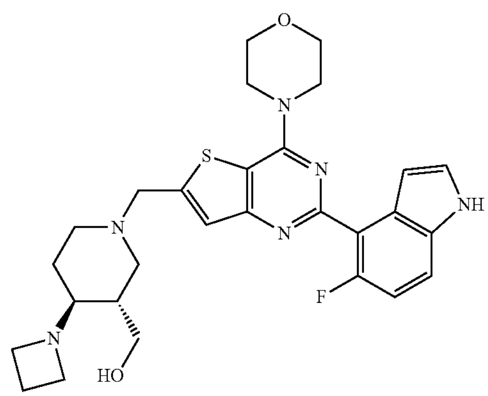 | (±)-{(trans)-4-Azetidin-1-yl-1-[2-(5-fluoro-1H-indol-4-yl)-4-morpholin-4-yl-thieno[3,2-d]pyrimidin-6-ylmethyl]-piperidin-3-yl}-methanol |
| 60 | 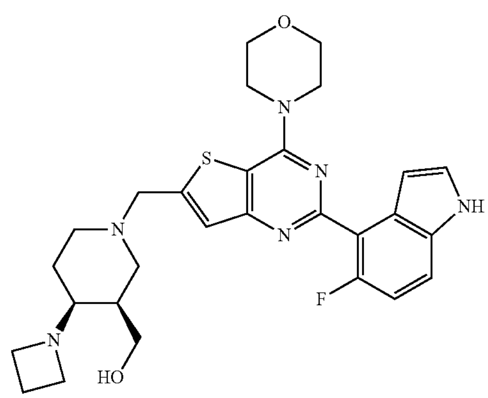 | (±)-{(Cis)-4-Azetidin-1-yl-1-[2-(5-fluoro-1H-indol-4-yl)-4-morpholin-4-yl-thieno[3,2-d]pyrimidin-6-ylmethyl]-piperidin-3-yl}-methanol |
| 61 | 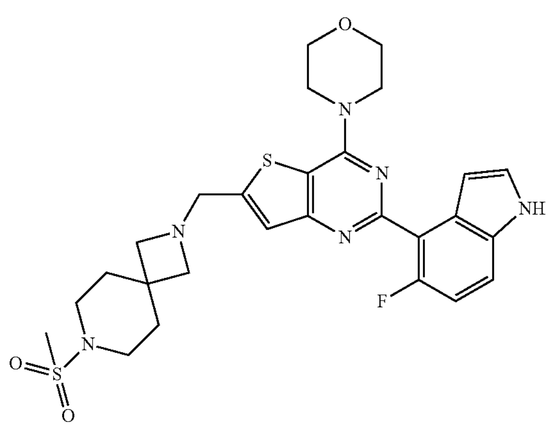 | 2-(5-Fluoro-1H-indol-4-yl)-6-(7-methanesulfonyl-2,7-diaza-spiro[3.5]non-2-ylmethyl)-4-morpholin-4-yl-thieno[3,2-d]pyrimidine |

TABLE 1-continued

| Compound No. | Structure | Name |
|---|---|---|
| 62 | 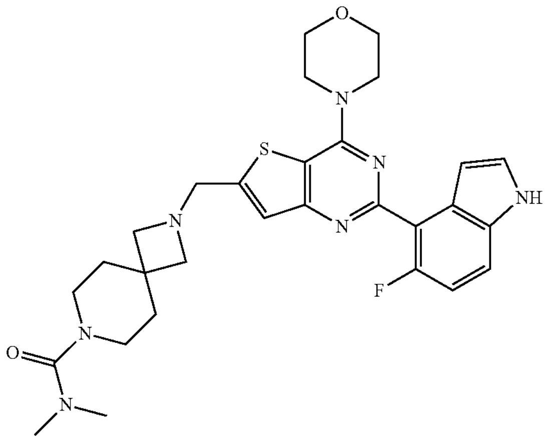 | 2-[2-(5-Fluoro-1H-indol-4-yl)-4-morpholin-4-yl-thieno[3,2-d]pyrimidin-6-ylmethyl]-2,7-diaza-spiro[3.5]nonane-7-carboxylic acid dimethylamide |
| 63 | 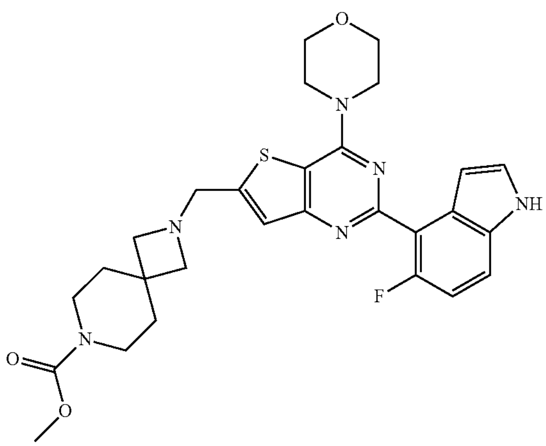 | 2-[2-(5-Fluoro-1H-indol-4-yl)-4-morpholin-4-yl-thieno[3,2-d]pyrimidin-6-ylmethyl]-2,7-diaza-spiro[3.5]nonane-7-carboxylic acid methyl ester |
| 64 | 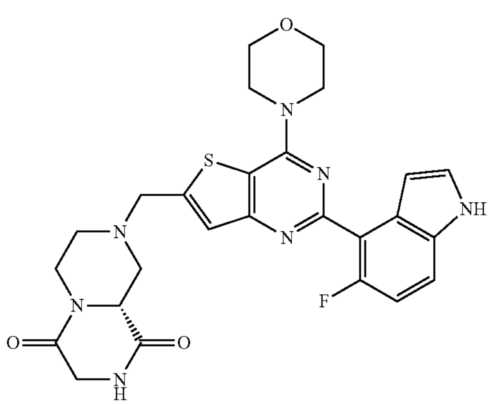 | (R)-8-[2-(5-Fluoro-1H-indol-4-yl)-4-morpholin-4-yl-thieno[3,2-d]pyrimidin-6-ylmethyl]-hexahydro-pyrazino[1,2-a]pyrazine-1,4-dione |

TABLE 1-continued

| Compound No. | Structure | Name |
|---|---|---|
| 65 | 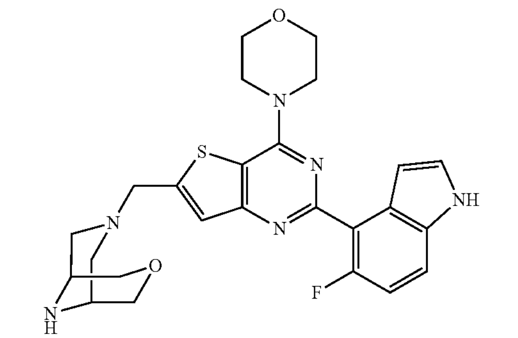 | 7-[2-(5-Fluoro-1H-indol-4-yl)-4-morpholin-4-yl-thieno[3,2-d]pyrimidin-6-ylmethyl]-3-oxa-7,9-diaza-bicyclo[3.3.1]nonane |
| 66 | 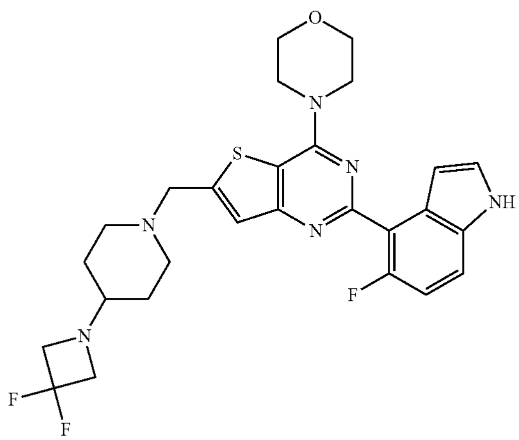 | 6-[4-(3,3-Difluoro-azetidin-1-yl)-piperidin-1-ylmethyl]-2-(5-fluoro-1H-indol-4-yl)-4-morpholin-4-yl-thieno[3,2-d]pyrimidine |
| 67 | 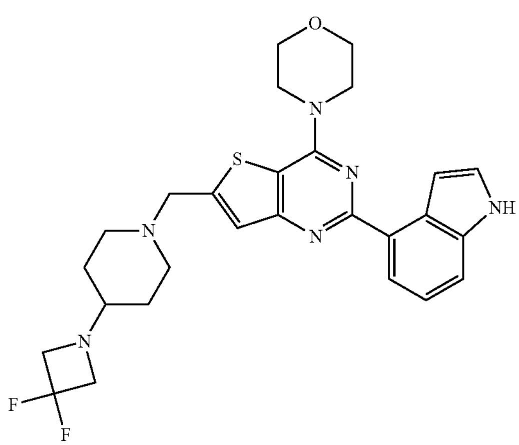 | 6-[4-(3,3-Difluoro-azetidin-1-yl)-piperidin-1-ylmethyl]-2-(1H-indol-4-yl)-4-morpholin-4-yl-thieno[3,2-d]pyrimidine |
| 68 | 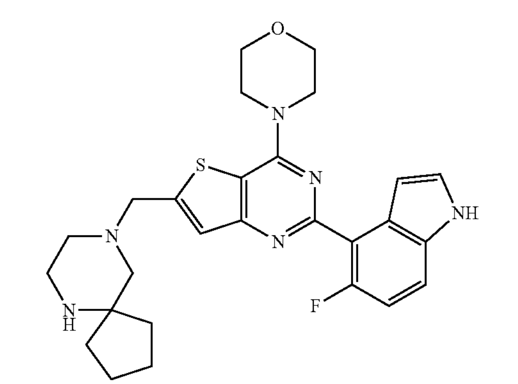 | 6-(6,9-Diaza-spiro[4.5]dec-9-ylmethyl)-2-(5-fluoro-1H-indol-4-yl)-4-morpholin-4-yl-thieno[3,2-d]pyrimidine |

TABLE 1-continued

| Compound No. | Structure | Name |
|---|---|---|
| 69 | 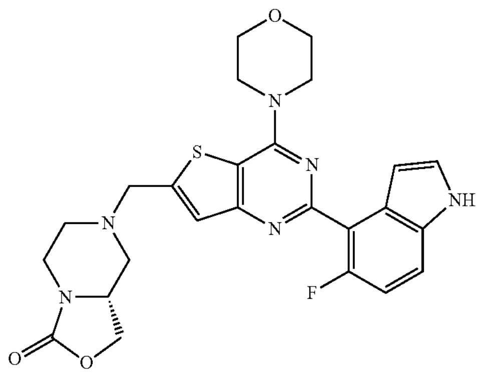 | (R)-7-[2-(5-Fluoro-1H-indol-4-yl)-4-morpholin-4-yl-thieno[3,2-d]pyrimidin-6-ylmethyl]-hexahydro-oxazolo[3,4-a]pyrazin-3-one |
| 70 | 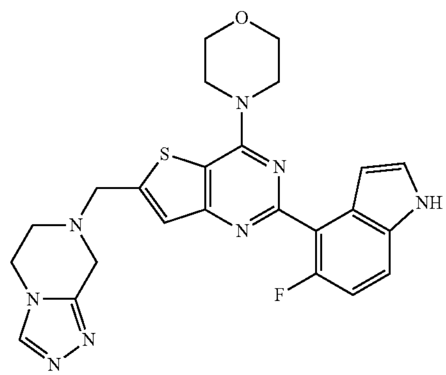 | 7-[2-(5-Fluoro-1H-indol-4-yl)-4-morpholin-4-yl-thieno[3,2-d]pyrimidin-6-ylmethyl]-5,6,7,8-tetrahydro-[1,2,4]triazolo[4,3-a]pyrazine |
| 71 | 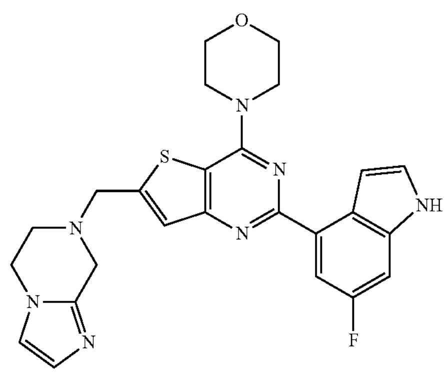 | 6-(5,6-Dihydro-8H-imidazo[1,2-a]pyrazin-7-ylmethyl)-2-(6-fluoro-1H-indol-4-yl)-4-morpholin-4-yl-thieno[3,2-d]pyrimidine |
| 72 | 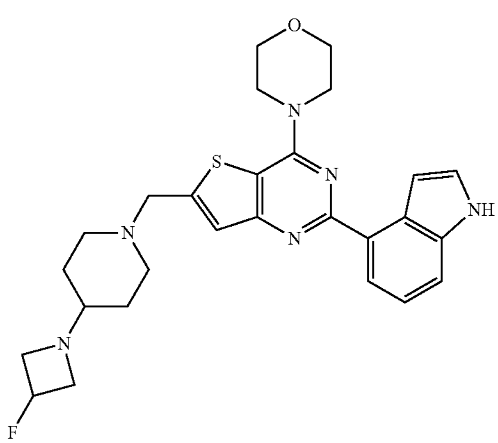 | 6-[4-(3-Fluoro-azetidin-1-yl)-piperidin-1-ylmethyl]-2-(1H-indol-4-yl)-4-morpholin-4-yl-thieno[3,2-d]pyrimidine |

TABLE 1-continued

| Compound No. | Structure | Name |
|---|---|---|
| 73 | 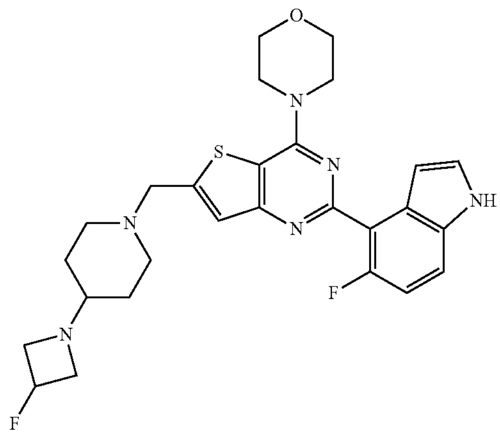 | 6-[4-(3-Fluoro-azetidin-1-yl)-piperidin-1-ylmethyl]-2-(5-fluoro-1H-indol-4-yl)-4-morpholin-4-yl-thieno[3,2-d]pyrimidine |
| 74 | 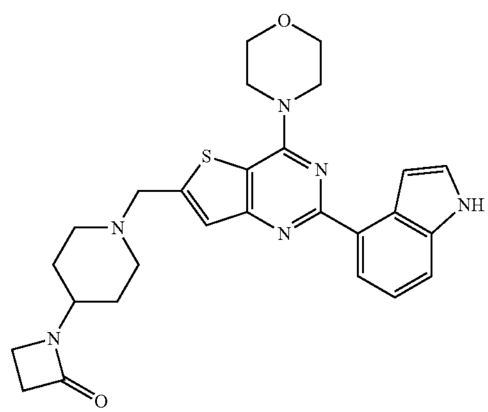 | 1-{1-[2-(1H-Indol-4-yl)-4-morpholin-4-yl-thieno[3,2-d]pyrimidin-6-ylmethyl]-piperidin-4-yl}-azetidin-2-one |
| 75 | 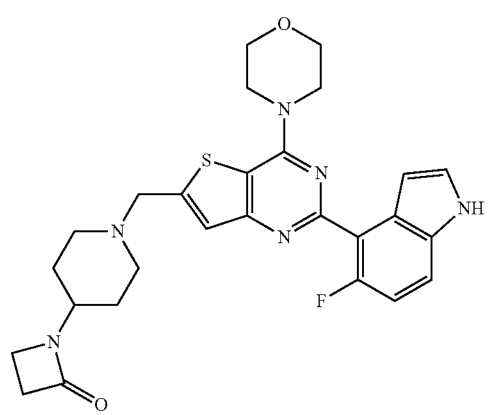 | 1-{1-[2-(5-Fluoro-1H-indol-4-yl)-4-morpholin-4-yl-thieno[3,2-d]pyrimidin-6-ylmethyl]-piperidin-4-yl}-azetidin-2-one |

TABLE 1-continued

| Compound No. | Structure | Name |
|---|---|---|
| 76 | 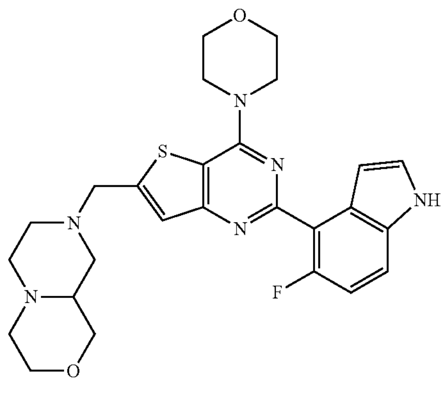 | (±)-8-[2-(5-Fluoro-1H-indol-4-yl)-4-morpholin-4-yl-thieno[3,2-d]pyrimidin-6-ylmethyl]-octahydro-pyrazino[2,1-c][1,4]oxazine |
| 77 | 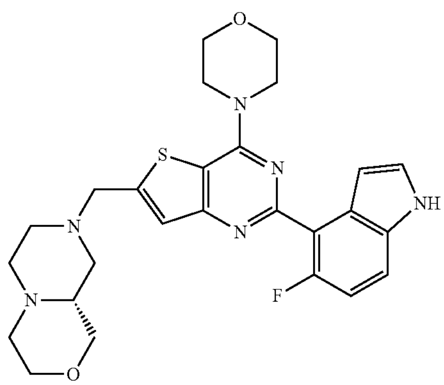 | (R)-8-[2-(5-Fluoro-1H-indol-4-yl)-4-morpholin-4-yl-thieno[3,2-d]pyrimidin-6-ylmethyl]-octahydro-pyrazino [2,1-c][1,4]oxazine |
| 78 | 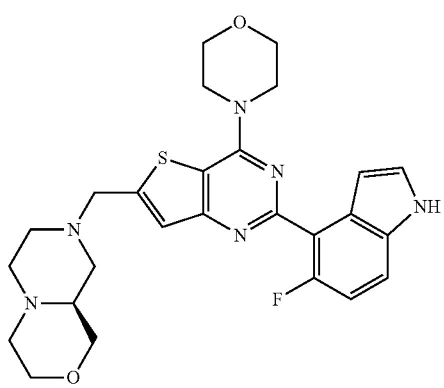 | (S)-8-[2-(5-Fluoro-1H-indol-4-yl)-4-morpholin-4-yl-thieno[3,2-d]pyrimidin-6-ylmethyl]-octahydro-pyrazino[2,1-c][1,4]oxazine |
| 79 | 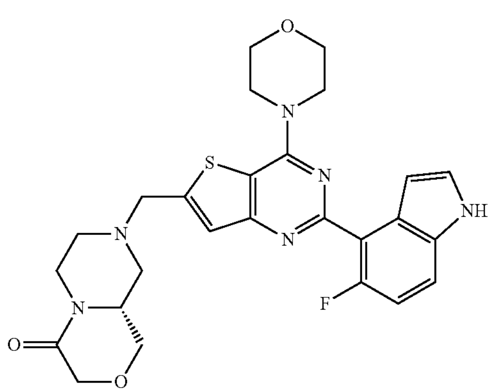 | (R)-8-[2-(5-Fluoro-1H-indol-4-yl)-4-morpholin-4-yl-thieno[3,2-d]pyrimidin-6-ylmethyl]-hexahydro-pyrazino[2,1-c][1,4]oxazin-4-one |

TABLE 1-continued

| Compound No. | Structure | Name |
|---|---|---|
| 80 | 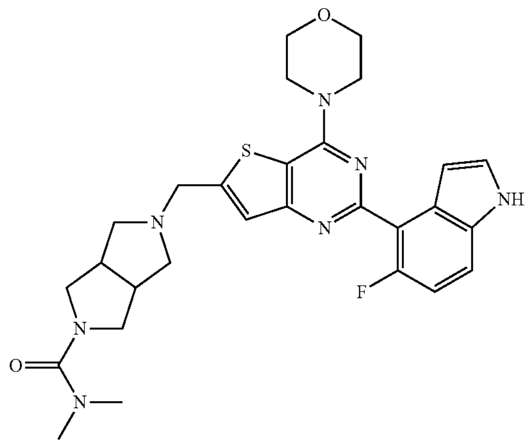 | 5-[2-(5-Fluoro-1H-indol-4-yl)-4-morpholin-4-yl-thieno[3,2-d]pyrimidin-6-ylmethyl]-hexahydro-pyrrolo[3,4-c]pyrrole-2-carboxylic acid dimethylamide |
| 81 | 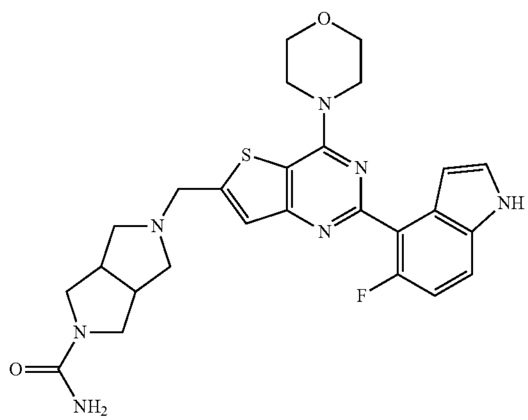 | 5-[2-(5-Fluoro-1H-indol-4-yl)-4-morpholin-4-yl-thieno[3,2-d]pyrimidin-6-ylmethyl]-hexahydro-pyrrolo[3,4-c]pyrrole-2-carboxylic acid amide |
| 82 | 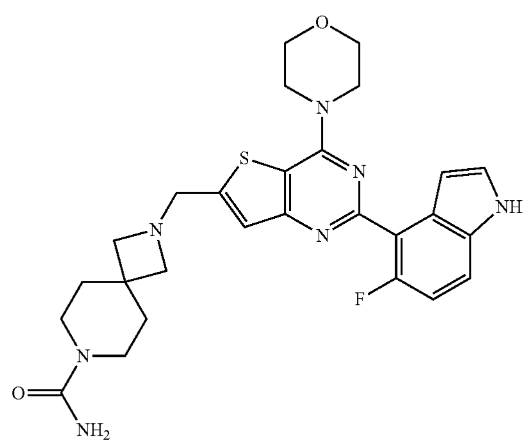 | 2-[2-(5-Fluoro-1H-indol-4-yl)-4-morpholin-4-yl-thieno[3,2-d]pyrimidin-6-ylmethyl]-2,7-diaza-spiro[3.5]nonane-7-carboxylic acid amide |

TABLE 1-continued

| Compound No. | Structure | Name |
|---|---|---|
| 83 | 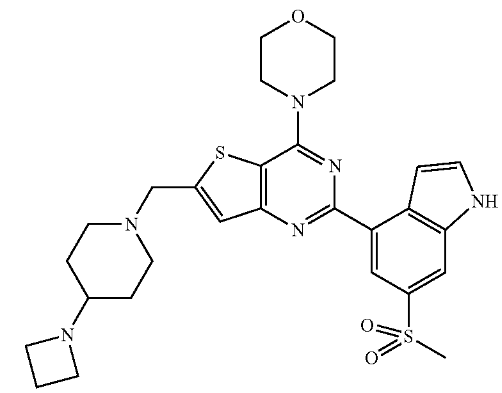 | 6-(4-Azetidin-1-yl-piperidin-1-ylmethyl)-2-(6-methanesulfonyl-1H-indol-4-yl)-4-morpholin-4-yl-thieno[3,2-d]pyrimidine |
| 84 | 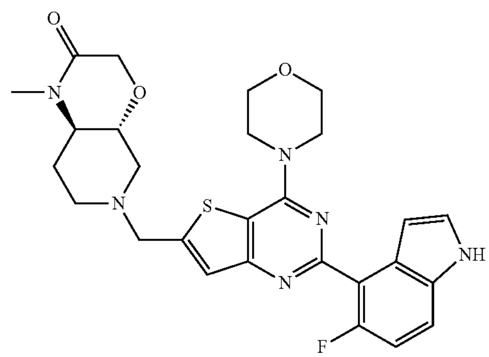 | (4aR*,8aR*)-6-[2-(5-Fluoro-1H-indol-4-yl)-4-morpholin-4-yl-thieno[3,2-d]pyrimidin-6-ylmethyl]-1-methyl-hexahydro-pyrido[3,4-b][1,4]oxazin-2-one |
| 85 | 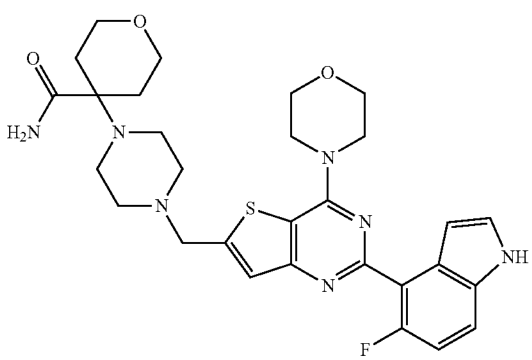 | 4-{4-[2-(5-Fluoro-1H-indol-4-yl)-4-morpholin-4-yl-thieno[3,2-d]pyrimidin-6-ylmethyl]-piperazin-1-yl}-tetrahydro-pyran-4-carboxylic acid amide |
| 86 | 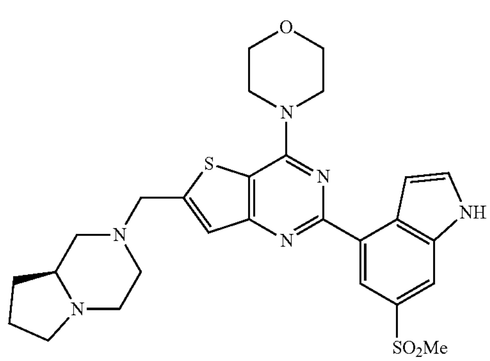 | 6-[(S)-1-(Hexahydro-pyrrolo[1,2-a]pyrazin-2-yl)methyl]-2-(6-methanesulfonyl-1H-indol-4-yl)-4-morpholin-4-yl-thieno[3,2-d]pyrimidine |

TABLE 1-continued

| Compound No. | Structure | Name |
|---|---|---|
| 87 | 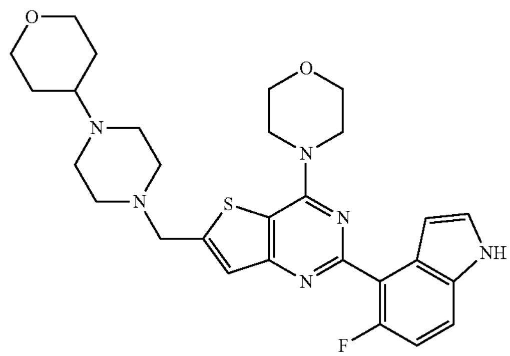 | 2-(5-Fluoro-1H-indol-4-yl)-4-morpholin-4-yl-6-[4-(tetrahydro-pyran-4-yl)-piperazin-1-ylmethyl]-thieno[3,2-d]pyrimidine |
| 88 | 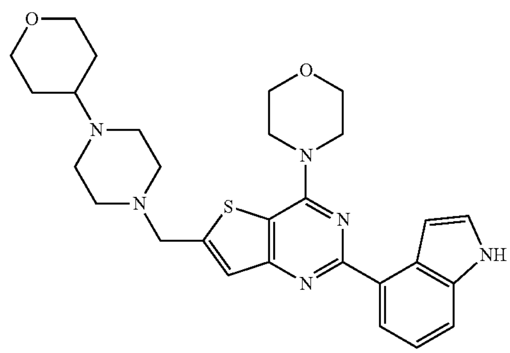 | 2-(1H-Indol-4-yl)-4-morpholin-4-yl6-[4-(tetrahydro-pyran-4-yl)-piperazin-1-ylmethyl]-thieno[3,2-d]pyrimidine. |
| 89 | 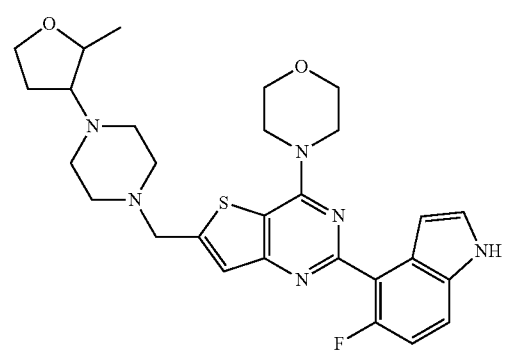 | (±)2-(5-Fluoro-1H-indol-4-yl)-6-[4-(2-methyl-tetrahydro-furan-3-yl)-piperazin-1-ylmethyl]-4-morpholin-4-yl-thieno[3,2-d]pyrimidine. |
| 90 | 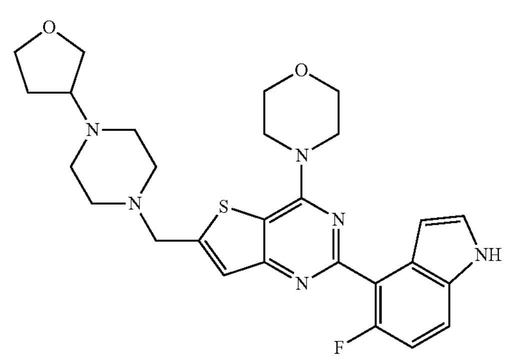 | (±)2-(5-Fluoro-1H-indol-4-yl)-4-morpholin-4-yl-6-[4-(tetrahydro-furan-3-yl)-piperazin-1-ylmethyl]-thieno[3,2-d]pyrimidine |

TABLE 1-continued

| Compound No. | Structure | Name |
|---|---|---|
| 91 | 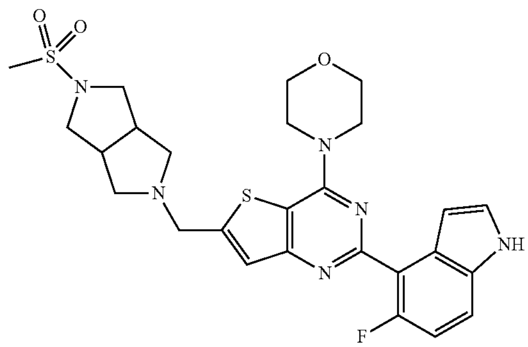 | 2-(5-Fluoro-1H-indol-4-yl)-6-(5-methanesulfonyl-hexahydro-pyrrolo[3,4-c]pyrrol-2-ylmethyl)-4-morpholin-4-yl-thieno[3,2-d]pyrimidine |
| 92 | 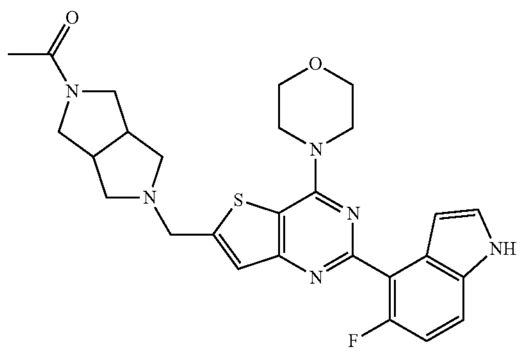 | 1-{5-[2-(5-Fluoro-1H-indol-4-yl)-4-morpholin-4-yl-thieno[3,2-d]pyrimidin-6-ylmethyl]-hexahydro-pyrrolo[3,4-c]pyrrol-2-yl}-ethanone |
| 93 | 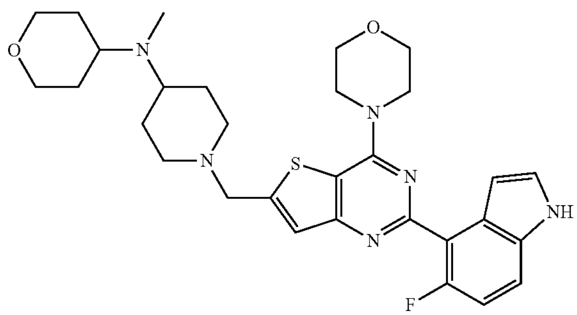 | {1-[2-(5-Fluoro-1H-indol-4-yl)-4-morpholin-4-yl-thieno[3,2-d]pyrimidin-6-ylmethyl]-piperidin-4-yl}-methyl-(tetrahydro-pyran-4-yl)-amine |
| 94 | 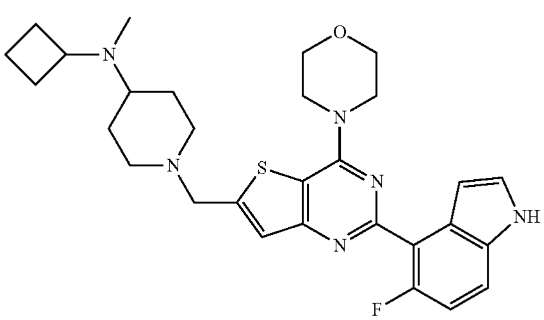 | Cyclobutyl-(1-[2-(5-fluoro-1H-indol-4-yl)-4-morpholin-4-yl-thieno[3,2-d]pyrimidin-6-ylmethyl]-piperidin-4-yl}-methyl-amine |

TABLE 1-continued

| Compound No. | Structure | Name |
|---|---|---|
| 95 | 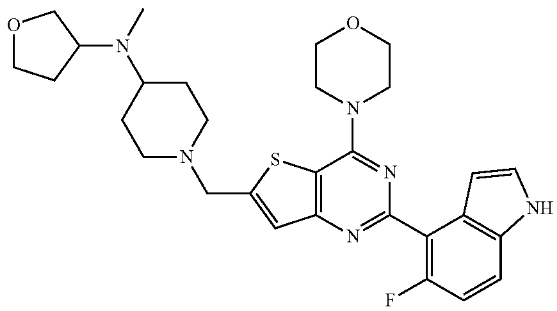 | (±)-{1-[2-(5-Fluoro-1H-indol-4-yl)-4-morpholin-4-yl-thieno[3,2-d]pyrimidin-6-ylmethyl]-piperidin-4-yl}-methyl-(tetrahydro-furan-3-yl)-amine |
| 96 | 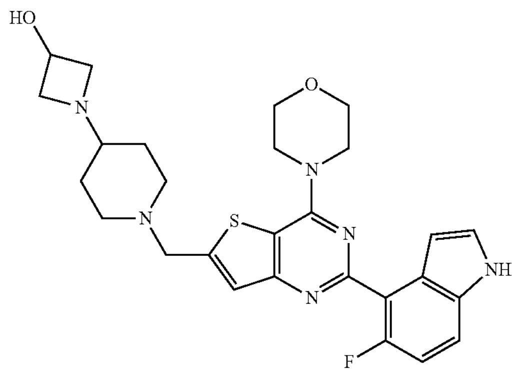 | 1-{1-[2-(5-Fluoro-1H-indol-4-yl)-4-morpholin-4-yl-thieno[3,2-d]pyrimidin-6-ylmethyl]-piperidin-4-yl}-azetidin-3-ol |
| 97 | 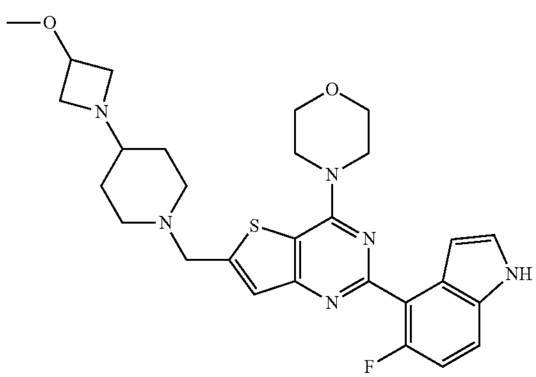 | 2-(5-Fluoro-1H-indol-4-yl)-6-[4-(3-methoxy-azetidin-1-yl)-piperidin-1-ylmethyl]-4-morpholin-4-yl-thieno[3,2-d]pyrimidine |
| 98 | | 4-[2-(5-Fluoro-1H-indol-4-yl)-4-morpholin-4-yl-thieno[3,2-d]pyrimidin-6-ylmethyl]-1-(tetrahydro-pyran-4-yl)-piperazin-2-one | and the pharmaceutically acceptable salts thereof.

Synthetic strategies for producing thienopyrimidines of formula (I) via suitable precursor compounds, and the production of those precursors, is depicted in the synthetic schemes 1 to 13 which follow in the Examples section.

One suitable synthetic strategy for producing a thienopyrimidine of formula (I) employs the precursor carboxaldehyde of formula (II):

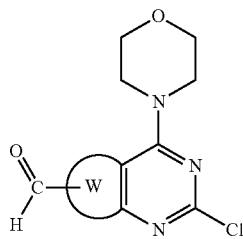

(II)

wherein W is as defined above. Starting from this precursor the synthesis comprises performing, in either order, a reductive amination and a palladium-mediated (Suzuki-type) cross-coupling reaction.

A compound of the invention may thus be produced by a process which comprises treating a compound of formula (II):

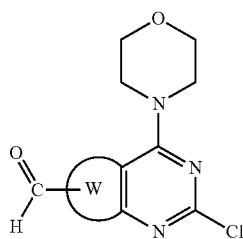

(II)

wherein W is as defined above, with an amine of formula $NHR^{1a}R^{2a}$ in which $R^{1a}$ and $R^{2a}$ are as defined above for $R^1$ and $R^2$, or $R^{1a}$ and $R^{2a}$ are as defined above for $R^1$ and $R^2$ wherein an N atom is present and is protected by an amine protecting group, in the presence of a suitable reducing agent; treating the resulting compound of formula (N):

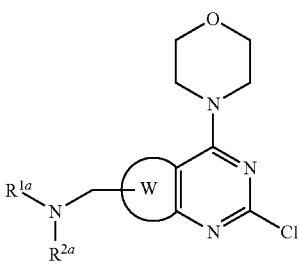

(IV)

wherein W, $R^{1a}$ and $R^{2a}$ are as defined above, with a boronic acid or ester thereof of formula $R^{4'}B(OR^{15})_2$ in which $R^{4'}$ is selected from a group $R^4$ as defined above and a group $R^4$ as defined above in which the indole N atom is protected, and each $R^{15}$ is H or $C_1$-$C_6$ alkyl or the two groups $OR^{15}$ form, together with the boron atom to which they are attached, a pinacolato boronate ester group, in the presence of a Pd catalyst; and, if $R^{4'}$, $R^{1a}$ and/or $R^{2a}$ includes an amine protecting group, removing the protecting group. Any suitable amine protecting groups may be used in $R^{1a}$ and/or $R^{2a}$, for instance a t-butoxycarbonyl (BOC) group. Any suitable group may be used to protect the indole N atom, for instance a t-butyldimethylsilyl group.

A compound of formula (I) may also be produced by a process which comprises treating a compound of formula (II):

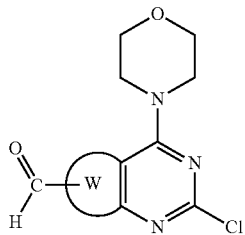

(II)

wherein W is as defined above, with a boronic acid or ester thereof of formula $R^4B(OR^{15})_2$ in which $R^4$ is as defined above and each $R^{15}$ is H or $C_1$-$C_6$ alkyl, or the two groups $OR^{15}$ form, together with the boron atom to which they are attached, a pinacolato boronate ester group, in the presence of a Pd catalyst; treating the resulting compound of formula (III):

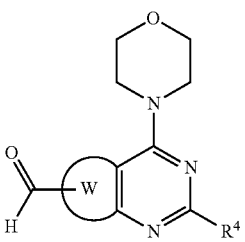

(III)

wherein W and $R^4$ are as defined above, with an amine of formula $NHR^{1a}R^{2a}$ in which $R^{1a}$ and $R^{2a}$ are as defined above, in the presence of a suitable reducing agent; and, if $R^{1a}$ and/or $R^{2a}$ includes an amine protecting group, removing the protecting group. In this embodiment of the process the N atom of the indole group $R^4$ may, if necessary, be protected before the compound of formula (III) is treated with the amine of formula $NHR^{1a}R^{2a}$. In that case the indole protecting group is removed in a subsequent step, using conventional methodology.

Both the reductive amination step and the Pd-mediated cross-coupling step take place under conventional conditions. The palladium catalyst may be any that is typically used for Suzuki-type cross-couplings, such as $PdCl_2(PPh_3)_2$. The reducing agent in the amination step is typically a borohydride, for instance $NaBH(OAc)_3$, $NaBH_4$ or $NaCNBH_3$, in particular $NaBH(OAc)_3$.

Alternatively, a compound of formula (I) may also be produced by a process which comprises treating a compound of formula (II) as defined above with a reducing agent, to reduce the —CHO functionality to —CH$_2$OH, and then treating the resulting compound with an agent which converts the OH moiety into a leaving group, thereby yielding a compound of formula (V):

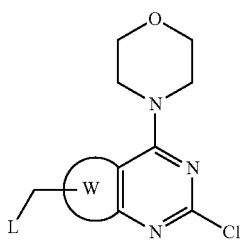

(V)

wherein L is a leaving group. Suitable examples of leaving groups include chloro, bromo, tosylate and mesylate groups. The compound of formula (V) is then treated with an amine of formula $NHR^{1a}R^{2a}$ in which $R^{1a}$ and $R^{2a}$ are as defined above, in the presence of a base such as potassium carbonate or cesium carbonate in a solvent such as DMF, to yield a compound of formula (I). This strategy is depicted in scheme 6 which follows.

A variation in the synthetic strategy for producing a thienopyrimidine of formula (I) entails attaching the group $R^4$ to the thienopyrimidine core by Suzuki coupling and then protecting the indole N atom of the group $R^4$. The process comprises treating a compound of formula (VI):

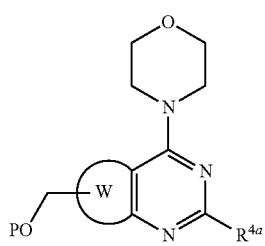

(VI)

in which W is as defined above, P is a toluenesulfonyl group and $R^{4a}$ is a group $R^4$ as defined above in which the indole N atom is protected by toluenesulfonyl, with a compound $NHR^{1a}R^{2a}$ as defined above under suitable conditions. The indole N atom is protected by any suitable protecting group, for instance a toluenesulfonyl group. All protecting groups are removed subsequently, using conventional methodology. This strategy is illustrated in scheme 8 which follows.

Thienopyrimidines of formula (I) may be converted into pharmaceutically acceptable salts, and salts may be converted into the free compound, by conventional methods. Pharmaceutically acceptable salts include salts of inorganic acids such as hydrochloric acid, hydrobromic acid and sulfuric acid, and salts of organic acids such as acetic acid, oxalic acid, malic acid, methanesulfonic acid, trifluoroacetic acid, benzoic acid, citric acid and tartaric acid. In the case of compounds of the invention bearing a free carboxy substituent, the salts include both the above-mentioned acid addition salts and the salts of sodium, potassium, calcium and ammonium. The latter are prepared by treating the free thienopyrimidine of formula (I), or an acid addition salt thereof, with the corresponding metal base or ammonia.

Compounds of the present invention have been found in biological tests to be inhibitors of PI3 kinase. The compounds are selective for the p110δ isoform, which is a class Ia PI3 kinase, over other class Ia PI3 kinases. They are thus selective for the p110δ isoform over both the p110α isoform and the p110β isoform. In particular they are selective for p110δ over p110β. The compounds are also selective for the p110δ isoform over p110γ, which is a class Ib kinase. The selectivity exhibited by compounds of the invention for p110δ over other isoforms of PI3 kinase is at least 2-fold. Typically the selectivity is 5-fold, or 10-fold, or 20-fold, or 50-fold, rising to 100-fold or higher in many cases. Thus the compounds may be 2-fold, 5-fold, 10-fold, 20-fold, 50-fold or 100-fold selective for p110δ over p110β. They may also be 2-fold, 5-fold, 10-fold, 20-fold, 50-fold or 100-fold selective for p110δ over p110α or over p110γ.

A compound of the present invention may be used as an inhibitor of PI3 kinase, in particular of a class Ia PI3 kinase. Accordingly, a compound of the present invention can be used to treat a disease or disorder arising from abnormal cell growth, function or behaviour associated with PI3 kinase, in particular the p110δ isoform of PI3 kinase. Examples of such diseases and disorders are discussed by Drees et al in Expert Opin. Ther. Patents (2004) 14(5):703-732. These include proliferative disorders such as cancer, immune disorders, cardiovascular disease, viral infection, inflammation, metabolism/endocrine disorders and neurological disorders. Examples of metabolism/endocrine disorders include diabetes and obesity. Examples of cancers which the present compounds can be used to treat include leukaemia, brain tumours, renal cancer, gastric cancer and cancer of the skin, bladder, breast, uterus, lung, colon, prostate, ovary and pancreas.

A compound of the present invention may be used as an inhibitor of PI3 kinase. A human or animal patient suffering from a disease or disorder arising from abnormal cell growth, function or behaviour associated with PI3 kinase, in particular with the p110δ isoform of PI3 kinase such as an immune disorder, cardiovascular disease, viral infection, inflammation, a metabolism/endocrine disorder or a neurological disorder, may thus be treated by a method comprising the administration thereto of a compound of the present invention as defined above. A human or animal patient suffering from cancer may also be treated by a method comprising the administration thereto of a compound of the present invention as defined above. The condition of the patient may thereby be improved or ameliorated.

A compound of the present invention can be administered in a variety of dosage forms, for example orally such as in the form of tablets, capsules, sugar- or film-coated tablets, liquid solutions or suspensions or parenterally, for example intramuscularly, intravenously or subcutaneously. The compound may therefore be given by injection or infusion.

The dosage depends on a variety of factors including the age, weight and condition of the patient and the route of administration. Daily dosages can vary within wide limits and will be adjusted to the individual requirements in each particular case. Typically, however, the dosage adopted for each route of administration when a compound is administered alone to adult humans is 0.0001 to 50 mg/kg, most commonly in the range of 0.001 to 10 mg/kg, body weight, for instance 0.01 to 1 mg/kg. Such a dosage may be given, for example, from 1 to 5 times daily. For intravenous injection a suitable daily dose is from 0.0001 to 1 mg/kg body weight, preferably from 0.0001 to 0.1 mg/kg body weight. A daily dosage can be administered as a single dosage or according to a divided dose schedule.

A compound of the invention is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. The compound may be administered in any conventional form, for instance as follows:

A) Orally, for example, as tablets, coated tablets, dragees, troches, lozenges, aqueous or oily suspensions, liquid solutions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, dextrose, saccharose, cellulose, corn starch, potato starch, calcium phosphate or sodium phosphate; granulating and disintegrating agents, for example, maize starch, alginic acid, alginates or sodium starch glycolate; binding agents, for example starch, gelatin or acacia; lubricating agents, for example silica, magnesium or calcium stearate, stearic acid or talc; effervescing mixtures; dyestuffs, sweeteners, wetting agents such as lecithin, polysorbates or lauryl sulphate. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. Such preparations may be manufactured in a known manner, for example by means of mixing, granulating, tableting, sugar coating or film coating processes.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is present as such, or mixed with water or an oil medium, for example, peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides for example polyoxyethylene sorbitan monooleate.

The said aqueous suspensions may also contain one or more preservatives, for example, ethyl or n-propyl p-hydroxybenzoate, one or more colouring agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavouring agents may be added to provide a palatable oral preparation. These compositions may be preserved by this addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occurring phosphatides, for example soy bean lecithin, and esters or partial esters derived from fatty acids an hexitol anhydrides, for example sorbitan mono-oleate, and condensation products of the said partial esters with ethylene oxide, for example polyoxyethylene sorbitan monooleate. The emulsion may also contain sweetening and flavouring agents. Syrups and elixirs may be formulated with sweetening agents, for example glycerol, sorbitol or sucrose. In particular a syrup for diabetic patients can contain as carriers only products, for example sorbitol, which do not metabolise to glucose or which only metabolise a very small amount to glucose.

Such formulations may also contain a demulcent, a preservative and flavouring and coloring agents.

B) Parenterally, either subcutaneously, or intravenously, or intramuscularly, or intrasternally, or by infusion techniques, in the form of sterile injectable aqueous or oleaginous suspensions. This suspension may be formulated according to the known art using those suitable dispersing of wetting agents and suspending agents which have been mentioned above. The sterile injectable preparation may also be a sterile injectable solution or suspension in a non-toxic paternally-acceptable diluent or solvent, for example as a solution in 1,3-butane diol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables.

C) By inhalation, in the form of aerosols or solutions for nebulizers.

D) Rectally, in the form of suppositories prepared by mixing the drug with a suitable non-irritating excipient which is solid at ordinary temperature but liquid at the rectal temperature and will therefore melt in the rectum to release the drug. Such materials are cocoa butter and poly-ethylene glycols.

E) Topically, in the form of creams, ointments, jellies, collyriums, solutions or suspensions.

The invention will be further described in the Examples which follow:

EXAMPLES

General Synthetic Procedure

Scheme 1

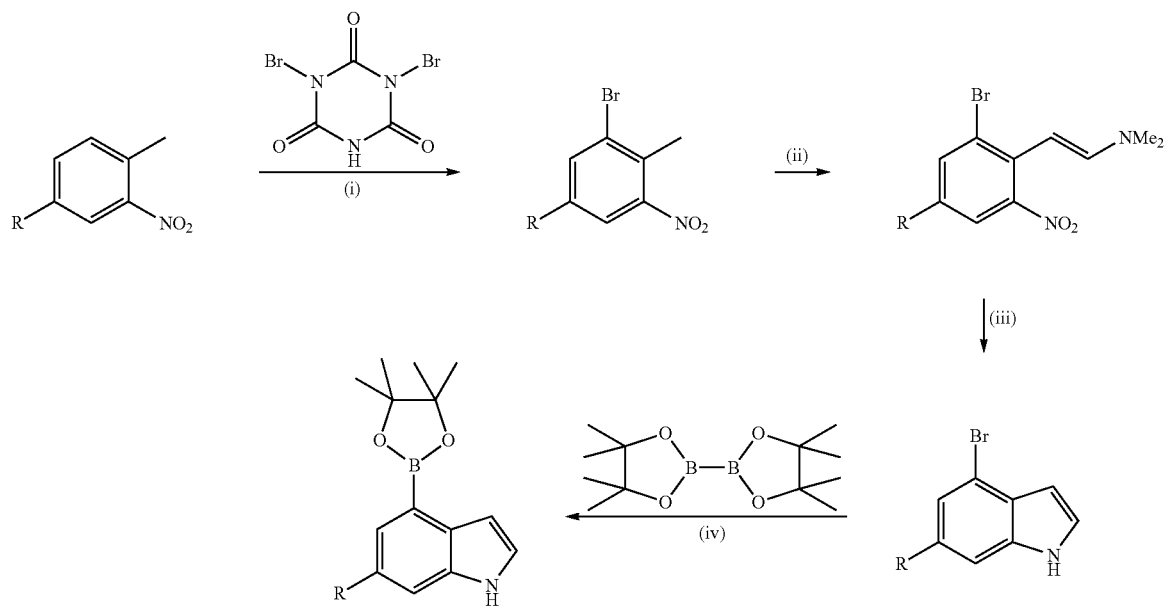

Conditions: (i) H$_2$SO$_4$, 21 h. (ii) Dioxane, DMF-DMA, 80° C. 24 h, 90° C. 16 h. (iii) MeOH—THF Raney® Nickel, NH$_2$NH$_2$•H$_2$O, RT, 40 min. (iv) DMSO, KOAc, Pd(dppf)$_2$Cl$_2$ 80° C.

Scheme 2

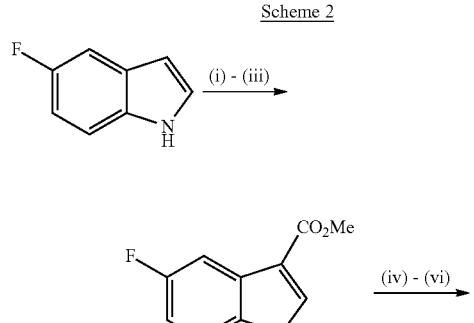

Scheme 3

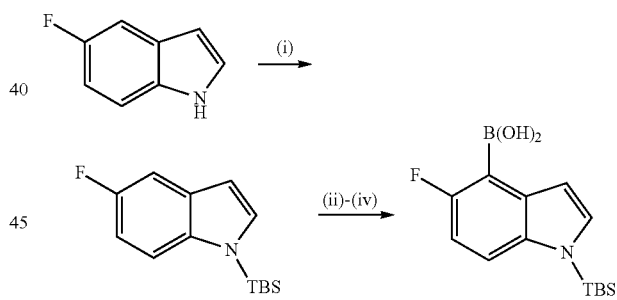

Conditions: (i) THF, NaH 0° C. then TBSCl, RT, 25 h. (ii) sBuLi, TMEDA, THF, -78° C., 2 h. (iii) B(OiPr)$_3$, THF, -78° C. →-10° C., 15 min. (iv) 2.4 M HCl.

Scheme 4

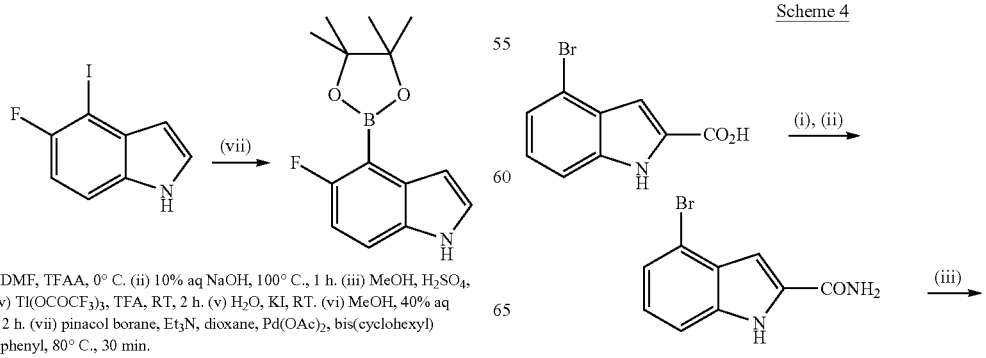

Conditions: (i) DMF, TFAA, 0° C. (ii) 10% aq NaOH, 100° C., 1 h. (iii) MeOH, H$_2$SO$_4$, 65° C., 18 h. (iv) Tl(OCOCF$_3$)$_3$, TFA, RT, 2 h. (v) H$_2$O, KI, RT. (vi) MeOH, 40% aq NaOH, 65° C., 2 h. (vii) pinacol borane, Et$_3$N, dioxane, Pd(OAc)$_2$, bis(cyclohexyl)phosphino-2-biphenyl, 80° C., 30 min.

67
-continued

68
-continued

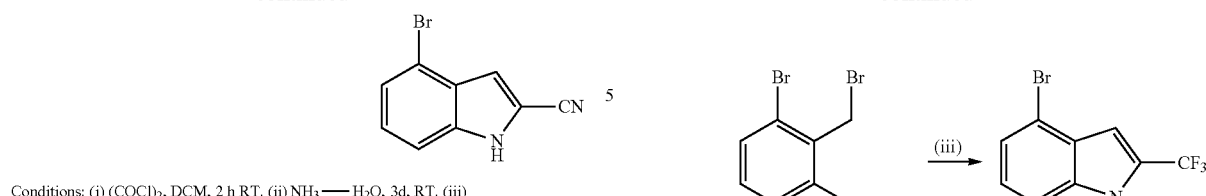

Conditions: (i) (COCl)₂, DCM, 2 h RT. (ii) NH₃—H₂O, 3d, RT. (iii) POCl₃, Toluene, 111° C., 45 min.

Scheme 5

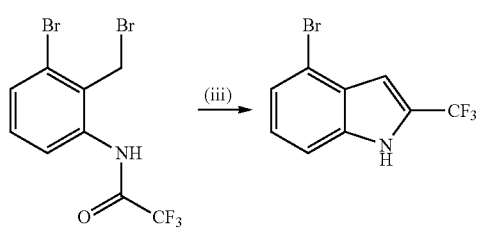

Conditions: (i) DCM-pyridine, 0° C., TFAA, 2 h, RT. (ii) benzoyl peroxide, CCl₄, 80° C., irradiation, Br₂, 16 h. (iii) Toluene, PPh₃, 60° C., 2 h then DMF, 16 h, reflux.

Scheme 6

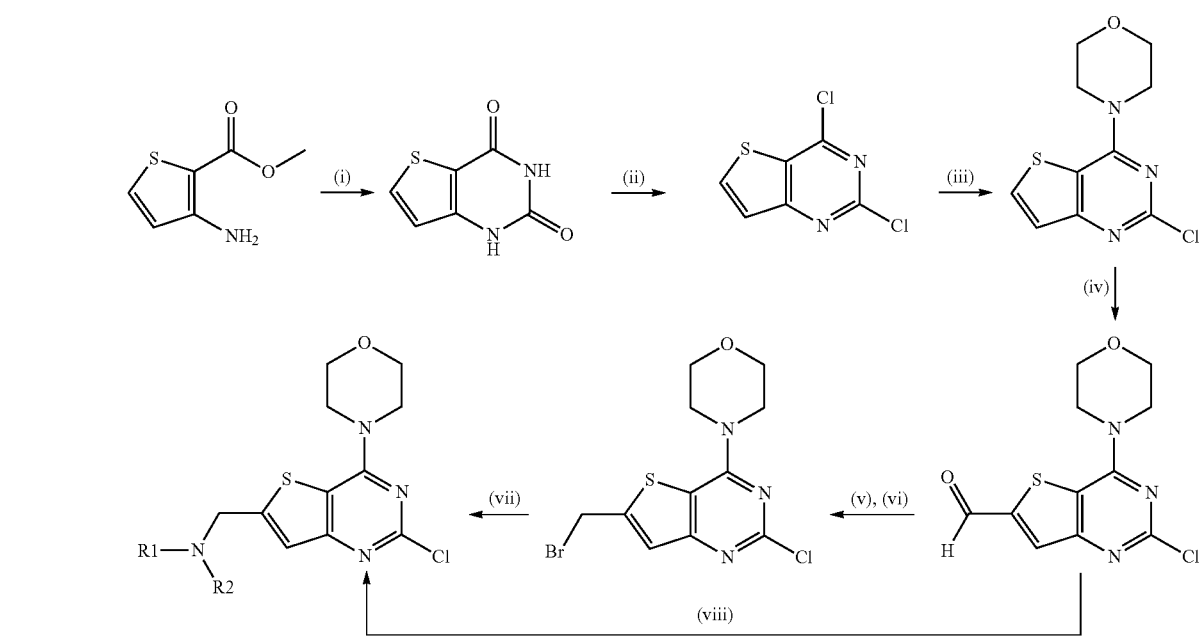

Conditions: (i) urea, 190° C., 2 h; (ii) POCl₃, 100° C., 24 h; (iii) morpholine, RT, 1 h; (iv) n-BuLi, -78° C., TMEDA, THF 1 h then DMF -78° C.→RT; (v) NaBH₄, THF-IMS, RT, 2 h. (vi) DCM, PPh₃, CBr₄, RT, 5 h. (vii) R1R2NH, K₂CO₃ or Cs₂CO₃, DMF, RT (viii) Na(OAc)₃BH, 1,2-dichloroethane, R1R2NH, HOAc, RT.

Scheme 7

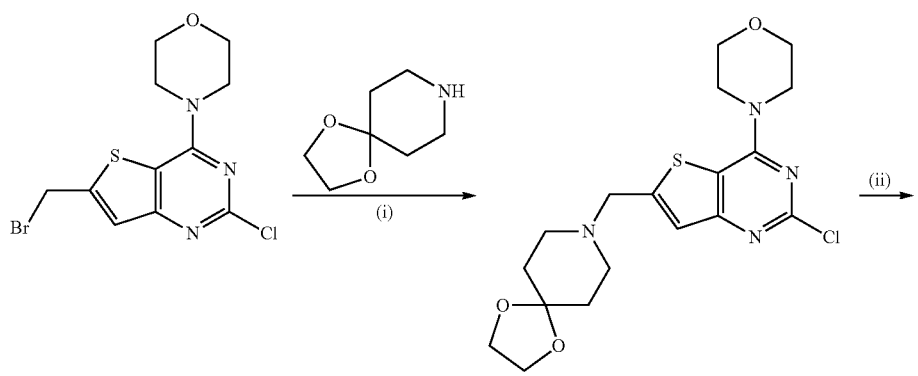

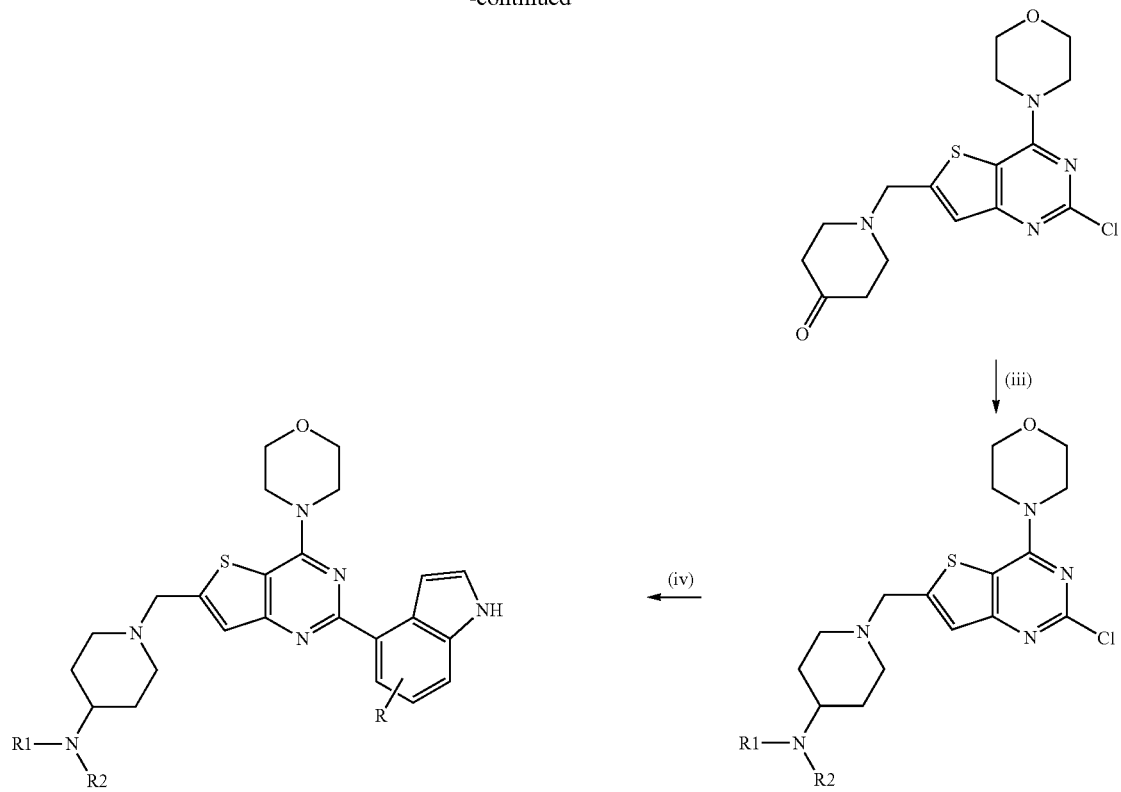
Conditions: (i) DMF, Cs$_2$CO$_3$, RT. (ii) dioxane-HCl, RT. (iii) Na(OAc)$_3$BH, 1,2-dicholoroethane, R1R2NH. (iv) Suzuki coupling.
Scheme 8
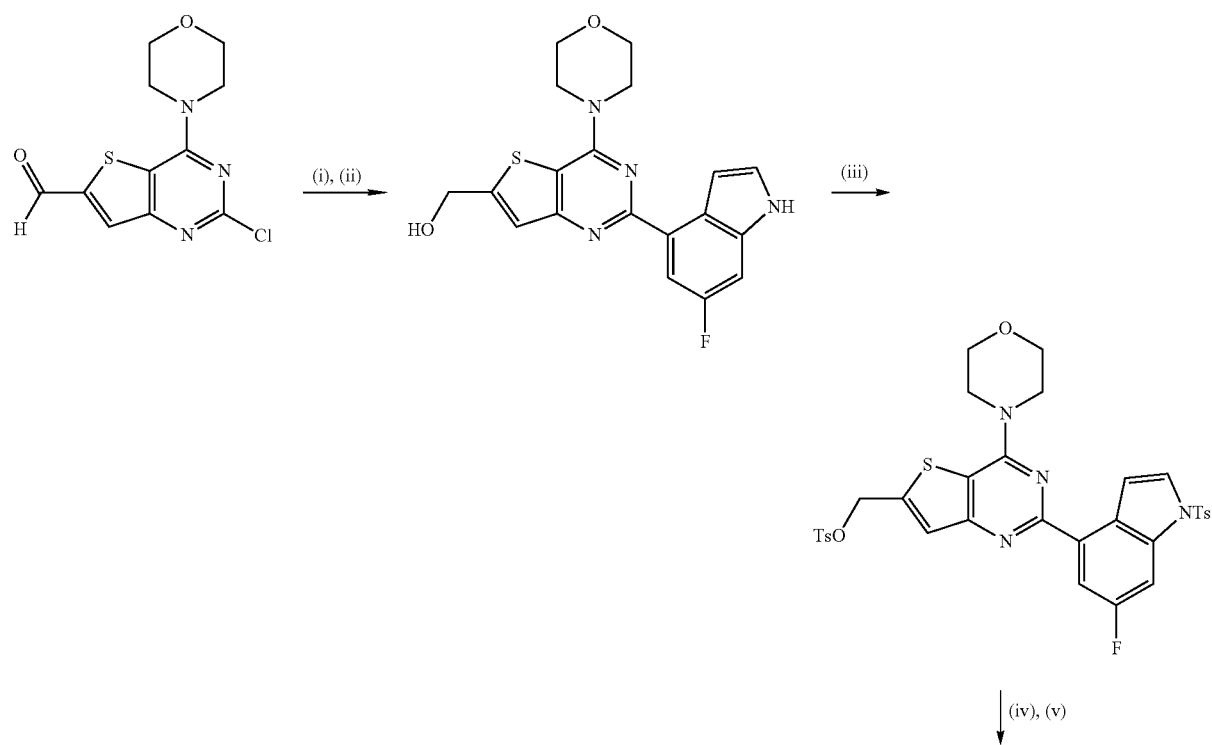

71  72

-continued

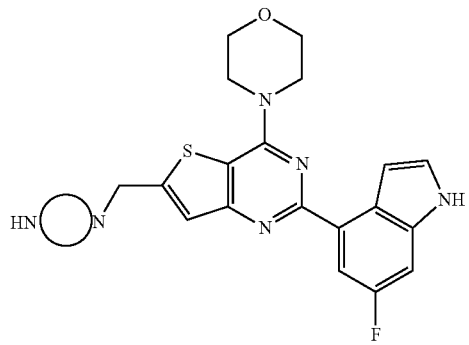 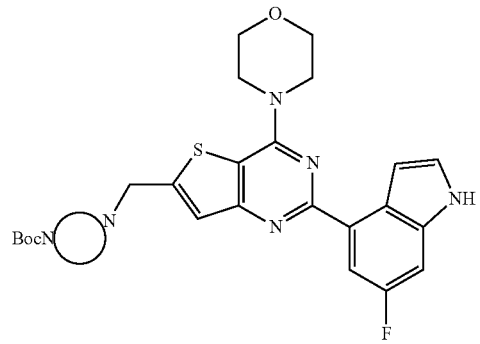

Conditions: (i) NaBH₄, THF-IMS, RT, 2 h. (ii) 4-indole boronate ester, CH₃CN-H₂O, Na₂CO₃, PdCl₂(PPh₃)₂, 140° C. microwave (iii) THF-DCM, NaH, RT, 10 min then TsCl, 40° C., 3 h. (iv) cyclic amine, DMF, K₂CO₃, 2 h, RT. (v) Dioxane-IMS, NaOH, H₂O RT, 3 h. (vi) TFA-CH₂Cl₂, RT.

Scheme 9

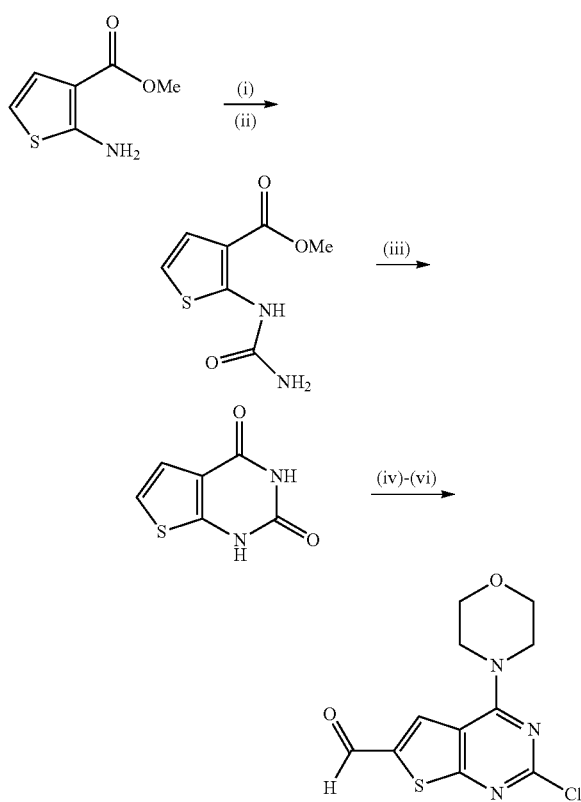

Conditions:
(i) ClSO₂NCO, CH₂Cl₂, -78° C. → RT. (ii) 6 N HCl, 100° C. (iii) iPrOH—H₂O, NaOH, 80° C., 3.5 h. (iv) POCl₃, 100° C., 24 h; (v) morpholine, RT, 1 h; (vi) n-BuLi, -78° C., TMEDA, THF 1 h then DMF -78° C. → RT Scheme 10

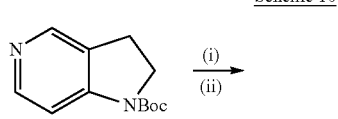

-continued

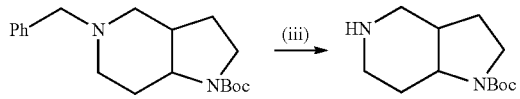

Conditions: (i) CH₃CN, PhCH₂Br, Δ, 2.5 h. (ii) NaBH₄, Δ, 2.5 h. (iii) IMS, Pd(OH₂)-C, H₂, RT, 10 h.

Scheme 11

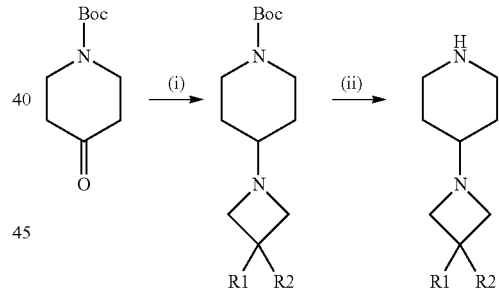

Condiitons:
(i) DCE, azetidine or substituted azetidine, Na(OAc)₃BH, 18 h. (ii) CH₂Cl₂-TFA, RT.

Scheme 12

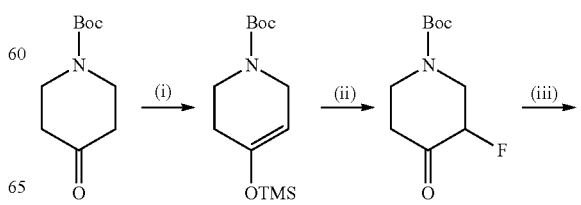

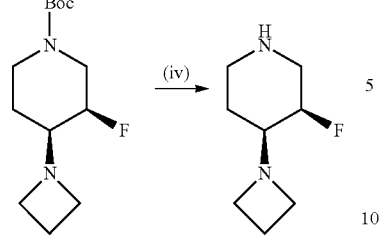
Conditions;
(i) DMF, TMSCl, 17 h, 80° C. (ii) CH₃CN, SelectFluor™, 2 h, RT. (iii) Na(OAc)₃BH, DCE, azetidine. (iv) CH₂Cl₂, TFA, RT.
Scheme 13
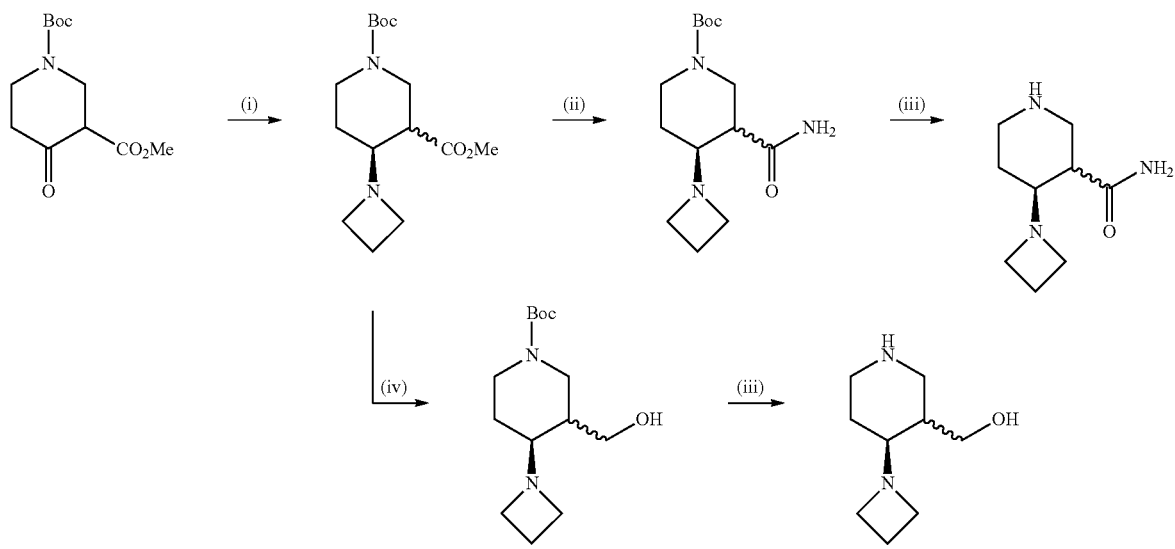
Conditions:
(i) DCE, azetidine, Na(OAc)₃BH, 2 h, RT. (ii) DMF, NH₂CHO, NaOMe, 100° C. (iii) CH₂Cl₂, TFA, RT, 1 h.
(iv) CH₂Cl₂, DIBAL, -70° C. → RT, 1.5 h.
Scheme 14
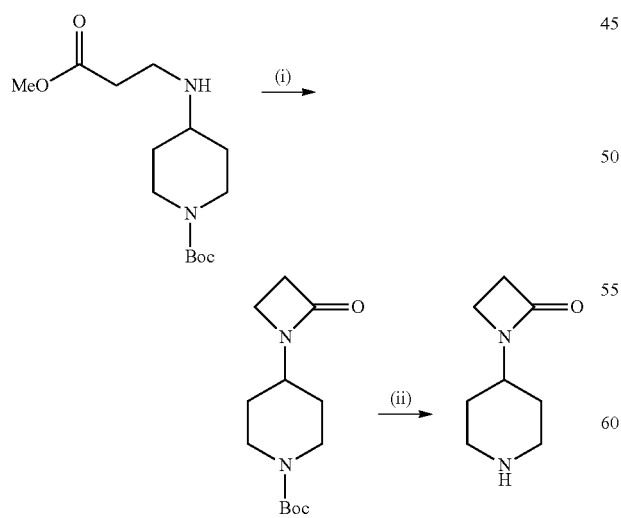
Conditions:
(i) THF, MeMgBr, 0° C., 3 h, then RT, 72 h. (ii) CH₂Cl₂-TFA.

Scheme 15

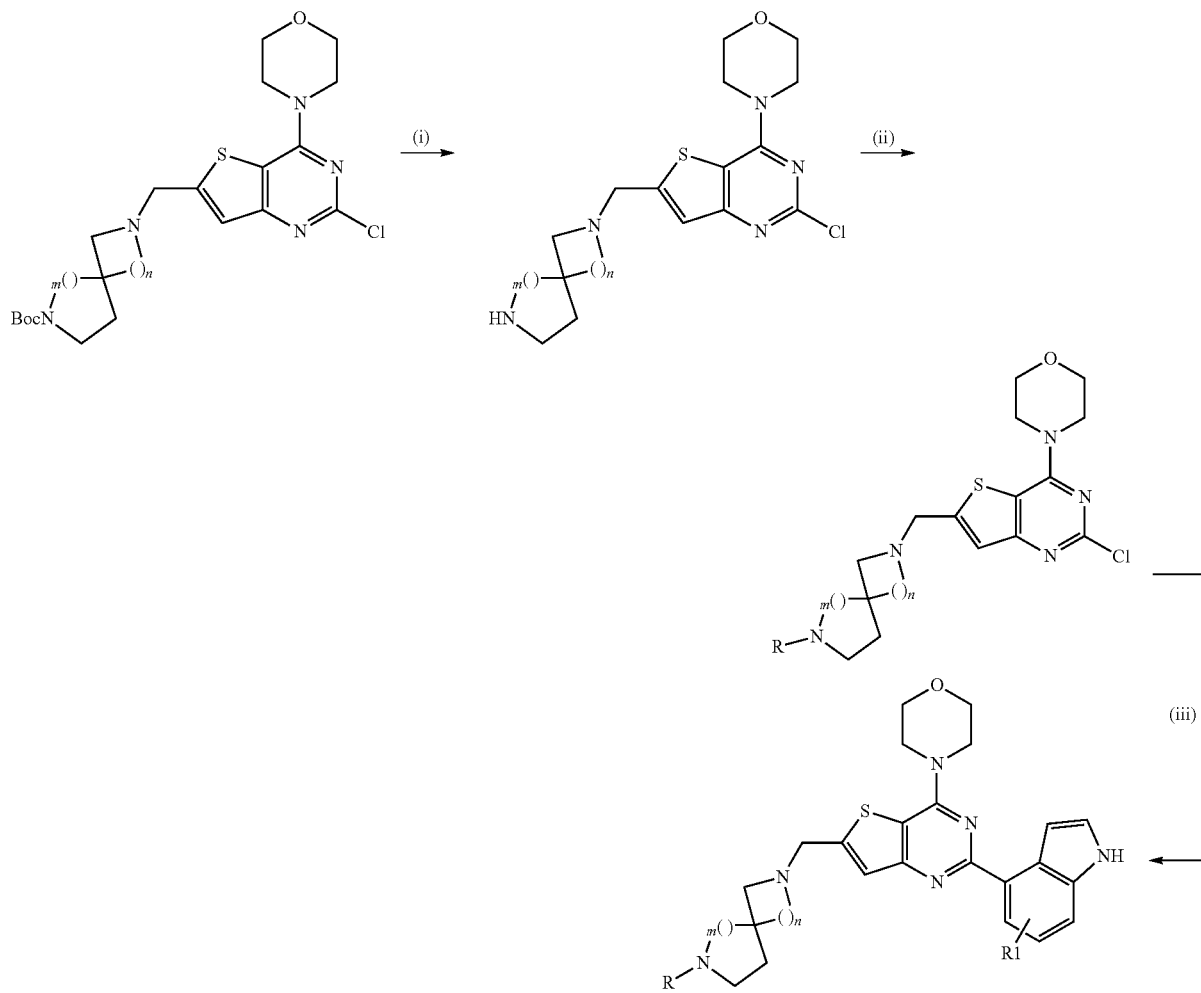

n = 1, m = 2 or n = 2, m = 1
Conditions:
(i) CH$_2$Cl$_2$-TFA. (ii) CH$_2$Cl$_2$, Et$_3$N, 18 h, RT, MeSO$_2$Cl or Me$_2$NC(O)Cl or TMSCNO. (iii) Suzuki coupling conditions.

Scheme 16

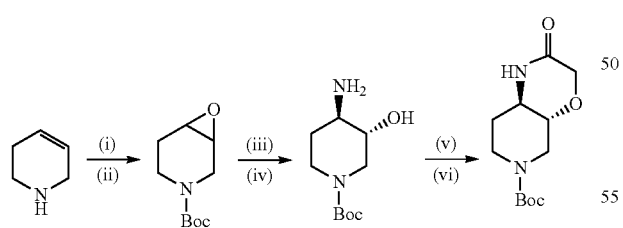

Conditions:
(i) CH$_2$Cl$_2$, (Boc)$_2$O, Et$_3$N, RT. (ii) CH$_2$Cl$_2$, mCPBA, 0° C.→RT, 4 h. (iii) EtOH, NaN$_3$, NH$_4$Cl, 78° C., 10 h. (iv) EtOH, Pd-C, H$_2$. (v) CH$_2$Cl$_2$, Et$_3$N, 0° C. then chloroacetyl chloride, 0° C.→RT, 10 h. (vi) THF, NaH, 0° C.→RT, 6 h. (vii) NaH, DMF, 0° C. then MeI, 0° C.→RT, 10 h. (viii) 2.0 M HCl-diethyl ether, CH$_2$Cl$_2$.

Scheme 17

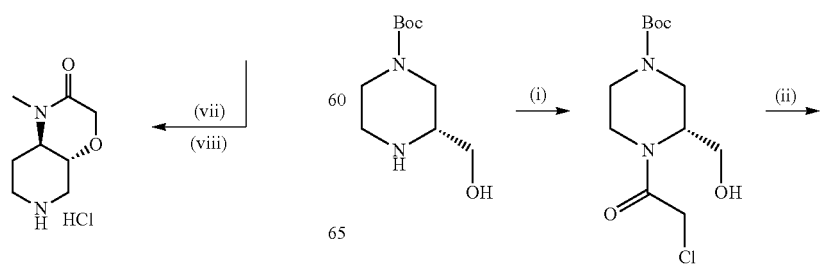

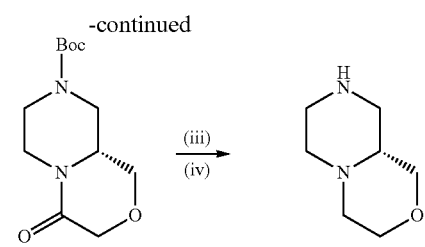

Conditions:
(i) CH₂Cl₂, Et₃N, chloroacetyl chloride, 0° C. →RT. (ii) THF, ᵗBuOK, 0° C. (iii) CH₂Cl₂-TFA, RT, 2 h. (iv) dioxane, LiAlH₄, 80° C., 2.5h.

Scheme 18

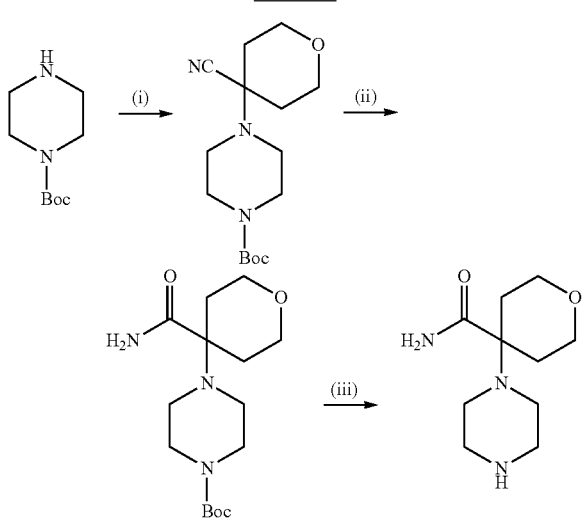

Conditions:
(i) MeOH—H₂O, KCN, tetrahydropyranone, RT. (ii) MeOH—H₂O, NaOH, H₂O₂, RT. (iii) 2.0 M HCl in Et₂O, CH₂Cl₂.

General Experimental Details:
NMR Spectroscopy

NMR spectra were obtained on a Varian Unity Inova 400 spectrometer with a 5 mm inverse detection triple resonance probe operating at 400 MHz or on a Bruker Avance DPX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane.

Purification by Column Chromatography:

Compounds purified by column chromatography were purified using silica gel or Isolute® cartridge or Redisep® cartridge, eluting with gradients from 100-0 to 0-100% of cyclohexane/EtOAc, or from 100-0 to 0-100% pentane/EtOAc or from 100-0 to 70-30% DCM/MeOH (with or without the addition of NH₃ 0.1%). 'Silica gel' refers to silica gel for chromatography, 0.035 to 0.070 mm (220 to 440 mesh) (e.g. Fluka silica gel 60), and an applied pressure of nitrogen up to 10 p.s.i accelerated column elution. Where thin layer chromatography (TLC) has been used, it refers to silica gel TLC using plates, typically 3×6 cm silica gel on aluminium foil plates with a fluorescent indicator (254 nm), (e.g. Fluka 60778).

Purification by Preparative HPLC:

Compounds purified by preparative HPLC were purified using a C18-reverse-phase column (100×22.5 mm i.d Genesis column with 7 µm particle size, UV detection at 230 or 254 nm, flow 5-15 mL/min), or a Phenyl-Hexyl column (250× 21.2 mm i.d. Gemini column with 5 µm particle size, UV detection at 230 or 254 nm, flow 5-20 mL/min), eluting with gradients from 100-0 to 0-100% water/acetonitrile or water/MeOH containing 0.1 TFA or water/acetonitrile containing 0.1% formic acid. The free base was liberated by partitioning between EtOAc and a saturated solution of sodium bicarbonate. The organic layer was dried (MgSO₄) and concentrated in vacuo. Alternatively, the free base was liberated by passing through an Isolute® SCX-2 cartridge, eluting with NH₃ in methanol.

Microwave Reactions:

Microwave experiments were carried out using a Smith Synthesiser or a Biotage Initiator™, which uses a single-mode resonator and dynamic field tuning, both of which give reproducibility and control. Temperatures from 40-250° C. can be achieved and pressures of up to 20 bar can be reached.

All solvents and commercial reagents were used as received. Non-commercially available reagents/reactants were prepared according to procedures described in the literature.

Abbreviations Used in the Experimental Section:
aq.=aqueous
BOC=t-Butoxycarbonyl
bs=broad singlet (NMR)
Cs₂CO₃=cesium carbonate
d=doublet (NMR)
DCE=1,2-dichloroethane
DCM=dichloromethane
DIPEA=diisopropylethylamine
DMA=dimethylacetamide
DMAP=dimethylaminopyridine
DMF=dimethylformamide
DMSO=dimethylsulfoxide
eq.=equivalents
EtOAc=ethyl acetate
EtOH=ethanol
h=hour(s)
HATU=O-(7-Azabenzotriazol-1-yl)-N,N,N',N'-tetramethyluronium hexafluorophosphate
HCl=hydrochloric acid
H₂O=water
HPLC=high pressure liquid chromatography
IPA=isopropanol
IMS=industrial methylated spirit
iPrOH=isopropanol
LCMS=liquid chromatography mass spectrometry
M=molar
m=multiplet (NMR)
MeOH=methanol
mg=milligram
MgSO₄=magnesium sulphate
min=minute(s)
mL=milliliter
Na₂CO₃=sodium carbonate
NaHCO₃=sodium hydrogen carbonate
NaOH=sodium hydroxide
Na₂SO₄=sodium sulfate
NH₄OH=ammonium hydroxide solution
NMR=nuclear magnetic resonance
q=quartet (NMR)
Rt=retention time
RT=room temperature
t=triplet (NMR)
TBAF=tetrabutylammonium fluoride
TBDMS=tert-Butyldimethylsilyl TFA=trifluoroacetic acid
THF=tetrahydrofuran
TLC=thin layer chromatography General Synthetic Strategies Reference Example 1

Formation of Boronate Esters

The boronate ester formed in scheme 1 was prepared as follows. To a solution of halide (1 eq.) and bis(pinacolato)diboron (1.3 eq.) in DMSO were added KOAc (3 eq.) and [1,1'-bis(diphenylphosphine)ferrocene]dichloropalladium (0.05 eq.). The mixture was heated at 90° C. until completion of the reaction. The reaction mixture was partioned between EtOAc and H₂O. The organic layer was washed successively with H₂O and brine, dried over Na₂SO₄ and evaporated to dryness. The resultant residue was then purified by column chromatography.

Reference Example 2

Suzuki Coupling

The Suzuki coupling reactions depicted generally in schemes 19 and 20 below were performed using one of the methods set out below. When R1=H in these methods, indole boronic acid was used as the reagent.

Scheme 19

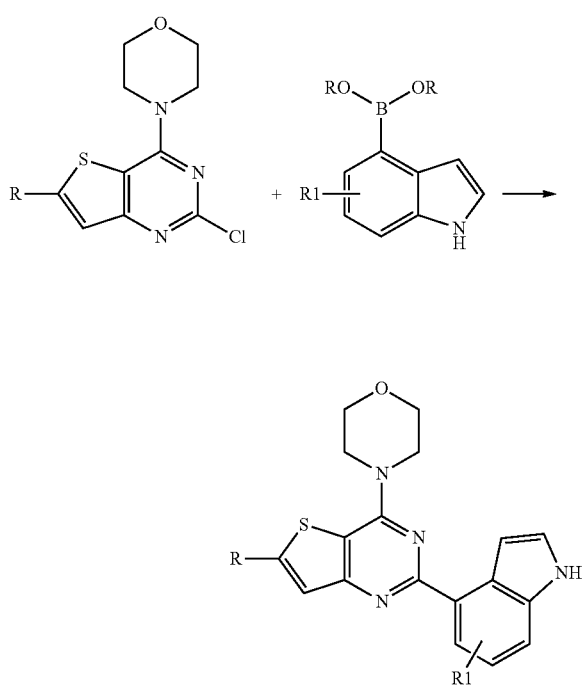

Scheme 20

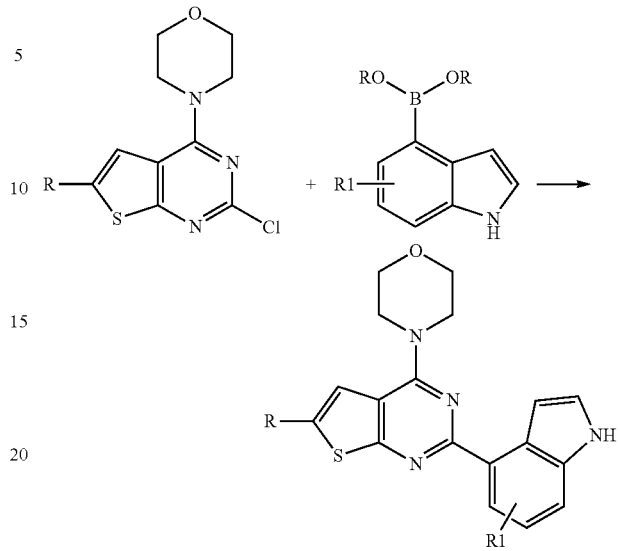

Method A

A mixture of the appropriate 2-chloro-thienopyrimidine (1 eq.), Cs₂CO₃ (1.5-2 eq.), indole boronate ester (1.2-1.5 eq.) or indole boronic acid (1.2 eq.) and tetrakis-(triphenylphosphine)palladium (0.05-0.1 eq.) in dioxane/water (3:1 or 2:1) was heated at 125° C.-140° C., for between 10 and 50 min in a microwave reactor (Smith synthesiser or CEM Discover). The resulting mixture was diluted with water then extracted with ethyl acetate. The combined organic extracts were dried (MgSO₄), filtered and concentrated then purified by either preparative HPLC or column chromatography to give the desired product. Alternatively, the reaction mixture was loaded onto an Isolute® SCX-2 cartridge, washed with MeOH then eluted with 2 M NH₃ in MeOH. The resulting residue was then purified by either preparative HPLC or column chromatography to give the desired product.

Method B

A mixture of the appropriate 2-chloro-thienopyrimidine (1 eq.), Na₂CO₃ (2 eq.), indole boronate ester or indole boronic acid (1.5 eq.) and bis(triphenylphosphine)palladium (II) chloride (0.1 eq.) in acetonitrile/water (2:1) was heated at 140° C. for 20-50 min in a microwave reactor (Smith synthetiser or CEM Discover). The resulting mixture was diluted with water then extracted with ethyl acetate. The combined organic extracts were dried (MgSO₄), filtered and concentrated then purified by either preparative HPLC or column chromatography to give the desired product. Alternatively, the reaction mixture was loaded onto an Isolute® SCX-2 cartridge, washed with MeOH then eluted with 2 M NH₃ in MeOH. The resulting residue was then purified by either preparative HPLC or column chromatography to give the desired product.

Method C

A mixture of the appropriate 2-chloro-thienopyrimidine (1 eq.), Na₂CO₃ (1.5 eq.), indole boronate ester or indole boronic acid (1.2 eq.) and tetrakis(triphenylphosphine)palladium (0.1 eq.) in acetonitrile/water (2:1) was heated at 140° C., for 10-30 min in a microwave reactor. The resulting mixture was diluted with water then extracted with ethyl acetate. The combined organic extracts were dried (MgSO₄), filtered and concentrated in vacuo then purified by either preparative HPLC or column chromatography to give the desired product. Alternatively, the reaction mixture was loaded onto an Isolute® SCX-2 cartridge, washed with MeOH then eluted with 2 M NH₃ in MeOH. The resulting residue was then purified by either preparative HPLC or column chromatography to give the desired product Method D A mixture of the appropriate 2-chloro-thienopyrimidine (0.1-0.2 mmol), K₃PO₄ (0.5 mL of a 1.27 M aqueous solution), dichlorobis(tricyclohexylphosphine)palladium (II) (0.05 eq.) and indole boronate ester (1.3-1.5 eq.) in dioxane (1 mL) was heated at 125° C. for 20-50 min in a microwave reactor (Smith synthesiser or CEM Discover). The resulting mixture was diluted with water then extracted with ethyl acetate. The combined organic extracts were dried (MgSO₄), filtered and concentrated then purified by either preparative HPLC or column chromatography to give the desired product. Alternatively, the reaction mixture was loaded onto an Isolute® SCX-2 cartridge, washed with MeOH then eluted with 2 M NH₃ in MeOH. The resulting residue was then purified by either preparative HPLC or column chromatography to give the desired product.

Reference Example 3

General Method for BOC-Deprotection

To a solution of the relevant BOC-protected amino-thienopyrimidine in DCM was added TFA and the resulting solution was stirred at RT for 30-180 min. The resulting mixture was diluted with water then extracted with DCM. The combined organic extracts were dried (MgSO₄ or Na₂SO₄), filtered and concentrated in vacuo, then purified by either preparative HPLC or column chromatography to give the desired product. Alternatively, the reaction mixture was loaded onto an Isolute® SCX-2 cartridge, washed with MeOH then eluted with 2 M NH₃ in MeOH. The resulting residue was then purified by either preparative HPLC or column chromatography to give the desired product.

Reference Example 4

General Method for TBDMS-Deprotection

To a solution of the relevant TBDMS-protected 5-fluoro-1H-indol-4-yl-thienopyrimidine in THF was added TBAF and the resulting solution was stirred at RT for 30 min, then concentrated in vacuo. The resultant residue was purified by either preparative HPLC or column chromatography to give the desired product.

Preparation of Intermediates

Reference Example 5

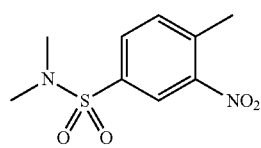

4-N,N-Trimethyl-3-nitro-benzenesulfonamide

To a solution of dimethylamine in H₂O (40% w/w, 15.0 mL, 120 mmol) at 0° C. was added a solution of 4-methyl-3-nitro-benzenesulfonyl chloride (9.42 g, 40 mmol) in DCM (60 mL) over 30 min. The resulting mixture was stirred at 0° C. for 30 min before being allowed to warm to RT and stirred overnight. The reaction mixture was diluted with H₂O (100 mL) and DCM (40 mL), and the layers were separated. The organic layer was washed in succession with water, HCl (aq., 0.1M) and brine before being dried over Na₂SO₄ and evaporated to dryness to give the title compound as a pale yellow solid (9.13 g, 94%).

[M+H]⁺ 244.9

Reference Example 6

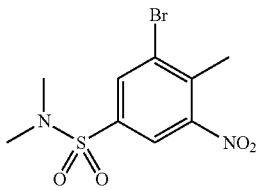

3-Bromo-4,N,N-trimethyl-5-nitro-benzenesulfonamide

To a solution of 4-N,N-trimethyl-3-nitro-benzenesulfonamide (8.57 g, 34.7 mmol) in concentrated sulfuric acid (80 mL) was added 1,3-dibromo-[1,3,5]triazinane-2,4,6-trione (5.97 g, 20.8 mmol) and the orange reaction mixture was stirred at RT for 16 h. A further 2 g of 1,3-dibromo-[1,3,5]triazinane-2,4,6-trione was added and stirring continued for 5 h. The reaction mixture was then poured onto ice and water and stirred for 15 min. The resulting milky/white solid was filtered and washed with H₂O, before being dissolved in EtOAc. The organic layer was dried over Na₂SO₄ and evaporated to dryness to give the title compound as a white solid (10.41 g, 93%).

[M+H]⁺ 32 3.1 (⁷⁹Br) 325.0 (⁸¹Br)

Reference Example 7

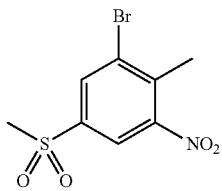

1-Bromo-5-methanesulfonyl-2-methyl-3-nitro-benzene

Prepared according to the method used in the preparation of 3-bromo-4-N,N-trimethyl-5-nitro-benzenesulfonamide using 4-methanesulfonyl-1-methyl-2-nitro-benzene in place of 4-N,N-trimethyl-3-nitro-benzenesulfonamide. The title compound was obtained as a white solid (17.0 g, 85%).

[M+H]⁺294.1 (⁷⁹Br) 296.0 (⁸¹Br)

Reference Example 8

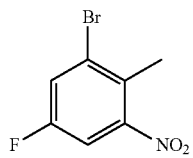

1-Bromo-5-fluoro-2-methyl-3-nitro-benzene

Prepared according to the method used in the preparation of 3-bromo-4-N,N-trimethyl-5-nitro-benzenesulfonamide using 4-fluoro-1-methyl-2-nitro-benzene in place of 4-N,N-trimethyl-3-nitro-benzenesulfonamide. The title compound was obtained as a yellow solid (68.0 g, 79%).

NMR $\delta_H$ (300 MHz, CDCl$_3$) 2.59 (s, 3H), 7.50 (dd, J=2.8, 7.6, 1H) and 7.58 (dd, J=2.9, 7.4, 1H).

Reference Example 9

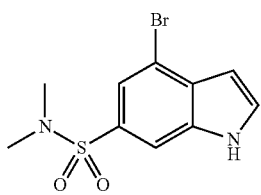

4-Bromo-1H-indole-6-sulfonic acid dimethylamide

To a solution of 3-bromo-4-N,N-trimethyl-5-nitro-benzenesulfonamide (9.15 g, 28.3 mmol) in dioxane (60 mL) was added DMF-DMA (11.3 mL, 84.9 mmol). The deep red reaction mixture was heated at 80° C. for 24 h followed by heating at 90° C. for 16 h. The mixture was cooled to RT and concentrated to 50% of the volume, poured into H$_2$O and extracted into EtOAc. The organic layer was isolated and washed with H$_2$O, then brine, dried over Na$_2$SO$_4$, and evaporated to dryness to give 3-bromo-4-(2-dimethylamino-vinyl)-N,N-dimethyl-5-nitro-benzenesulfonamide as a red solid (10.4 g, 91%). To a suspension of the amide (10.4 g, 25.7 mmol) and Raney®-Nickel (suspension in H$_2$O, 20 mL) in MeOH:THF (1:1, 200 mL) was added hydrazine monohydrate (1.9 mL, 38.6 mmol) at 0° C. and the mixture stirred at RT for 40 min.

The reaction mixture was then filtered through Celite and the filter cake washed with EtOAc and H$_2$O. The aqueous layer was isolated and then extracted with EtOAc. The combined organic layers were washed with H$_2$O, followed by brine, dried over Na$_2$SO$_4$ then evaporated to dryness. The resulting pink solid was purified by column chromatography, and subsequently recrystallised from iPrOH and EtOH to give the title compound as a white solid (3.5 g, 41%).

NMR $\delta_H$ (400 MHz, CDCl$_3$) 2.72 (s, 6H), 6.70 (m, 1H), 7.49 (apparent t, J=2.7, 1H), 7.68 (d, J=1.1, 1H), 7.94 (m, 1H) and 9.04 (bs, 1H).

Reference Example 10

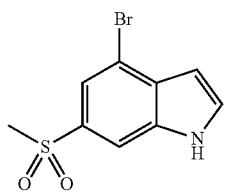

4-Bromo-6-methanesulfonyl-1H-indole

Prepared according to the method used in the preparation of 4-bromo-1H-indole-6-sulfonic acid dimethylamide using 1-bromo-5-methanesulfonyl-2-methyl-3-nitro-benzene in place of 3-bromo-4-N,N-trimethyl-5-nitro-benzenesulfonamide. The title compound was obtained as a white solid (1.8 g, 76%).

NMR $\delta_H$ (300 MHz, CDCl$_3$) 3.11 (s, 3H), 6.70 (m, 1H), 7.52 (dd, J=2.5, 3.0, 1H), 7.81 (d, J=1.5, 1H), 8.10 (dd, J=1.0, 1.5, 1H) and 9.34 (bs, 1H).

Reference Example 11

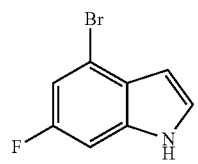

4-Bromo-6-fluoro-1H-indole

Prepared according to the method used in the preparation of 4-bromo-1H-indole-6-sulfonic acid dimethylamide using 1-bromo-5-fluoro-2-methyl-3-nitro-benzene in place of 3-bromo-4-N,N-trimethyl-5-nitro-benzenesulfonamide. The title compound was obtained as a white solid (6.06 g, 33%).

NMR $\delta_H$ (300 MHz, CDCl$_3$) 6.57 (apparent t, J=2.7, 1H), 7.04 (dd, J=2.1, 9.1, 1H), 7.12 (dd, J=2.1, 9.1, 1H), 7.20-7.25 (m, 1H) and 8.25 (s, 1H).

Reference Example 12

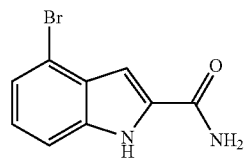

4-Bromo-1H-indole-2-carboxylic acid amide

Oxalyl chloride (0.9 mL, 10 mmol) was added to a suspension of 4-bromo-1H-indole-2-carboxylic acid (2.1 g, 8.8 mmol) in DCM and the mixture was stirred for 2 h. The solution formed was added drop-wise to a stirring mixture of ammonia (37%, 50 mL) and ice (50 mL). The resulting mixture was allowed to stand for 3 days. The mixture was filtered and the filtrate extracted with EtOAc. The solid from the filtration was dissolved in EtOAc and the organic solutions were combined, dried (MgSO$_4$) and then evaporated to afford the title compound as a brown solid (2.1 g, 100%).

NMR $\delta_H$ (400 MHz, CD$_3$OD) 7.11 (dd, J=7.5, 8.3, 1H), 7.16 (d, J=0.9, 1H), 7.25 (dd, J=0.78, 7.54, 1H) and 7.43 (d, J=8.3, 1H).

Reference Example 13

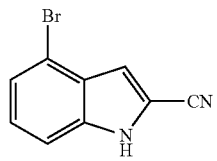

4-Bromo-1H-indole-2-carbonitrile

Phosphorous oxychloride (1.9 mL, 20 mmol) was added to a suspension of 4-bromo-1H-indole-2-carboxylic acid amide (1.32 g, 5.5 mmol.) in toluene (10 mL) and the mixture was stirred at reflux for 45 min. On cooling, the mixture was poured into an aqueous Na$_2$CO$_3$ solution (sat., 50 mL) and the mixture stirred until effervescence had subsided. The layers were separated, the aqueous phase extracted with EtOAc and the combined organic layers dried (MgSO$_4$) and evaporated to dryness. The crude material was purified by column chromatography to afford the title compound as a solid (1.00 g, 82%).

NMR $\delta_H$ (400 MHz, CDCl$_3$) 7.22-7.28 (m, 2H), 7.35-7.40 (m, 2H) and 8.79 (s, 1H).

Reference Example 14

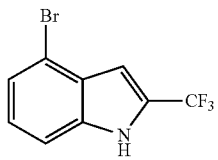

4-Bromo-2-trifluoromethyl-1H-indole

A solution of 2-methyl-3-bromo-aniline (6.05 g, 37 mmol) in pyridine (8 mL) and DCM (150 mL) was cooled to 0° C. and treated drop-wise with trifluoroacetic anhydride (11.5 mL, 81.4 mmol). The reaction mixture was stirred at RT for 2 h, then quenched with an aqueous solution of ammonium chloride. The organic layer was dried over MgSO$_4$, and evaporated to dryness to give N-(3-bromo-2-methyl-phenyl)-2,2,2-trifluoro-acetamide as an off-white solid, which was used without further purification (10 g).

NMR $\delta_H$ (400 MHz, CDCl$_3$) 2.38 (s, 3H), 7.14 (apparent t, J=8.0, 1H), 7.53 (d, J=8.0, 1H), 7.66 (d, J=8.0, 1H) and 7.75 (bs, 1H).

A solution of N-(3-bromo-2-methyl-phenyl)-2,2,2-trifluoro-acetamide (2.1 g, 7.4 mmol) and benzoyl peroxide (100 mg) in carbon tetrachloride (50 mL) was heated to reflux under irradiation (150 W tungsten lamp). A solution of bromine (0.55 mL, 10.4 mmol) in carbon tetrachloride (3 mL) was then added drop-wise to the refluxing solution, and heating was pursued for 16 h. The reaction mixture was left to cool to RT and diluted with DCM. The organic layer was washed with sodium thiosulfate, and evaporated to dryness to give N-(3-bromo-2-bromomethyl-phenyl)-2,2,2-trifluoro-acetamide as a brown residue which was used without further purification (2.9 g).

NMR $\delta_H$ (400 MHz, CDCl$_3$) 4.71 (s, 2H), 7.30 (apparent t, J=8.0, 1H), 7.55 (d, J=8.0, 1H), 7.82 (d, J=8.0, 1H) and 8.79 (bs, 1H).

A solution of N-(3-bromo-2-bromomethyl-phenyl)-2,2,2-trifluoro-acetamide (2.9 g) in toluene (40 mL) was treated with triphenylphosphine (2.3 g, 8.7 mmol). The solution was stirred at 60° C. for 2 h, then cooled to 0° C. The beige solid that precipitated was collected by filtration, washed with diethyl ether, then dissolved in DMF (60 mL), and heated to reflux under nitrogen for 16 h. The reaction mixture was evaporated to dryness, then partitioned between EtOAc and a sat. sodium carbonate solution. The organic layer was isolated, dried (MgSO$_4$), and purified by column chromatography to give the title compound as a yellow solid (1.55 g, 84%).

NMR $\delta_H$ (400 MHz, CDCl$_3$) 7.00 (s, 1H), 7.19 (apparent t, J=7.9, 1H), 7.36-7.41 (m, 2H) and 8.53 (bs, 1H).

Reference Example 15

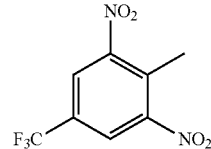

2-Methyl-1,3-dinitro-5-trifluoromethyl-benzene

To a solution of 4-methylbenzo-trifluoride (9.51 g, 59.4 mmol) in concentrated sulphuric acid (120 mL) was added potassium nitrate (15.0 g, 0.149 mol) and the resulting mixture stirred at RT for 16 h. The reaction mixture was poured onto ice and water then extracted into EtOAc. The organic layer was washed successively with H$_2$O and brine, dried over Na$_2$SO$_4$ and evaporated to dryness to give the title compound as a yellow solid (13.84 g, 93%)

NMR $\delta_H$ (400 MHz, CDCl$_3$) 2.67 (s, 3H) and 8.27 (s, 2H).

Reference Example 16

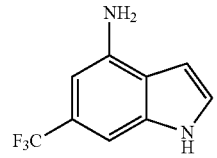

6-Trifluoromethyl-1H-indol-4-ylamine

Prepared according to the method used in the preparation of 4-bromo-1H-indole-6-sulfonic acid dimethylamide using 2-methyl-1,3-dinitro-5-trifluoromethyl-benzene in place of 3-bromo-4,N,N-trimethyl-5-nitro-benzenesulfonamide. The title compound was obtained as a white solid (10.7 g, 99%).

[M+H]+ 201.1

Reference Example 17

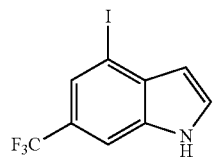

4-Iodo-6-trifluoromethyl-1H-indole

To a suspension of 6-trifluoromethyl-1H-indol-4-ylamine (10.7 g, 53.4 mmol) in HCl (aq., 15%, 240 mL) was added a solution of sodium nitrite (5.52 g, 80.1 mmol) in H$_2$O (10 mL) slowly at 0° C. The reaction mixture was stirred at RT for 1 h before a solution of sodium tetrafluoroborate (23.5 g, 0.214 mol) in H$_2$O (30 mL) was added. After stirring for 15 min, the resulting precipitate was collected by filtration and washed with a sodium tetrafluoroborate solution (aq., sat) before dissolving in acetonitrile (100 mL). This solution was added slowly to a suspension of sodium iodide (24.0 g, 0.160 mol) in acetonitrile (100 mL) and the mixture stirred at RT for 16 h. The reaction mixture was concentrated to 30% of the volume and partioned between EtOAc and H$_2$O. The organic layer was isolated then washed in succession with sodium thiosulfate, H$_2$O and brine, dried over Na$_2$SO$_4$ and evaporated to dryness. The resulting brown oil was purified by column chromatography to give the title compound (9.77 g, 59%).

[M−H]− 310.1

Reference Example 18

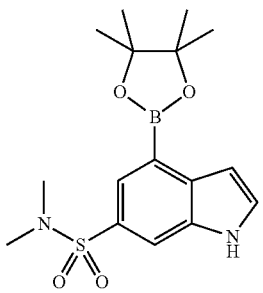

4-(4,4,5,5-Tetramethyl-[1,3,2]dioxaborolan-2-yl)-1H-indole-6-sulfonic acid dimethylamide Prepared by using the general method (Scheme 1). The title compound was obtained as a white solid (1.85 g, 46%).

[M+H]+350.2 (10B) 351.2 (11B)

Reference Example 19

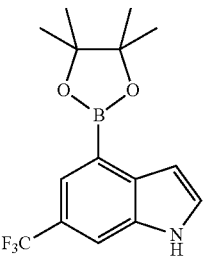

4-(4,4,5,5-Tetramethyl-[1,3,2]dioxaborolan-2-yl)-6-trifluoromethyl-1H-indole

Prepared by using the general method (Scheme 1). The title compound was obtained as a pale yellow solid (1.37 g, 92%).

[M+H]+311.2 (10B) 312.2 (11B)

Reference Example 20

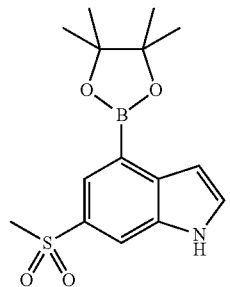

6-Methanesulfonyl-4-(4,4,5,5-tetramethyl-[1,3,2]dioxaborolan-2-yl)-1H-indole

Prepared by using the general method (Scheme 1). The title compound was obtained as a pale yellow solid (2.4 g, 51%).

NMR δ$_H$ (300 MHz, DMSO-d$_6$) 1.36 (s, 12H), 3.18 (s, 3H), 6.87 (m, 1H), 7.73 (apparent t, J=2.5, 1H), 7.85 (d, J=1.5, 1H), 8.07 (dd, J=1.0, 1.5, 1H) and 11.73 (bs, 1H).

Reference Example 21

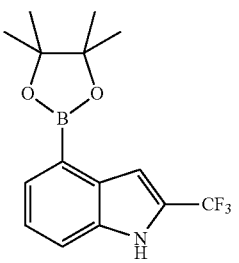

4-(4,4,5,5-Tetramethyl-[1,3,2]dioxaborolan-2-yl)-2-trifluoromethyl-1H-indole

Prepared by using the general method (Scheme 1). The title compound was obtained as a white solid (1.5 g, 55%).

NMR δ$_H$ (400 MHz, CDCl$_3$) 1.40 (s, 12H), 7.33 (dd, J=7.0, 8.3, 1H), 7.42 (s, 1H), 7.53 (d, J=8.3, 1H), 7.70 (d, J=7.0, 1H) and 8.37 (bs, 1H).

Reference Example 22

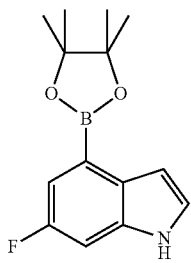

6-Fluoro-4-(4,4,5,5-tetramethyl-[1,3,2]dioxaborolan-2-yl)-1H-indole

Prepared by using the general method (Scheme 1). The title compound was obtained as a white solid (4.6 g, 61%).

NMR δ$_H$ (300 MHz, CDCl$_3$) 1.39 (s, 12H), 7.02 (m, 1H), 7.14-7.19 (m, 1H), 7.20-7.26 (m, 1H), 7.38 (dd, J=2.4, 9.9, 1H) and 8.16 (s, 1H).

Reference Example 23

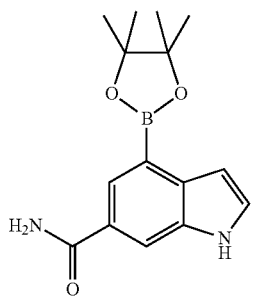

4-(4,4,5,5-Tetramethyl-[1,3,2]dioxaborolan-2-yl)-1H-indole-6-carboxylic acid amide A solution of 4-bromo-1H-indole-6-carbonitrile (1 g, 4.50 mmol) in methanol (10 mL) was treated with 30% aqueous hydrogen peroxide (2.7 mL, 4.95 mmol) and a 1 M aqueous sodium hydroxide solution (5 mL) then heated at 40° C. for 1 h. The reaction mixture was cooled, treated with water and cooled in an ice-bath. The resulting precipitate was collected by filtration, washed with water and dried in vacuo to obtain 4-bromo-1H-indole-6-carboxylic acid amide (1.05 g, 97%), which was transformed into the title boronic ester by the general method (Scheme 1) (0.80 g, 67%).

NMR δ$_H$ (300 MHz, DMSO-d$_6$) 1.35 (s, 12H), 6.78 (m, 1H), 7.10 (s, 1H), 7.51-7.54 (m, 1H), 7.94-7.97 (m, 2H), 8.06 (s, 1H) and 11.40 (bs, 1H).

Reference Example 24

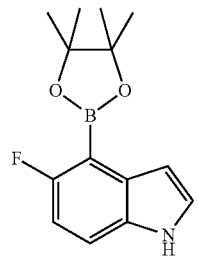

5-Fluoro-4-(4,4,5,5-tetramethyl-[1,3,2]dioxaborolan-2-yl)-1H-indole

A solution of 5-fluoroindole (5 g, 37.0 mmol) in DMF (40 mL) was treated at 0° C. with trifluoroacetic anhydride (6.1 mL, 42.6 mmol). After 30 min, the reaction was poured into water and the resulting precipitate collected by filtration, washed with water, then dried in vacuo. The solid was then dissolved in 10% aqueous NaOH (200 mL) and heated at reflux for 1 h. The reaction mixture was then cooled, washed with dichloromethane and acidified with aqueous HCl. The resulting white precipitate was collected by filtration, washed with water, taken up in dichloromethane, washed with water, dried (MgSO$_4$) and evaporated in vacuo. The resulting material (5 g, 75%) was dissolved in methanol (80 mL) and treated with concentrated sulphuric acid (2 mL) then heated at reflux overnight. The reaction was cooled and the resulting precipitate collected, washed with water and evaporated in vacuo to give 5-fluoro-1H-indole-3-carboxylic acid methyl ester as a peach-coloured solid (4.5 g, 83%).

A solution of thallium tris(trifluoroacetate) (8.45 g, 15.6 mmol) in TFA (35 mL) was added to a solution of 5-fluoro-1H-indole-3-carboxylic acid methyl ester (2 g, 10.4 mmol) in TFA (10 mL) at room temperature and stirred for 2 h. The reaction mixture was evaporated in vacuo and the resulting residue suspended in water (25 mL) before being treated with a solution of potassium iodide (5.2 g, 31.3 mmol) in water (50 mL). The reaction mixture was treated with dichloromethane (100 mL) and methanol (5 mL) and the resulting precipitate removed by filtration through celite.

The organic layer was separated, washed successively with sodium thiosulfate solution and brine, then dried (MgSO$_4$) and evaporated in vacuo. The resultant material was dissolved in methanol (60 mL) and treated with 40% aqueous NaOH solution (60 mL) then refluxed for 2 h. The reaction mixture was cooled and extracted with DCM/MeOH (ratio 95:5), dried (MgSO$_4$), filtered and evaporated in vacuo to give a crude solid. Purification by column chromatography gave 5-fluoro-4-iodo-1H-indole as a pale brown solid (1.05 g, 39%).

NMR δ$_H$ (300 MHz, CDCl$_3$) 6.49-6.52 (m, 1H), 6.95 (apparent dt, J=0.4, 8.6, 1H), 7.26-7.33 (m, 2H) and 8.35 (s, 1H).

A solution of 5-fluoro-4-iodo-1H-indole (261 mg, 1.0 mmol) in dioxane (1 mL) was treated with triethylamine (0.2 mL, 1.4 mmol), palladium acetate (4.5 mg, 0.02 mmol) and bis(cyclohexyl)phosphino-2-biphenyl (28 mg, 0.08 mmol) then heated to 80° C. A solution of pinacolborane (1 M in THF, 2.66 mL, 2.66 mmol) was added via syringe. After 30 min, the reaction mixture was cooled, then diluted with water (10 mL) and DCM (10 mL). The resulting mixture was passed through a phase separation cartridge, and the dichloromethane layer was evaporated in vacuo to obtain the title compound which was used without further purification.

Reference Example 25

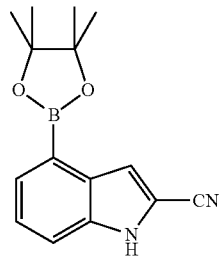

4-(4,4,5,5-Tetramethyl-[1,3,2]dioxaborolan-2-yl)-1H-indole-2-carbonitrile 4,4,5,5-Tetramethyl-[1,3,2]dioxaborolane (2.1 mL, 14.5 mmol) was added drop-wise to a mixture of 4-bromo-1H-indole-2-carbonitrile (1.27 g, 5.8 mmol), palladium acetate (33 mg, 0.145 mmol), triethylamine (1.21 mL, 8.7 mmol) and 2-(dicyclohexylphosphino)biphenyl (203 mg, 0.58 mmol) in dioxane at 80° C. The reaction mixture was stirred at 80° C. for 5 h then allowed to stand at RT overnight. The reaction mixture was diluted with DCM and washed with water, then the organic layer was isolated, dried (MgSO$_4$) then concentrated in vacuo. The resultant crude material was purified by column chromatography to afford the title compound as a brown solid (1.02 g, 66%).

NMR $\delta_H$ (400 MHz, CDCl$_3$) 1.40 (s, 12H), 7.36-7.42 (m, 1H), 7.51 (apparent dt, J=1.0, 8.3, 1H), 7.67-7.74 (m, 2H) and 8.51 (s, 1H).

Reference Example 26

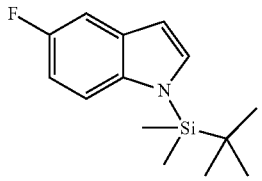

1-(tert-Butyl-dimethyl-silanyl)-5-fluoro-1H-indole

To a solution of 5-fluoro-1H-indole (30.0 g, 0.222 mol) in anhydrous THF (250 mL) was added sodium hydride (60% suspension in mineral oil, 10.22 g, 0.255 mol) portionwise and maintaining the solution at 0° C. The reaction mixture was stirred at 0° C. for 20 min, then a solution of tert-butyl-chloro-dimethyl-silane (40.15 g, 0.266 mol) in anhydrous THF (20 mL) was added and the solution stirred at RT for 25 h. The reaction mixture was poured into H$_2$O and the layers separated. The aqueous layer was extracted with EtOAc and the combined organic layers were dried (MgSO$_4$), then concentrated in vacuo. The resultant residue was purified by column chromatography (silica gel, cyclohexane:DCM 100% to 50:50) to provide the title compound was obtained as a colourless oil (41.2 g, 74%).

$^1$H NMR (400 MHz, CDCl$_3$): δ 0.60 (s, 6H), 0.94 (s, 9H), 6.58 (dd, J=3.2, 1.0 Hz, 1H), 6.87-6.93 (m, 1H), 7.23 (d, J=3.2 Hz, 1H), 7.24-7.29 (m, 1H) and 7.41 (m, 1H).

Reference Example 27

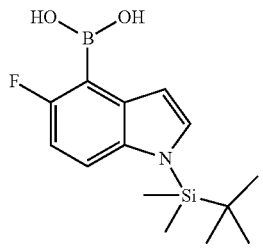

[1-(tert-Butyl-dimethyl-silanyl)-5-fluoro-1H-indol-4-yl]boronic acid

To a solution of 1-(tert-butyl-dimethyl-silanyl)-5-fluoro-1H-indole (30.0 g, 0.12 mol) in anhydrous THF (1000 mL) were added N,N,N',N'-tetramethylethylenediamine (36.6 mL, 0.241 mol) and a solution of s-butyl lithium (1.4 M in cyclohexane, 172 mL, 0.241 mmol) at –78° C. The resulting mixture was stirred at –78° C. for 2 h, then triisopropyl borate (37.5 mL, 162.7 mmol) was added dropwise. The resulting solution was stirred at –78° C. for 40 min, then allowed to warm to –20° C. An aqueous solution of HCl (2.4 M, 250 mL) was added and the resulting mixture was poured into H$_2$O. The layers were separated and the aqueous layer extracted with EtOAc. The combined organic layers were dried (MgSO$_4$) and concentrated in vacuo. The resultant yellow solid was then crystallised from DCM and cyclohexane to give the title compound as a white solid (25.0 g, 71%).

$^1$H NMR (400 MHz, CD$_3$OD): δ 0.62 (s, 6H), 0.92 (s, 9H), 6.51 (d, J=3.2 Hz, 1H), 6.79-6.90 (m, 1H), 7.30-7.36 (m, 1H) and 7.54 (dd, J=9.0, 4.6 Hz, 1H).

Reference Example 28

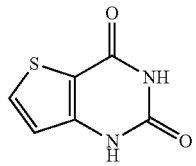

1H-Thieno[3,2-d]pyrimidine-2,4-dione

A mixture of methyl 3-amino-2-thiophenecarboxylate (13.48 g, 85.85 mmol) and urea (29.75 g, 5 equivalents) was heated at 190° C. for 2 hours. The hot reaction mixture was then poured onto sodium hydroxide solution (2N, 300 mL) and any insoluble material removed by filtration. The mixture was then acidified to pH 6 by the addition concentrated HCl with cooling. The resultant white precipitate was collected by filtration and air dried (9.49 g, 66%).

δH (400 MHz, d-6 DMSO) 11.60-11.10 (2H, br, s), 8.10 (1H, d, J 5.2), 6.90 (1H, d, J 5.2).

Reference Example 29

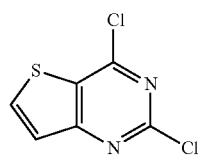

2,4-Dichloro-thieno[3,2-d]pyrimidine

To a suspension of 1H-thieno[3,2-d]pyrimidine-2,4-dione (10.0 g, 59.52 mmol) in acetonitrile (50 mL) was added phosphorous oxychloride (300 mmol, 5 equivalents, 28 mL) and the mixture heated at reflux for 24 hours in a flask fitted with a mechanical stirrer. The reaction mixture was then cooled and poured cautiously onto ice-water (250 mL) maintaining the temperature below 20° C. The mixture was filtered to yield 2,4-dichloro-thieno[3,2-d]pyrimidine as an off-white solid (9.15 g, 75%).

δH (400 MHz, CDCl$_3$) 8.13 (1H, d, J 5.5), 7.56 (1H, d, J 5.5).

Reference Example 30

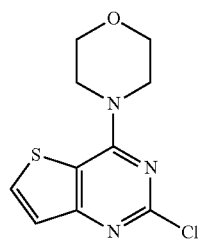

2-Chloro-4-morpholin-4-yl-thieno[3,2-d]pyrimidine

A mixture of 2,4-dichloro-thieno[3,2-d]pyrimidine (8.68 g, 42.34 mmol), morpholine (8.11 mL, 2.2 equivalents) and methanol (150 mL) was stirred at room temperature for 1 hour. The reaction mixture was then filtered, washed with water to yield the title compound a a white solid (11.04 g, 100%).

δH (400 MHz, d-6 DMSO) 8.30 (1H, d, J 5.6), 7.40 (1H, d, J 5.6), 3.90 (4H, t, J 4.9), 3.74 (4H, t, J 4.9).

Reference Example 31

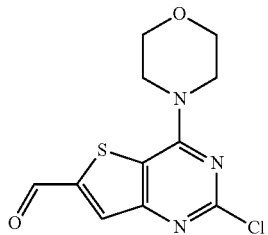

2-Chloro-4-morpholin-4-yl-thieno[3,2-d]pyrimidine-6-carbaldehyde

To a solution of 2-chloro-4-morpholin-4-yl-thieno[3,2-d] pyrimidine (1.0 g, 3.91 mmol) in anhydrous THF (50 mL) was added N,N,N',N'-tetramethylethylenediamine (0.68 mL, 4.53 mmol) and the resulting mixture was cooled to −78° C. n-Butyl lithium (2.5 M in hexanes, 1.9 mL, 4.75 mmol) was added dropwise and the resulting suspension allowed to warm to −30° C. over 1 h. The reaction mixture was cooled to −78° C. and treated with DMF (0.7 mL, 9.04 mmol), then stirred at RT for 30 min. The reaction mixture was cooled to 0° C. before an aqueous solution of HCl (0.5 M) was added and the mixture stirred for another 30 min. The precipitate that formed was collected by filtration, washed twice with water then dried in vacuo at 70° C. for 3 h. The title compound was obtained as a pale yellow solid (1.0 g 90%).

NMR δ$_H$ (300 MHz, DMSO-d$_6$) 3.77 (m, 4H), 3.95 (m, 4H), 8.29 (s, 1H) and 10.21 (s, 1H)

Reference Example 32

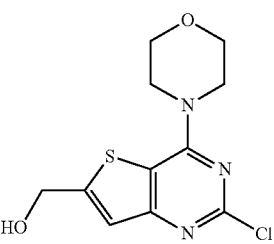

(2-Chloro-4-morpholin-4-yl-thieno[3,2-d]pyrimidin-6-yl)-methanol

To a suspension of 2-chloro-4-morpholin-4-yl-thieno[3,2-d]pyrimidine-6-carbaldehyde (3.2 g, 11.31 mmol) in anhydrous THF (100 mL) and IMS (70 mL) was added sodium borohydride (0.47 g, 12.42 mmol) and the resulting mixture stirred at RT for 2 h. The reaction mixture was partitioned between DCM and a saturated aqueous solution of NaHCO$_3$. The organic layer was isolated, dried (MgSO$_4$) and concentrated in vacuo. The resultant residue was triturated with water to give the title compound as a white solid (2.9 g, 91%).

NMR δ$_H$ (300 MHz, DMSO-d$_6$) 3.75 (m, 4H), 3.89 (m, 4H), 4.81 (d, J=5.0 Hz, 2H), 5.96 (t, J=5.0 Hz, 1H) and 7.22 (s, 1H).

Reference Example 33

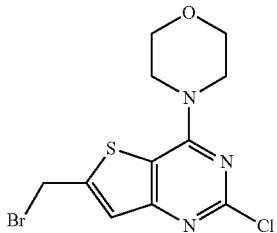

6-Bromomethyl-2-chloro-4-morpholin-4-yl-thieno[3,2-d]pyrimidine

To a solution of (2-chloro-4-morpholin-4-yl-thieno[3,2-d]pyrimidin-6-yl)-methanol (1.46 g, 5.11 mmol) in anhydrous DCM (30 mL) at 0° C. were added triphenylphosphine (1.74 g, 6.64 mmol) and carbon tetrabromide (2.03 g, 6.13 mmol). The resulting brown solution was stirred at RT for 5 h, before additional quantities of triphenylphosphine and carbon tetrabromide were added (0.4 g and 0.34 g, respectively) and stirring continued at RT for 1 h. The reaction mixture was concentrated in vacuo and DCM and EtOAc were added. The resultant white precipitate was collected by filtration and air dried to give the title compound as a white solid (0.82 g, 46%).

[M+H]$^+$ 348.1 ($^{79}$Br) 350.1 ($^{81}$Br)

Reference Example 34

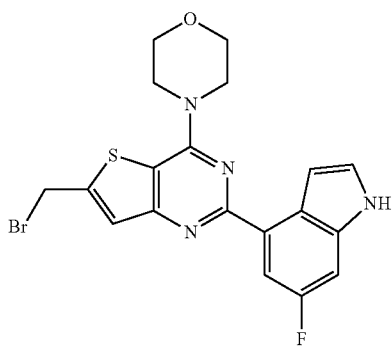

[2-(6-Fluoro-1H-indol-4-yl)-4-morpholin-4-yl-thieno[3,2-d]pyrimidin-6-yl]-methanol Prepared by using general Suzuki coupling method A of Reference Example 2. The title compound was obtained as a white solid (1.2 g, 40%).

NMR δ$_H$ (300 MHz, DMSO-d$_6$) 3.83 (m, 4H), 4.00 (m, 4H), 4.85 (d, J=5.8 Hz, 2H), 5.92 (t, J=5.8 Hz, 1H), 7.31 (dd, J=2.7, 9.5 Hz, 1H), 7.39 (s, 1H), 7.41-7.47 (m, 2H), 7.90 (dd, J=2.7, 11.5 Hz, 1H) and 11.30 (bs, 1H).

Reference Example 35

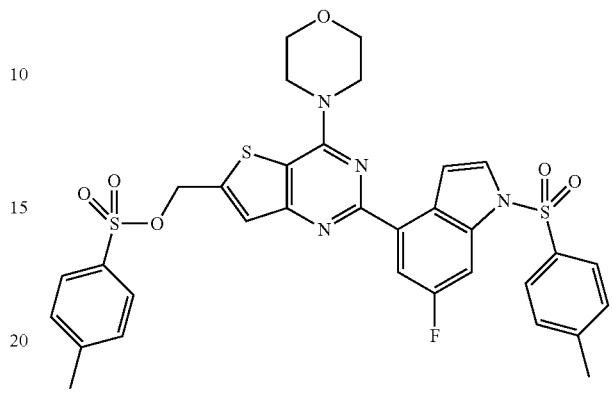

Toluene-4-sulfonic acid 2-[6-fluoro-1-(toluene-4-sulfonyl)-1H-indol-4-yl]-4-morpholin-4-yl-thieno[3,2-d]pyrimidin-6-ylmethyl ester To a suspension of [2-(6-fluoro-1H-indol-4-yl)-4-morpholin-4-yl-thieno[3,2-d]pyrimidin-6-yl]-methanol (0.54 g, 1.41 mmol) in anhydrous THF (20 mL) and DMF (5 mL) was added sodium hydride (60% suspension in mineral oil, 0.34 g, 8.5 mmol). The resulting mixture was stirred at RT for 10 min, then p-toluenesulfonyl chloride (1.08 g, 5.66 mmol) was added and the reaction mixture was heated at 40° C. for 3 h. The resulting solution was partitioned between EtOAc and a saturated aqueous solution of ammonium chloride. The organic layer was isolated, dried (MgSO$_4$) and concentrated in vacuo. The resultant residue was purified by column chromatography to give the title compound as a white solid (0.60 g, 62%).

NMR δ$_H$ (300 MHz, CDCl$_3$) 2.35 (s, 3H), 2.44 (s, 3H), 3.89 (m, 4H), 4.01 (m, 4H), 5.33 (s, 2H), 7.23 (d, J=8.7 Hz, 2H), 7.34 (m, 3H), 7.63 (d, J=3.7 Hz, 1H), 7.68 (d, J=3.7 Hz, 1 H), 7.77 (d, J=8.3 Hz, 2H), 7.81-7.86 (m, 3H) and 7.98 (dd, J=10.6, 2.5 Hz, 1H).

Reference Example 36

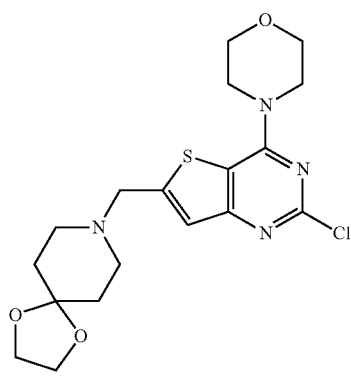

8-(2-Chloro-4-morpholin-4-yl-thieno[3,2-d]pyrimidin-6-ylmethyl)-1,4-dioxa-8-aza-spiro[4.5]decane To a solution of 6-bromomethyl-2-chloro-4-morpholin-4-yl-thieno[3,2-d]pyrimidine (1.00 g, 2.87 mmol) in DMF (20 mL) were added 1,4-dioxa-8-aza-spiro[4.5]decane (1.06 mL, 8.62 mmol) and cesium carbonate (1.8 g, 5.75 mmol). The resulting mixture was stirred at RT for 90 min. The reaction mixture was diluted with water then extracted with EtOAc. The organic extracts were dried (Na$_2$SO$_4$) and concentrated in vacuo to give the title compound as an orange solid (0.97 g, 82%).
[M+H]$^+$ 411.2

Reference Example 37

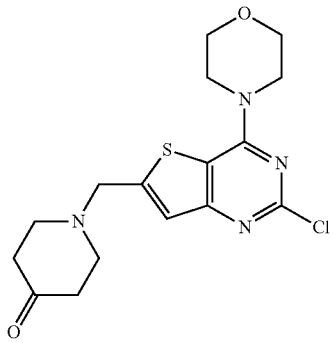

1-(2-Chloro-4-morpholin-4-yl-thieno[3,2-d]pyrimidin-6-ylmethyl)-piperidin-4-one

To a solution of 8-(2-chloro-4-morpholin-4-yl-thieno[3,2-d]pyrimidin-6-ylmethyl)-1,4-dioxa-8-aza-spiro[4.5]decane (0.97 g, 2.36 mmol) in 1,4-dioxane (16 mL) was slowly added concentrated HCl (24 mL) and the resulting solution was stirred at RT for 2 h. The reaction mixture was cooled to 0° C. and the pH was adjusted to 12 by careful addition of an aqueous solution of NaOH (50% w/v). EtOAc was added, the layers were separated and the aqueous layer was extracted further with EtOAc. The combined organic layers were dried (Na$_2$SO$_4$), then concentrated in vacuo to give the title compound as a yellow solid (0.9 g, 100%).
[M+H]$^+$ 367.3

Reference Example 38

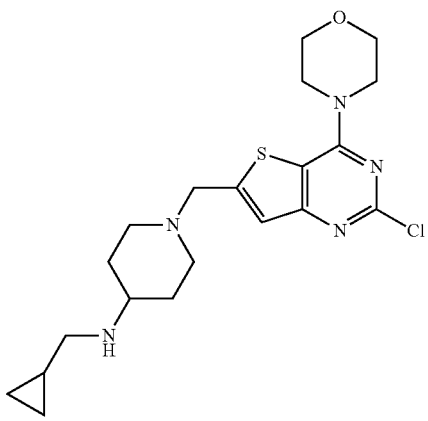

[1-(2-Chloro-4-morpholin-4-yl-thieno[3,2-d]pyrimidin-6-ylmethyl)-piperidin-4-yl]-cyclopropylmethyl-amine To a solution of 1-(2-chloro-4-morpholin-4-yl-thieno[3,2-d]pyrimidin-6-ylmethyl)-piperidin-4-one (0.2 g, 0.545 mmol) in 1,2-dichloroethane (3 mL) were added cyclopropanemethylamine (71 μL, 0.812 mmol) and sodium triacetoxyborohydride (0.15 g, 0.71 mmol). The resulting suspension was stirred at RT for 17 h, then diluted with water and DCM. The aqueous layer was separated and extracted with DCM. The combined organic layers were dried (Na$_2$SO$_4$), then concentrated in vacuo to give the title compound as an off-white solid (0.10 g, 44%).
[M]$^+$ 422.3

Reference Example 39

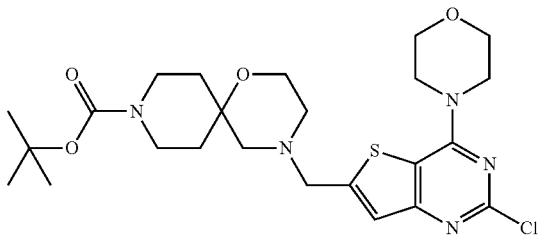

4-(2-Chloro-4-morpholin-4-yl-thieno[3,2-d]pyrimidin-6-ylmethyl)-1-oxa-4,9-diaza-spiro[5.5]undecane-9-carboxylic acid tert-butyl ester To a suspension of 2-chloro-4-morpholin-4-yl-thieno[3,2-d]pyrimidine-6-carbaldehyde (100 mg, 0.352 mmol) in dichloroethane (10 mL) were added 1-oxa-4,9-diaza-spiro[5.5]undecane-9-carboxylic acid tert-butyl ester (110 mg, 0.376 mmol) and sodium triacetoxyborohydride (113 mg, 0.533 mmol) and the resulting solution stirred at RT for 3 h. The reaction was quenched with water and loaded onto an Isolute® SCX-2 cartridge, washed with MeOH then eluted with 2 M NH$_3$ in MeOH. The resulting residue was then purified by column chromatography to give the title compound as a white solid (98 mg, 53%) [M+H]$^+$ 524.3

Reference Example 40

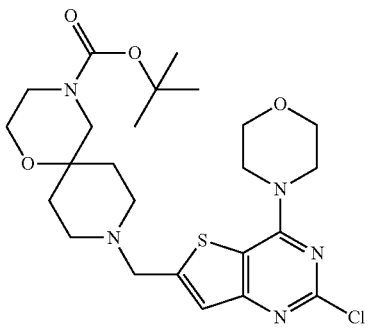

9-(2-Chloro-4-morpholin-4-yl-thieno[3,2-d]pyrimidin-6-ylmethyl)-1-oxa-4,9-diaza-spiro[5.5]undecane-4-carboxylic acid tert-butyl ester Prepared according to the method used in the preparation of 4-(2-chloro-4-morpholin-4-yl-thieno[3,2-d]pyrimidin-6-ylmethyl)-1-oxa-4,9-diaza-spiro[5.5]undecane-9-carboxylic acid tert-butyl ester using 1-oxa-4,9-diaza-spiro[5.5]undecane-4-carboxylic acid tert-butyl ester in place of 4-ethoxy-4-methylaminomethyl-piperidine-1-carboxylic acid tert-butyl ester. The title compound was obtained as a white solid (110 mg, 60%).

[M+H]$^+$ 524.3

Reference Example 41

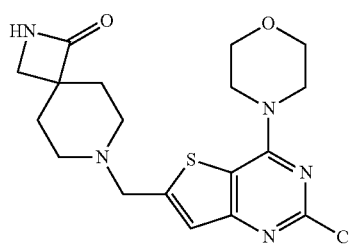

7-(2-Chloro-4-morpholin-4-yl-thieno[3,2-d]pyrimidin-6-ylmethyl)-2,7-diaza-spiro[3.5]nonan-1-one To a solution of 1-oxo-2,7-diaza-spiro[3.5]nonane-7-carboxylic acid tert-butyl ester (150 mg, 0.624 mmol) in DCM (6 mL) was added TFA (3 mL) and the resulting solution stirred at RT for 1 h. The crude reaction mixture was loaded onto a Isolute® SCX-2 cartridge, washed with MeOH then eluted with 2 M NH$_3$ in MeOH to provide 2,7-diaza-spiro[3.5]nonan-1-one as a colourless oil. To a suspension of 2,7-diaza-spiro[3.5]nonan-1-one (0.624 mmol) in dichloroethane (13 mL) were added 2-chloro-4-morpholin-4-yl-thieno[3,2-d]pyrimidine-6-carbaldehyde (130 mg, 0.458 mmol) and sodium triacetoxyborohydride (146 mg, 0.689 mmol) and the resulting suspension stirred at RT for 18 h. The reaction was quenched with water and loaded onto an Isolute® SCX-2 cartridge, washed with MeOH then eluted with 2 M NH$_3$ in MeOH. The resulting residue was then purified by column chromatography to give the title compound as a white solid (93 mg, 50%)

[M+H]$^+$ 408.2

Reference Example 42

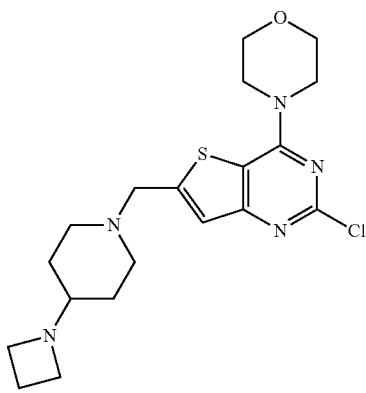

6-(4-Azetidin-1-yl-piperidin-1-ylmethyl)-2-chloro-4-morpholin-4-yl-thieno[3,2-d]pyrimidine Method A:

Prepared according to the method used in the preparation of [1-(2-chloro-4-morpholin-4-yl-thieno[3,2-d]pyrimidin-6-ylmethyl)-piperidin-4-yl]-cyclopropylmethyl-amine using azetidine hydrochloride in place of cyclopropanemethylamine. The title compound was obtained as an orange solid (102 mg, 57%).

[M+H]$^+$ 408.2

Method B:

Prepared according to the method used in the preparation of 4-(2-chloro-4-morpholin-4-yl-thieno[3,2-d]pyrimidin-6-ylmethyl)-1-oxa-4,9-diaza-spiro[5.5]undecane-9-carboxylic acid tert-butyl ester using 4-azetidin-1-yl-piperidine in place of 4-ethoxy-4-methylaminomethyl-piperidine-1-carboxylic acid tert-butyl ester. The title compound was obtained as an off-white solid (219 mg, 48%).

[M+H]$^+$ 408.2

Reference Example 43

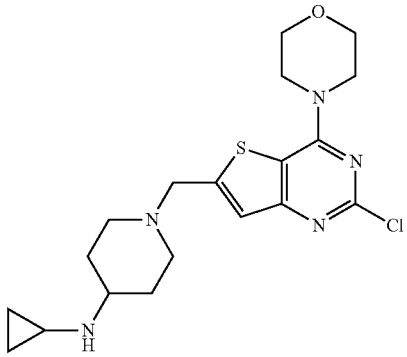

[1-(2-Chloro-4-morpholin-4-yl-thieno[3,2-d]pyrimidin-6-ylmethyl)-piperidin-4-yl]-cyclopropyl-amine Prepared according to the method used in the preparation of [1-(2-chloro-4-morpholin-4-yl-thieno[3,2-d]pyrimidin-6-ylmethyl)-piperidin-4-yl]-cyclopropylmethyl-amine using cyclopropylamine in place of cyclopropanemethylamine. The title compound was obtained as a pale yellow solid (38 mg, 17%).

[M+H]$^+$ 408.2

Reference Example 44

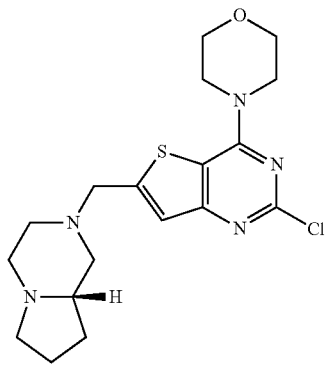

2-Chloro-6-[(S)-1-(hexahydro-pyrrolo[1,2-a]pyrazin-2-yl)methyl]-4-morpholin-4-yl-thieno[3,2-d]pyrimidine To a solution of 6-bromomethyl-2-chloro-4-morpholin-4-yl-thieno[3,2-d]pyrimidine (150 mg, 0.43 mmol) in DMF (4 mL) were added (S)-octahydro-pyrrolo[1,2-a]pyrazine (81 mg, 0.642 mmol) and potassium carbonate (117 mg, 0.847 mmol). The resulting mixture was stirred at RT for 17 h, then concentrated in vacuo. The resulting residue was triturated with water to give the title compound as an off-white solid (130 mg, 77%).
[M+H]$^+$ 394.3

Reference Example 45

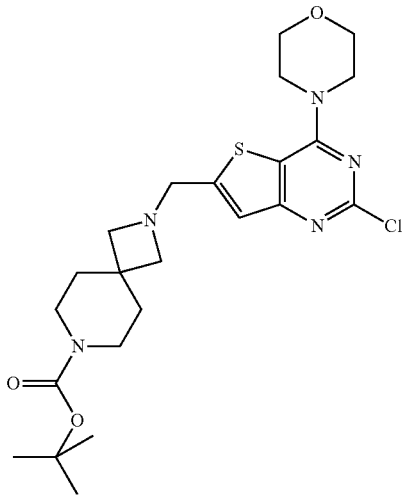

2-(2-Chloro-4-morpholin-4-yl-thieno[3,2-d]pyrimidin-6-ylmethyl)-2,7-diaza-spiro[3.5]nonane-7-carboxylic acid tert-butyl ester Prepared according to the method used in the preparation of 2-chloro-6-[(S)-1-(hexahydro-pyrrolo[1,2-d]pyrazin-2-yl)methyl]-4-morpholin-4-yl-thieno[3,2-d]pyrimidine using 2,7-diaza-spiro[3.5]nonane-7-carboxylic acid tert-butyl ester hydrochloride in place of (S)-octahydro-pyrrolo[1,2-a]pyrazine. The title compound was obtained as a tan solid (209 mg, 84%).
[M+H]$^+$ 494.3

Reference Example 46

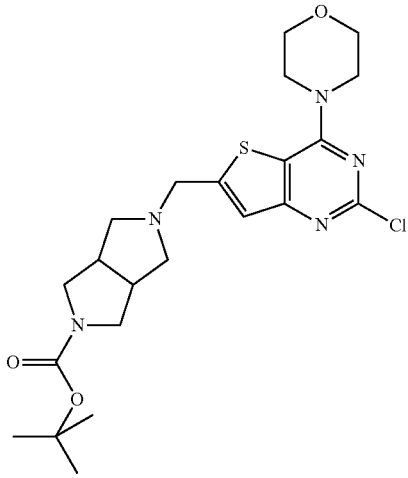

5-(2-Chloro-4-morpholin-4-yl-thieno[3,2-d]pyrimidin-6-ylmethyl)-hexahydro-pyrrolo[3,4-c]pyrrole-2-carboxylic acid tert-butyl ester To a solution of 6-bromomethyl-2-chloro-4-morpholin-4-yl-thieno[3,2-d]pyrimidine (175 mg, 0.50 mmol) in DMF (5 mL) were added hexahydro-pyrrolo[3,4-c]pyrrole-2-carboxylic acid tert-butyl ester (160 mg, 0.754 mmol) and potassium carbonate (136 mg, 0.984 mmol). The resulting mixture was stirred at RT for 2 h, then diluted with water and EtOAc. The organic layer was isolated, then washed with brine, dried (MgSO$_4$) and concentrated in vacuo. The resulting residue was purified by column chromatography to give the title compound as an off-white solid (218 mg, 90%).
[M H]$^+$ 480.3

Reference Example 47

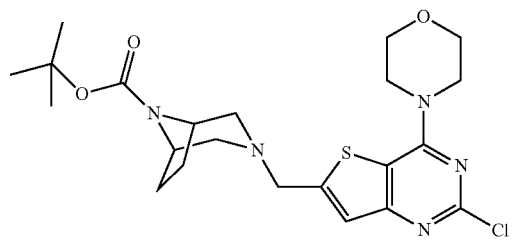

3-(2-Chloro-4-morpholin-4-yl-thieno[3,2-d]pyrimidin-6-ylmethyl)-3,8-diaza-bicyclo[3.2.1]octane-8-carboxylic acid tert-butyl ester Method A:
Prepared according to the method used in the preparation of 5-(2-chloro-4-morpholin-4-yl-thieno[3,2-d]pyrimidin-6- ylmethyl)-hexahydro-pyrrolo[3,4-c]pyrrole-2-carboxylic acid tert-butyl ester using 3,8-diaza-bicyclo[3.2.1]octane-8-carboxylic acid tert-butyl ester in place of hexahydro-pyrrolo[3,4-c]pyrrole-2-carboxylic acid tert-butyl ester. The title compound was obtained as a tan solid (103 mg, 74%).

[M+H]+ 480.3

Method B:

Prepared according to the method used in the preparation of 4-(2-chloro-4-morpholin-4-yl-thieno[3,2-d]pyrimidin-6-ylmethyl)-1-oxa-4,9-diaza-spiro[5.5]undecane-9-carboxylic acid tert-butyl ester using 3,8-diaza-bicyclo[3.2.1]octane-8-carboxylic acid tert-butyl ester in place of 4-ethoxy-4-methylaminomethyl-piperidine-1-carboxylic acid tert-butyl ester. The title compound was obtained as a cream solid (245 mg, 58%).

[M+H]+ 480.3

Reference Example 48

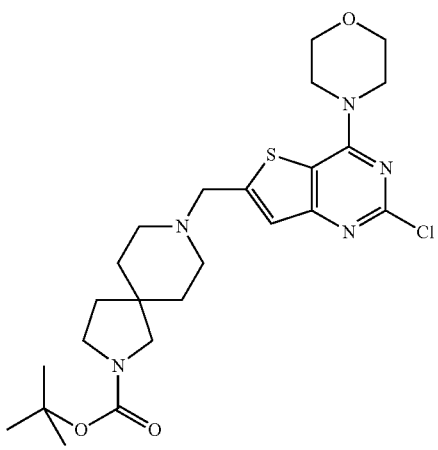

8-(2-Chloro-4-morpholin-4-yl-thieno[3,2-d]pyrimidin-6-ylmethyl)-2,8-diaza-spiro[4.5]decane-2-carboxylic acid tert-butyl ester Prepared according to the method used in the preparation of 5-(2-chloro-4-morpholin-4-yl-thieno[3,2-d]pyrimidin-6-ylmethyl)-hexahydro-pyrrolo[3,4-c]pyrrole-2-carboxylic acid tert-butyl ester using 2,8-diaza-spiro[4.5]decane-2-carboxylic acid tert-butyl ester hydrochloride in place of hexahydro-pyrrolo[3,4-c]pyrrole-2-carboxylic acid tert-butyl ester. The title compound was obtained as a tan solid (104 mg, 71%).

[M+H]+ 508.3

Reference Example 49

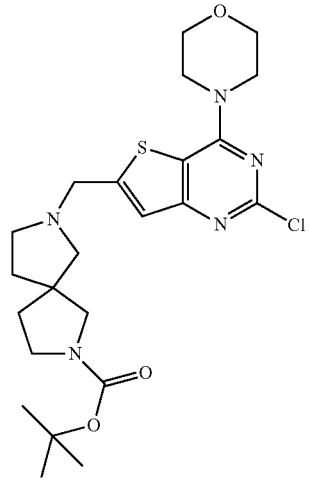

7-(2-Chloro-4-morpholin-4-yl-thieno[3,2-d]pyrimidin-6-ylmethyl)-2,7-diaza-spiro[4.4]nonane-2-carboxylic acid tert-butyl ester Prepared according to the method used in the preparation of 5-(2-chloro-4-morpholin-4-yl-thieno[3,2-d]pyrimidin-6-ylmethyl)-hexahydro-pyrrolo[3,4-c]pyrrole-2-carboxylic acid tert-butyl ester using 2,7-diaza-spiro[4.4]nonane-2-carboxylic acid tert-butyl ester hydrochloride in place of hexahydro-pyrrolo[3,4-c]pyrrole-2-carboxylic acid tert-butyl ester. The title compound was obtained as a pale yellow oil (96 mg, 67%).

[M+H]+ 494.3

Reference Example 50

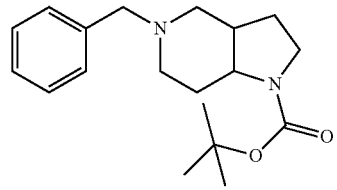

5-Benzyl-octahydro-pyrrolo[3,2-c]pyridine-1-carboxylic acid tert-butyl ester

To a solution of 2,3-dihydro-pyrrolo[3,2-c]pyridine-1-carboxylic acid tert-butyl ester (1.0 g, 4.2 mmol) in acetonitrile (20 mL) was added benzyl bromide and the mixture heated at reflux for 2.5 h. The reaction mixture was concentrated in vacuo and the resultant black oil was dissolved in MeOH (50 mL). To this solution was slowly added sodium borohydride (1.2 g, 32.0 mmol) over 10 min, then the mixture was heated at reflux for 2.5 h. After cooling to RT, the reaction mixture was concentrated in vacuo before EtOAc and an aqueous saturated solution of ammonium chloride were added. The reaction mixture was stirred at RT for 1 h. The organic layer was isolated, dried (Na₂SO₄) and concentrated in vacuo to give the title compound as a cream solid (0.78 g, 59%).

[M+H]⁺ 317.2

Reference Example 51

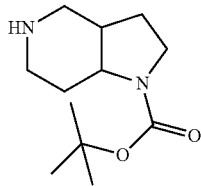

Octahydro-pyrrolo[3,2-c]pyridine-1-carboxylic acid tert-butyl ester

To a solution of (5-benzyl-octahydro-pyrrolo[3,2-c]pyridine-1-carboxylic acid tert-butyl ester (777 mg, 2.46 mmol) in IMS (20 mL) was added palladium hydroxide on carbon (5%, 50 mg) and the mixture stirred under a hydrogen atmosphere at RT for 10 h. The reaction mixture was filtered through Celite and the filtrate concentrated in vacuo to give the title compound as a straw coloured oil (550 mg, 99%).

[M+H]⁺ 227.3

Reference Example 52

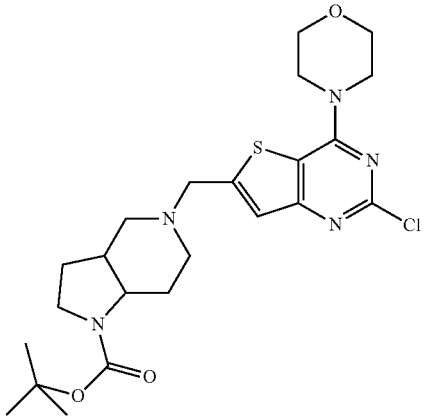

5-(2-Chloro-4-morpholin-4-yl-thieno[3,2-d]pyrimidin-6-ylmethyl)-octahydro-pyrrolo[3,2-c]pyridine-1-carboxylic acid tert-butyl ester Prepared according to the method used in the preparation of 8-(2-chloro-4-morpholin-4-yl-thieno[3,2-d]pyrimidin-6-ylmethyl)-1,4-dioxa-8-aza-spiro[4.5]decane using octahydro-pyrrolo[3,2-c]pyridine-1-carboxylic acid tert-butyl ester in place of 1,4-dioxa-8-aza-spiro[4.5]decane. The title compound was obtained as white solid (153 mg, 90%).

[M+H]⁺ 494.1

Reference Example 53

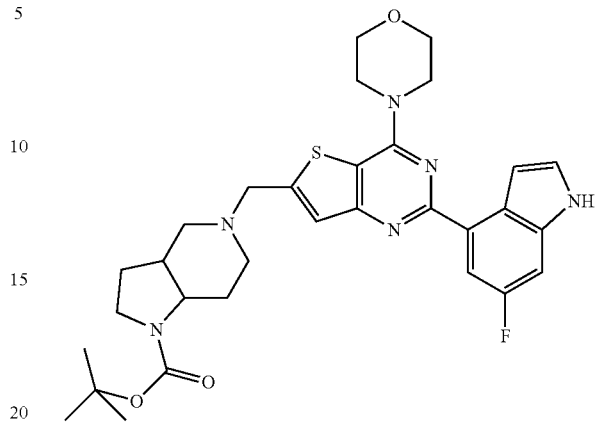

5-[2-(6-Fluoro-1H-indol-4-yl)-4-morpholin-4-yl-thieno[3,2-c]pyrimidin-6-ylmethyl]-octahydro-pyrrolo[3,2-c]pyridine-1-carboxylic acid tert-butyl ester Prepared by using general Suzuki coupling method A of Reference Example 2 above. The title compound was obtained as a yellow oil (105 mg, 51%).

NMR $\delta_H$ (400 MHz, CDCl₃) 1.46 (s, 9H), 1.71-1.85 (m, 2H), 1.96-2.19 (m, 3H), 2.21-2.31 (m, 2H), 2.40-2.50 (m, 1H), 2.71-2.92 (m, 2H), 3.32-3.41 (m, 1H), 3.45-3.58 (m, 1H), 3.80 (d, J=9.80 Hz, 2H), 3.92 (t, J=4.7 Hz, 4H), 4.08 (t, J=4.7 Hz, 4H), 7.13-7.18 (m, 1H), 7.29 (m, 1H), 7.34 (s, 1H), 7.52 (m, 1H), 7.96 (dd, J=11.2, 2.3 Hz, 1H) and 8.32 (bs, 1H).

Reference Example 54

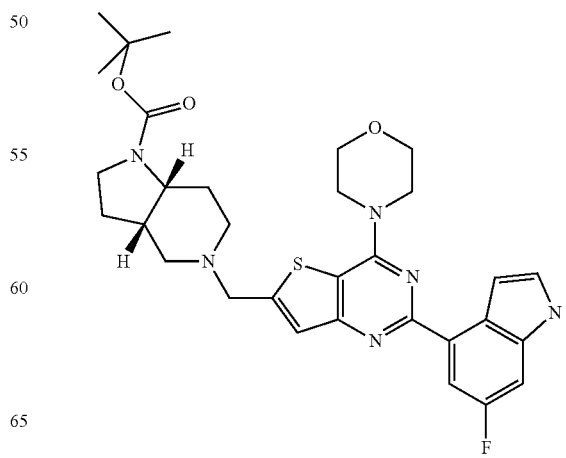

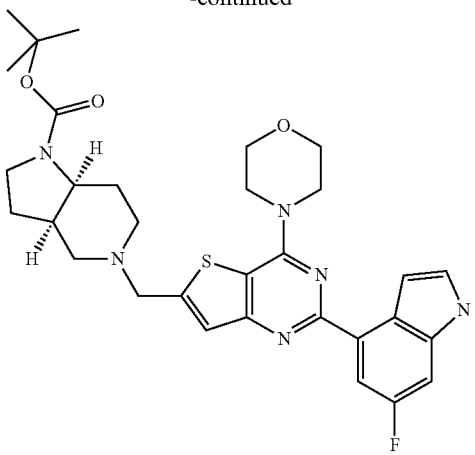

(3aS,7aR)-5-[2-(6-Fluoro-1H-indol-4-yl)-4-morpholin-4-yl-thieno[3,2-d]pyrimidin-6-ylmethyl]-octahydro-pyrrolo[3,2-c]pyridine-1-carboxylic acid tert-butyl ester And (3aR,7aS)-5-[2-(6-Fluoro-1H-indol-4-3H)-4-morpholin-4-yl-thieno[3,2-d]pyrimidin-6-ylmethyl]-octahydro-pyrrolo[3,2-c]pyridine-1-carboxylic acid tert-butyl ester After Suzuki coupling, the two enantiomers were separated by chiral HPLC using a Chiralpak® IA column (250×20 mm i.d column with 5 μm particle size, UV detection at 254 nm, flow 9 mL/min), eluting with 100% EtOH containing 0.1% diethylamine. 100 mg dissolved in 4 mL of eluting solvent (injection volume 1500 μL, sensitivity 0.04) gave the title compounds as two distinct enantiomers. Both enantiomers have analytical data identical to those obtained for the racemic mixture Reference Example 55

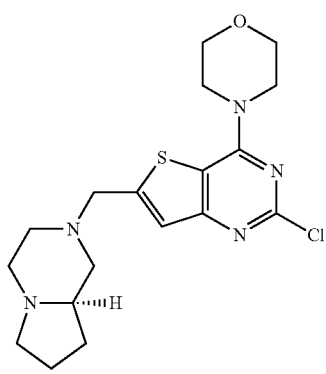

2-Chloro-6-[(R)-1-(hexahydro-pyrrolo[1,2-a]pyrazin-2-yl)methyl]-4-morpholin-4-yl-thieno[3,2-d]pyrimidine Prepared according to the method used in the preparation of 5-(2-chloro-4-morpholin-4-yl-thieno[3,2-d]pyrimidin-6-ylmethyl)-hexahydro-pyrrolo[3,4-c]pyrrole-2-carboxylic acid tert-butyl ester using (R)-octahydro-pyrrolo[1,2-a]pyrazine in place of hexahydro-pyrrolo[3,4-c]pyrrole-2-carboxylic acid tert-butyl ester. The title compound was obtained as white solid (90 mg, 61%).
[M+H]$^+$ 394.0

Reference Example 56

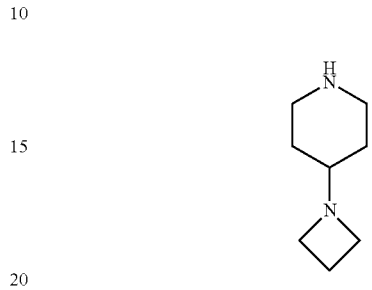

4-Azetidin-1-yl-piperidine

To a solution of 4-oxo-piperidine-1-carboxylic acid tert-butyl ester (1.75 g, 8.88 mmol) in dichloroethane (80 mL) was added azetidine (0.6 g, 10.53 mmol) and the mixture was stirred at RT for 30 min. Sodium triacetoxyborohydride (3.9 g, 18.44 mmol) was added and the resulting solution was stirred at RT for 18 h. The reaction mixture was partitioned between water and DCM and the layers separated. The organic layer was extracted further with DCM and the combined aqueous layers were concentrated in vacuo. The resultant white semi-solid was suspended in DCM and a saturated aqueous solution of NaHCO$_3$ was added. The layers were thoroughly mixed, the organic layer isolated and the aqueous layer further extracted with DCM. The combined organic layers were washed with brine, dried (Na$_2$SO$_4$) and concentrated in vacuo to give 4-azetidin-1-yl-piperidine-1-carboxylic acid tert-butyl ester as a white solid (2.0 g, 95%). BOC-deprotection of 4-azetidin-1-yl-piperidine-1-carboxylic acid tert-butyl ester (400 mg, 1.67 mmol) using TFA:DCM (1:4) gave the title compound as a yellow oil (185 mg, 79%)
NMR δ$_H$ (400 MHz, CDCl$_3$) 1.04-1.16 (m, 2H), 1.68 (d, J=12.8 Hz, 2H), 1.98-2.08 (m, 3 H), 2.55 (td, J=12.1, 2.6 Hz, 2H), 3.06 (dt, J=12.8, 3.6 Hz, 2H) and 3.15 (t, J=6.9 Hz, 4 H).

Reference Example 57

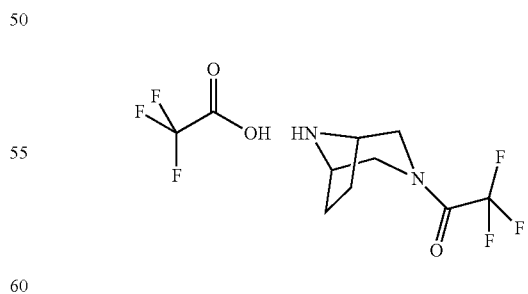

1-(3,8-Diaza-bicyclo[3.2.1]oct-3-yl)-2,2,2-trifluoroethanone trifluoroacetic acid salt To a solution of 3,8-diaza-bicyclo[3.2.1]octane-8-carboxylic acid tert-butyl ester (212 mg, 1.0 mmol) in DCM (4 mL) were added triethylamine (208 μL, 1.5 mmol) and trifluoroacetic anhydride (169 μL, 1.2 mmol) at 0° C. and the mixture stirred at 0° C. for 2 h. The reaction mixture was concentrated in vacuo and the resultant residue was purified by column chromatography to give 3-(2,2,2-trifluoro-acetyl)-3,8-diaza-bicyclo[3.2.1]octane-8-carboxylic acid tert-butyl ester as a colourless oil. To a solution of 3-(2,2,2-trifluoro-acetyl)-3,8-diaza-bicyclo[3.2.1]octane-8-carboxylic acid tert-butyl ester in DCM (4 mL) was added TFA (1 mL) and the solution stirred at RT for 1 h. The reaction mixture was concentrated in vacuo to give the title compound as a colourless oil (212 mg, 66%).

NMR $\delta_H$ (400 MHz, CDCl$_3$) 1.92-2.04 (m, 2H), 2.27 (m, 2H), 3.40 (d, J=14.6 Hz, 1H), 3.83 (d, J=14.6 Hz, 1H), 3.93 (d, J=14.6 Hz, 1H), 4.22 (m, 2H), 4.47 (d, J=14.6 Hz, 1 H); 8.68 (bs, 1H) and 8.90 (bs, 1H).

Reference Example 58

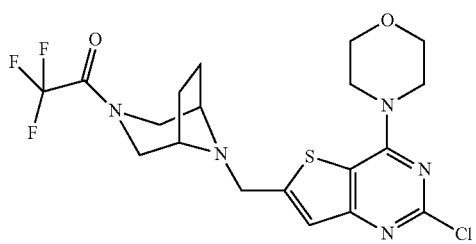

1-[8-(2-Chloro-4-morpholin-4-yl-thieno[3,2-d]pyrimidin-6-ylmethyl)-3,8-diaza-bicyclo[3.2.1]oct-3-yl]-2,2,2-trifluoro-ethanone To a solution of 1-(3,8-diaza-bicyclo[3.2.1]oct-3-yl)-2,2,2-trifluoro-ethanone trifluoroacetic acid salt (106 mg, 0.33 mmol) in THF (5 mL) were added triethylamine (161 μL, 1.16 mmol) and 6-bromomethyl-2-chloro-4-morpholin-4-yl-thieno[3,2-d]pyrimidine (100 mg, 0.29 mmol). The reaction mixture was stirred at RT for 17 h, then concentrated in vacuo. The resultant residue was purified by column chromatography to give the title compound as a white solid (98 mg, 71%).

NMR $\delta_H$ (400 MHz, CDCl$_3$) 1.67-1.73 (m, 2H), 1.98-2.06 (m, 2H), 3.11 (d, J=12.6 Hz, 1H), 3.28 (bs, 1H), 3.34 (bs, 1H), 3.48 (d, J=12.6 Hz, 1H), 3.65 (d, J=12.6 Hz, 1H), 3.79 (s, 2H), 3.80-3.85 (m, 4H), 3.95-4.00 (m, 4H), 4.16 (d, J=12.8 Hz, 1H) and 7.13 (s, 1H).

Reference Example 59

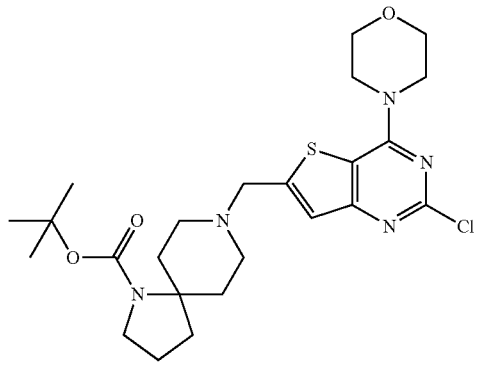

8-(2-Chloro-4-morpholin-4-yl-thieno[3,2-d]pyrimidin-6-ylmethyl)-1,8-diaza-spiro[4.5]decane-1-carboxylic acid tert-butyl ester Prepared according to the method used in the preparation of [1-(2-chloro-4-morpholin-4-yl-thieno[3,2-d]pyrimidin-6-ylmethyl)-piperidin-4-yl]-cyclopropylmethyl-amine using 1,8-diaza-spiro[4.5]decane-1-carboxylic acid tert-butyl ester in place of cyclopropanemethylamine. The title compound was obtained as a white solid (184 mg, 45%).

NMR $\delta_H$ (400 MHz, CDCl$_3$) 1.22-1.31 (m, 2H), 1.51 (m, 9H), 1.72 (m, 2H), 1.88 (m, 2H), 2.18 (m, 2H), 2.68 (m, 1H), 2.90 (m, 3H), 3.42 (m, 2H), 3.77 (s, 2H), 3.84 (s, 4H), 3.98 (m, 4H) and 7.11 (s, 1H).

Reference Example 60

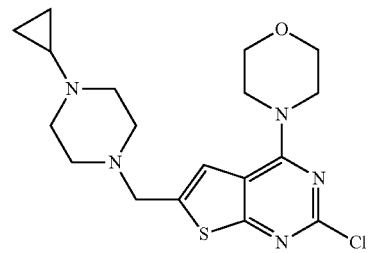

2-Chloro-6-(4-cyclopropyl-piperazin-1-ylmethyl)-4-morpholin-4-yl-thieno[2,3-d]pyrimidine A mixture of 2-chloro-4-morpholin-4-yl-thieno[2,3-d]pyrimidine-6-carbaldehyde (254 mg), 1-cyclopropyl-piperazine di-HCl (264 mg), sodium triacetoxyborohydride (619 mg) and trimethylorthoformate (968 μL), was stirred in anhydrous 1,2-dichloroethane (25 mL) for 12 hours at room temperature, then diluted with dichloromethane (50 mL), and washed with 50% sodium bicarbonate solution. The organic phase was dried (MgSO$_4$) and the solvents removed in vacuo to give a residue which was purified using flash silica chromatography to yield the title compound (217 mg) as a buff solid.

$\delta_H$ (400 MHz, CDCl$_3$) 0.37 (m, 4H); 1.51 (m, 1H); 2.59 (m, 8H); 3.63 (s, 2H); 3.77 (m, 4H);
3.85 (m, 4H); 7.02 (s, 1H).

Reference Example 61

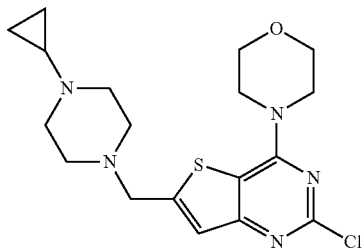

2-Chloro-6-(4-cyclopropyl-piperazin-1-ylmethyl)-4-morpholin-4-yl-thieno[3,2-d]pyrimidine A mixture of 2-chloro-4-morpholin-4-yl-thieno[3,2-d]pyrimidine-6-carbaldehyde (254 mg) and 1-cyclopropylpiperazine di-HCl (352 mg) was reacted under the reductive amination conditions described for 2-chloro-6-(4-cyclopropyl-piperazin-1-ylmethyl)-4-morpholin-4-yl-thieno[2,3-d]pyrimidine, to give the title compound (279 mg) as a white solid.

$\delta_H$ (400 MHz, CDCl$_3$) 0.40 (m, 4H); 1.65 (m, 4H); 2.63 (m, 8H); 3.81 (s, 2H); 3.86 (m, 4H); 4.01 (m, 4H); 7.18 (s, 1H).

Reference Example 62

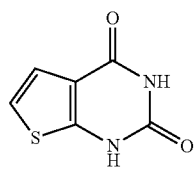

1H-Thieno[2,3-d]pyrimidine-2,4-dione

To a stirring solution of methyl-2-aminothiophene-3-carboxylate (10.0 g, 63.7 mmol) in anhydrous dichloromethane (270 mL) cooled down to −78° C. was added dropwise chlorosulfonyl isocyanate (7.6 mL, 87.2 mmol) over 25 minutes. The temperature was warmed to room temperature and stirred for 40 minutes. The reaction mixture was evaporated down. The resulting crude solid was treated with 6M hydrochloric acid (250 mL) and heated at 100° C. for 35 minutes. The cooled reaction mixture was neutralised to pH 3 with solid sodium carbonate. The precipitate was filtered, washed with water and dried to give 3-ureido-thiophene-2-carboxylic acid methyl ester (13.5 g).

To a stirring suspension of 3-ureido-thiophene-2-carboxylic acid methyl ester (13.5 g, 67.5 mmol) in 2-propanol (100 mL) was added sodium hydroxide (5.5 g, 137.5 mmol) in water (40 mL). The mixture was stirred at 80° C. for 3.5 hours. The cooled reaction mixture was poured onto 2M sodium hydroxide solution (100 mL) and acidified to pH 3 with careful addition of concentrated hydrochloric acid. The precipitate was filtered under vacuum, washed with water and dried to give 1H-thieno[2,3-d]pyrimidine-2,4-dione (8.83 g).

Reference Example 63

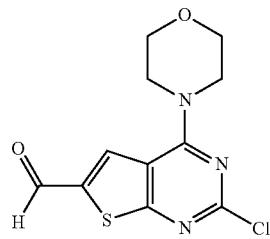

2-Chloro-4-morpholin-4-yl-thieno[2,3-d]pyrimidine-6-carbaldehyde

Prepared from 1H-thieno[2,3-d]pyrimidine-2,4-dione using the same procedures as described for 1H-thieno[3,2-d]pyrimidine-2,4-dione.

Reference Example 64

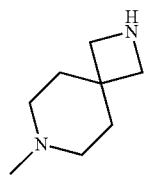

7-Methyl-2,7-diaza-spiro[3.5]nonane

To a solution of 2,7-diaza-spiro[3.5]nonane-2-carboxylic acid tert-butyl ester hydrochloride (100 mg, 0.381 mmol) in DCE (10 mL) was added an aqueous solution of formaldehyde (37% w/w, 40 µL, 0.537 mmol). The mixture was stirred at RT for 10 min, then sodium triacetoxyborohydride (121 mg, 0.571 mmol) was added and stirring was continued for 1 h. Water was added to the reaction mixture before being loaded onto an Isolute® SCX-2 cartridge. The cartridge was washed with MeOH then eluted with 2 M NH$_3$ in MeOH to give 7-methyl-2,7-diaza-spiro[3.5]nonane-2-carboxylic acid tert-butyl ester. To a solution of 7-methyl-2,7-diaza-spiro[3.5]nonane-2-carboxylic acid tert-butyl ester in DCM (5 mL) was added TFA (1 mL) and the resulting mixture was stirred at RT for 1 h. The reaction mixture was loaded onto an Isolute® SCX-2 cartridge, washed with MeOH then eluted with 2 M NH$_3$ in MeOH to give the title compound as a colourless oil (45 mg, 84%).

$^1$H NMR (400 MHz, CDCl$_3$): δ 1.81 (m, 4H), 2.22 (s, 3H), 2.28 (m, 2H), 3.22 (bs, 4H) and 3.38 (bs, 2H).

Reference Example 65

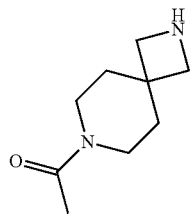

1-(2,7-Diaza-spiro[3.5]non-7-yl)-ethanone

To a solution of 2,7-diaza-spiro[3.5]nonane-2-carboxylic acid tert-butyl ester (70 mg, 0.309 mmol) in DCM (3 mL) were added acetyl chloride (32 μL, 0.450 mmol) and triethylamine (54 μL, 0.526 mmol). The resulting mixture was stirred at RT for 2 h. The reaction mixture was loaded onto an Isolute® SCX-2 cartridge, and washed with MeOH then eluted with 2 M NH$_3$ in MeOH to give 7-acetyl-2,7-diaza-spiro[3.5]nonane-2-carboxylic acid tert-butyl ester. To a solution of 7-acetyl-2,7-diaza-spiro[3.5]nonane-2-carboxylic acid tert-butyl ester in DCM (3 mL) was added TFA (1 mL) and the resulting mixture was stirred at RT for 1 h. The reaction mixture was loaded onto an Isolute® SCX-2 cartridge, washed with MeOH then eluted with 2 M NH$_3$ in MeOH to give the title compound as a colourless oil (41 mg, 79%).

$^1$H NMR (400 MHz, CDCl$_3$): δ 1.69-1.79 (m, 2H), 1.78-1.83 (m, 2H), 2.08 (s, 3H), 3.32-3.37 (m, 2H), 3.39-3.45 (m, 2H) and 3.37-3.57 (m, 4H).

Reference Example 66

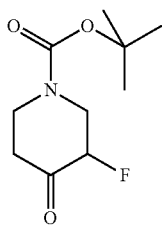

3-Fluoro-4-oxo-piperidine-1-carboxylic acid tert-butyl ester

To a solution of 4-oxo-piperidine-1-carboxylic acid tert-butyl ester (2.5 g, 12.55 mmol) in anhydrous DMF (5 mL) were added chlorotrimethylsilane (1.95 mL, 15.37 mmol) and triethylamine (4.18 mL, 30.0 mmol). The resulting milky mixture was heated at 80° C. for 17 h, then cooled to RT. The reaction mixture was diluted with water and extracted with EtOAc. The organic layer was separated, dried (MgSO$_4$) and concentrated in vacuo. The resultant residue was purified by column chromatography to give 4-trimethylsilanyloxy-3,6-dihydro-2H-pyridine-1-carboxylic acid tert-butyl ester as a pale yellow oil (1.86 g, 55%). To a solution of 4-trimethylsilanyloxy-3,6-dihydro-2H-pyridine-1-carboxylic acid tert-butyl ester (1.86 g, 6.852 mmol) in acetonitrile (80 mL) was added Selectfluor™ (2.7 g, 7.622 mmol) and the mixture was stirred at RT for 2 h. The resulting solution was diluted with water and extracted with EtOAc. The organic layer was separated, dried (MgSO$_4$) and concentrated in vacuo. The resultant residue was purified by column chromatography to give the title compound as a colourless oil (1.13 g, 76%).

$^1$H NMR (400 MHz, CDCl$_3$): δ 1.46-1.54 (s, 9H), 2.42-2.65 (m, 3H), 3.19-3.33 (m, 1H), 4.15 (m, 1H), 4.45 (m, 1H) and 4.83 (dt, J=47.8, 7.8 Hz, 1H).

Reference Example 67

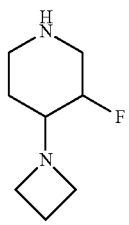

(±)-(cis)-4-Azetidin-1-yl-3-fluoro-piperidine

Prepared according to the method used in the preparation of 7-methyl-2,7-diaza-spiro[3.5]nonane using 3-fluoro-4-oxo-piperidine-1-carboxylic acid tert-butyl ester in place of formaldehyde and azetidine in place of 2,7-diaza-spiro[3.5]nonane-2-carboxylic acid tert-butyl ester hydrochloride. The title compound was obtained as a colourless oil (205 mg, 56%).

To the product in DCM (3 mL) was added TFA (1 mL) and the resulting mixture was stirred at RT for 1 h. The reaction mixture was loaded onto an Isolute® SCX-2 cartridge, washed with MeOH then eluted with 2 M NH$_3$ in MeOH to give the title compound as a colourless oil (205 mg, 56%).

$^1$H NMR (400 MHz, CDCl$_3$): δ 1.40-1.57 (m, 2H), 2.01-2.24 (m, 3H), 2.48-2.72 (m, 2H), 3.06-3.12 (m, 1H), 3.18-3.34 (m, 5H) and 4.48 (d, J=50.0 Hz, 1H).

Reference Example 68

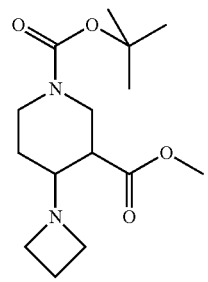

(±)-4-Azetidin-1-yl-piperidine-1,3-dicarboxylic acid 1-tert-butyl ester 3-methyl ester To a solution of 4-oxo-piperidine-1,3-dicarboxylic acid 1-tert-butyl ester 3-methyl ester (100 mg, 0.389 mmol) in DCE (11 mL) was added azetidine (33 mg, 0.578 mmol). The mixture was stirred at RT for 10 min, then sodium triacetoxyborohydride (132 mg, 0.623 mmol) was added and stirring was continued for 2 h. Water was added to the reaction mixture before being loaded onto an Isolute® SCX-2 cartridge. The cartridge was washed with MeOH then eluted with 2 M $NH_3$ in MeOH to give the title compound as a colourless oil (102 mg, 88%).

[M+H]⁺ 299.2

Reference Example 69

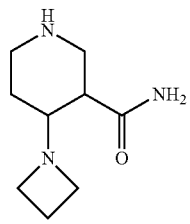

(±)-(cis)-4-Azetidin-1-yl-piperidine-3-carboxylic acid amide and (±)-(trans)-4-Azetidin-1-yl-piperidine-3-carboxylic acid amide To a solution of 4-azetidin-1-yl-piperidine-1,3-dicarboxylic acid 1-tert-butyl ester 3-methyl ester (0.66 g, 2.21 mmol) in anhydrous DMF (13 mL) was added formamide (370 µL, 9.32 mmol). The mixture was heated to 100° C. and a solution of sodium methoxide in MeOH (25 w/w. 330 µL, 1.44 mmol) was added with heating being continued for 2 h. The reaction mixture was cooled to RT, then loaded onto an Isolute® SCX-2 cartridge. The cartridge was washed with MeOH then eluted with 2 M $NH_3$ in MeOH to give 4-azetidin-1-yl-3-carbamoyl-piperidine-1-carboxylic acid tert-butyl ester. To a solution of 4-azetidin-1-yl-3-carbamoyl-piperidine-1-carboxylic acid tert-butyl ester in DCM (40 mL) was added TFA (5 mL) and the resulting mixture was stirred at RT for 1 h. The reaction mixture was loaded onto an Isolute® SCX-2 cartridge, washed with MeOH then eluted with 2 M $NH_3$ in MeOH to give a 1:1 cis:trans mixture of the title compound as a colourless oil (280 mg, 69%).

[M+H]⁺ 184.3

Reference Example 70

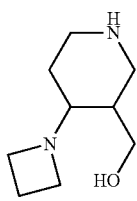

(±)-(cis)-(4-Azetidin-1-yl-piperidin-3-yl)-methanol and (±)-(trans)-(4-Azetidin-1-yl-piperidin-3-yl)-methanol To a solution of 4-azetidin-1-yl-piperidine-1,3-dicarboxylic acid 1-tert-butyl ester 3-methyl ester (373 mg, 1.25 mmol) in anhydrous DCM (10 mL) was slowly added a solution of diisobutylaluminum hydride in hexanes (1M, 3.8 mL, 3.8 mmol) at −70° C. The reaction mixture was allowed to warm to −10° C. over 90 min, then stirred at RT for 15 min. Water was added to the reaction mixture before being loaded onto an Isolute® SCX-2 cartridge. The cartridge was washed with MeOH then eluted with 2 M $NH_3$ in MeOH to give 4-azetidin-1-yl-3-hydroxymethyl-piperidine-1-carboxylic acid tert-butyl ester. To a solution of 4-azetidin-1-yl-3-hydroxymethyl-piperidine-1-carboxylic acid tert-butyl ester in DCM (10 mL) was added TFA (1 mL) and the resulting mixture was stirred at RT for 30 min. The reaction mixture was loaded onto an Isolute® SCX-2 cartridge, washed with MeOH then eluted with 2 M $NH_3$ in MeOH to give a 1:1 cis:trans mixture of the title compound as a colourless oil (188 mg, 88%).

[M+H]⁺ 171.1

Reference Example 71

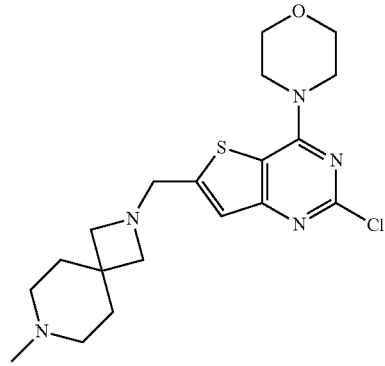

2-Chloro-6-(7-methyl-2,7-diaza-spiro[3.5]non-2-ylmethyl)-4-morpholin-4-yl-thieno[3,2-d]pyrimidine To a solution of 2-chloro-4-morpholin-4-yl-thieno[3,2-d]pyrimidine-6-carbaldehyde (72 mg, 0.254 mmol) in DCE (7 mL) was added 7-methyl-2,7-diaza-spiro[3.5]nonane (45 mg, 0.321 mmol). The mixture was stirred at RT for 10 min, then sodium triacetoxyborohydride (81 mg, 0.382 mmol) was added and stirring was continued for 3 h. To the reaction mixture was added water and the resulting solution was loaded onto an Isolute® SCX-2 cartridge. The cartridge was washed with MeOH and the desired product was eluted with 2 M $NH_3$ in MeOH an concentrated in vacuo. The resultant residue was purified by column chromatography to give the title compound as a yellow oil (31 mg, 30%).

[M+H]⁺ 408.2

Reference Example 72

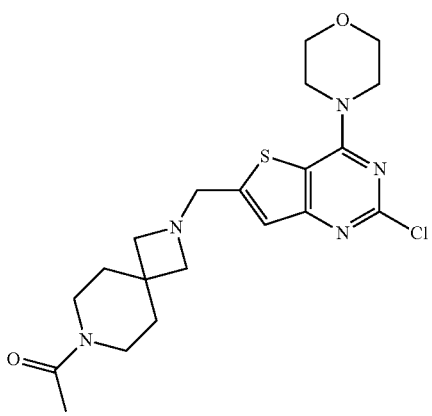

1-[2-(2-Chloro-4-morpholin-4-yl-thieno[3,2-d]pyrimidin-6-ylmethyl)-2,7-diaza-spiro[3.5]non-7-yl]ethanone Prepared according to the method used in the preparation of 2-chloro-6-(7-methyl-2,7-diaza-spiro[3.5]non-2-ylmethyl)-4-morpholin-4-yl-thieno[3,2-d]pyrimidine using 1-(2,7-diaza-spiro[3.5]non-7-yl)-ethanone in place of 7-methyl-2,7-diaza-spiro[3.5]nonane. The title compound was obtained as a colourless solid (47 mg, 61%).

[M+H]$^+$ 436.5

Reference Example 73

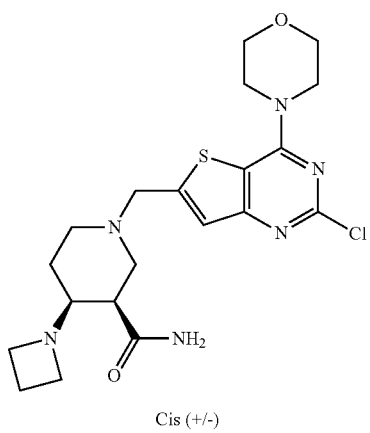

Cis (+/-)

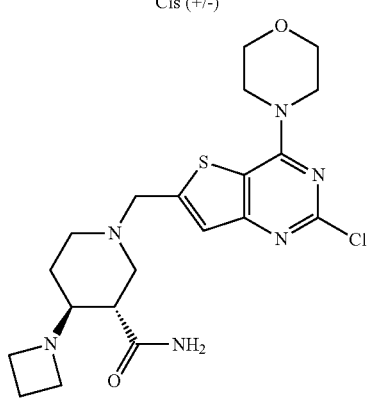

Trans (+/-)

(±)-(cis)-4-Azetidin-1-yl-1-(2-chloro-4-morpholin-4-yl-thieno[3,2-d]pyrimidin-6-ylmethyl)-piperidine-3-carboxylic acid amide and (±)-(trans)-4-azetidin-1-yl-1-(2-chloro-4-morpholin-4-yl-thieno[3,2-d]pyrimidin-6-ylmethyl)-piperidine-3-carboxylic acid amide Prepared according to the method used in the preparation of 2-chloro-6-(7-methyl-2,7-diaza-spiro[3.5]non-2-ylmethyl)-4-morpholin-4-yl-thieno[3,2-d]pyrimidine using 4-azetidin-1-yl-piperidine-3-carboxylic acid amide in place of 7-methyl-2,7-diaza-spiro[3.5]nonane. The title compounds were separated by column chromatography.

(±)-(cis)-4-Azetidin-1-yl-1-(2-chloro-4-morpholin-4-yl-thieno[3,2-d]pyrimidin-6-ylmethyl)-piperidine-3-carboxylic acid amide: tan solid (62 mg, 10%).

$^1$H NMR (400 MHz, CDCl$_3$): δ 1.51-1.73 (m, 2H), 2.00-2.12 (m, 3H), 2.15 (dd, J=11.4, 3.1 Hz, 1H), 2.22-2.30 (m, 1H), 2.47 (m, 1H), 2.93 (bd, J=11.4 Hz, 1H), 3.16-3.28 (m, 4H), 3.56 (dt, J=11.3, 2.3 Hz, 1H), 3.76-3.88 (m, 6H), 0.93-3.98 (m, 4H), 5.46-5.51 (m, 1H), 7.13 (s, 1H) and 9.07 (bs, 1H).

(±)-(trans)-4-Azetidin-1-yl-1-(2-chloro-4-morpholin-4-yl-thieno[3,2-d]pyrimidin-6-ylmethyl)-piperidine-3-carboxylic acid amide: white solid (153 mg, 25%).

$^1$H NMR (400 MHz, CDCl$_3$): δ 1.48-1.54 (m, 1H), 1.78-1.83 (m, 1H), 1.98-2.06 (m, 2H), 2.30-2.35 (m, 1H), 2.41 (m, 1H), 2.53-2.60 (m, 2H), 2.72 (m, 1H), 2.91 (dd, J=11.6, 3.5 Hz, 1H), 3.20-3.27 (m, 4H), 3.79 (d, J=2.4 Hz, 2H), 3.84 (m, 4H), 3.94-3.99 (m, 4H), 5.46 (s, 1H), 7.16 (s, 1H) and 7.75 (bs, 1H).

Reference Example 74

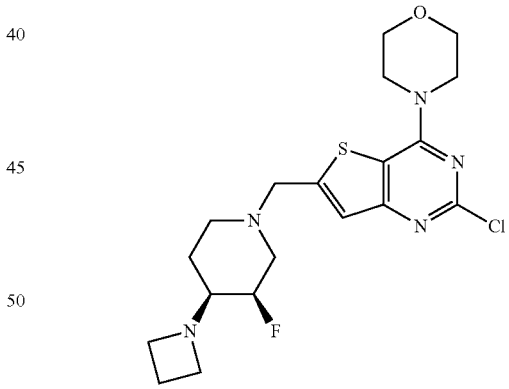

6-(((cis)-4-Azetidin-1-yl-3-fluoro-piperidin-1-ylmethyl)-2-chloro-4-morpholin-4-yl-thieno[3,2-d]pyrimidine Prepared according to the method used in the preparation of 2-chloro-6-(7-methyl-2,7-diaza-spiro[3.5]non-2-ylmethyl)-4-morpholin-4-yl-thieno[3,2-d]pyrimidine using (cis)-4-azetidin-1-yl-3-fluoro-piperidine in place of 7-methyl-2,7-diaza-spiro[3.5]nonane. The title compound was obtained as a tan solid (284 mg, 57%)

[M+H]$^+$ 426.5 .

Reference Example 75

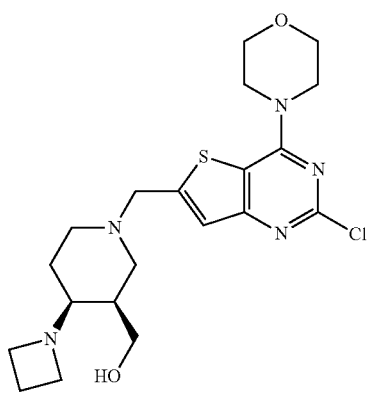

Cis (+/-)

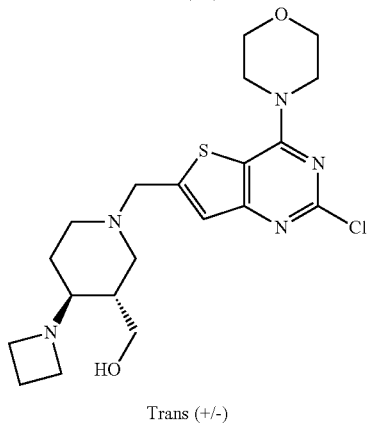

Trans (+/-)

(±)-[(cis)-4-Azetidin-1-yl-1-(2-chloro-4-morpholin-4-yl-thieno[3,2-d]pyrimidin-6-ylmethyl)-piperidin-3-yl]-methanol and (±)-[(trans)-4-azetidin-1-yl-1-(2-chloro-4-morpholin-4-yl-thieno[3,2-d]pyrimidin-6-ylmethyl)-piperidin-3-yl]-methanol Prepared according to the method used in the preparation of 2-chloro-6-(7-methyl-2,7-diaza-spiro[3.5]non-2-ylmethyl)-4-morpholin-4-yl-thieno[3,2-d]pyrimidine using (4-azetidin-1-yl-piperidin-3-yl)-methanol in place of 7-methyl-2,7-diaza-spiro[3.5]nonane. The title compounds were separated by column chromatography.

[(cis)-4-Azetidin-1-yl-1-(2-chloro-4-morpholin-4-yl-thieno[3,2-d]pyrimidin-6-ylmethyl)-piperidin-3-yl]-methanol: tan solid (83 mg, 19%).

$^1$H NMR (400 MHz, CDCl$_3$): δ 1.61 (m, 1H), 1.81 (m, 1H), 2.04-2.12 (m, 4H), 2.12-2.19 (m, 1H), 2.44 (m, 1H), 2.79 (d, J=11.5 Hz, 1H), 3.00 (d, J=11.1 Hz, 1H), 3.18-3.37 (m, 4H), 3.59-3.74 (m, 3H), 3.85 (t, J=4.8 Hz, 4H), 3.98 (m, 4H), 4.40 (t, J=10.6 Hz, 1H) and 7.11 (s, 1H).

[(trans)-4-Azetidin-1-yl-1-(2-chloro-4-morpholin-4-yl-thieno[3,2-d]pyrimidin-6-ylmethyl)-piperidin-3-yl]-methanol: tan solid (42 mg, 9%).

$^1$H NMR (400 MHz, CDCl$_3$): δ 1.61 (m, 2H), 1.81 (m, 1H), 2.04-2.12 (m, 3H), 2.12-2.19 (m, 1H), 2.34 (m, 1H), 2.79 (d, J=11.5 Hz, 1H), 2.86 (m, 1H), 3.18-3.37 (m, 4H), 3.59-3.74 (m, 2H), 3.77 (m, 2H), 3.85 (t, J=4.8 Hz, 4H), 3.98 (m, 4H) and 7.11 (s, 1H).

Reference Example 76

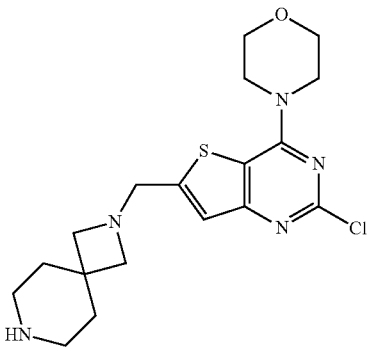

2-Chloro-6-(2,7-diaza-spiro[3.5]non-2-ylmethyl)-4-morpholin-4-yl-thieno[3,2-d]pyrimidine 2-(2-Chloro-4-morpholin-4-yl-thieno[3,2-d]pyrimidin-6-ylmethyl)-2,7-diaza-spiro[3.5]nonane-7-carboxylic acid tert-butyl ester was prepared according to the method used in the preparation of 2-chloro-6-(7-methyl-2,7-diaza-spiro[3.5]non-2-ylmethyl)-4-morpholin-4-yl-thieno[3,2-d]pyrimidine using 2,7-diaza-spiro[3.5]-nonane-7-carboxylic acid tert-butyl ester in place of 7-methyl-2,7-diaza-spiro[3.5]nonane. 2-(2-chloro-4-morpholin-4-yl-thieno[3,2-d]pyrimidin-6-ylmethyl)-2,7-diaza-spiro[3.5]nonane-7-carboxylic acid tert-butyl ester was subsequently BOC-deprotected to give the title compound as a pale yellow oil (287 mg, 58%).
[M+H]$^+$ 394.3

Reference Example 77

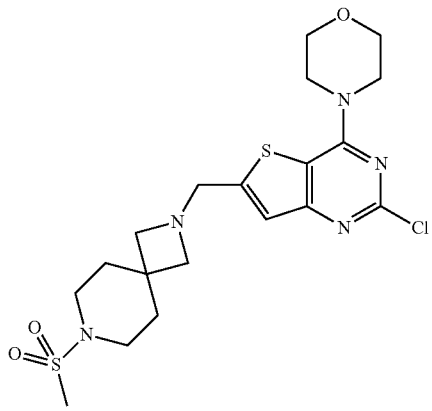

2-Chloro-6-(7-methanesulfonyl-2,7-diaza-spiro[3.5]non-2-ylmethyl)-4-morpholin-4-yl-thieno[3,2-d]pyrimidine To a solution of 2-chloro-6-(2,7-diaza-spiro[3.5]non-2-ylmethyl)-4-morpholin-4-yl-thieno[3,2-d]pyrimidine (71 mg, 0.18 mmol) in anhydrous DCM (3 mL) was added triethylamine (160 μL, 1.46 mmol) and a solution of methanesulfonyl chloride (17 μL, 0.22 mmol) in anhydrous DCM (0.5 mL). The resulting mixture was stirred at RT for 18 h, then diluted with DCM and brine. The organic layer was separated, dried (Na$_2$SO$_4$) and concentrated in vacuo. The resultant residue was purified by column chromatography to give the title compound as a yellow oil (55 mg, 65%).

[M+H]$^+$ 472.3

Reference Example 78

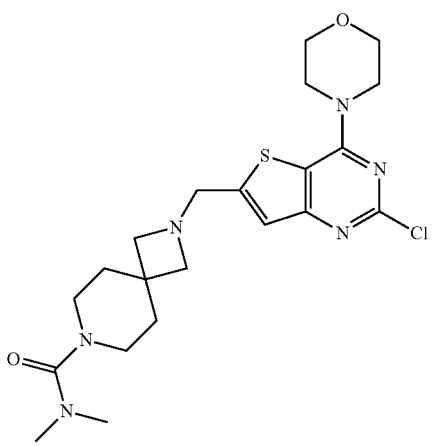

2-(2-Chloro-4-morpholin-4-yl-thieno[3,2-d]pyrimidin-6-ylmethyl)-2,7-diaza-spiro[3.5]nonane-7-carboxylic acid dimethylamide Prepared according to the method used in the preparation of 2-chloro-6-(7-methanesulfonyl-2,7-diaza-spiro[3.5]non-2-ylmethyl)-4-morpholin-4-yl-thieno[3,2-d]pyrimidine using dimethylcarbamoyl chloride in place of methanesulfonyl chloride. The title compound was obtained as a yellow oil (39 mg, 42%).

[M+H]$^+$ 465.4

Reference Example 79

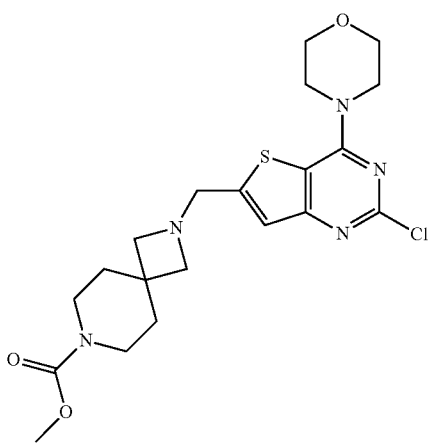

2-(2-Chloro-4-morpholin-4-yl-thieno[3,2-d]pyrimidin-6-ylmethyl)-2,7-diaza-spiro[3.5]nonane-7-carboxylic acid methyl ester Prepared according to the method used in the preparation of 2-chloro-6-(7-methanesulfonyl-2,7-diaza-spiro[3.5]non-2-ylmethyl)-4-morpholin-4-yl-thieno[3,2-d]pyrimidine using methyl chloroformate in place of methanesulfonyl chloride. The title compound was obtained as a colourless oil (20 mg, 28%).

[M+H]$^+$ 452.4

Reference Example 80

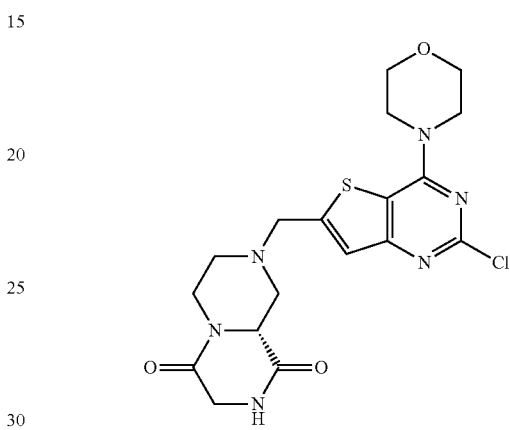

(R)-8-(2-Chloro-4-morpholin-4-yl-thieno[3,2-d]pyrimidin-6-ylmethyl)-hexahydro-pyrazino[1,2-a]pyrazine-1,4-dione Prepared according to the method used in the preparation of 4-(2-chloro-4-morpholin-4-yl-thieno[3,2-d]pyrimidin-6-ylmethyl)-3,3-dimethyl-piperazin-2-one using (R)-hexahydro-pyrazino[1,2-a]pyrazine-1,4-dione in place of 3,3-dimethyl-piperazin-2-one. The title compound was obtained as a cream solid (23 mg, 29%).

[M+H]$^+$ 437.2

Reference Example 81

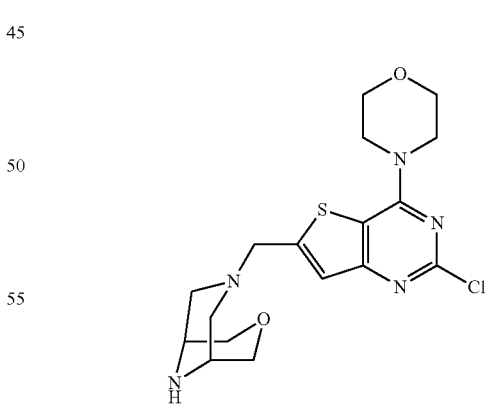

7-(2-Chloro-4-morpholin-4-yl-thieno[3,2-d]pyrimidin-6-ylmethyl)-3-oxa-7,9-diaza-bicyclo[3.3.1]nonane Prepared according to the method used in the preparation of 4-(2-chloro-4-morpholin-4-yl-thieno[3,2-c]pyrimidin-6- ylmethyl)-3,3-dimethyl-piperazin-2-one using 3-oxa-7,9-diaza-bicyclo[3.3.1]nonane in place of 3,3-dimethyl-piperazin-2-one. The title compound was obtained as a white solid (28 mg, 52%).

[M+H]+ 396.3

Reference Example 82

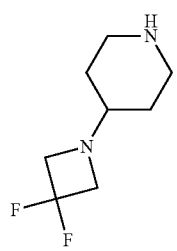

4-(3,3-Difluoroazetidin-1-yl)-piperidine

To a solution of 4-oxo-piperidine-1-carboxylic acid tert-butyl ester (1.0 g, 5.0 mmol) in DCE (50 mL) was added 3,3-difluoroazetidine hydrochloride (712 mg, 5.5 mmol). The mixture was stirred at RT for 15 min, then sodium triacetoxyborohydride (1.59 g, 7.5 mmol) was added and stirring was continued for 17 h. The reaction mixture was diluted with brine and extracted with DCM. The organic layer was separated, dried (Na$_2$SO$_4$) and concentrated in vacuo. The resultant residue was purified by column chromatography to give 4-(3,3-difluoroazetidin-1-yl)-piperidine-1-carboxylic acid tert-butyl ester as a pale yellow solid (1.2 g, 88%). To a solution of 4-(3,3-difluoro-azetidin-1-yl)-piperidine-1-carboxylic acid tert-butyl ester (552 mg, 2.0 mmol) in DCM (4 mL) was added TFA (2 mL) and the resulting mixture was stirred at RT for 45 min. The reaction mixture was loaded onto an Isolute® SCX-2 cartridge. The cartridge was washed with MeOH then eluted with 2 M NH$_3$ in MeOH to give the title compound as a pale yellow solid (271 mg, 77%).

$^1$H NMR (400 MHz, CDCl$_3$): δ 1.16-1.27 (m, 2H), 1.63-1.72 (m, 2H), 2.14-2.23 (m, 1H), 2.54-2.62 (m, 2H), 3.09 (dt, J=12.7, 3.9 Hz, 2H) and 3.46-3.57 (m, 4H).

Reference Example 83

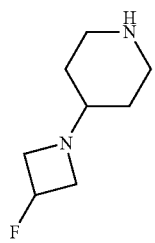

4-(3-Fluoroazetidin-1-yl)-piperidine

Prepared according to the method used in the preparation of 4-(3,3-difluoroazetidin-1-yl)-piperidine using 3-fluoroazetidine in place of 3,3-difluoroazetidine hydrochloride. The title compound was obtained as a colourless oil (180 mg, 39%).

$^1$H NMR (400 MHz, CDCl$_3$): δ 1.13-1.24 (m, 2H), 1.64 (dd, J=12.6, 4.3 Hz, 2H), 2.16-2.23 (m, 1H), 2.82-2.91 (m, 2H), 3.01-3.14 (m, 2H), 3.59-3.67 (m, 2H), 3.78-3.95 (m, 2H), 5.10 (dm, J=55.8 Hz, 1H).

Reference Example 84

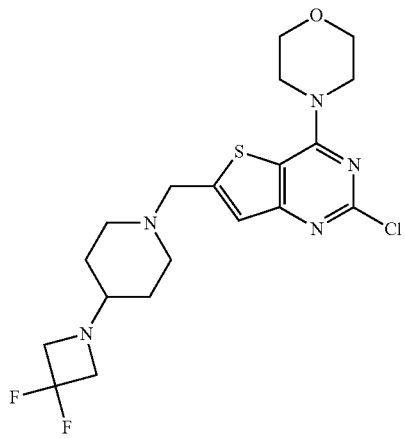

2-Chloro-6-[4-(3,3-difluoroazetidin-1-yl)-piperidin-1-ylmethyl]-4-morpholin-4-yl-thieno[3,2-d]pyrimidine Prepared according to the method used in the preparation of 2-chloro-6-(7-methyl-2,7-diaza-spiro[3.5]non-2-ylmethyl)-4-morpholin-4-yl-thieno[3,2-d]pyrimidine using 4-(3,3-difluoroazetidin-1-yl)-piperidine in place of 7-methyl-2,7-diaza-spiro[3.5]nonane. The title compound was obtained as a white solid (115 mg, 74%).

[M+H]+ 444.4

Reference Example 85

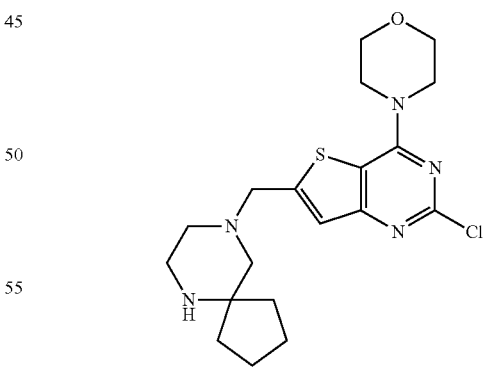

2-Chloro-6-(6,9-diaza-spiro[4.5]dec-9-ylmethyl)-4-morpholin-4-yl-thieno[3,2-d]pyrimidine Prepared according to the method used in the preparation of 2-chloro-6-(7-methyl-2,7-diaza-spiro[3.5]non-2-ylmethyl)-4-morpholin-4-yl-thieno[3,2-d]pyrimidine using 6,9-diaza-spiro[4.5]decane dihydrochloride in place of 7-methyl- 2,7-diaza-spiro[3.5]nonane. The title compound was obtained as a white solid (76 mg, 53%).
[M+H]+ 408.5

Reference Example 86

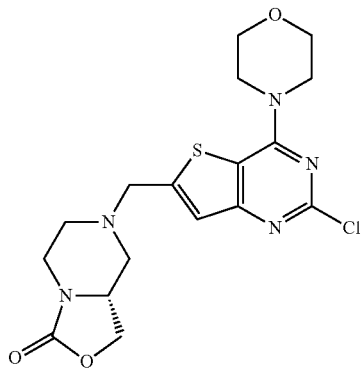

(R)-7-(2-Chloro-4-morpholin-4-yl-thieno[3,2-d]pyrimidin-6-ylmethyl)-hexahydro-oxazolo[3,4-a]pyrazin-3-one Prepared according to the method used in the preparation of 2-chloro-6-(7-methyl-2,7-diaza-spiro[3.5]non-2-ylmethyl)-4-morpholin-4-yl-thieno[3,2-d]pyrimidine using (R)-hexahydro-oxazolo[3,4-a]pyrazin-3-one in place of 7-methyl-2,7-diaza-spiro[3.5]nonane. The title compound was obtained as a white solid (71 mg, 50%).
[M+H]+ 410.5

Reference Example 87

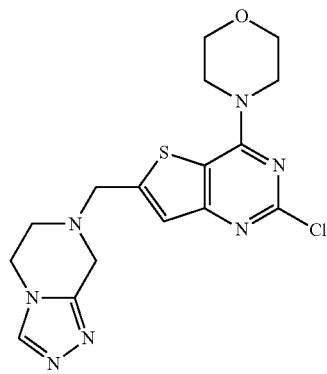

7-(2-Chloro-4-morpholin-4-yl-thieno[3,2-d]pyrimidin-6-ylmethyl)-5,6,7,8-tetrahydro-[1,2,4]triazolo[4,3-a]pyrazine Prepared according to the method used in the preparation of 4-(2-chloro-4-morpholin-4-yl-thieno[3,2-d]pyrimidin-6-ylmethyl)-3,3-dimethyl-piperazin-2-one using 5,6,7,8-tetrahydro-[1,2,4]triazolo[4,3-a]pyrazine in place of 3,3-dimethyl-piperazin-2-one. The title compound was obtained as a white solid (115 mg, 84%)
[M+H]+ 392.3 .

Reference Example 88

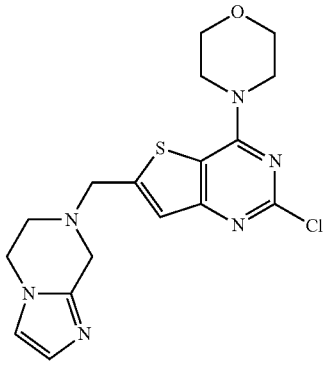

2-Chloro-6-(5,6-dihydro-8H-imidazo[1,2-a]pyrazin-7-ylmethyl)-4-morpholin-4-yl-thieno[3,2-d]pyrimidine Prepared according to the method used in the preparation of 4-(2-chloro-4-morpholin-4-yl-thieno[3,2-d]pyrimidin-6-ylmethyl)-3,3-dimethyl-piperazin-2-one using 5,6,7,8tetrahydro-imidazo[1,2-a]pyrazine in place of 3,3-dimethyl-piperazin-2-one. The title compound was obtained as a pale brown solid (50 mg, 52%).
[M H]+ 391.3

Reference Example 89

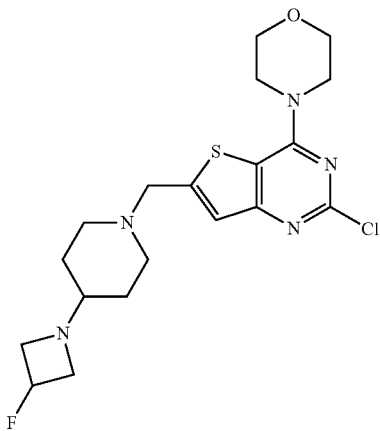

2-Chloro-6-[4-(3-fluoro-azetidin-1-yl)-piperidin-1-ylmethyl]-4-morpholin-4-yl-thieno[3,2-d]pyrimidine Prepared according to the method used in the preparation of 2-chloro-6-(7-methyl-2,7-diaza-spiro[3.5]non-2-ylmethyl)-4-morpholin-4-yl-thieno[3,2-d]pyrimidine using 4-(3-fluoro-azetidin-1-yl)-piperidine in place of 7-methyl-2,7-diaza-spiro[3.5]nonane. The title compound was obtained as a white solid (201 mg, 47%).
[M+H]+ 426.1

Reference Example 90

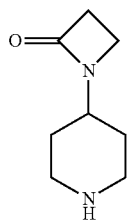

1-Piperidin-4-yl-azetidin-2-one

To a solution of 4-(2-methoxycarbonyl-ethylamino)-piperidine-1-carboxylic acid tert-butyl ester (3.4 g, 12.0 mmol) in anhydrous THF (75 mL) was slowly added a solution of methyl magnesium bromide in diethyl ether (3 M, 6 mL, 18 mmol) at 0° C. The reaction mixture was stirred at 0° C. for 3 h, then allowed to warm to RT and stirring was continued for 72 h. The reaction mixture was concentrated in vacuo and the resulting residue was partitioned between EtOAc and an aqueous solution of ammonium chloride. The organic layer was separated and washed with brine, then dried ($Na_2SO_4$) and concentrated in vacuo. The resultant residue was purified by column chromatography to give 4-(2-oxo-azetidin-1-yl)-piperidine-1-carboxylic acid tert-butyl ester as a pale yellow oil (598 mg, 20%). To a solution of 4-(2-oxo-azetidin-1-yl)-piperidine-1-carboxylic acid tert-butyl ester (595 mg, 2.34 mmol) in DCM (6 mL) was added TFA (2 mL). The resulting mixture was stirred at RT for 1.5 h, then concentrated in vacuo. The resultant residue was loaded onto an Isolute® SCX-2 cartridge, washed with MeOH then eluted with 2 M $NH_3$ in MeOH to give the title compound as a pale yellow solid (325 mg, 90%).

$^1$H NMR (400 MHz, $CDCl_3$): δ 1.48-1.61 (m, 2H), 1.83 (dd, J=12.6, 3.7 Hz, 2H), 2.54-2.67 (m, 2H), 2.86 (t, J=4.0 Hz, 2H), 3.10 (dt, J=12.6, 3.5 Hz, 2H), 3.22 (t, J=4.0 Hz, 2H) and 3.66 (m, 1H).

Reference Example 91

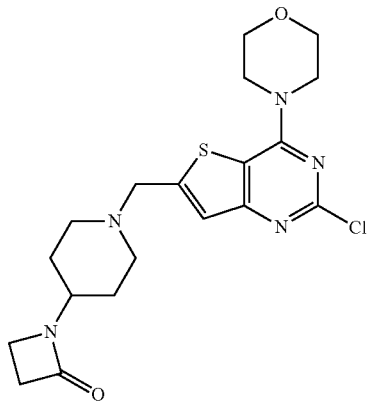

1-[1-(2-Chloro-4-morpholin-4-yl-thieno[3,2-d]pyrimidin-6-ylmethyl)-piperidin-4-yl]-azetidin-2-one Prepared according to the method used in the preparation of 2-chloro-6-(7-methyl-2,7-diaza-spiro[3.5]non-2-ylmethyl)-4-morpholin-4-yl-thieno[3,2-d]pyrimidine using 1-piperidin-4-yl-azetidin-2-one in place of 7-methyl-2,7-diazaspiro[3.5]nonane. The title compound was obtained as a pale yellow solid (205 mg, 81%).

[M+H]$^+$ 422.3

Reference Example 92

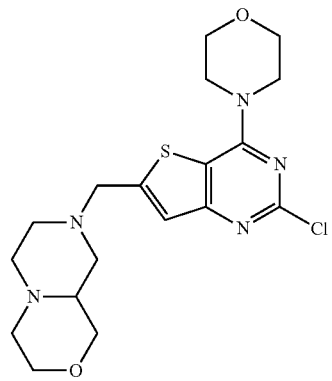

(±)-8-(2-Chloro-4-morpholin-4-yl-thieno[3,2-d]pyrimidin-6-ylmethyl)-octahydro-pyrazino[2,1-c][1,4]oxazine Prepared according to the method used in the preparation of 4-(2-chloro-4-morpholin-4-yl-thieno[3,2-d]-pyrimidin-6-ylmethyl)-piperazin-2-one using octahydro-pyrazino[2,1-c][1,4]oxazine in place of piperazin-2-one. The title compound was obtained as a white solid (79 mg, 64%).

[M+H]$^+$ 410.2

Reference Example 93

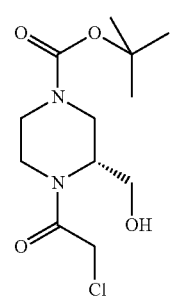

(R)-4-(2-Chloro-acetyl)-3-hydroxymethyl-piperazine-1-carboxylic acid tert-butyl ester To a solution of (R)-3-hydroxymethyl-piperazine-1-carboxylic acid tert-butyl ester (795 mg, 3.68 mmol) in DCM (20 mL) was added triethylamine (1.53 mL, 11.04 mmol). The resulting mixture was cooled to 0° C. before the dropwise addition of chloroacetyl chloride (325 μL, 4.05 mmol). The mixture was warmed to RT and stirred for 5 h. The reaction mixture was partitioned between a saturated aqueous solution of NaHCO$_3$ and DCM. The organic layer was separated and the aqueous layer extracted with DCM. The combined organic fractions were dried (Na$_2$SO$_4$) and concentrated in vacuo. The resulting residue was purified by column chromatography to give the title compound as a colourless oil which was a mixture of rotamers (710 mg, 66%).

$^1$H NMR (400 MHz, CDCl$_3$): δ 1.48 (s, 9H), 2.80-2.92 (m, 1H), 2.95-3.10 (m, 2H), 3.34-3.44 (m, ½H), 3.60-3.74 (m, 2½H), 3.96-4.16 (m, 3½H), 4.22-4.30 (m, ½H), 4.32-4.40 (m, ½H) and 4.63 (bs, ½H).

Reference Example 94

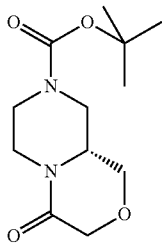

(R)-4-Oxo-hexahydro-pyrazino[2,1-c][1,4]oxazine-8-carboxylic acid tert-butyl ester To a solution of (R)-4-(2-chloro-acetyl)-3-hydroxymethyl-piperazine-1-carboxylic acid tert-butyl ester (710 mg, 2.45 mmol) in THF (16 mL) at 0° C. was added potassium tert-butoxide (326 mg, 2.91 mmol). The resulting mixture was stirred for 75 min before the addition of AcOH (0.6 mL). The resulting mixture was partitioned between water and DCM and the aqueous layer extracted with further DCM. The combined organic fractions were dried (Na$_2$SO$_4$) and concentrated in vacuo. The resulting residue was purified by column chromatography to give the title compound as a colourless oil (570 mg, 91%).

$^1$H NMR (400 MHz, CDCl$_3$): δ 1.48 (s, 9H), 2.69 (td, J=12.9, 3.0 Hz, 2H), 2.78-2.89 (m, 1H), 3.48-3.58 (m, 2H), 3.96-4.10 (m, 3H), 4.14 (d, J=16.2 Hz, 1H), 4.20 (d, J=16.8 Hz, 1H) and 4.57 (m, 1H).

Reference Example 95

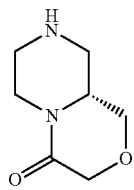

(R)-Hexahydro-pyrazino[2,1-c][1,4]oxazin-4-one

To a solution of (R)-4-oxo-hexahydro-pyrazino[2,1-c][1,4]oxazine-8-carboxylic acid tert-butyl ester in DCM (5 mL) was added TFA (1 mL). The resulting mixture was stirred at RT for 2 h then concentrated in vacuo. The resulting residue was azeotroped with toluene then purified by SCX column to give the title compound as a colourless oil (60 mg, 76%).

$^1$H NMR (400 MHz, MeOD): δ 2.46-2.55 (m, 1H), 2.59-2.76 (m, 2H), 2.90-3.03 (m, 2H), 3.50-3.60 (m, 2H), 3.94-4.02 (m, 1H), 4.10 (s, 2H) and 4.42-4.48 (m, 1H).

Reference Example 96

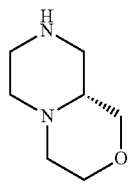

(R)-Octahydro-pyrazino[2,1-c][1,4]oxazine

To a solution of (R)-hexahydro-pyrazino[2,1-c][1,4]oxazin-4-one (60 mg, 0.39 mmol) in dioxane (5 mL) was added LiAlH$_4$ (1.5 mL, 1M solution in THF). The resulting mixture was heated at 80° C. for 2.5 h before the addition of $^i$PrOH (0.5 mL) followed by a saturated aqueous solution of Na$_2$SO$_4$ (3 mL). Further Na$_2$SO$_4$ was added and the resulting mixture filtered through celite, washing with EtOAc. The resulting residue was purified by NH$_2$ column to give the title compound as an oil (40 mg, 73%).

$^1$H NMR (400 MHz, CDCl$_3$): δ 2.17-2.30 (m, 2H), 2.36-2.47 (m, 2H), 2.61 (d, J=11.9 Hz, 1H), 2.69-2.79 (m, 2H), 2.92-2.99 (m, 2H), 3.23 (t, J=10.3 Hz, 1H), 3.61-3.75 (m, 2H) and 3.79-3.87 (m, 1H).

Reference Example 97

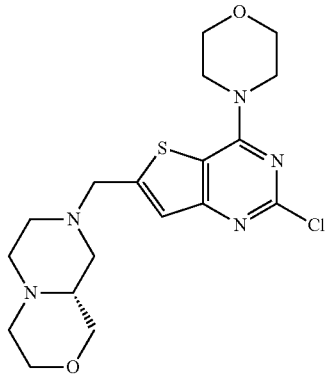

(R)-8-(2-Chloro-4-morpholin-4-yl-thieno[3,2-d]pyrimidin-6-ylmethyl)-octahydro-pyrazino[2,1-c][1,4]oxazine Prepared according to the method used in the preparation of (S)-4-(2-chloro-4-morpholin-4-yl-thieno[3,2-d]pyrimidin-6-ylmethyl)-3-isopropyl-piperazin-2-one using (R)-octahydro-pyrazino[2,1-c][1,4]oxazine in place of (S)-3-isopropyl-piperazin-2-one. The title compound was obtained as a pale yellow solid (57 mg, 62%)

[M+H]$^+$ 410.3.

Reference Example 98

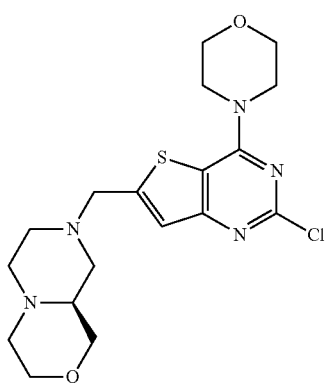

(S)-8-(2-Chloro-4-morpholin-4-yl-thieno[3,2-d]pyrimidin-6-ylmethyl)-octahydro-pyrazino[2,1-c][1,4]oxazine Prepared according to the method used in the preparation of (S)-4-(2-chloro-4-morpholin-4-yl-thieno[3,2-d]pyrimidin-6-ylmethyl)-3-isopropyl-piperazin-2-one using (S)-octahydro-pyrazino[2,1-c][1,4]oxazine in place of (S)-3-isopropyl-piperazin-2-one. The title compound was obtained as a pale yellow solid (210 mg, 90%).

[M+H]⁺ 410.3

Reference Example 99

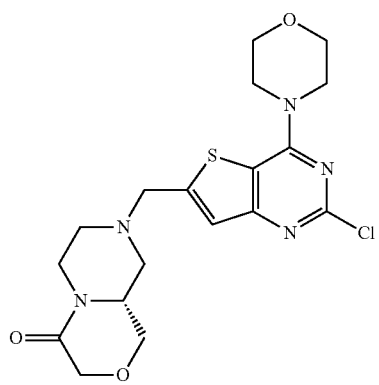

(R)-8-(2-Chloro-4-morpholin-4-yl-thieno[3,2-d]pyrimidin-6-ylmethyl)-hexahydro-pyrazino[2,1-c][1,4]oxazin-4-one Prepared according to the method used in the preparation of (S)-4-(2-chloro-4-morpholin-4-yl-thieno[3,2-d]pyrimidin-6-ylmethyl)-3-isopropyl-piperazin-2-one using (R)-hexahydro-pyrazino[2,1-c][1,4]oxazin-4-one in place of (S)-3-isopropyl-piperazin-2-one. The title compound was obtained as a tan solid (79 mg, 69%).

¹H NMR (400 MHz, CDCl₃): δ 1.96-2.03 (m, 1H), 2.20 (m, 1H), 2.78-2.85 (m, 2H), 2.94 (m, 1H), 3.48 (dd, J=11.9, 7.7 Hz, 1H), 3.63-3.68 (m, 1H), 3.78-3.83 (m, 6H), 3.92 (m, 1 H), 3.93-3.99 (m, 4H), 4.05-4.18 (m, 2H), 4.57 (m, 1H) and 7.16 (s, 1H).

Reference Example 100

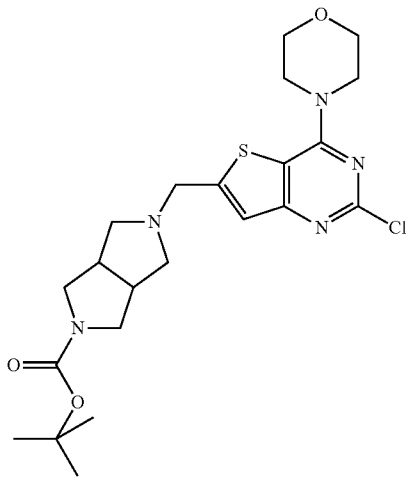

5-(2-Chloro-4-morpholin-4-yl-thieno[3,2-d]pyrimidin-6-ylmethyl)-hexahydro-pyrrolo[3,4-c]pyrrole-2-carboxylic acid tert-butyl ester To a solution of 6-bromomethyl-2-chloro-4-morpholin-4-yl-thieno[3,2-d]pyrimidine (175 mg, 0.50 mmol) in DMF (5 mL) were added hexahydro-pyrrolo[3,4-c]pyrrole-2-carboxylic acid tert-butyl ester (160 mg, 0.754 mmol) and potassium carbonate (136 mg, 0.984 mmol). The resulting mixture was stirred at RT for 2 h, then diluted with water and EtOAc. The organic layer was isolated, then washed with brine, dried (MgSO₄) and concentrated in vacuo. The resulting residue was purified by column chromatography to give the title compound as an off-white solid (218 mg, 90%).

[M+H]⁺ 480.3

Reference Example 101

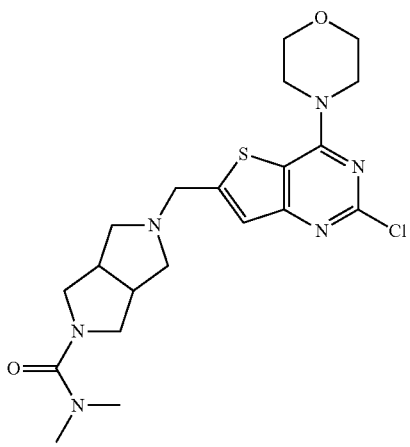

5-(2-Chloro-4-morpholin-4-yl-thieno[3,2-d]pyrimidin-6-ylmethyl)-hexahydro-pyrrolo[3,4-c]pyrrole-2-carboxylic acid dimethylamide To a solution of 5-(2-chloro-4-morpholin-4-yl-thieno[3,2-d]pyrimidin-6-ylmethyl)-hexahydro-pyrrolo[3,4-c]pyrrole-2-carboxylic acid tert-butyl ester (250 mg, 0.52 mmol) in DCM (4.5 mL) was added TFA (0.5 mL). The reaction mixture stirred at RT for 1 h, then loaded onto an Isolute® SCX-2 cartridge. The cartridge was washed with MeOH then eluted with 2 M $NH_3$ in MeOH, and concentrated in vacuo. The resultant residue was dissolved in DCM (6 mL) and triethylamine (0.48 mL, 3.28 mmol) was added. The reaction mixture was cooled to 0° C. then a solution of dimethylcarbamoyl chloride (57 µL, 0.615 mmol) in DCM (0.5 mL) was added. The reaction mixture was stirred at RT for 1 h, then partitioned between water and DCM. The organic layer was separated and washed with brine, then dried ($Na_2SO_4$) and concentrated in vacuo. The resultant residue was purified by column chromatography to give the title compound as a colourless oil (55 mg, 24%).

$^1$H NMR (400 MHz, $CDCl_3$): δ 2.51 (m, 2H), 2.66-2.73 (m, 2H), 2.76-2.80 (m, 2H), 2.84 (s, 6H), 3.17-3.24 (m, 2H), 3.47-3.55 (m, 2H), 3.82 (m, 4H), 3.85 (s, 2H), 3.94-3.99 (m, 4H) and 7.12 (s, 1H).

Reference Example 102

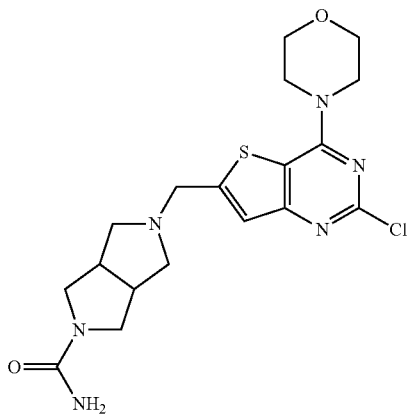

5-(2-Chloro-4-morpholin-4-yl-thieno[3,2-d]pyrimidin-6-ylmethyl)-hexahydro-pyrrolo[3,4-c]pyrrole-2-carboxylic acid amide To a solution of 5-(2-chloro-4-morpholin-4-yl-thieno[3,2-d]pyrimidin-6-ylmethyl)-hexahydro-pyrrolo[3,4-c]pyrrole-2-carboxylic acid tert-butyl ester (250 mg, 0.52 mmol) in DCM (4.5 mL) was added TFA (0.5 mL). The reaction mixture stirred at RT for 1 h, then loaded onto an Isolute® SCX-2 cartridge. The cartridge was washed with MeOH then eluted with 2 M $NH_3$ in MeOH, and concentrated in vacuo. The resultant residue was dissolved in DCM (5 mL) and trimethylsilyl isocyanate (139 µL, 1.0 mmol) was added. The reaction mixture was stirred at RT for 1 h, then partitioned between DCM and a saturated aqueous solution of $NaHCO_3$. The organic layer was separated and washed with brine, then dried ($Na_2SO_4$) and concentrated in vacuo to give the title compound as a colourless oil (185 mg, 84%).

$^1$H NMR (400 MHz, $CDCl_3$): δ 2.63 (m, 2H), 2.71 (m, 2H), 2.89-2.96 (m, 2H), 3.29 (m, 2 H), 3.57-3.67 (m, 2H), 3.82-3.86 (m, 4H), 3.89 (s, 2H), 3.95-4.00 (m, 4H), 4.32 (bs, 2H) and 7.13 (s, 1H).

Reference Example 103

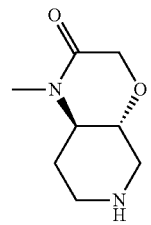

(4R*,4aR*)-1-Methyl-hexahydro-pyrido[3,4-b][1,4]oxazin-2-one

To a stirring solution of 1,2,3,6-tetrahydropyridine (2.96 g, 35.6 mmol), in dichloromethane (100 mL) was added portionwise di-tert-butyldicarbonate (8.54 g, 39.1 mmol) followed by triethylamine (5.46 mL, 39.1 mmol). The reaction mixture was stirred at room temperature overnight and partitioned between dichloromethane and saturated sodium bicarbonate solution. The combined organic layers were washed with brine, separated and dried ($MgSO_4$) to give 3,6-dihydro-2H-pyridine-1-carboxylic acid tert-butyl ester as a yellow liquid (6.27 g).

To a stirring solution of 3,6-dihydro-2H-pyridine-1-carboxylic acid tert-butyl ester (6.27 g, 34.2 mmol) in dichloromethane (35 mL) cooled down to 0° C. was added dropwise a solution of m-chloroperoxybenzoic acid (8.65 g, 1.1 eq) in dichloromethane (50 mL). The mixture stirred at room temperature for 4 hours. The mixture was partitioned between dichloromethane and 5% potassium carbonate solution. The combined organic layers were washed with brine, separated and dried ($MgSO_4$). The crude product was purified by column chromatography to yield a (±)-7-oxa-3-azabicyclo[4.1.0]heptane-3-carboxylic acid tert-butyl ester (4.43 g) as a pale yellow liquid.

To a stirring solution of (±)-7-oxa-3-aza-bicyclo[4.1.0]heptane-3-carboxylic acid tert-butyl ester (2.4 g, 12.06 mmol) in ethanol (20 mL) was added sodium azide (1.00 g, 15.62 mmol) and ammonium chloride (840 mg, 15.79 mmol). The resulting mixture was heated to reflux overnight and then partitioned between ethyl acetate and water. The combined organic layers were washed with brine, separated and dried ($MgSO_4$). The crude product was purified by column chromatography to yield (3R*,4R*)-4-azido-3-hydroxy-piperidine-1-carboxylic acid tert-butyl ester (1.95 g) and (3S*, 4S*)-3-azido-4-hydroxy-piperidine-1-carboxylic acid tert-butyl ester (312 mg).

The structures of these regioisomers were confirmed by COSY-4/HSQC/NOESY/DEPT-Q experiments.

A solution of (3R*,4R*)-4-azido-3-hydroxy-piperidine-1-carboxylic acid tert-butyl ester (2.96 g, 12.23 mmol) in ethanol (50 mL) was flushed out with nitrogen. Palladium (10 wt % on activated carbon) (~300 mg) was added and the mixture flushed out with hydrogen and then stirred under a hydrogen balloon at room temperature overnight. The reaction mixture was filtered through celite and the filtrate evaporated to give (3R*,4R*)-4-amino-3-hydroxy-piperidine-1-carboxylic acid tert-butyl ester (2.73 g).

To a stirring solution of (3R*,4R*)-4-amino-3-hydroxy-piperidine-1-carboxylic acid tert-butyl ester (2.64 g, 12.22 mmol) in dichloromethane (30 mL) was added triethylamine (1.87 mL, 13.41 mmol) and cooled down to 0° C. Chloroacetyl chloride (0.97 mL, 12.18 mmol) was added dropwise. The mixture was warmed to room temperature and stirred overnight. The mixture was partitioned between dichloromethane and brine. The combined organic layers were washed with brine, separated and dried (MgSO$_4$). The crude product was purified by column chromatography to yield (3R*,4R*)-4-(2-chloro-acetylamine)-3-hydroxy-piperidine-1-carboxylic acid tert-butyl ester (2.70 g).

To a stirring solution of (3R*,4R*)-4-(2-chloro-acetylamino)-3-hydroxy-piperidine-1-carboxylic acid tert-butyl ester (2.70 g, 9.23 mmol) in tetrahydrofuran (30 mL) cooled down to 0° C. was added sodium hydride, 60% dispersion in mineral oil (830 mg, 1.1 eq) portionwise. The mixture was warmed to room temperature and stirred for 6 hours. The mixture was partitioned between dichloromethane and brine. The combined organic layers were washed with brine, separated and dried (MgSO$_4$). The crude product was purified by column chromatography to yield (4aR*,8aR*)-2-oxo-octahydro-pyrido[3,4-b][1,4]oxazine-6-carboxylic acid tert-butyl ester (1.31 g).

To a stirring solution of (4aR*,8aR*)-2-oxo-octahydro-pyrido[3,4-b][1,4]oxazine-6-carboxylic acid tert-butyl ester (700 mg, 2.73 mmol) in dimethylformamide (10 mL) at 0° C. was added sodium hydride, 60% dispersion in mineral oil (180 mg, 1.1 eq). The mixture was stirred at 0° C. for 30 minutes and then iodomethane (0.19 mL, 3.05 mmol) was added. The mixture was warmed to room temperature and stirred overnight.

The mixture was partitioned between ethyl acetate and water. The combined organic layers were washed with brine, separated and dried (MgSO$_4$) to yield (4aR*,8aR*)-1-methyl-2-oxo-octahydro-pyrido[3,4-b][1,4]oxazine-6-carboxylic acid tert-butyl ester (513 mg). Removal of the Boc-protecting group using 2.0 M HCl in diethyl ether in dichloromethane gave the hydrochloride salt of the title compound as an off-white foam (290 mg).

Reference Example 104

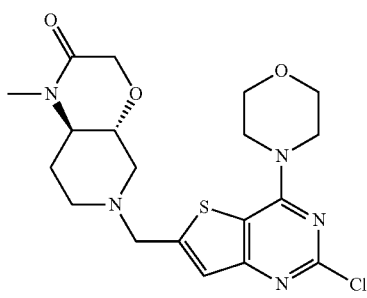

(4aR*,8aR*)-6-(2-Chloro-4-morpholin-4-yl-thieno[3,2-d]pyrimidin-6-ylmethyl)-1-methyl-hexahydro-pyrido[3,4-b][1,4]oxazin-2-one The title compound was prepared under the standard reductive-amination conditions using (4R*,4aR*)-1-methyl-hexahydro-pyrido[3,4-b][1,4]oxazin-2-one hydrochloride salt in the presence of triethylamine to give an off-white foam (48 mg).

$\delta_H$ (400 MHz, CDCl$_3$) 1.52 (m, 1H), 2.04-2.17 (m, 3H), 2.88 (s, 3H), 2.96 (m, 1H), 3.09 (m, 2H), 3.52 (m, 1H), 3.77 (t, J=4.8, 4H), 8.81 (s, 2H), 3.91 (t, J=4.8, 4H), 4.21 (m, 2H), 6.93 (s, 1H).

Reference Example 105

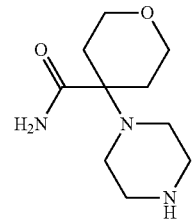

4-piperazin-1-yl-tetrahydro-pyran-4-carboxylic acid amide

To a mixture of tetrahydro-4H-pyran-4-one (500 mg, 5.00 mmol) and 1-Boc-piperazine (930 mg, 5.00 mmol) in methanol (10 mL) at 0° C. was added dropwise a solution of potassium cyanide (325 mg, 5.00 mmol) in water (1 mL). The mixture was warmed to room temperature and stirred overnight. The mixture was partitioned between ethyl acetate and water. The combined organic layers were washed with brine, separated and dried (MgSO$_4$) to yield a 1:1 mixture of 4-(4-cyano-tetrahydro-pyran-4-yl)-piperazine-1-carboxylic acid tert-butyl ester and unreacted starting material (1.15 g). The crude mixture was dissolved in methanol (10 mL) and 1M sodium hydroxide solution (5 mL, 5.00 mmol) was added followed by the dropwise addition of hydrogen peroxide, (30 wt % solution in water; 2.5 mL) The mixture was stirred at room temperature overnight. The mixture was evaporated in vacuo and the crude product was purified by column chromatography to yield 4-(4-carbamoyl-tetrahydro-pyran-4-yl)-piperazine-1-carboxylic acid tert-butyl ester (307 mg). Removal of the Boc-protecting group using 2.0 M HCl in diethyl ether in dichloromethane gave the di-hydrochloride salt of the title compound as a pale solid (260 mg).

Reference Example 106

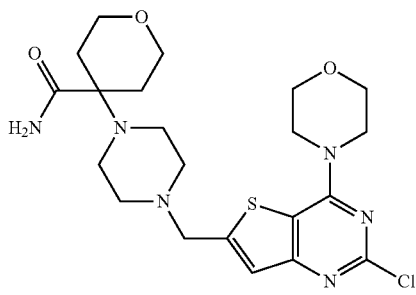

4-[4-(2-Chloro-4-morpholin-4-yl-thieno[3,2-d]pyrimidin-6-ylmethyl)-piperazin-1-yl]-tetrahydro-pyran-4-carboxylic acid amide The title compound was prepared under the standard reductive-amination conditions using 4-piperazin-1-yl-tetrahydro-pyran-4-carboxylic acid amide di-hydrochloride salt in the presence of triethylamine to give an off-white foam (46 mg).

$\delta_H$ (400 MHz, CDCl$_3$) 1.69 (m, 2H), 1.81 (m, 2H), 2.49 (m, 4H), 2.57 (m, 4H), 3.65-3.85 (m, 10H), 3.91 (t, J=4.8, 4H), 5.11 (br s, 1H), 6.46 (br s, 1H), 7.07 (s, 1H).

Reference Example 107

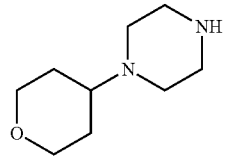

1-(Tetrahydro-pyran-4-yl)-piperazine

To a solution of piperazine-1-carboxylic acid tert-butyl ester (1.5 g, 8.05 mmol) stirring in anhydrous THF (20 mL) and water (0.2 mL) was added glacial acetic acid (1.45 mL, 24.2 mmol), followed by sodium cyanoborohydride (758 mg, 12.1 mmol). The reaction mixture was stirred at 60° C. for 12 h, quenched with 10% aqueous NaHCO$_3$ (50 mL), extracted with EtOAc and dried (MgSO$_4$) to give a colourless oil which was purified by silica chromatography to give 4-(tetrahydro-pyran-4-yl)-piperazine-1-carboxylic acid tert-butyl ester (0.54 g, 25%), as a white solid. BOC-deprotection was carried out as in Reference Example 3 to give the title compound (0.30 g, 88%).

Reference Example 108

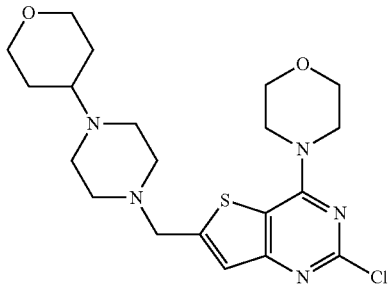

2-Chloro-4-morpholin-4-yl-6-[4-(tetrahydro-pyran-4-yl)-piperazin-1-ylmethyl]-thieno[3,2-d]pyrimidine Prepared from 1-(tetrahydro-pyran-4-yl)-piperazine and 2-chloro-4-morpholin-4-yl-thieno[3,2-d]pyrimidine-6-carbaldehyde under reductive amination conditions described in Reference Example 39, to give, after silica chromatography purification, the title compound as a white solid (190 mg, 61%) [M+H]$^+$ 439.4

Reference Example 109

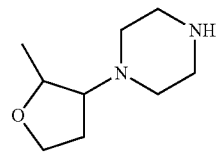

(±)-1-(2-Methyl-tetrahydro-furan-3-yl)-piperazine 4-(2-Methyl-tetrahydro-furan-3-yl)-piperazine-1-carboxylic acid tert-butyl ester (1.01 g, 53%) was prepared in an analogous fashion to 4-(tetrahydro-pyran-4-yl)-piperazine-1-carboxylic acid tert-butyl ester. This was BOC-deprotected as in Reference Example 3 to give the title compound as a white solid (370 mg, 98%).

NMR $\delta_H$ (400 MHz, CDCl$_3$): 1.16 (d, 3H); 1.96 (m, 2H); 2.70 (m, 2H); 2.86 (m, 2H); 2.97 (m, 1H); 3.22 (m, 4H); 3.79 (m, 1H); 3.99 (m, 2H); 8.25 (bs, 1H).

Reference Example 110

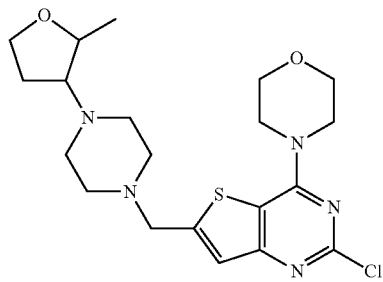

(±)2-Chloro-6-[4-(2-methyl-tetrahydro-furan-3-yl)-piperazin-1-ylmethyl]-4-morpholin-4-yl-thieno[3,2-d]pyrimidine 1-(2-methyl-tetrahydro-furan-3-yl)-piperazine was reacted with 2-chloro-4-morpholin-4-yl-thieno[3,2-d]pyrimidine-6-carbaldehyde under reductive amination conditions described in Reference Example 39, to give, after silica chromatography purification the title compound as a white solid (110 mg, 43%).

[M+H]$^+$ 439.2

Reference Example 111

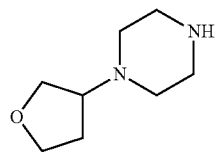

(±)-1-(Tetrahydro-furan-3-yl)-piperazine

To tetrahydro-furan-3-ol (1.0 g, 11.4 mmol) in anhydrous dichloromethane (15 mL) with triethylamine (2.37 mL, 17.03 mmol), was added methane sulfonyl chloride (12.5 mmol) at 0° C. The reaction mixture was stirred at RT for 3.5 hours, diluted with dichloromethane (50 mL) and washed with water. The organic phase was dried (MgSO$_4$) and evaporated in-vacuo to give methanesulfonic acid tetrahydro-furan-3-yl ester as light orange oil (1.68 g, 89%). A mixture of piperazine-1-carboxylic acid tert-butyl ester (1.0 g, 5.38 mmol), methanesulfonic acid tetrahydrofuran-3-yl ester (1.07 g, 6.45 mmol) and K$_2$CO$_3$ (2.96 g, 21.5 mmol) was stirred in anhydrous acetonitrile (50 mL) under reflux conditions for 12 hours. The reaction mixture was cooled and poured onto water and extracted with dichloromethane to give after silica chromatography, 4-(tetrahydro-furan-3-yl)-piperazine-1-carboxylic acid tert-butyl ester, as a colourless oil (0.57 g, 41%).

NMR δ$_H$(400 MHz, CDCl$_3$): 1.54 (s, 9H); 1.85-2.10 (m, 2H); 2.37-2.48 (m, 4H); 3.06 (m, 1H); 3.46 (m, 4H); 3.67-3.97 (m, 4H).

4-(Tetrahydro-furan-3-yl)-piperazine-1-carboxylic acid tert-butyl ester (0.57 g, 2.21 mmol) was BOC-deprotected as in Reference Example 3, to give, the title compound as a gummy residue (264 mg, 76%).

Reference Example 112

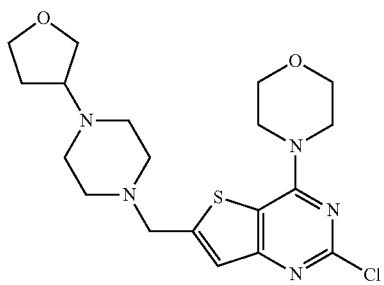

(±)-2-Chloro-4-morpholin-4-yl-6-[4-(tetrahydro-furan-3-yl)-piperazin-1-ylmethyl]-thieno[3,2-d]pyrimidine Prepared from 2-chloro-4-morpholin-4-yl-thieno[3,2-d]pyrimidine-6-carbaldehyde and 1-(tetrahydro-furan-3-yl)-piperazine under reductive amination conditions described in Reference Example 39, to give after silica chromatography, the title compound as a white solid (217 mg, 60%).

NMR δ$_H$(400 MHz, CDCl$_3$): 1.87 (m, 1H); 2.06 (m, 1H); 2.49-2.61 (bs, 8H); 3.01 (m, 1H); 3.64-4.02 (m, 14H); 7.19 (s, 1H).

Reference Example 113

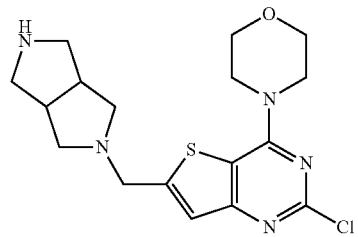

2-Chloro-6-(hexahydro-pyrrolo[3,4-c]pyrrol-2-ylmethyl)-4-morpholin-4-yl-thieno[3,2-d]pyrimidine To a stirred solution of 5-(2-chloro-4-morpholin-4-yl-thieno[3,2-d]pyrimidin-6-ylmethyl)-hexahydro-pyrrolo[3,4-c]pyrrole-2-carboxylic acid tert-butyl ester (390 mg; 0.81 mmol) in CH$_2$Cl$_2$ (4 mL) was added TFA (6 mL). The reaction mixture was stirred at RT for 4 h upon which time volatiles were removed in vacuo. Purification by SCX-2 gave the title compound as an off-white solid (273 mg; 89%).

δ$_H$(400 MHz, CDCl$_3$) 1.72 (br s, 1H), 2.49-3.01 (m, 10H), 3.85-3.90 (m, 6H), 3.99-4.01 (m, 4H), 7.15 (s, 1H).

Reference Example 114

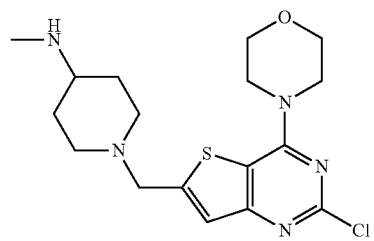

[1-(2-Chloro-4-morpholin-4-yl-thieno[3,2-d]pyrimidin-6-ylmethyl)-piperidin-4-yl]-methyl-amine To a stirred suspension of 2-chloro-4-morpholin-4-yl-thieno[3,2-d]pyrimidine-6-carbaldehyde (1.0 g; 3.5 mmol), 4-N-Boc-4-N-methylaminopiperidine (1.0 g; 4.7 mmol) and AcOH (0.2 mL) in 1,2-dichloroethane (25 mL) was added NaB(OAc)$_3$H (1.0 g; 4.7 mmol). The reaction mixture was stirred at RT for 5 h upon which time it was quenched with saturated NaHCO$_3$ solution (30 mL), diluted with H$_2$O (50 mL) and extracted with EtOAc (200 mL). The organic layer was dried (Na$_2$SO$_4$) and concentrated to a yellow foam (1.84 g). This foam was dissolved in CH$_2$Cl$_2$ (20 mL) and treated with TFA (10 mL) at RT overnight (17 h). Volatiles were removed in vacuo, the residue was taken up in 2M HCl (30 mL) and washed with CH$_2$Cl$_2$ (40 mL). The aqueous layer was basified with saturated Na$_2$CO$_3$ solution, extracted into CH$_2$Cl$_2$, the organic layer separated (hydrophobic frit) and solvent evaporated to give the title compound as a pale yellow solid (1.18 g; 88%).

δ$_H$ (400 MHz, CDCl$_3$) 1.18-1.42 (m, 3H), 1.7-1.75 (m, 2H), 1.99-2.05 (m, 2H), 2.20-2.27 (m, 1H), 2.28 (s, 3H), 2.73-2.76 (m, 2H), 3.62 (s, 2H), 3.66-3.69 (m, 4H), 3.81-3.84 (m, 4H), 6.98 (s, 1H).

Reference Example 115

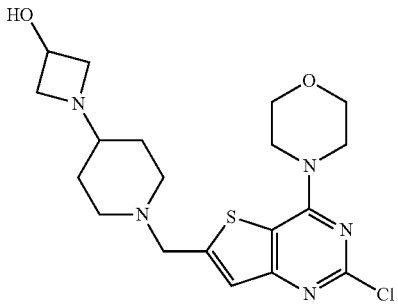

1-[1-(2-Chloro-4-morpholin-4-yl-thieno[3,2-c]pyrimidin-6-ylmethyl)-piperidin-4-yl]-azetidin-3-ol To a stirred solution of 1-Boc-4-piperidone (1.2 g; 6.0 mmol), 3-hydroxyazetidine (0.43 g; 5.9 mmol) in 1,2-dichloroethane (30 mL) was added NaB(OAc)$_3$H (3.81 g; 18.0 mmol). The reaction mixture was stirred at RT overnight (16 h), quenched with saturated NaHCO$_3$ solution (20 mL), the layers separated (hydrophobic frit) and solvent evaporated. The resulting residue (926 mg; 3.6 mmol) was Boc-deprotected (TFA/CH$_2$Cl$_2$) and after evaporation of volatiles 1-piperidin-4-yl-azetidin-3-ol trifluoroacetate was obtained as a thick oil.

To a stirred suspension of 2-chloro-4-morpholin-4-yl-thieno[3,2-d]pyrimidine-6-carbaldehyde (1.13 g; 4.0 mmol) in 1,2-dichloroethane (20 mL) was added a solution of 1-piperidin-4-yl-azetidin-3-ol trifluoroacetate (3.6 mmol) in THF (5 mL) followed by NaB(OAc)$_3$H (2.12 g; 10.0 mmol). The reaction mixture was stirred at RT overnight (16 h) and product isolated by acid/base extraction. Purification by ISCO gave the title compound as a white solid (0.50 g; 30%).

δ$_H$ (400 MHz, CDCl$_3$) 1.30-1.47 (m, 2H). 1.60-1.80 (m, 3H), 2.04-2.21 (m, 3H), 2.81-2.90 (m, 4H), 3.59-3.68 (m, 2H), 3.80 (s, 2H), 3.84-3.87 (m, 4H), 3.98-4.01 (m, 4H), 4.47 (quintet, J=5.6, 1H), 7.15 (s, 1H).

Reference Example 116

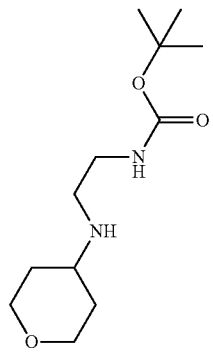

[2-(Tetrahydro-pyran-4-ylamino)-ethyl]-carbamic acid tert-butyl ester

To a solution of (2-amino-ethyl)-carbamic acid tert-butyl ester (5 g, 31.2 mmol) in DCE (150 mL) was added tetrahydro-pyran-4-one (2.7 mg, 27.1 mmol). The mixture was stirred at RT for 1 h, then sodium triacetoxyborohydride (8.63 g, 40.7 mmol) was added and stirring was continued for 18 h. The reaction mixture was diluted with NH$_4$OH 10% in water and extracted with DCM. The organic layer was separated, dried (Na$_2$SO$_4$) and concentrated in vacuo to give the title compound as colourless oil (6.60 g, 99%).

[M+H]$^+$ 245.1

Reference Example 117

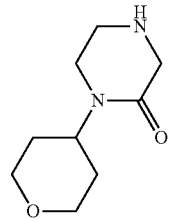

1-(Tetrahydro-pyran-4-yl)-piperazin-2-one

To a solution of [2-(tetrahydro-pyran-4-ylamino)-ethyl]-carbamic acid tert-butyl ester (6.60 g, 27.0 mmol) in DCM (100 mL) was added triethylamine (11.3 mL, 81.1 mmol) followed by chloroacetyl chloride (3.64 g, 32.4 mmol) dropwise. The reaction mixture was stirred at RT for 24 h, then partitioned between DCM and saturated NaHCO$_3$ aqueous solution. The organic layer was isolated, dried (Na$_2$SO$_4$) and concentrated in vacuo. To a solution of the resulting residue in THF (50 mL) was added sodium hydride (60% in mineral oil) (1.62 g, 40.6 mmol). The reaction mixture was stirred at RT for 20 h, then partitioned between DCM and water. The organic layer was dried (Na$_2$SO$_4$) and concentrated in vacuo to yield an orange residue. The residue (7.66 g, 27.0 mmol) was dissolved in dichloromethane (15 mL) and TFA (15 mL) was added. The resulting solution was stirred at RT for 4 h before being concentrated in vacuo. The resultant residue was loaded onto an Isolute® SCX-2 cartridge, washed with MeOH then eluted with 2 M NH$_3$ in MeOH to give the title compound as yellow oil (4.26 g, 86%).

[M+H]$^+$ 184.9

Reference Example 118

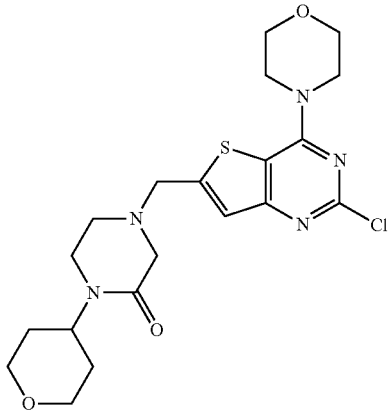

4-(2-Chloro-4-morpholin-4-yl-thieno[3,2-d]pyrimidin-6-ylmethyl)-1-(tetrahydro-pyran-4-yl)-piperazin-2-one To a solution of 6-bromomethyl-2-chloro-4-morpholin-4-yl-thieno[3,2-d]pyrimidine (200 mg, 0.57 mmol), in DMF (4 mL), was added 1-(tetrahydro-pyran-4-yl)-piperazin-2-one (116 mg, 0.63 mmol) and potassium carbonate (238 mg, 1.72 mmol). The mixture was stirred at RT for 4 h, then the reaction mixture was diluted with water and extracted with DCM. The organic layer was separated, dried ($Na_2SO_4$) and concentrated in vacuo to give the title compound as a yellow solid (212 mg, 82%).
[M+H]$^+$ 452.2

Preparation of Compounds of Formula (I)

Example 1

6-(4-Azetidin-1-yl-piperidin-1-ylmethyl)-2-(6-fluoro-1H-indol-4-yl)-4-morpholin-4-yl-thieno[3,2-d]pyrimidine Prepared by using general Suzuki coupling method A. The title compound was obtained as an orange gum (12.1 mg, 24%).
[M+H]$^+$ 507.2
NMR δ$_H$ (400 MHz, CDCl$_3$) 1.42-1.78 (m, 6H), 2.16 (m, 4H), 2.95 (m, 2H), 3.33 (m, 3H), 3.84 (s, 2H), 3.91 (m, 4H), 4.08 (m, 4H), 7.17 (dd, J=8.9, 2.1 Hz, 1H), 7.30 (dd, J=3.2, 2.5 Hz, 1H), 7.33 (s, 1H), 7.53 (m, 1H), 7.96 (dd, J=10.9, 2.1 Hz, 1H) and 8.27 (bs, 1H).

Example 2

Cyclopropylmethyl-{1-[2-(5-fluoro-1H-indol-4-yl)-4-morpholin-4-yl-thieno[3,2-d]pyrimidin-6-ylmethyl]-piperidin-4-yl}-amine Prepared by using general Suzuki coupling method A. The title compound was obtained as a cream solid (55 mg, 67%).
[M+H]$^+$ 521.3
NMR δ$_H$ (400 MHz, CD$_3$OD) 0.16 (m, 2H), 0.51 (m, 2H), 0.94 (m, 1H), 1.46 (m, 2H), 1.90 (d, J=12.1 Hz, 2H), 2.14 (dt, J=12.1, 2.2 Hz, 2H), 2.48 (d, J=6.9 Hz, 2H), 2.56 (m, 1H), 2.98 (d, J=12.0 Hz, 2H), 3.82 (m, 6H), 4.03 (m, 4H), 6.63 (dd, J=3.1, 0.8 Hz, 1H), 6.98 (dd, J=10.8, 8.8 Hz, 1H), 7.29 (s, 1H), 7.32 (d, J=3.1 Hz, 1H) and 7.44 (ddd, J=8.8, 4.0, 0.8 Hz, 1H).

Example 3

Cyclopropylmethyl-{1-[2-(6-fluoro-1H-indol-4-yl)-4-morpholin-4-yl-thieno[3,2-d]pyrimidin-6-ylmethyl]-piperidin-4-yl}-amine Prepared by using general Suzuki coupling method A. The title compound was obtained as a cream solid (21 mg, 17%).
[M+H]$^+$ 521.3
NMR δ$_H$ (400 MHz, CDCl$_3$) 0.12 (m, 2H), 0.49 (m, 2H), 0.96 (m, 1H), 1.43-1.54 (m, 2H), 1.89 (m, 2H), 2.18 (m, 2H), 2.48-2.58 (m, 3H), 2.97 (d, J=11.9 Hz, 2H), 3.83 (m, 2H), 3.91 (m, 4H), 4.07 (m, 4H), 7.17 (ddd, J=8.8, 2.3, 0.8 Hz, 1H), 7.30 (d, J=2.3 Hz, 1H) 7.33 (s, 1H), 7.53 (m, 1H), 7.96 (dd, J=11.2, 2.3 Hz, 1H) and 8.27 (bs, 1H).

Example 4

Cyclopropyl-{1-[2-(6-fluoro-1H-indol-4-yl)-4-morpholin-4-yl-thieno[3,2-d]pyrimidin-6-ylmethyl]-piperidin-4-yl}-amine Prepared by using general Suzuki coupling method A. The title compound was obtained as a white solid (40 mg, 63%).
[M+H]$^+$ 507.3
NMR δ$_H$ (400 MHz, CDCl$_3$) 0.38 (bs, 2H), 0.47 (m, 2H), 1.43-1.57 (m, 2H), 1.96 (d, J=12.7 Hz, 2H), 2.11-2.22 (m, 3H), 2.60-2.69 (m, 1H), 2.95 (d, J=11.3 Hz, 2H), 3.82 (d, J=1.0 Hz, 2H), 3.87-3.92 (m, 4H), 4.03-4.08 (m, 4H), 7.15 (ddd, J=8.8, 2.4, 1.0 Hz, 1H), 7.28 (dd, J=3.3, 2.4 Hz, 1H), 7.32 (s, 1H), 7.51 (m, 1H), 7.95 (dd, J=11.2, 2.4 Hz, 1H) and 8.26 (bs, 1H).

Example 5

6-[(S)-1-(Hexahydro-pyrrolo[1,2-a]pyrazin-2-yl)methyl]-2-(1H-indol-4-yl)-4-morpholin-4-yl-thieno[3,2-d]pyrimidine Prepared by using general Suzuki coupling method A. The title compound was obtained as a tan solid (71 mg, 91%).
[M+H]$^+$ 475.3
NMR δ$_H$ (400 MHz, CDCl$_3$) 1.60 (bs, 2H), 1.84 (m, 2H), 2.07 (m, 1H), 2.23 (bs, 2H), 2.45 (bs, 2H), 2.95 (d, J=8.7 Hz, 1H), 3.09 (m, 3H), 3.87-3.95 (m, 6H), 4.08 (m, 4H), 7.29-7.34 (m, 2H), 7.38 (s, 1H), 7.49 (d, J=8.0 Hz, 1H), 7.50-7.56 (m, 1H), 8.18 (dd, J=8.0, 1.0 Hz, 1H) and 8.29 (bs, 1H).

Example 6

2-(5-Fluoro-1H-indol-4-yl)-6-[(S)-1-(hexahydro-pyrrolo[1,2-a]pyrazin-2-yl)methyl]-4-morpholin-4-yl-thieno[3,2-t]pyrimidine Prepared by using general Suzuki coupling method A. The title compound was obtained as a tan solid (55 mg, 68%).
[M+H]$^+$ 493.3
NMR δ$_H$ (400 MHz, CD$_3$OD) 1.34-1.45 (m, 1H), 1.73-1.86 (m, 3H), 2.04 (t, J=10.3 Hz, 1 H), 2.14-2.24 (m, 2H), 2.33-2.42 (m, 2H), 2.89-2.94 (m, 1H), 2.97-3.08 (m, 3H), 3.78-3.83 (m, 4H), 3.93 (d, J=1.0 Hz, 1H), 3.94 (d, J=1.0 Hz, 1H), 4.03 (m, 4H), 6.58 (dd, J=3.0, 0.9 Hz, 1H), 6.95 (m, 1H), 7.29 (d, J=3.0 Hz, 2H) and 7.41 (ddd, J=8.8, 4.0, 0.9 Hz, 1H).

Example 7

2-(6-Fluoro-1H-indol-4-yl)-6-[(S)-1-(hexahydro-pyrrolo[1,2-a]pyrazin-2-yl) methyl]-4-morpholin-4-yl-thieno[3,2-d]pyrimidine To a solution of toluene-4-sulfonic acid 2-[6-fluoro-1-(toluene-4-sulfonyl)-1H-indol-4-yl]-4-morpholin-4-yl-thieno[3,2-d]pyrimidin-6-ylmethyl ester (100 mg, 0.144 mmol) in DMF (1 mL) were added potassium carbonate (100 mg, 0.724 mmol) and (S)-octahydro-pyrrolo[1,2-a]pyrazine (36 mg, 0.289 mmol). The reaction mixture was stirred at RT for 2 h before water and DCM were added. The phases were separated using a hydrophobic frit and the organic phase was concentrated in vacuo.

The resultant residue was dissolved in dioxane (1 mL) and IMS (1 mL), and an aqueous solution of NaOH (12 M, 1 mL, 12 mmol) was added. The mixture was stirred at RT for 3 h before a saturated aqueous solution of ammonium chloride and DCM were added. The phases were separated using a hydrophobic frit and the organic phase was concentrated in vacuo. The resultant residue was purified by column chromatography to give the title compound as a white solid (35 mg, 49%).

[M+H]$^+$ 493.3

NMR $\delta_H$ (400 MHz, DMSO-d$_6$) 1.21-1.31 (m, 1H), 1.59-1.75 (m, 3H), 1.87-1.96 (m, 1H), 1.97-2.11 (m, 2H), 2.14-2.31 (m, 2H), 2.84 (d, J=9.6 Hz, 1H), 2.89-3.01 (m, 3H), 3.82 (m, 4H), 3.90 (d, J=14.8 Hz, 1H), 3.94 (d, J=14.8 Hz, 1H), 3.99 (m, 4H), 7.30 (dd, J=9.3, 2.5 Hz, 1H), 7.42-7.45 (m, 3H), 7.89 (dd, J=11.5, 2.5 Hz, 1H) and 11.28 (bs, 1H).

Example 8

6-(Hexahydro-pyrrolo[3,4-c]pyrrol-2-ylmethyl)-2-(1H-indol-4-yl)-4-morpholin-4-yl-thieno[3,2-yl]pyrimidine Prepared by using general Suzuki coupling method A, followed by BOC-deprotection using TFA:DCM (1:2). The title compound was obtained as a tan solid (27 mg, 28%).

[M+H]$^+$ 461.3

NMR $\delta_H$ (400 MHz, CD$_3$OD) 2.60-2.66 (m, 4H), 2.78 (m, 4H), 2.99-3.06 (m, 2H), 3.86 (t, J=4.7 Hz, 4H), 3.92 (s, 2H), 4.08 (t, J=4.7 Hz, 4H), 7.17-7.24 (m, 2H), 7.32 (m, 2H), 7.50 (d, J=8.0 Hz, 1H) and 7.89 (d; J=7.4 Hz, 1H).

Example 9

2-(5-Fluoro-1H-indol-4-yl)-6-(hexahydro-pyrrolo[3,4-c]pyrrol-2-ylmethyl)-4-morpholin-4-yl-thieno[3,2-d]pyrimidine Prepared by using general Suzuki coupling method A, followed by BOC-deprotection using TFA:DCM (1:5). The title compound was obtained as a tan solid (36 mg, 36%).

[M+H]$^+$ 479.3

NMR $\delta_H$ (400 MHz, DMSO-d$_6$) 2.37 (d, J=8.8 Hz, 2H), 2.50-2.59 (m, 4H), 2.67 (t, J=6.9 Hz, 2H), 2.77-2.83 (m, 2H), 3.17 (d, J=3.6 Hz, 1H), 3.77 (t, J=4.7 Hz, 4H), 3.89 (s, 2H), 3.90-3.95 (m, 4H), 6.67 (t, J=2.4 Hz, 1H), 7.00 (dd, J=11.1, 8.8 Hz, 1H), 7.35 (s, 1H), 7.41-7.47 (m, 2H) and 11.23 (bs, 1H).

Example 10

2-(6-Fluoro-1H-indol-4-yl)-6-(hexahydro-pyrrolo[3,4-c]pyrrol-2-ylmethyl)-4-morpholin-4-yl-thieno[3,2-d]pyrimidine Prepared according to the method used in the preparation of 2-(6-fluoro-1H-indol-4-yl)-6-[(S)-1-(hexahydro-pyrrolo[1,2-d]pyrazin-2-yl)methyl]-4-morpholin-4-yl-thieno-[3,2-d]pyrimidine using hexahydro-pyrrolo[3,4-c]pyrrole-2-carboxylic acid tert-butyl ester in place of (S)-octahydro-pyrrolo[1,2-a]pyrazine, followed by BOC-deprotection using TFA:DCM (1:1). The title compound was obtained as a white solid (34 mg, 47%).

[M+H]$^+$ 479.3

NMR $\delta_H$ (400 MHz, DMSO-d$_6$) 2.38 (dd, J=8.4, 2.5 Hz, 2H), 2.53-2.61 (m, 4H), 2.64-2.70 (m, 2H), 2.78-2.85 (m, 2H), 3.82 (m, 4H), 3.90 (s, 2H), 3.99 (m, 4H), 7.30 (dd, J=9.2, 2.6 Hz, 1H), 7.40-7.46 (m, 3H), 7.89 (dd, J=11.4, 2.6 Hz, 1H) and 11.29 (bs, 1H).

Example 11

6-(2,7-Diaza-spiro[3.5]non-2-ylmethyl)-2-(1H-indol-4-yl)-4-morpholin-4-yl-thieno[3,2-d]pyrimidine Prepared by using general Suzuki coupling method A, followed by BOC-deprotection using TFA:DCM (1:3). The title compound was obtained as a tan solid (57 mg, 59%).

[M+H]$^+$ 475.3

NMR $\delta_H$ (400 MHz, CD$_3$OD) 1.74 (t, J=5.2 Hz, 4H), 2.73 (t, J=5.2 Hz, 4H), 3.18 (s, 4H), 3.85 (t, J=4.7 Hz, 4H), 3.97 (s, 2H), 4.06 (t, J=4.7 Hz, 4H), 7.16-7.23 (m, 2H), 7.31 (m, 2 H), 7.48 (dt, J=8.1, 1.0 Hz, 1H) and 7.88 (dd, J=7.5, 1.0 Hz, 1H).

Example 12

6-(2,7-Diaza-spiro[3.5]non-2-ylmethyl)-2-(5-fluoro-1H-indol-4-yl)-4-morpholin-4-yl-thieno[3,2-d]pyrimidine Prepared by using general Suzuki coupling method A, followed by BOC-deprotection using TFA:DCM (1:5). The title compound was obtained as a tan solid (18 mg, 18%).

[M+H]$^+$ 493.3

NMR $\delta_H$ (400 MHz, DMSO-d$_6$) 1.67 (t, J=5.1 Hz, 4H), 2.65-2.72 (m, 4H), 2.99-3.11 (m, 5 H), 3.77 (m, 4H), 3.84-3.95 (m, 6H), 6.66 (m, 1H), 6.99 (dd, J=11.1, 8.8 Hz, 1H), 7.32 (m, 1H), 7.41-7.47 (m, 21-1) and 11.24 (bs, 1H).

Example 13

6-(2,7-Diaza-spiro[3.5]non-2-ylmethyl)-2-(6-fluoro-1H-indol-4-yl)-4-morpholin-4-yl-thieno[3,2-d]pyrimidine Prepared according to the method used in the preparation of 2-(6-fluoro-1H-indol-4-yl)-6-[(S)-1-(hexahydro-pyrrolo[1,2-a]pyrazin-2-yl)methyl]-4-morpholin-4-yl-thieno-[3,2-d]pyrimidine using 2,7-diaza-spiro[3.5]nonane-7-carboxylic acid tert-butyl ester hydrochloride in place of (S)-octahydropyrrolo[1,2-c]pyrazine, followed by BOC-deprotection using TFA:DCM (1:1). The title compound was obtained as a white solid (29 mg, 49%).

[M+H]+ 493.1

NMR δ$_H$ (400 MHz, DMSO-d$_6$) 1.63 (t, J=5.1 Hz, 4H), 2.64 (t, J=5.1 Hz, 4H), 3.05 (s, 4 H), 3.81 (t, J=4.6 Hz, 4H), 3.94 (s, 2H), 3.97 (t, J=4.6 Hz, 4H), 7.29 (m, 1H), 7.38 (s, 1 H), 7.42 (m, 2H), 7.82-7.91 (m, 1H) and 11.27 (bs, 1H).

Example 14

6-(3,8-Diaza-bicyclo[3.2.1]oct-3-ylmethyl)-2-(6-fluoro-1H-indol-4-yl)-4-morpholin-4-yl-thieno[3,2-d]pyrimidine Prepared by using general Suzuki coupling method A, followed by BOC-deprotection using TFA:DCM (1:3). The title compound was obtained as an off-white solid (68 mg, 68%).

[M+H]+ 479.2

NMR δ$_H$ (400 MHz, CDCl$_3$) 1.70-1.76 (m, 2H), 1.94-2.05 (m, 2H), 2.32 (d, J=10.6 Hz, 2 H), 2.78 (dd, J=10.6, 2.6 Hz, 2H), 3.44 (bs, 2H), 3.77 (s, 2H), 3.88-3.93 (m, 4H), 4.07 (m, 4H), 7.15 (m, 1H), 7.28 (t, J=2.5 Hz, 1H), 7.32 (s, 1H), 7.51 (s, 1H), 7.94 (dd, J=11.2, 2.5 Hz, 1H) and 8.32 (bs, 1H).

Example 16

6-[(1S,5S)-1-(3,6-Diaza-bicyclo[3.1.1]hept-6-yl) methyl]-2-(6-fluoro-1H-indol-4-yl)-4-morpholin-4-yl-thieno[3,2-d]pyrimidine Prepared according to the method used in the preparation of 2-(6-fluoro-1H-indol-4-yl)-6-[(S)-1-(hexahydro-pyrrolo [1,2-c]pyrazin-2-yl)methyl]-4-morpholin-4-yl-thieno-[3,2-d]pyrimidine using ((1S,5S)-3,6-diaza-bicyclo[3.1.1]heptane-3-carboxylic acid tert-butyl ester in place of (S)-octahydro-pyrrolo[1,2-a]pyrazine, followed by BOC-deprotection using TFA:DCM (1:1). The title compound was obtained as a white solid (27 mg, 38%).

[M+H]+ 465.3

NMR δ$_H$ (400 MHz, DMSO-d$_6$) 1.50 (d, J=9.5 Hz, 1H), 1.78 (d, J=9.5 Hz, 1H), 2.53 (d, J=9.6 Hz, 1H), 2.77 (dd, J=10.0, 2.1 Hz, 1H), 2.85 (dd, J=9.6, 2.4 Hz, 1H), 3.08 (d, J=10.0 Hz, 1H), 3.47 (s, 1H), 3.56 (s, 1H), 3.82 (m, 4H), 3.97-4.13 (m, 6H), 7.30 (ddd, J=9.3, 2.4, 0.8 Hz, 1H), 7.39-7.46 (m, 3H), 7.89 (dd, J=11.5, 2.4 Hz, 1H) and 11.28 (bs, 1H).

Example 18

6-(2,7-Diaza-spiro[3.5]non-7-ylmethyl)-2-(6-fluoro-1H-indol-4-yl)-4-morpholin-4-yl-thieno[3,2-d]pyrimidine Prepared according to the method used in the preparation of 2-(6-fluoro-1H-indol-4-yl)-6-[(S)-1-(hexahydro-pyrrolo [1,2-a]pyrazin-2-yl)methyl]-4-morpholin-4-yl-thieno-[3,2-d]pyrimidine using 2,7-diaza-spiro[3.5]nonane-2-carboxylic acid tert-butyl ester hydrochloride in place of (S)-octahydro-pyrrolo[1,2-a]pyrazine, followed by BOC-deprotection using TFA:DCM (1:1). The title compound was obtained as a white solid (27 mg, 44%).

[M+H]+ 493.3

NMR δ$_H$ (400 MHz, DMSO-d$_6$) 1.74 (bs, 4H), 2.39 (bs, 4H), 3.42 (bs, 4H), 3.81 (m, 6H), 3.97 (m, 4H), 7.29 (dd, J=9.3, 2.5 Hz, 1H), 7.40-7.45 (m, 3H), 7.88 (dd, J=11.5, 2.5 Hz, 1 H) and 11.29 (bs, 1H).

Example 19

6-(2,8-Diaza-spiro[4.5]dec-8-ylmethyl)-2-(6-fluoro-1H-indol-4-yl)-4-morpholin-4-yl-thieno[3,2-d]pyrimidine Prepared by using general Suzuki coupling method A, followed by BOC-deprotection using TFA:DCM (1:1). The title compound was obtained as a tan solid (50 mg, 49%).

[M+H]+ 507.3

NMR δ$_H$ (400 MHz, DMSO-d$_6$) 1.59 (t, J=6.7 Hz, 6H), 2.48 (s, 4H), 2.74 (m, 3H), 2.98 (t, J=6.7 Hz, 2H), 3.79 (s, 2H), 3.87 (t, J=4.7 Hz, 4H), 4.04 (t, J=4.7 Hz, 4H), 7.12 (ddd, J=8.9, 2.4, 0.9 Hz, 1H), 7.25 (d, J=3.3 Hz, 1H), 7.31 (s, 1H), 7.49 (m, 1H), 7.92 (dd, J=11.2, 2.4 Hz, 1H) and 8.38 (bs, 1H).

Example 20

6-(2,7-Diaza-spiro[4.4]non-2-ylmethyl)-2-(6-fluoro-1H-indol-4-yl)-4-morpholin-4-yl-thieno[3,2-d]pyrimidine Prepared by using general Suzuki coupling method A, followed by BOC-deprotection using TFA:DCM (1:1). The title compound was obtained as a tan solid (21 mg, 23%).

[M+H]+ 493.3

NMR δ$_H$ (400 MHz, DMSO-d$_6$) 1.73-1.92 (m, 4H), 2.43-2.59 (m, 2H), 2.58-2.68 (m, 1H), 2.66-2.77 (m, 1H), 2.76-2.87 (m, 2H), 2.90-3.08 (m, 3H), 3.83-3.94 (m, 4H), 3.96 (s, 2H), 4.04-4.09 (m, 4H), 7.15 (ddd, J=10.1, 2.4, 0.9 Hz, 1H), 7.28 (d, J=3.3 Hz, 1H), 7.33 (s, 1 H), 7.52 (d, J=3.3 Hz, 1H), 7.95 (dd, J=10.1, 2.4 Hz, 1H) and 8.41 (bs, 1H).

Example 21

2-(6-Fluoro-1H-indol-4-yl)-4-morpholin-4-yl-6-(octahydro-pyrrolo[3,2-c]pyridin-5-ylmethyl)-thieno[3,2-d]pyrimidine Prepared by BOC-deprotection of 5-[2-(6-fluoro-1H-indol-4-yl)-4-morpholin-4-yl-thieno[3,2-d]pyrimidin-6-ylmethyl]-octahydro-pyrrolo[3,2-c]pyridine-1-carboxylic acid tert-butyl ester using TFA:DCM (1:6). The title compound was obtained as a white solid (8.3 mg, 7%).

[M+H]+ 493.2

NMR δ$_H$ (400 MHz, DMSO-d$_6$) 1.74-1.98 (m, 4H), 2.20-2.29 (m, 2H), 2.39-2.47 (m, 1H), 2.50-2.63 (m, 2H), 2.96 (td, J=10.3, 5.6 Hz, 1H), 3.08-3.16 (m, 2H), 3.81 (s, 2H), 3.91 (m, 4H), 4.05-4.10 (m, 4H), 7.17 (ddd, J=8.9, 2.4, 0.9 Hz, 1H), 7.30 (dd, J=3.3, 2.4 Hz, 1H), 7.35 (s, 1H), 7.53 (m, 1H), 7.96 (dd, J=11.2, 2.4 Hz, 1H) and 8.26 (bs, 1H).

Example 22

2-(6-Fluoro-1H-indol-4-yl)-4-morpholin-4-yl-6-[(3aS,7aR)-1-(octahydro-pyrrolo[3,2-c]pyridin-5-yl) methyl]-thieno[3,2-d]pyrimidine Prepared by BOC-deprotection of (3aS,7aR)-5-[2-(6-fluoro-1H-indol-4-yl)-4-morpholin-4-yl-thieno[3,2-d]pyrimidin-6-ylmethyl]-octahydro-pyrrolo[3,2-c]pyridine-1-carboxylic acid tert-butyl ester using TFA:DCM (1:6). The title compound was obtained as a beige solid.

The analytical data are identical to those obtained for the racemic mixture.

Example 23

2-(6-Fluoro-1H-indol-4-yl)-4-morpholin-4-yl-6-[(3aR,7aS)-1-(octahydro-pyrrolo[3,2-c]pyridin-5-yl)methyl]-thieno[3,2-d]pyrimidine Prepared by BOC-deprotection of (3aR,7aS)-5-[2-(6-fluoro-1H-indol-4-yl)-4-morpholin-4-yl-thieno[3,2-d]pyrimidin-6-ylmethyl]-octahydro-pyrrolo[3,2-c]pyridine-1-carboxylic acid tert-butyl ester using TFA:DCM (1:6). The title compound was obtained as a beige solid.

The analytical data are identical to those obtained for the racemic mixture.

Example 24

2-(6-Fluoro-1H-indol-4-yl)-6-[(R)-1-(hexahydro-pyrrolo[1,2-a]pyrazin-2-yl)methyl]-4-morpholin-4-yl-thieno[3,2-d]pyrimidine Prepared by using general Suzuki coupling method A. The title compound was obtained as a white solid (98 mg, 92%).
[M+H]+ 493.2
NMR $\delta_H$ (400 MHz, CDCl$_3$) 1.42 (m, 1H), 1.70-1.90 (m, 3H), 1.98-2.07 (m, 1H), 2.14-2.23 (m, 2H), 2.35-2.47 (m, 2H), 2.92-2.97 (m, 1H), 3.01-3.14 (m, 3H), 3.88-3.96 (m, 6H), 4.05-4.10 (m, 4H), 7.17 (ddd, J=8.9, 2.4, 0.9 Hz, 1H), 7.29 (dd, J=3.3, 2.4 Hz, 1H), 7.37 (m, 1H), 7.53 (m, 1H), 7.93-7.98 (m, 1H) and 8.30 (bs, 1H).

Example 27

4-[2-(5-Fluoro-1H-indol-4-yl)-4-morpholin-4-yl-thieno[3,2-d]pyrimidin-6-ylmethyl]-1-oxa-4,9-diaza-spiro[5.5]undecane Prepared by using general Suzuki coupling method A, followed by TBDMS-deprotection using TBAF:THF (1:10) and BOC-deprotection using TFA:DCM (1:2). The title compound was obtained as a white solid (37 mg, 38%).
[M+H]+ 523.2
NMR $\delta_H$ (400 MHz, CD$_3$OD) 1.51-1.61 (m, 2H), 1.95 (m, 2H), 2.38 (s, 2H), 2.56 (t, J=4.6 Hz, 2H), 2.72 (dt, J=12.7, 4.6 Hz, 2H), 2.83-2.92 (m, 2H), 3.77 (t, J=4.6 Hz, 2H), 3.83 (m, 6H), 4.05 (t, J=4.7 Hz, 4H), 6.59 (dd, J=3.1, 0.9 Hz, 1H), 6.97 (dd, J=10.9, 8.8 Hz, 1 H), 7.31 (m, 2H) and 7.43 (ddd, J=8.8, 4.0, 0.9 Hz, 1H).

Example 28

9-[2-(5-Fluoro-1H-indol-4-yl)-4-morpholin-4-yl-thieno[3,2-d]pyrimidin-6-ylmethyl]-1-oxa-4,9-diaza-spiro[5.5]undecane Prepared by using general Suzuki coupling method A, followed by TBDMS-deprotection using TBAF:THF (1:10) and BOC-deprotection using TFA:DCM (1:2). The title compound was obtained as a tan solid (51 mg, 46%).
[M+H]+ 523.2
NMR $\delta_H$ (400 MHz, CD$_3$OD) 1.54-1.64 (m, 2H), 1.97 (d, J=13.7 Hz, 2H), 2.50 (t, J=11.0 Hz, 2H), 2.67 (m, 4H), 2.74 (t, J=4.8 Hz, 2H), 3.63 (t, J=4.8 Hz, 2H), 3.84 (m, 4H), 3.87 (t, J=4.7 Hz, 4H), 3.89 (s, 2H), 4.05 (t, J=4.7 Hz, 4H), 6.60 (dd, J=3.1, 0.9 Hz, 1H), 6.98 (dd, J=10.8, 8.8 Hz, 1H), 7.31 (m, 2H) and 7.43 (ddd, J=8.8, 4.0, 0.9 Hz, 1H).

Example 29

7-[2-(5-Fluoro-1H-indol-4-yl)-4-morpholin-4-yl-thieno[3,2-d]pyrimidin-6-ylmethyl]-2,7-diaza-spiro[3.5]nonan-1-one Prepared by using general Suzuki coupling method A. The title compound was obtained as a tan solid (47 mg, 41%).
[M+H]+ 507.2
NMR $\delta_H$ (400 MHz, CD$_3$OD) 1.84 (d, J=13.4 Hz, 2H), 2.01 (ddd, J=13.3, 9.8, 3.8 Hz, 2 H), 2.38 (t, J=10.5 Hz, 2H), 2.89-2.96 (m, 2H), 3.17 (s, 2H), 3.85 (t, J=4.7 Hz, 4H), 3.90 (s, 2H), 4.06 (t, J=4.7 Hz, 4H), 6.61 (dd, J=3.1, 0.9 Hz, 1H), 6.98 (dd, J=10.9, 8.8 Hz, 1 H), 7.32 (m, 2H) and 7.44 (ddd, J=8.8, 4.0, 0.9 Hz, 1H).

Example 31

6-(4-Azetidin-1-yl-piperidin-1-ylmethyl)-2-(1H-indol-4-yl)-4-morpholin-4-yl-thieno[3,2-d]pyrimidine Prepared by using general Suzuki coupling method A. The title compound was obtained as a tan solid (99 mg, 84%).
[M+H]+ 489.2
NMR $\delta_H$ (400 MHz, CDCl$_3$) 1.35-1.46 (m, 2H), 1.71 (d, J=13.6 Hz, 2H), 2.01-2.12 (m, 3 H), 2.13-2.23 (m, 2H), 2.93 (d, J=11.2 Hz, 2H), 3.21 (t, J=6.9 Hz, 4H), 3.83 (s, 2H), 3.91 (t, J=4.7 Hz, 4H), 4.08 (t, J=4.7 Hz, 4H), 7.27-7.34 (m, 3H), 7.49 (d, J=8.1 Hz, 1H), 7.53 (t, J=2.5 Hz, 1H), 8.16 (m, 1H) and 8.34 (bs, 1H).

Example 32

6-(4-Azetidin-1-yl-piperidin-1-ylmethyl)-2-(5-fluoro-1H-indol-4-yl)-4-morpholin-4-yl-thieno[3,2-d]pyrimidine Prepared by using general Suzuki coupling method A, followed by TBDMS-deprotection using TBAF:THF (1:10). The title compound was obtained as a cream oil (74 mg, 50%).
[M+H]+ 507.2
NMR $\delta_H$ (400 MHz, CDCl$_3$) 1.31-1.43 (m, 2H), 1.68 (m, 2H), 1.99-2.09 (m, 3H), 2.15 (m, 2 H), 2.90 (d, J=11.2 Hz, 2H), 3.17 (m, 4H), 3.80 (s, 2H), 3.84 (t, J=4.7 Hz, 4H), 4.02 (t, J=4.7 Hz, 4H), 6.87 (t, J=2.5 Hz, 1H), 6.96-7.05 (m, 1H), 7.25 (m, 1H), 7.29 (s, 1H), 7.33 (dd, J=8.8, 3.8 Hz, 1H) and 8.36 (bs, 1H).

Example 33

6-(3,8-Diaza-bicyclo[3.2.1]oct-3-ylmethyl)-2-(1H-indol-4-yl)-4-morpholin-4-yl-thieno[3,2-d]pyrimidine Prepared by using general Suzuki coupling method A, followed by TBDMS-deprotection using TBAF:THF (1:10) and BOC-deprotection using TFA:DCM (1:2). The title compound was obtained as a cream solid (25 mg, 45%).
[M+H]+ 461.2
NMR $\delta_H$ (400 MHz, DMSO-d$_6$) 1.57-1.62 (m, 2H), 1.80-1.86 (m, 2H), 2.25 (d, J=10.2 Hz, 2H), 2.64-2.70 (m, 2H), 3.33 (m, 2H), 3.79 (s, 2H), 3.82 (t, J=4.6 Hz, 4H), 3.98 (t, J=4.6 Hz, 4H), 7.18 (apparent t, J=7.8 Hz, 1H), 7.38 (s, 1H), 7.38-7.45 (m, 2H), 7.50 (d, J=7.8 Hz, 1H), 8.10 (dd, J=7.8, 0.9 Hz, 1H) and 11.20 (bs, 1H).

Example 34

6-(3,8-Diaza-bicyclo[3.2.1]oct-3-ylmethyl)-2-(5-fluoro-1H-indol-4-yl)-4-morpholin-4-yl-thieno[3,2-d]pyrimidine Prepared by using general Suzuki coupling method A, followed by TBDMS-deprotection using TBAF:THF (1:10) and BOC-deprotection using TFA:DCM (1:2). The title compound was obtained as a cream solid (91.8 mg, 77%).
[M+H]$^+$ 479.1
NMR $\delta_H$ (400 MHz, DMSO-d$_6$) 1.74 (m, 2H), 1.91 (d, J=7.2 Hz, 2H), 2.41 (d, J=10.6 Hz, 2H), 2.73 (d, J=10.6 Hz, 2H), 3.60 (bs, 2H), 3.77 (d, J=5.0 Hz, 4H), 3.85 (s, 2H), 3.92 (d, J=5.0 Hz, 4H), 6.66 (d, J=2.6 Hz, 1H), 6.99 (dd, J=11.0, 8.8 Hz, 1H), 7.32-7.40 (m, 1 H), 7.40-7.46 (m, 2H) and 11.23 (bs, 1H).

Example 35

6-(3,8-Diaza-bicyclo[3.2.1]oct-8-ylmethyl)-2-(6-fluoro-1H-indol-4-yl)-4-morpholin-4-yl-thieno[3,2-d]pyrimidine Prepared by using general Suzuki coupling method A. The title compound was obtained as a white solid (35 mg, 37%).
[M+H]$^+$ 479.2
NMR $\delta_H$ (400 MHz, CDCl$_3$) 1.85-1.97 (m, 2H), 2.05-2.12 (m, 2H), 2.77 (dd, J=12.1, 2.5 Hz, 3H), 3.16 (d, J=12.1 Hz, 2H), 3.23 (s, 2H), 3.82 (d, J=1.2 Hz, 2H), 3.89-4.00 (m, 4 H), 4.07-4.12 (m, 4H), 7.17 (ddd, J=10.0, 2.4, 0.9 Hz, 1H), 7.3 (m, 1H), 7.32 (m, 1H), 7.53 (d, J=3.1 Hz, 1H), 7.97 (dd, J=10.0, 2.4 Hz, 1H) and 8.33 (bs, 1H).

Example 36

6-(4-Cyclopropyl-piperazin-1-ylmethyl)-4-morpholin-4-yl-2-(2-trifluoromethyl-1H-indol-4-yl)-thieno[2,3-d]pyrimidine Prepared by using general Suzuki coupling method A. The title compound was obtained as a pale yellow solid (80 mg, 74%).
[M+H]$^+$ 543.1
NMR $\delta_H$ (400 MHz, DMSO-d$_6$) 0.28 (m, 2H), 0.37-0.43 (m, 2H), 1.59-1.65 (m, 1H), 2.44 (m, 4H), 2.56 (m, 4H), 3.77 (s, 2H), 3.81 (m, 4H), 3.93 (m, 4H), 7.43 (apparent t, J=7.9 Hz, 1H), 7.54 (s, 1H), 7.62 (dd, J=7.9, 0.9 Hz, 1H), 7.90 (s, 1H), 8.26 (dd, J=7.9, 0.9 Hz, 1H) and 12.44 (bs, 1H).

Example 37

4-[6-(4-Cyclopropyl-piperazin-1-ylmethyl)-4-morpholin-4-yl-thieno[2,3-d]pyrimidin-2-yl]-1H-indole-6-sulfonic acid dimethylamide Prepared by using general Suzuki coupling method B. The title compound was obtained as a white solid (68 mg, 53%).
[M+H]$^+$ 582.3
NMR $\delta_H$ (400 MHz, CDCl$_3$) 0.36-0.48 (m, 4H), 1.58-1.68 (m, 1H), 2.54 (m, 4H), 2.68 (m, 4 H), 2.73 (s, 6H), 3.76 (s, 2H), 3.90 (m, 4H), 3.96 (m, 4H), 7.14 (s, 1H), 7.52 (m, 1H), 7.67 (m, 1H), 7.97 (m, 1H), 8.60 (d, J=1.6 Hz, 1H) and 8.82 (bs, 1H).

Example 38

4-[6-(4-Cyclopropyl-piperazin-1-ylmethyl)-4-morpholin-4-yl-thieno[2,3-d]pyrimidin-2-yl]-1H-indole-6-carboxylic acid amide Prepared by using general Suzuki coupling method B. The title compound was obtained as a white solid (37 mg, 28%).
[M+H]$^+$ 518.3
NMR $\delta_H$ (400 MHz, DMSO-d$_6$) δ 0.27 (m, 2H), 0.40 (m, 2H), 1.57-1.64 (m, 1H), 2.43 (m, 4H), 2.56 (m, 4H), 3.76 (s, 2H), 3.82 (t, J=4.5 Hz, 4H), 3.94 (t, J=4.5 Hz, 4H), 7.18 (bs, 1 H), 7.39 (s, 1H), 7.53 (s, 1H), 7.60 (m, 1H), 8.00 (bs, 1H), 8.05 (s, 1H), 8.60 (m, 1H) and 11.53 (bs, 1H).

Example 39

6-(4-Cyclopropyl-piperazin-1-ylmethyl)-4-morpholin-4-yl-2-(6-trifluoromethyl-1H-indol-4-yl)-thieno[2,3-d]pyrimidine Prepared by using general Suzuki coupling method B. The title compound was obtained as a white solid (75 mg, 63%).
[M+H]$^+$ 543.4
NMR $\delta_H$ (400 MHz, CDCl$_3$) 0.38 (m, 2H), 0.40-0.47 (m, 2H), 1.59-1.66 (m, 1H), 2.54 (m, 4H), 2.67 (m, 4H), 3.75 (s, 2H), 3.88-3.93 (m, 4H), 3.94-3.99 (m, 4H), 7.14 (s, 1H), 7.44 (t, J=2.7 Hz, 1H), 7.63 (t, J=2.7 Hz, 1H), 7.71 (s, 1H), 8.47 (s, 1H) and 8.62 (bs, 1H).

Example 40

6-(4-Cyclopropyl-piperazin-1-ylmethyl)-2-(6-fluoro-1H-indol-4-yl)-4-morpholin-4-yl-thieno[2,3-d]pyrimidine Prepared by using general Suzuki coupling method A. The title compound was obtained as a white solid (65 mg, 65%).
[M+H]$^+$ 493.3
NMR $\delta_H$ (400 MHz, DMSO-d$_6$) 0.24-0.33 (m, 2H), 0.37-0.42 (m, 2H), 1.58-1.65 (m, 1H), 2.44 (m, 4H), 2.56 (m, 4H), 3.76 (s, 2H), 3.81 (t, J=4.6 Hz, 4H), 3.92 (t, J=4.6 Hz, 4H), 7.31 (dd, J=10.2, 2.6 Hz, 1H), 7.39 (d, J=2.6 Hz, 1H), 7.46 (apparent t, J=2.6 Hz, 1H), 7.53 (s, 1H), 7.89 (dd, J=10.2, 2.6 Hz, 1H) and 11.31 (bs, 1H).

Example 41

6-(4-Cyclopropyl-piperazin-1-ylmethyl)-2-(6-methanesulfonyl-1H-indol-4-yl)-4-morpholin-4-yl-thieno[2,3-d]pyrimidine Prepared by using general Suzuki coupling method B. The title compound was obtained as a white solid (54 mg, 44%).
[M+H]$^+$ 553.3
NMR $\delta_H$ (400 MHz, DMSO-d$_6$) 0.27 (m, 2H), 0.37-0.43 (m, 2H), 1.58-1.65 (m, 1H), 2.44 (m, 4H), 2.48-2.64 (m, 4H), 3.23 (s, 3H), 3.78 (s, 2H), 3.83 (m, 4H), 3.87-3.98 (m, 4H), 7.51 (d, J=2.5 Hz, 1H), 7.56 (s, 1H), 7.81 (s, 1H), 8.08 (dd, J=2.5, 1.3 Hz, 1H), 8.57 (d, J=1.3 Hz, 1H) and 11.85 (bs, 1H).

Example 42

6-(4-Cyclopropyl-piperazin-1-ylmethyl)-2-(5-fluoro-1H-indol-4-yl)-4-morpholin-4-yl-thieno[2,3-d]pyrimidine Prepared by using general Suzuki coupling method B. The title compound was obtained as a white solid (39 mg, 35%).
[M+H]+ 493.3
NMR δ$_H$ (400 MHz, CD$_3$OD) 0.37-0.42 (m, 2H), 0.43-0.50 (m, 2H), 1.63-1.70 (m, 1H), 2.56 (m, 4H), 2.69 (m, 4H), 3.79-3.84 (m, 6H), 3.95-4.00 (m, 4H), 6.66 (dd, J=3.1, 0.8 Hz, 1H), 6.97 (dd, J=11.0, 8.8 Hz, 1H), 7.32 (d, J=3.1 Hz, 1H) and 7.43 (m, 2H).

Example 43

4-[6-(4-Cyclopropyl-piperazin-1-ylmethyl)-4-morpholin-4-yl-thieno[2,3-d]pyrimidin-2-yl]-1H-indole-2-carbonitrile Prepared by using general Suzuki coupling method A. The title compound was obtained as a white solid (36 mg, 24%).
[M+H]+ 500.1
NMR δ$_H$(400 MHz, CDCl$_3$) 0.39-0.49 (m, 4H), 1.65 (m, 1H), 2.56 (m, 4 μl), 2.69 (m, 4H), 3.78 (s, 2H), 3.89-3.94 (m, 4H), 3.94-3.99 (m, 4H), 7.15 (s, 1H), 7.45-7.51 (m, 2H), 8.30-8.34 (m, 2H) and 8.73 (s, 1H).

Example 44

4-[6-(4-Cyclopropyl-piperazin-1-ylmethyl)-4-morpholin-4-yl-thieno[2,3-d]pyrimidin-2-yl]-1H-indole-6-carbonitrile A mixture of 2-chloro-6-(4-cyclopropyl-piperazin-1ylmethyl)-4-morpholin-4-yl-thieno[2,3-d]pyrimidine-6-carbaldehyde (217 mg), 4-(4,4,5,5-tetramethyl-[1,3,2]dioxaborolan-2-yl)-1-H-indole-6-carbonitrile (256 mg), bis(triphenylphosphine)palladium chloride (19 mg), and sodium carbonate (175 mg) in water (1.7 mL) and acetonitrile (6 mL) was heated in a microwave reactor at 140° C. for 1 hour. The reaction mixture was cooled, diluted with dichloromethane (20 mL), washed with water, dried (MgSO$_4$) and the solvents removed in vacuo to give, after purification using flash chromatography, the title compound (59 mg) as a white solid.
δ$_H$ (400 MHz, CDCl$_3$) 0.43 (m, 41-1); 1.56 (m, 1H); 2.58 (m, 411); 2.71 (m, 4H); 3.80 (s, 2H); 3.95 (m, 414); 4.02 (m, 4H); 7.28 (s, 1H); 7.56 (s, 1H); 7.75 (s, 1H); 7.83 (s, 1H); 8.52 (s, 1H); 8.53 (br s, 1H).
[M+H]+ 500.3

Example 45

4-[6-(4-Cyclopropyl-piperazin-1-ylmethyl)-4-morpholin-4-yl-thieno[3,2-d]pyrimidine-2-yl]-1H-indole-6-carbonitrile A mixture of 2-chloro-6-(4-cyclopropyl-piperazin-1-ylmethyl)-4-morpholin-4-yl-thieno[3,2-d]pyrimidine (200 mg) and 4-(4,4,5,5-tetramethyl-[1,3,2]dioxaborolan-2-yl)-1-H-indole-6-carbonitrile (273 mg) were reacted using Suzuki coupling method B, to give the title compound (55 mg) as a white solid.

δ$_H$ (400 MHz, CDCl$_3$) 0.36 (m, 4H); 1.57 (m, 1H); 2.51 (br s, 4H); 2.63 (br s, 4H); 3.77 (s, 2H); 3.85 (m, 4H); 4.02 (m, 4H); 7.29 (s, 1H); 7.45 (t, 1H); 7.61 (t, 1H); 7.72 (s, 1H); 8.38 (s, 1H); 8.46 (br s, 1H).
[M+H]+ 500.3.

Example 46

4-[6-(4-Cyclopropyl-piperazin-1-ylmethyl)-4-morpholin-4-yl-thieno[3,2-d]pyrimidine-2-yl]-1H-indole-6-carboxylic acid amide Prepared Suzuki coupling method B to give the title compound (59 mg) as a white solid.
δ$_H$ (400 MHz, CDCl$_3$) 0.38 (m, 4H); 1.58 (m, 1H); 2.51-2.63 (m, 8H); 3.76 (s, 2H); 3.85 (m, 4H); 4.06 (m, 4H); 7.29 (s, 1H); 7.41 (t, 1H); 7.49 (s, 1H); 8.11 (s, 1H); 8.45 (s, 1H); 8.46 (br s, 1H).
[M+H]+ 518.4

Example 47

6-(4-Cyclopropyl-piperazin-1-ylmethyl)-2-(6-fluoro-1H-indol-4-yl)-4-morpholin-4-yl-thieno[3,2-d]pyrimidine Prepared by Suzuki coupling method B to give an off-white foam (46 mg).
δ$_H$ (400 MHz, CDCl$_3$) 0.45 (m, 4H), 1.67 (m, 1H), 2.59 (br m, 4H), 2.72 (br m, 4H), 3.85 (s, 2H), 3.93 (t, J=4.8, 4H), 4.10 (t, J=4.8, 4H), 7.19 (dd, J=1.8, 7.1, 1H), 7.31 (m, 1H), 7.38 (s, 1H), 7.57 (m, 1H), 8.00 (dd, J=2.3, 8.9, 1H), 8.22 (br s, 1H).
[M+H]+ 493.

Example 48

6-(4-Cyclopropyl-piperazin-1-ylmethyl)-4-morpholin-4-yl-2-(2-trifluoromethyl-1H-indol-4-yl)-thieno[3,2-d]pyrimidine Prepared using Suzuki coupling method A to give a yellow solid (53 mg).
δH (400 MHz, CDCl$_3$) 0.40-0.50 (m, 4H), 1.64-1.70 (m, 1H), 2.60 (br s, 411), 2.72 (br s, 4H, 3.86 (s, 2H), 3.94 (t, J=4.8, 4H), 4.11 (t, J=4.8, 4H), 7.41 (s, 1H), 7.46 (t, J=8.0, 1H), 8.03 (s, 1H), 8.28 (d, J=8.0, 1H), 8.49 (br s, 1H).
[M+H]+543

Example 49

6-(4-Cyclopropyl-piperazin-1-ylmethyl)-4-morpholin-4-yl-2-(6-trifluoromethyl-1H-indol-4-yl)-thieno[3,2-d]pyrimidine Prepared by the Suzuki coupling method A to give a white foam (14 mg).
δ$_H$ (400 MHz, CDCl$_3$) 0.46 (m, 4H), 1.67 (m, 1H), 2.60 (br m, 4H), 2.72 (br m, 4H), 3.86 (s, 2H), 3.94 (t, J=4.8, 4H), 4.11 (t, J=4.8, 4H), 7.40 (s, 1H), 7.49 (m, 1H), 7.64 (m, 1H), 7.78 (s, 1H), 8.46 (s, 1H), 8.49 (br s, 1H).
[M+H]+ 543.

Example 50

6-(4-Cyclopropyl-piperazin-1-ylmethyl)-2-(6-methyl-1H-indol-4-yl)-4-morpholin-4-yl-thieno[3,2-d]pyrimidine Prepared using Suzuki coupling method A to give a white solid (80 mg).

δ$_H$(400 MHz, CDCl$_3$) 0.44 (m, 2H), 0.47 (m, 2H), 1.67 (m, 1H), 2.60 (br s, 4H), 2.72 (br s, 4H), 2.76 (s, 6H), 3.87 (s, 2H), 3.93 (t, J=4.8, 4H), 4.10 (t, J=4.8, 4H), 7.39 (s, 1H), 7.56 (t, J=2.8, 1H), 7.68, (m, 1H), 8.00 (s, 1H), 8.59 (d, J=1.5, 1H), 8.70 (br s, 1H).
[M+H]$^+$ 582.31

Example 51

6-(4-Cyclopropyl-piperazin-1-ylmethyl)-2-(6-methanesulfonyl-1H-indol-4-yl)-4-morpholin-4-yl-thieno[3,2-d]pyrimidine Prepared using Suzuki coupling method A to give an off-white solid (72 mg).
δ$_H$(400 MHz, d$_6$-DMSO) 0.28-0.31 (m, 2H), 0.40-0.44 (m, 2H), 1.60-1.65 (m, 1H), 2.42-2.60 (m, 8H), 3.23 (s, 3H), 3.83-3.87 (m, 6H), 4.00-4.03 (m, 4H), 7.49 (s, 1H), 7.52 (br s, 1H), 7.81 (br s, 1H), 8.06 (s, 1H), 8.57 (s, 1H), 11.88 (br s, 1H).
[M+H]$^+$ 553.

Example 52

6-(4-Cyclopropyl-piperazin-1-ylmethyl)-2-(5-fluoro-1H-indol-4-yl)-4-morpholin-4-yl-thieno[3,2-d]pyrimidine Prepared using Suzuki coupling method A to give an off-white solid (63 mg).
δ$_H$ (400 MHz, CDCl$_3$) 0.31-0.41 (m, 4H), 1.54-1.60 (m, 1H), 2.50 (br s, 4H), 2.63 (br s, 4H), 3.76 (s, 2H), 3.80 (t, J=4.8, 4H), 4.06 (t, J=4.8, 4H), 6.82-6.84 (m, 1H), 6.98 (dd, J=10.8 and 8.8, 1H), 7.20-7.25 (m, 1H), 7.30-7.34 (m, 2H), 8.13 (br s, 1H).
[M+H]$^+$ 493.

Example 53

6-(1,8-Diaza-spiro[4.5]dec-8-ylmethyl)-2-(5-fluoro-1H-indol-4-yl)-4-morpholin-4-yl-thieno[3,2-d]pyrimidine Prepared by using general coupling method A, followed by BOC-deprotection using TFA:DCM (1:2) and TBDMS-deprotection using TBAF:THF (1:10). The title compound was obtained as a beige solid (37 mg, 32%).
[M+H]$^+$ 507.2
NMR δ$_H$ (400 MHz, CDCl$_3$) 1.53-1.70 (m, 4H), 1.67-1.84 (m, 4H), 2.49 (m, 2H), 2.63 (m, 2H), 2.96 (t, J=6.8 Hz, 2H), 3.84 (m, 6H), 4.03 (t, J=4.7 Hz, 4H), 6.88 (t, J=2.3 Hz, 1H), 6.96-7.05 (m, 1H), 7.26 (s, 1H), 7.34 (m, 2H) and 8.35 (bs, 1H).

Example 54

2-(5-Fluoro-1H-indol-4-yl)-6-(7-methyl-2,7-diaza-spiro[3.5]non-2-ylmethyl)-4-morpholin-4-yl-thieno[3,2-d]pyrimidine Prepared by using Suzuki coupling Method A, followed by TBDMS-deprotection. The title compound was obtained as a white solid (12 mg, 33%).
[M+H]$^+$ 507.2
$^1$H NMR (400 MHz, CDCl$_3$): δ 1.84 (m, 4H), 2.26 (s, 3H), 2.35 (m, 4H), 3.09 (s, 4H), 3.80-3.90 (m, 4H), 3.89 (s, 2H), 3.98-4.03 (m, 4H), 6.86 (m, 1H), 7.02 (dd, J=10.9, 8.8 Hz, 1 H), 7.25 (d, J=2.9 Hz, 1H), 7.29 (s, 1H), 7.33 (ddd, J=8.8, 3.9, 0.9 Hz, 1H) and 8.25 (bs, 1H).

Example 55

1-{2-[2-(5-Fluoro-1H-indol-4-yl)-4-morpholin-4-yl-thieno[3,2-d]pyrimidin-6-ylmethyl]-2,7-diaza-spiro[3.5]non-7-yl}-ethanone Prepared by using Suzuki coupling Method A. The title compound was obtained as a white solid (13 mg, 23%).
[M+H]$^+$ 535.1
$^1$H NMR (400 MHz, CDCl$_3$): δ 1.76 (t, J=5.6 Hz, 2H), 1.83 (m, 2H), 2.08 (s, 3H), 3.23 (m, 4H), 3.37 (t, J=5.6 Hz, 2H), 3.52 (t, J=5.6 Hz, 2H), 3.86 (t, J=4.7 Hz, 4H), 4.00 (s, 2H), 4.05 (t, J=4.7 Hz, 4H), 6.88 (d, J=2.6 Hz, 1H), 7.04 (dd, J=10.9, 8.8 Hz, 1H), 7.28 (t, J=2.8 Hz, 1H), 7.34-7.39 (m, 2H) and 8.33 (bs, 1H).

Example 56

(3R*,4S*)-4-Azetidin-1-yl-1-[2-(5-fluoro-1H-indol-4-yl)-4-morpholin-4-yl-thieno[3,2-d]pyrimidin-6-ylmethyl]-piperidine-3-carboxylic acid amide Prepared by using Suzuki coupling Method A. The title compound was obtained as a tan solid (55 mg, 75%).
[M+H]$^+$ 550.2
$^1$H NMR (400 MHz, CDCl$_3$): δ 1.67 (m, 2H), 2.00-2.12 (m, 3H), 2.19 (dd, J=11.5, 3.2 Hz, 1H), 2.23-2.31 (m, 1H), 2.50 (m, 1H), 2.98 (d, J=11.5 Hz, 1H), 3.18-3.28 (m, 4H), 3.52 (d, J=11.5 Hz, 1H), 3.77-3.91 (m, 6H), 4.01 (t, J=4.7 Hz, 4H); 5.44 (d, J=5.0 Hz, 1H), 6.86 (m, 1H), 7.02 (dd, J=10.9, 8.8 Hz, 1H), 7.27 (m, 1H), 7.34 (m, 2H), 8.26 (bs, 1H) and 8.91 (bs, 1H).
The two enantiomers were separated by chiral HPLC using a Chiralpak® IA column (250×20 mm i.d column with 5 μm particle size, UV detection at 254 nm, flow 18 mL/min). Elution with 20% EtOH in tert-butyl methyl ether containing 0.1% diethylamine. 32 mg dissolved in 3 mL of eluting solvent (injection volume 500 μL, sensitivity 0.04) gave the title compound as two distinct enantiomers:
Enantiomer A: first eluting enantiomer, white solid; 11.4 mg.
Enantiomer B: second eluting enantiomer; white solid; 13.2 mg.
Both enantiomers have analytical data identical to those obtained for the racemic mixture.

Example 57

(3R*,4R*)-4-Azetidin-1-yl-1-[2-(5-fluoro-1H-indol-4-yl)-4-morpholin-4-yl-thieno[3,2-d]pyrimidin-6-ylmethyl]-piperidine-3-carboxylic acid amide Prepared by using Suzuki coupling Method A. The title compound was obtained as a white solid (84 mg, 45%).
[M+H]$^+$ 550.2
$^1$H NMR (400 MHz, CDCl$_3$): δ 1.50-1.58 (m, 1H), 1.78-1.88 (m, 1H), 1.98-2.08 (m, 2H), 2.39 (m, 1H), 2.49 (m, 1H), 2.56-2.74 (m, 3H), 2.90 (d, J=11.6 Hz, 1H), 3.22-3.29 (m, 4 H), 3.83 (s, 2H), 3.86 (t, J=4.7 Hz, 4H), 4.03 (t, J=4.7 Hz, 4H), 5.45 (s, 1H), 6.89 (t, J=2.5 Hz, 1H), 7.04 (dd, J=10.9, 8.8 Hz, 1H), 7.28 (m, 1H), 7.36 (m, 2H), 7.86 (bs, 1H) and 8.27 (bs, 1H).
The two enantiomers were separated by chiral HPLC using a Chiralpak® IA column (250×20 mm i.d column with 5 μm particle size, UV detection at 254 nm, flow 18 mL/min)

Elution with 20% EtOH in tert-butyl methyl ether containing 0.1% diethylamine. 59 mg dissolved in 3 mL of eluting solvent (injection volume 500 μL, sensitivity 0.04) gave the title compound as two distinct enantiomers;
Enantiomer A; first eluting enantiomer; white solid; 22.6 mg.
Enantiomer B; second eluting enantiomer; white solid; 26.9 mg.
Both enantiomers have analytical data identical to those obtained for the racemic mixture.

Example 58

(±)-6-(Cis)-4-Azetidin-1-yl-3-fluoro-piperidin-1-ylmethyl)-2-(5-fluoro-1H-indol-4-yl)-4-morpholin-4-yl-thieno[3,2-d]pyrimidine Prepared by using Suzuki coupling Method A. The title compound was obtained as a white solid (56 mg, 45%).
[M+H]$^+$ 525.1
$^1$H NMR (400 MHz, CDCl$_3$): δ 1.62 (m, 1H), 1.81 (m, 1H), 2.12 (m, 2H), 2.33 (m, 2H), 2.51 (dd, J=29.3, 12.3 Hz, 1H), 2.90 (m, 1H), 3.20 (m, 1H), 3.29 (m, 4H), 3.84-3.89 (m, 4H), 3.93 (s, 2H), 4.03-4.08 (m, 4H), 4.65 (d, J=48.5 Hz, 1H), 6.91 (m, 1H), 7.06 (dd, J=10.9, 8.8 Hz, 1H), 7.29 (m, 1H), 7.34-7.40 (m, 2H) and 8.28 (bs, 1H).

Example 59

(±)-{(trans)-4-Azetidin-1-yl-1-[2-(5-fluoro-1H-indol-4-yl)-4-morpholin-4-yl-thieno[3,2-d]pyrimidin-6-ylmethyl]-piperidin-3-yl}-methanol Prepared by using Suzuki coupling Method A. The title compound was obtained as a cream solid (19 mg, 38%).
[M+H]$^+$ 537.2
$^1$H NMR (400 MHz, CDCl$_3$): δ 1.65 (m, 2H), 1.91 (m, 1H), 1.95-2.09 (m, 3H), 2.20 (m, 1H), 2.31 (m, 1H), 2.81 (dd, J=11.2, 3.7 Hz, 1H), 2.86-2.93 (m, 1H), 3.23-3.34 (m, 4H), 3.58-3.66 (m, 2H), 3.78 (s, 2H), 3.86 (t, J=4.7 Hz, 4H), 4.04 (t, J=4.7 Hz, 4H), 6.89 (m, 1 H), 7.04 (dd, J=10.9, 8.8 Hz, 1H), 7.27 (m, 1H), 7.32 (s, 1H), 7.35 (ddd, J=8.8, 3.8, 0.9 Hz, 1H) and 8.23 (bs, 1H).

Example 60

(±)-{(Cis)-4-Azetidin-1-yl-1-[2-(5-fluoro-1H-indol-4-yl)-4-morpholin-4-yl-thieno[3,2-d]pyrimidin-6-ylmethyl]-piperidin-3-yl}-methanol Prepared by using Suzuki coupling Method A. The title compound was obtained as a cream solid (69 mg, 71%).
[M+H]$^+$ 537.1
$^1$H NMR (400 MHz, CDCl$_3$): δ 1.62 (m, 1H), 1.71-1.85 (m, 1H), 1.98-2.18 (m, 5H), 2.34-2.41 (m, 1H), 2.82 (d, J=11.5 Hz, 1H), 3.04 (d, J=11.5 Hz, 1H), 3.16 (m, 2H), 3.25 (m, 2 H), 3.62-3.71 (m, 2H), 3.76 (dd, J=14.4, 1.1 Hz, 1H), 3.86 (t, J=4.7 Hz, 4H), 4.03 (t, J=4.7 Hz, 4H), 4.40 (dd, J=11.2, 9.8 Hz, 1H), 6.88 (m, 1H), 7.04 (dd, J=10.9, 8.8 Hz, 1H), 7.27 (m, 1H), 7.29 (s, 1H), 7.35 (ddd, J=8.9, 4.0, 0.9 Hz, 1H) and 8.23 (bs, 1H).

Example 61

2-(5-Fluoro-1H-indol-4-yl)-6-(7-methanesulfonyl-2,7-diaza-spiro[3.5]non-2-ylmethyl)-4-morpholin-4-yl-thieno[3,2-d]pyrimidine Prepared by using Suzuki coupling Method A. The title compound was obtained as a cream solid (33 mg, 47%).
[M+H]$^+$ 571.1
$^1$H NMR (400 MHz, CDCl$_3$): δ 1.90 (m, 4H), 2.74 (s, 3H), 3.11-3.21 (m, 8H), 3.85 (t, J=4.7 Hz, 4H), 3.94 (s, 2H), 4.04 (t, J=4.7 Hz, 4H), 6.88 (m, 1H), 7.04 (dd, J=10.9, 8.8 Hz, 1H), 7.27 (t, J=2.8 Hz, 1H), 7.32 (s, 1H), 7.36 (ddd, J=8.8, 3.9, 0.8 Hz, 1H) and 8.24 (bs, 1H).

Example 62

2-[2-(5-Fluoro-1H-indol-4-yl)-4-morpholin-4-yl-thieno[3,2-d]pyrimidin-6-ylmethyl]-2,7-diaza-spiro[3.5]nonane-7-carboxylic acid dimethylamide Prepared by using Suzuki coupling Method A. The title compound was obtained as an colourless oil (13 mg, 27%).
[M+H]$^+$ 564.2
$^1$H NMR (400 MHz, CDCl$_3$): δ 1.75-1.80 (m, 4H), 2.80 (s, 6H), 3.13 (m, 8H), 3.82-3.87 (m, 4H), 3.95 (s, 2H), 4.04 (m, 4H), 6.88 (m, 1H), 7.04 (dd, J=10.9, 8.8 Hz, 1H), 7.28 (m, 1 H), 7.32 (s, 1H), 7.36 (dd, J=8.8, 3.9 Hz, 1H) and 8.22 (bs, 1H).

Example 63

2-[2-(5-Fluoro-1H-indol-4-yl)-4-morpholin-4-yl-thieno[3,2-d]pyrimidin-6-ylmethyl]-2,7-diaza-spiro[3.5]nonane-7-carboxylic acid methyl ester Prepared by using Suzuki coupling Method A. The title compound was obtained as a cream solid (8 mg, 35%).
[M+H]$^+$ 551.3
$^1$H NMR (400 MHz, CDCl$_3$): δ 1.74 (t, J=5.2 Hz, 4H), 3.19 (s, 4H), 3.37 (t, J=5.2 Hz, 4 H), 3.67 (s, 3H), 3.85 (t, J=4.7 Hz, 4H), 3.97 (s, 2H), 4.04 (t, J=4.7 Hz, 4H), 6.86 (t, J=2.5 Hz, 1H), 7.03 (dd, J=10.9, 8.8 Hz, 1H), 7.27 (t, J=2.5 Hz, 1H), 7.35 (m, 2H) and 8.29 (bs, 1H).

Example 64

(R)-8-[2-(5-Fluoro-1H-indol-4-yl)-4-morpholin-4-yl-thieno[3,2-d]pyrimidin-6-ylmethyl]-hexahydro-pyrazino[1,2-a]pyrazine-1,4-dione Prepared by using Suzuki coupling Method A. The title compound was obtained as a cream solid (13 mg, 47%).
[M+H]$^+$ 536.1
$^1$H NMR (400 MHz, DMSO-d$_6$): δ 2.06-2.15 (m, 2H), 2.73 (td, J=12.7, 3.2 Hz, 1H), 2.97 (d, J=11.4 Hz, 1H), 3.27 (m, 1H), 3.77 (t, J=4.6 Hz, 4H), 3.83 (d, J=10.5 Hz, 2H), 3.88-3.96 (m, 4H), 3.98 (s, 2H), 4.03 (dd, J=11.4, 3.2 Hz, 1H), 4.30 (d, J=12.7 Hz, 1H), 6.67 (m, 1H), 6.99 (dd, J=11.0, 8.7 Hz, 1H), 7.40-7.46 (m, 3H), 8.17 (bs, 1H) and 11.22 (bs, 1 H).

Example 65

7-[2-(5-Fluoro-1H-indol-4-yl)-4-morpholin-4-yl-thieno[3,2-d]pyrimidin-6-ylmethyl]-3-oxa-7,9-diaza-bicyclo[3.3.1]nonane Prepared by using Suzuki coupling Method A. The title compound was obtained as a white solid (25 mg, 50%).
[M+H]$^+$ 495.1
$^1$H NMR (400 MHz, CDCl$_3$): δ 2.73 (d, J=11.2 Hz, 2H), 3.07 (m, 4H), 3.82-3.88 (m, 6H), 3.91 (d, J=11.6 Hz, 2H), 3.98-4.07 (m, 6H), 6.89 (m, 1H), 7.04 (dd, J=10.9, 8.8 Hz, 1H), 7.26 (t, J=2.8 Hz, 1H), 7.35 (m, 2H) and 8.23 (bs, 1H).

Example 66

6-[4-(3,3-Difluoro-azetidin-1-yl)-piperidin-1-ylmethyl]-2-(5-fluoro-1H-indol-4-yl)-4-morpholin-4-yl-thieno[3,2-d]pyrimidine Prepared by using Suzuki coupling Method C. The title compound was obtained as a white solid (108 mg, 80%).
[M+H]+ 543.2
$^1$H NMR (400 MHz, CDCl$_3$): δ 1.49 (m, 2H), 1.70 (m, 2H), 2.20 (m, 3H), 2.91 (m, 2H), 3.54 (apparent t, J=11.9 Hz, 4H), 3.82-3.87 (m, 6H), 4.03 (t, J=4.7 Hz, 4H), 6.88 (m, 1H), 7.03 (dd, J=10.9, 8.8 Hz, 1H), 7.24-7.28 (m, 1H), 7.30-7.37 (m, 2H) and 8.29 (bs, 1H).

Example 67

6-[4-(3,3-Difluoro-azetidin-1-yl)-piperidin-1-ylmethyl]-2-(1H-indol-4-yl)-4-morpholin-4-yl-thieno[3,2-d]pyrimidine Prepared by using Suzuki coupling Method C. The title compound was obtained as a cream solid (96 mg, 61%).
[M+H]+ 525.1
$^1$H NMR (400 MHz, CDCl$_3$): δ 1.41-1.52 (m, 2H), 1.70 (m, 2H), 2.21 (m, 3H), 2.90 (m, 2H), 3.54 (apparent t, J=11.9 Hz, 4H), 3.82 (s, 2H), 3.90 (t, J=4.7 Hz, 4H), 4.07 (t, J=4.7 Hz, 4H), 7.25-7.34 (m, 3H), 7.47 (d, J=8.0 Hz, 1H), 7.52 (m, 1H), 8.16 (dd, J=7.5, 1.0 Hz, 1H) and 8.31 (bs, 1H).

Example 68

6-(6,9-Diaza-spiro[4.5]dec-9-ylmethyl)-2-(5-fluoro-1H-indol-4-yl)-4-morpholin-4-yl-thieno[3,2-d]pyrimidine Prepared by using Suzuki coupling Method C. The title compound was obtained as a white solid (35 mg, 36%).
[M+H]+ 507.2
$^1$H NMR (400 MHz, CDCl$_3$): δ 1.50-1.84 (m, 8H), 2.32 (m, 2H), 2.52 (m, 2H), 2.95 (t, J=5.0 Hz, 2H), 3.70 (s, 2H), 3.83-3.88 (m, 4H), 4.04 (t, J=4.7 Hz, 4H), 6.88 (m, 1H), 6.97-7.06 (m, 1H), 7.26 (m, 1H), 7.34 (m, 2H) and 8.38 (bs, 1H).

Example 69

(R)-7-[2-(5-Fluoro-1H-indol-4-yl)-4-morpholin-4-yl-thieno[3,2-d]pyrimidin-6-ylmethyl]-hexahydro-oxazolo[3,4-a]pyrazin-3-one Prepared by using Suzuki coupling Method C. The title compound was obtained as a white solid (58 mg, 67%).
[M+H]+ 509.2
$^1$H NMR (400 MHz, DMSO-d$_6$): δ 1.94-2.03 (m, 1H), 2.10 (td, J=11.7, 3.7 Hz, 1H), 2.90 (d, J=11.7 Hz, 1H), 2.99-3.11 (m, 2H), 3.60 (dd, J=13.1, 3.3 Hz, 1H), 3.77 (t, J=4.6 Hz, 4H), 3.80-4.01 (m, 8H), 4.32 (t, J=8.1 Hz, 1H), 6.66 (m, 1H), 7.00 (dd, J=11.1, 8.7 Hz, 1H), 7.40-7.47 (m, 3H) and 11.23 (bs, 1H).

Example 70

7-[2-(5-Fluoro-1H-indol-4-yl)-4-morpholin-4-yl-thieno[3,2-d]pyrimidin-6-ylmethyl]-5,6,7,8-tetrahydro-[1,2,4]triazolo[4,3-a]pyrazine Prepared by using Suzuki coupling Method B. The title compound was obtained as a white solid (115 mg, 84%).
[M+H]+ 491.1
$^1$H NMR (400 MHz, DMSO-d$_6$): δ 2.99 (t, J=5.5 Hz, 2H), 3.75 (t, J=4.6 Hz, 4H), 3.89-3.94 (m, 6H), 4.09 (t, J=5.5 Hz, 2H), 4.17 (s, 2H), 6.68 (t, J=2.4 Hz, 1H), 7.00 (dd, J=11.1, 8.7 Hz, 1H), 7.45 (m, 3H), 8.46 (bs, 1H) and 11.24 (bs, 1H).

Example 71

6-(5,6-Dihydro-8H-imidazo[1,2-a]pyrazin-7-ylmethyl)-2-(6-fluoro-1H-indol-4-yl)-4-morpholin-4-yl-thieno[3,2-d]pyrimidine Prepared by using Suzuki coupling Method B (Scheme 1). The title compound was obtained as a white solid (5 mg, 10%).
[M+H]+ 490.2
NMR δ$_H$ (400 MHz, CDCl$_3$) 2.99 (t, J=5.4 Hz, 2H), 3.86-3.91 (m, 4H), 3.94 (s, 2H), 3.99-4.08 (m, 8H), 6.85 (d, J=1.4 Hz, 1H), 7.04 (d, J=1.4 Hz, 1H), 7.14-7.19 (m, 1H), 7.29 (dd, J=3.3, 2.4 Hz, 1H), 7.42 (s, 1H), 7.51 (m, 1H), 7.96 (dd, J=11.2, 2.4 Hz, 1H) and 8.29 (bs, 1H).

Example 72

6-[4-(3-Fluoro-azetidin-1-yl)-piperidin-1-ylmethyl]-2-(1H-indol-4-yl)-4-morpholin-4-yl-thieno[3,2-d]pyrimidine Prepared by using Suzuki coupling Method C. The title compound was obtained as a white solid (87 mg, 75%).
[M+H]+ 507.1
$^1$H NMR (400 MHz, CDCl$_3$): δ 1.35-1.46 (m, 2H), 1.72 (m, 2H), 2.06-2.23 (m, 3H), 2.90 (m, 2H), 3.04-3.15 (m, 2H), 3.60-3.69 (m, 2H), 3.83 (s, 2H), 3.90 (t, J=4.7 Hz, 4H), 4.08 (t, J=4.7 Hz, 4H), 5.12 (dp, J=57.4, 5.4 Hz, 1H), 7.27-7.34 (m, 3H), 7.48 (d, J=8.0 Hz, 1H), 7.53 (m, 1H), 8.17 (dd, J=7.5, 1.0 Hz, 1H) and 8.31 (bs, 1H).

Example 73

6-[4-(3-Fluoro-azetidin-1-yl)-piperidin-1-ylmethyl]-2-(5-fluoro-1H-indol-4-yl)-4-morpholin-4-yl-thieno[3,2-d]pyrimidine Prepared by using Suzuki coupling Method C. The title compound was obtained as a white solid (94 mg, 79%).
[M+H]+ 525.1
$^1$H NMR (400 MHz, CDCl$_3$): δ 1.34-1.45 (m, 2H), 1.71 (m, 2H), 2.07-2.23 (m, 3H), 2.89 (m, 2H), 3.03-3.14 (m, 2H), 3.59-3.68 (m, 2H), 3.82 (s, 2H), 3.82-3.87 (m, 4H), 4.03 (t, J=4.7 Hz, 4H), 5.00-5.21 (m, 1H), 6.88 (m, 1H), 6.97-7.06 (m, 1H), 7.26 (m, 1H), 7.33 (m, 2 H) and 8.32 (bs, 1H).

Example 74

1-{1-[2-(1H-Indol-4-yl)-4-morpholin-4-yl-thieno[3,2-d]pyrimidin-6-ylmethyl]-piperidin-4-yl}-azetidin-2-one Prepared by using Suzuki coupling Method C. The title compound was obtained as a pale yellow solid (74 mg, 61%).
[M+H]+ 503.3
$^1$H NMR (400 MHz, CDCl$_3$): δ 1.74-1.88 (m, 4H), 2.17 (td, J=11.5, 2.7 Hz, 2H), 2.86 (t, J=4.0 Hz, 2H), 2.98 (bd, J=11.4 Hz, 2H), 3.23 (t, J=4.0 Hz, 2H), 3.53-3.62 (m, 1H), 3.81 (s, 2H), 3.90 (t, J=4.7 Hz, 4H), 4.07 (t, J=4.7 Hz, 4H), 7.27-7.32

(m, 2H), 7.34 (s, 1H), 7.47 (dt, J=8.0, 1.0 Hz, 1H), 7.51 (m, 1H), 8.16 (dd, J=7.5, 1.0 Hz, 1H) and 8.29 (bs, 1 H).

Example 75

1-{1-[2-(5-Fluoro-1H-indol-4-yl)-4-morpholin-4-yl-thieno[3,2-d]pyrimidin-6-ylmethyl]-piperidin-4-yl}-azetidin-2-one Prepared by using Suzuki coupling Method C. The title compound was obtained as a pale grey solid (44 mg, 35%).
[M+H]$^+$ 521.3
$^1$H NMR (400 MHz, CDCl$_3$): δ 1.70-1.87 (m, 4H), 2.17 (td, J=11.5, 2.7 Hz, 2H), 2.86 (t, J=4.0 Hz, 2H), 2.98 (d, J=11.5 Hz, 2H), 3.23 (t, J=4.0 Hz, 2H), 3.53-3.62 (m, 1H), 3.80 (s, 2H), 3.85 (t, J=4.7 Hz, 4H), 4.04 (t, J=4.7 Hz, 4H), 6.88 (m, 1H), 6.99-7.05 (m, 1H), 7.25 (m, 1H), 7.31-7.37 (m, 2H) and 8.31 (bs, 1H).

Example 76

(±)-8-[2-(5-Fluoro-1H-indol-4-yl)-4-morpholin-4-yl-thieno[3,2-d]pyrimidin-6-ylmethyl]-octahydro-pyrazino[2,1-c][1,4]oxazine Prepared by using Suzuki coupling Method C, followed by TBDMS-deprotection. The title compound was obtained as a colourless needles (4 mg, 4%).
[M+H]$^+$ 509.1
$^1$H NMR (400 MHz, CDCl$_3$): δ 1.91 (s, 1H), 2.43 (m, 4H), 2.63-2.79 (m, 3H), 2.90-2.99 (m, 1H), 3.25 (m, 1H), 3.60-3.73 (m, 2H), 3.80-3.88 (m, 7H), 4.04 (t, J=4.7 Hz, 4H), 6.88 (m, 1H), 7.03 (dd, J=10.9, 8.8 Hz, 1H), 7.26 (m, 1H), 7.33-7.37 (m, 2H) and 8.27 (bs, 1H).

Example 77

(R)-8-[2-(5-Fluoro-1H-indol-4-yl)-4-morpholin-4-yl-thieno[3,2-d]pyrimidin-6-ylmethyl]-octahydro-pyrazino[2,1-c][1,4]oxazine Prepared by using Suzuki coupling Method A. The title compound was obtained as a cream solid (16 mg, 23%).
[M+H]$^+$ 509.2
$^1$H NMR (400 MHz, CDCl$_3$): δ 1.91 (m, 1H), 2.36-2.47 (m, 4H), 2.63-2.78 (m, 3H), 2.95 (d, J=8.6 Hz, 1H), 3.25 (m, 1H), 3.62-3.74 (m, 2H), 3.81-3.89 (m, 7H), 4.05 (t, J=4.7 Hz, 4H), 6.88-6.90 (m, 1H), 7.05 (dd, J=10.9, 8.8 Hz, 1H), 7.28 (m, 1H), 7.34-7.39 (m, 2H) and 8.22 (bs, 1H).

Example 78

(S)-8-[2-(5-Fluoro-1H-indol-4-yl)-4-morpholin-4-yl-thieno[3,2-d]pyrimidin-6-ylmethyl]-octahydro-pyrazino[2,1-c][1,4]oxazine Prepared by using Suzuki coupling Method A. The title compound was obtained as a cream solid (73 mg, 60%).
[M+H]$^+$ 509.2
$^1$H NMR (400 MHz, CDCl$_3$): δ 1.91 (t, J=10.0 Hz, 1H), 2.34-2.50 (m, 4H), 2.63-2.78 (m, 3 H), 2.94-2.99 (m, 1H), 3.25 (t, J=10.0 Hz, 1H), 3.61-3.73 (m, 2H), 3.81-3.89 (m, 7H), 4.05 (t, J=4.7 Hz, 4H), 6.88-6.90 (m, 1H), 7.05 (dd, J=10.9, 8.8 Hz, 1H), 7.28 (m, 1H), 7.33-7.38 (m, 2H) and 8.28 (bs, 1H).

Example 79

(R)-8-[2-(5-Fluoro-1H-indol-4-yl)-4-morpholin-4-yl-thieno[3,2-d]pyrimidin-6-ylmethyl]-hexahydro-pyrazino[2,1-c][1,4]oxazin-4-one Prepared by using Suzuki coupling Method A. The title compound was obtained as a tan solid (70 mg, 72%).
[M+H]$^+$ 523.2
$^1$H NMR (400 MHz, CDCl$_3$): δ 2.03 (t, J=10.9 Hz, 1H), 2.26 (td, J=11.7, 3.2 Hz, 1H), 2.85-2.94 (m, 2H), 3.00-3.07 (m, 1H), 3.52 (dd, J=11.9, 8.0 Hz, 1H), 3.68-3.76 (m, 1H), 3.86-3.92 (m, 6H), 3.93-4.00 (m, 1H), 4.06 (t, J=4.7 Hz, 4H), 4.13 (d, J=16.3 Hz, 1H), 4.21 (d, J=16.3 Hz, 1H), 4.62 (ddd, J=13.2, 3.2, 1.8 Hz, 1H), 6.91 (m, 1H), 7.06 (dd, J=10.9, 8.8 Hz, 1H), 7.29 (m, 1H), 7.36-7.40 (m, 2H) and 8.27 (bs, 1H).

Example 80

5-[2-(5-Fluoro-1H-indol-4-yl)-4-morpholin-4-yl-thieno[3,2-d]pyrimidin-6-ylmethyl]-hexahydro-pyrrolo[3,4-c]pyrrole-2-carboxylic acid dimethylamide Prepared by using Suzuki coupling Method A, followed by TBDMS-deprotection. The title compound was obtained as a white solid (40 mg, 66%).
[M+H]$^+$ 550.2
$^1$H NMR (400 MHz, CDCl$_3$): δ 2.54 (d, J=7.9 Hz, 2H), 2.73-2.84 (m, 4H), 2.86 (s, 6H), 3.24 (dd, J=11.0, 3.0 Hz, 2H), 3.51-3.59 (m, 2H), 3.86 (t, J=4.7 Hz, 4H), 3.92 (s, 2H), 4.04 (t, J=4.7 Hz, 4H), 6.88 (m, 1H), 6.98-7.07 (m, 1H), 7.27 (m, 1H), 7.33-7.38 (m, 2H) and 8.36 (bs, 1H).

Example 81

5-[2-(5-Fluoro-1H-indol-4-yl)-4-morpholin-4-yl-thieno[3,2-d]pyrimidin-6-ylmethyl]-hexahydro-pyrrolo[3,4-c]pyrrole-2-carboxylic acid amide Prepared by using Suzuki coupling Method A. The title compound was obtained as a white solid (40 mg, 17%).
[M+H]$^+$ 522.2
$^1$H NMR (400 MHz, CDCl$_3$): δ 2.65 (dd, J=9.4, 2.7 Hz, 2H), 2.74 (dd, J=9.4, 6.1 Hz, 2H), 2.93 (m, 2H), 3.30 (dd, J=10.2, 3.4 Hz, 2H), 3.63 (dd, J=10.2, 7.6 Hz, 2H), 3.83-3.88 (m, 4H), 3.93 (s, 2H), 4.04 (m, 4H), 4.54 (bs, 2H), 6.88 (m, 1H); 7.04 (dd, J=10.9, 8.8 Hz, 1H), 7.27 (m, 1H), 7.35 (m, 2H) and 8.22 (bs, 1H).

Example 82

2-[2-(5-Fluoro-1H-indol-4-yl)-4-morpholin-4-yl-thieno[3,2-d]pyrimidin-6-ylmethyl]-2,7-diaza-spiro[3.5]nonane-7-carboxylic acid amide To a solution of 6-(2,7-diaza-spiro[3.5]non-2-ylmethyl)-2-(5-fluoro-1H-indol-4-yl)-4-morpholin-4-yl-thieno[3,2-d]pyrimidine (125 mg, 0.254 mmol) in anhydrous DCM (10 mL) was added trimethylsilyl isocyanate (35 μL, 0.254 mmol). The reaction mixture was stirred at RT for 1 h, then partitioned between DCM and a saturated aqueous solution of NaHCO$_3$. The organic layer was separated and washed with brine, then dried (Na$_2$SO$_4$) and concentrated in vacuo. The resultant residue was purified by preparative HPLC to give the title compound as a white solid (41 mg, 30%).
[M+H]$^+$ 536.2

¹H NMR (400 MHz, CDCl₃): δ 1.76-1.81 (m, 4H), 3.17 (s, 4H), 3.31 (m, 4H), 3.82-3.87 (m, 4H), 3.95 (s, 2H), 4.04 (t, J=4.7 Hz, 4H), 4.46 (bs, 2H), 6.88 (t, J=2.5 Hz, 1H), 7.04 (dd, J=10.9, 8.7 Hz, 1H), 7.28 (m, 1H), 7.32-7.38 (m, 2H) and 8.20 (bs, 1H).

Example 83

6-(4-Azetidin-1-yl-piperidin-1-ylmethyl)-2-(6-methanesulfonyl-1H-indol-4-yl)-4-morpholin-4-yl-thieno[3,2-d]pyrimidine The title compound was prepared using Suzuki coupling Method A to give a white solid (35 mg).
NMR $\delta_H$(400 MHz, CDCl₃) 1.42 (m, 2H), 1.63 (m, 2H), 1.73 (m, 2H), 2.08 (m, 2H), 2.21 (m, 2H), 2.93 (m, 2H), 3.17 (s, 3H), 3.21 (m, 3H), 3.86 (s, 2H), 3.94 (t, J=4.7, 4H), 4.10 (t, J=4.7, 4H), 7.35 (s, 1H), 7.58 (t, J=2.7, 1H), 7.70 (m, 1H), 8.14 (s, 1H), 8.69 (br s, 1H), 8.74 (s, 1H).
[M+H]⁺ 567.25

Example 84

(4aR*,8aR*)-6-[2-(5-Fluoro-1H-indol-4-yl)-4-morpholin-4-yl-thieno[3,2-d]pyrimidin-6-ylmethyl]-1-methyl-hexahydro-pyrido[3,4-b][1,4]oxazin-2-one The title compound was prepared using Suzuki coupling Method A to give an off-white foam (50 mg).
NMR $\delta_H$ (400 MHz, CDCl₃) 1.48-1.60 (m, 1H), 2.03-2.17 (m, 3H), 2.88 (s, 3H), 2.95-3.18 (m, 3H), 3.53 (m, 1H), 3.81 (t, J=4.8, 4H), 3.85 (s, 2H), 3.97 (t, J=4.8, 4H), 4.21 (m, 2H), 6.83 (m, 1H), 6.97 (m, 1H), 7.20 (m, 1H), 7.29 (m, 2H), 8.15 (br s, 1H).
[M+H]⁺ 537.15

Example 85

4-{4-[2-(5-Fluoro-1H-indol-4-yl)-4-morpholin-4-yl-thieno[3,2-d]pyrimidin-6-ylmethyl]-piperazin-1-yl}-tetrahydro-pyran-4-carboxylic acid amide The title compound was prepared using Suzuki coupling Method A to give an off-white solid (17 mg).
NMR $\delta_H$ (400 MHz, CDCl₃) 1.80 (m, 2H), 1.93 (m, 2H), 2.62 (m, 4H), 2.68 (m, 4H), 3.78-3.94 (m, 10H), 4.07 (t, J=4.8, 4H), 5.21 (br s, 1H), 6.61 (br s, 1H), 6.92 (m, 1H), 7.07 (m, 1H), 7.27 (m, 1H), 7.39 (m, 2H), 8.25 (br s, 1H).
[M+H]⁺ 580.13

Example 86

6-[(S)-1-(Hexahydro-pyrrolo[1,2-a]pyrazin-2-yl)methyl]-2-(6-methanesulfonyl-1H-indol-4-yl)-4-morpholin-4-yl-thieno[3,2-d]pyrimidine Prepared from 2-chloro-6-[(S)-1-(hexahydro-pyrrolo[1,2-a]pyrazin-2-yl)methyl]-4-morpholin-4-yl-thieno[3,2-d]pyrimidine using Suzuki coupling Method A to give a white powder (59 mg).
NMR $\delta_H$(400 MHz, CDCl₃) 1.33 (1H, m), 1.35-1.75 (m, 3H), 1.94 (t, J=10.1, 1H), 2.09 (m, 2H), 2.31 (m, 2H), 2.87 (d, J=8.6, 1H), 2.99 (m, 3H), 3.06 (s, 3H), 3.79-3.88 (m, 6H), 4.01 (t, J=4.8, 4H), 7.30 (s, 1H), 7.5 (t, J=2.8, 1H), 7.6 (t, J=2.1, 1H), 8.1 (s, 1H), 8.64 (d, J=1.6, 1H), 8.6 (d, J=1.6, 1H), 9.00 (br s, 1H)
[M=H]⁺ 553. .

Example 87

2-(5-Fluoro-1H-indol-4-yl)-4-morpholin-4-yl-6-[4-(tetrahydro-pyran-4-yl)-piperazin-1-ylmethyl]-thieno[3,2-d]pyrimidine This was prepared using Suzuki coupling Method B, to give, after TBDMS-deprotection carried out as in Reference Example 4, the title compound as a white solid (67 mg, 61%).
[M+H]⁺ 537.4.
NMR $\delta_H$ (400 MHz, CDCl₃) 1.47 (m, 2H); 1.80 (m, 2H); 2.47 (m, 1H); 2.66 (bs, 8H); 3.40 (m, 2H); 3.88 (m, 2H); 4.04 (s, 2H); 4.07 (m, 4H); 6.93 (s, 1H); 7.06 (m, 1H); 7.29 (m, 2H); 7.39 (m, 2H); 8.24 (bs, 1H).

Example 88

2-(1H-Indol-4-yl)-4-morpholin-4-yl6-[4-(tetrahydropyran-4-yl)-piperazin-1-ylmethyl]-thieno[3,2-d]pyrimidine A mixture of 2-chloro-4-morpholin-4-yl-6-[4-(tetrahydro-pyran-4-yl)-piperazin-1-ylmethyl]-thieno[3,2-d]pyrimidine (100 mg, 0.23 mmol) and indole-4-boronic acid was reacted using Suzuki coupling Method B, to give after silica chromatography, the title compound as a white solid (76 mg, 64%).
[M+H]⁺ 519.3
NMR $\delta_H$(400 MHz, CDCl₃) 1.51 (m, 2H); 1.70 (m, 2H); 2.37 (m, 1H); 2.56 (bs, 8H); 3.31 (m, 2H); 3.77 (s, 2H); 3.84 (m, 4H); 3.95 (m, 2H); 4.01 (m, 4H); 7.24 (m, 2H); 7.30 (s, 1H); 7.43 (m, 1H); 7.48 (m, 1H); 8.11 (d, 1H); 8.20 (bs, 1H).

Example 89

(±)-2-(5-Fluoro-1H-indol-4-yl)-6-[4-(2-methyl-tetrahydro-furan-3-yl)-piperazin-1-ylmethyl]-4-morpholin-4-yl-thieno[3,2-d]pyrimidine Prepared using Suzuki coupling Method B, to give after TBDMS-deprotection carried out as in Reference Example 4, the title compound as a white solid (60 mg, 44%).
[M+H]⁺ 537.3
NMR $\delta_H$(400 MHz, CDCl₃): 1.15 (d, 3H); 1.94 (m, 2H); 2.56 (m, 8H); 2.85 (m, 1H); 3.86 (m, 7H); 4.00 (m, 6H); 6.93 (s, 1H); 7.06 (m, 1H); 7.31 (m, 1H); 7.39 (m, 2H); 8.23 (bs, 1H).

Example 90

(±)-2-(5-Fluoro-1H-indol-4-yl)-4-morpholin-4-yl-6-[4-(tetrahydro-furan-3-yl)-piperazin-1-ylmethyl]-thieno[3,2-d]pyrimidine Prepared using Suzuki coupling Method B, to give after TBDMS-deprotection carried out as in Reference Example 4, the title compound as a white solid (48 mg, 26%)
[M+H]⁺ 523.3
NMR $\delta_H$(400 MHz, CDCl₃): 1.88 (m, 1H); 2.07 (m, 1H); 2.63 (m, 8H); 3.03 (m, 1H); 3.67 (m, 1H); 3.86 (m, 9H); 4.07 (m, 4H); 6.93 (s, 1H); 7.07 (m, 1H); 7.33 (m, 1H); 7.54 (m, 2H); 8.26 (bs, 1H).

Example 91

2-(5-Fluoro-1H-indol-4-yl)-6-(5-methanesulfonyl-hexahydro-pyrrolo[3,4-c]pyrrol-2-ylmethyl)-4-morpholin-4-yl-thieno[3,2-d]pyrimidine To a stirred solution of 2-chloro-6-(hexahydro-pyrrolo[3,4-c]pyrrol-2-ylmethyl)-4-morpholin-4-yl-thieno[3,2-d]pyrimidine (60 mg; 0.16 mmol) and NEt$_3$ (36 µL; 0.26 mmol) in CH$_2$Cl$_2$ (2 mL) at 0° C. was added methanesulfonyl chloride (20 µL; 0.26 mmol). The reaction mixture was stirred at 0° C. for 2 h then RT overnight (18 h) upon which time it was quenched with saturated NaHCO$_3$ solution (4 mL). The organic layer was separated using a hydrophobic frit and solvent evaporated to give a yellow solid (70 mg). This solid was reacted using Suzuki coupling Method D to give the title compound as a buff-coloured solid (26 mg; 30%).

δ$_H$ (400 MHz, CDCl$_3$) 2.62-2.66 (m, 2H), 2.77-2.81 (m, 4H), 2.89 (s, 3H), 2.91-3.01 (m, 2H), 3.19 (dd, J=10 and 4, 2H), 3.49-3.55 (m, 2H), 3.88-3.90 (m, 4H), 3.96 (s, 2H), 4.06-4.08 (m, 4H), 6.93 (br s, 1H), 7.08 (dd, J=10.8 and 8.8, 1H), 7.28-7.31 (m, 1H), 7.36-7.41 (m, 2H), 8.24 (br s, 1H).

[M+H]$^+$ 557

Example 92

1-{5-[2-(5-Fluoro-1H-indol-4-yl)-4-morpholin-4-yl-thieno[3,2-d]pyrimidin-6-ylmethyl]-hexahydro-pyrrolo[3,4-c]pyrrol-2-yl}-ethanone To a stirred solution of 2-chloro-6-(hexahydro-pyrrolo[3,4-c]pyrrol-2-ylmethyl)-4-morpholin-4-yl-thieno[3,2-d]pyrimidine (60 mg; 0.16 mmol) and NEt$_3$ (36 µL; 0.26 mmol) in CH$_2$Cl$_2$ (2 mL) at RT was added acetyl chloride (18.5 µL; 0.26 mmol) and the resulting solution was stirred at RT overnight (17 h) upon which time it was quenched with saturated NaHCO$_3$ solution (4 mL). The organic layer was separated using a hydrophobic frit and solvent evaporated to give a yellow solid (62 mg). This solid was reacted using Suzuki coupling Method D to give the title compound as a buff-coloured solid (53 mg; 70%).

δ$_H$ (400 MHz, CDCl$_3$) 2.10 (s, 3H), 2.61-3.07 (m, 4H), 3.44-3.56 (m, 2H), 3.66-3.81 (m, 2H), 3.88-3.92 (m, 4H), 3.92 (s, 2H), 3.95-4.00 (m, 4H), 6.92-6.94 (m, 1H), 7.07 (dd, J=10.8 and 8.8, 1H), 7.28-7.31 (m, 1H), 7.35 (s, 1H), 7.37-7.41 (m, 1H), 8.25 (br s, 1H).

[M+H]$^+$ 521

Example 93

{1-[2-(5-Fluoro-1H-indol-4-yl)-4-morpholin-4-yl-thieno[3,2-d]pyrimidin-6-ylmethyl]-piperidin-4-yl}-methyl-(tetrahydro-pyran-4-yl)-amine To a stirred suspension of [1-(2-chloro-4-morpholin-4-yl-thieno[3,2-d]pyrimidin-6-ylmethyl)-piperidin-4-yl]-methyl-amine (229 mg; 0.6 mmol) and NaB(OAc)$_3$H (276 mg; 1.3 mmol) in 1,2-dichloroethane (5 mL) was added tetrahydro-4H-pyran-4-one (0.12 mL; 1.3 mmol) and the reaction mixture was stirred at RT overnight (16 h). The 2-chloro-pyrimidine intermediate was isolated by acid-base extraction and reacted using Suzuki coupling Method D to give the title compound as an off-white solid (58 mg).

δ$_H$ (400 MHz, CDCl$_3$) 1.50-1.65 (m, 6H), 1.91-2.05 (m, 2H), 2.18 (s, 3H), 2.42-2.69 (m, 2H), 2.94-2.96 (m, 2H), 3.25-3.31 (m, 2H), 3.55-3.63 (m, 2H), 3.72 (s, 2H), 3.76-3.78 (m, 4H), 3.90-3.97 (m, 6H), 6.80-6.81 (m, 1H), 6.95 (dd, J=10.8 and 8.8, 1H), 7.16-7.18 (m, 1H), 7.24 (s, 1H), 7.26 (dd, J=8.8 and 3.6, 1H), 8.14 (br s, 1H).

[M+H]$^+$ 565

Example 94

Cyclobutyl-{1-[2-(5-fluoro-1H-indol-4-yl)-4-morpholin-4-yl-thieno[3,2-d]pyrimidin-6-ylmethyl]-piperidin-4-yl}-methyl-amine To a stirred suspension of [1-(2-chloro-4-morpholin-4-yl-thieno[3,2-d]pyrimidin-6-ylmethyl)-piperidin-4-yl]-methyl-amine (229 mg; 0.6 mmol) and NaB(OAc)$_3$H (0.85 g; 4.0 mmol) in 1,2-dichloroethane (5 mL) was added cyclobutanone (0.3 mL; 4.0 mmol) and the reaction mixture was stirred at RT overnight (16 h). The 2-chloro-pyrimidine intermediate was isolated by acid-base extraction and reacted using Suzuki coupling Method D to give the title compound as an off-white solid (18 mg).

δ$_H$ (400 MHz, CDCl$_3$) 1.50-1.59 (m, 5H), 1.68-2.04 (m, 9H), 2.28-2.40 (m, 1H), 2.94-3.05 (m, 3H), 3.60-3.64 (m, 1H), 3.72 (s, 2H), 3.75-3.78 (m, 4H), 3.94-3.97 (m, 4H), 6.80-6.81 (m, 1H), 6.95 (dd, J=10.8 and 8.8, 1H), 7.16-7.18 (m, 1H), 7.23 (s, 1H), 7.26 (dd, J=8.8 and 4.0, 1H), 8.14 (br s, 1H).

[M+H]$^+$ 535

Example 95

(±)-{1-[2-(5-Fluoro-1H-indol-4-yl)-4-morpholin-4-yl-thieno[3,2-d]pyrimidin-6-ylmethyl]-piperidin-4-yl}-methyl-(tetrahydro-furan-3-yl)-amine To a stirred suspension of [1-(2-chloro-4-morpholin-4-yl-thieno[3,2-d]pyrimidin-6-ylmethyl)-piperidin-4-yl]-methyl-amine (229 mg; 0.6 mmol) and NaB(OAc)$_3$H (0.85 g; 4.0 mmol) in 1,2-dichloroethane (5 mL) was added dihydrofuran-3-one (0.3 mL; 3.7 mmol) and the reaction mixture was stirred at RT overnight (16 h). The 2-chloro-pyrimidine intermediate was isolated by acid-base extraction and reacted (0.2 mmol) using Suzuki coupling Method D to give the title compound as an off-white solid (26 mg).

δ$_H$ (400 MHz, CDCl$_3$) 1.54-1.63 (m, 4H), 1.68-2.04 (m, 4H), 2.15 (s, 3H), 2.32-2.38 (m, 1H), 2.95-2.98 (m, 2H), 3.19-3.50 (m 2H), 3.53-3.84 (m, 9H), 3.94-3.97 (m, 4H), 6.81 (br s, 1H), 6.93-6.97 (m, 1H), 7.17-7.28 (m, 3H), 8.14 (br s, 1H).

[M+H]$^+$ 551

Example 96

1-{1-[2-(5-Fluoro-1H-indol-4-yl)-4-morpholin-4-yl-thieno[3,2-d]pyrimidin-6-ylmethyl]-piperidin-4-yl}-azetidin-3-ol 1-[1-(2-Chloro-4-morpholin-4-yl-thieno[3,2-d]pyrimidin-6-ylmethyl)-piperidin-4-yl]-azetidin-3-ol (0.2 mmol) was reacted using Suzuki coupling Method D to give the title compound as an off-white solid (56 mg; 54%).

δ$_H$ (400 MHz, CDCl$_3$) 1.30-2.21 (m, 7H), 2.79-2.95 (m, 4H), 3.61-3.65 (m, 2H), 3.81-4.04 (m, 10H), 4.43 (quintet, J=5.6, 1H), 6.88 (s, 1H), 7.03 (dd, J=10.8 and 8.8, 1H), 7.24-7.27 (m, 1H), 7.30 (s, 1H), 7.34 (dd, J=8.8 and 3.6, 1H), 8.22 (br s, 1H).

[M+H]$^+$ 523

Example 97

2-(5-Fluoro-1H-indol-4-yl)-6-[4-(3-methoxy-azetidin-1-yl)-piperidin-1-ylmethyl]-4-morpholin-4-yl-thieno[3,2-d]pyrimidine To a stirred solution of 1-[1-(2-chloro-4-morpholin-4-yl-thieno[3,2-d]pyrimidin-6-ylmethyl)-piperidin-4-yl]-azetidin-3-ol (100 mg; 0.24 mmol) in anhydrous DMF at 0° C. was added NaH (60 wt %; 20 mg; 0.5 mmol). Stirring was continued at 0° C. for 40 min. upon which time iodomethane (16 μL; 0.26 mmol) was added and the reaction mixture was allowed to warm to RT whilst stirring over 4 h. The reaction was purified by acid-base extraction to give a crude residue that was reacted using Suzuki coupling Method D to give the title compound as an off-white solid (33 mg; 26%).

$\delta_H$ (400 MHz, CDCl$_3$) 1.36-1.71 (m, 5H), 2.10-2.26 (m, 3H), 2.81-2.98 (m, 4H), 3.29 (s, 3H), 3.64 (br s, 2H), 3.85 (s, 2H), 3.87-3.90 (m, 4H), 4.05-4.08 (m, 4H), 6.92-6.93 (m, 1H), 7.07 (dd, J=10.8 and 8.8, 1H), 7.28-7.30 (m, 1H), 7.34 (s, 1H), 7.38 (dd, J=8.8 and 4.0, 1H), 8.26 (br s, 1H).

[M+H]$^+$ 537

Example 98

4-[2-(5-Fluoro-1H-indol-4-yl)-4-morpholin-4-yl-thieno[3,2-d]pyrimidin-6-ylmethyl]-1-(tetrahydropyran-4-A-piperazin-2-one Prepared by using Suzuki coupling method A. The title compound was obtained as a white solid (78 mg, 30%).

[M+H]$^+$ 551.1

$^1$H NMR (400 MHz, CDCl$_3$): δ 1.63 (d, J=4.1 Hz, 2H), 1.79 (qd, J=12.3, 4.6 Hz, 2H), 2.78 (t, J=5.3 Hz, 2H), 3.30 (t, J=5.3 Hz, 2H), 3.36 (s, 2H), 3.51 (td, J=11.8, 1.9 Hz, 2H), 3.86 (t, J=4.8 Hz, 4H), 3.90 (s, 2H), 4.00-4.07 (m, 6H), 4.69-4.78 (m, 1H), 6.90 (m, 1H), 7.05 (dd, J=10.9, 8.8 Hz, 1H), 7.27 (m, 1H), 7.37 (m, 2H) and 8.27 (bs, 1H).

Biological Evaluation and Pharmaceutical Formulations

Example 99

Biological Testing

Compounds of the invention, prepared as described in the preceding Examples, were submitted to the following biological assay:

PI3K Biochemical Screening

Compound inhibition of PI3K was determined in a radiometric assay using purified, recombinant enzyme and ATP at a concentration of 1 uM. All compounds were serially diluted in 100% DMSO. The kinase reaction was incubated for 1 hour at room temperature, and the reaction was terminated by the addition of PBS. IC$_{50}$ values were subsequently determined using sigmoidal dose-response curve fit (variable slope). All of the compounds tested had an IC$_{50}$ against PI3K of 50 μM or less. Typically the IC$_{50}$ against the p110δ isoform of PI3K was less than 500 nM.

Example 100

Tablet Composition

Tablets, each weighing 0.15 g and containing 25 mg of a compound of the invention were manufactured as follows:

Composition for 10,000 tablets
Compound of the invention (250 g)
Lactose (800 g)
Corn starch (415 g)
Talc powder (30 g)
Magnesium stearate (5 g)

The compound of the invention, lactose and half of the corn starch were mixed. The mixture was then forced through a sieve 0.5 mm mesh size. Corn starch (10 g) is suspended in warm water (90 ml). The resulting paste was used to granulate the powder. The granulate was dried and broken up into small fragments on a sieve of 1.4 mm mesh size. The remaining quantity of starch, talc and magnesium was added, carefully mixed and processed into tablets.

Example 101

Injectable Formulation

| | |
|---|---|
| Compound of the invention | 200 mg |
| Hydrochloric Acid Solution 0.1 M or | 4.0 to 7.0 |
| Sodium Hydroxide Solution 0.1 M q.s. to pH | |
| Sterile water q.s. to | 10 ml |

The compound of the invention was dissolved in most of the water (35°-40° C.) and the pH adjusted to between 4.0 and 7.0 with the hydrochloric acid or the sodium hydroxide as appropriate. The batch was then made up to volume with water and filtered through a sterile micropore filter into a sterile 10 ml amber glass vial (type 1) and sealed with sterile closures and overseals.

Example 102

Intramuscular Injection

| | |
|---|---|
| Compound of the invention | 200 mg |
| Benzyl Alcohol | 0.10 g |
| Glycofurol 75 | 1.45 g |
| Water for injection q.s to | 3.00 ml |

The compound of the invention was dissolved in the glycofurol. The benzyl alcohol was then added and dissolved, and water added to 3 ml. The mixture was then filtered through a sterile micropore filter and sealed in sterile 3 ml glass vials (type 1).

Example 103

Syrup Formulation

| | |
|---|---|
| Compound of invention | 250 mg |
| Sorbitol Solution | 1.50 g |
| Glycerol | 2.00 g |
| Sodium benzoate | 0.005 g |
| Flavour | 0.0125 ml |
| Purified Water q.s. to | 5.00 ml |

The compound of the invention was dissolved in a mixture of the glycerol and most of the purified water. An aqueous solution of the sodium benzoate was then added to the solution, followed by addition of the sorbital solution and finally the flavour. The volume was made up with purified water and mixed well.

The invention claimed is:

1. A compound which is a thienopyrimidine of formula (I):

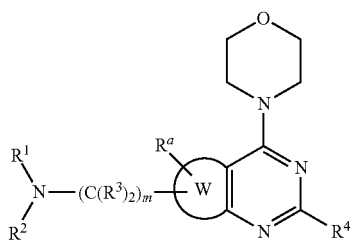

wherein
W represents a thiophene ring;
$R^1$ and $R^2$ form, together with the N atom to which they are attached, a group of the following formula (IIa):

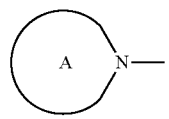

in which A is selected from:
(a) a group selected from homopiperazine, piperazine, piperidine, pyrrolidine and azetidine, which group is substituted by one or more substituents selected from $C_3$-$C_{10}$ cycloalkyl which is unsubstituted or substituted, an O-containing ring which is tetrahydrofuran, tetrahydropyran or oxetane and which is unsubstituted or substituted, —NR'—(CR'$_2$)$_r$—X wherein each R' is independently H or $C_1$-$C_6$ alkyl, r is 0 or 1 and X is selected from $C_3$-$C_{10}$ cycloalkyl which is unsubstituted or substituted, an O-containing ring which is tetrahydrofuran, tetrahydropyran or oxetane and which is unsubstituted or substituted, and a 4-membered saturated N-containing heterocyclic ring which is unsubstituted or substituted, and which group is optionally substituted by one or more further substituents;
(b) a 4- to 7-membered saturated N-containing heterocyclic ring which includes 0 or 1 additional heteroatoms selected from N, S and O, the ring being fused to a second ring selected from a 4- to 7-membered saturated N-containing heterocyclic ring as defined above, a 5- to 12-membered unsaturated heterocyclic ring, a 5- to 7-membered saturated O-containing heterocyclic ring, a 3- to 12-membered saturated carbocyclic ring and an unsaturated 5- to 12-membered carbocyclic ring to form a heteropolycyclic ring system, the heteropolycyclic ring system being unsubstituted or substituted;
(c) a 4- to 7-membered saturated N-containing heterocyclic ring which includes 0 or 1 additional heteroatoms selected from N, S and O and which further comprises, linking two constituent atoms of the ring, a bridgehead group selected from —(CR'$_2$)$_n$— and —(CR'$_2$)$_r$—O—(CR'$_2$)$_s$— wherein each R' is as defined above, n is 1, 2 or 3, r is as defined above and s is 0 or 1, the remaining ring positions being unsubstituted or substituted; and
(d) a group of formula (IIb):

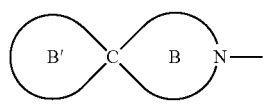

wherein ring B is a 4- to 7-membered saturated N-containing heterocyclic ring which includes 0 or 1 additional heteroatoms selected from N, S and O and ring B' is a 3- to 12-membered saturated carbocyclic ring, a 5- to 7-membered saturated O-containing heterocyclic ring or a 4- to 7-membered saturated N-containing heterocyclic ring as defined above, each of B and B' being unsubstituted or substituted;
m is 0, 1 or 2;
$R^3$ is H or $C_1$-$C_6$ alkyl;
$R^a$ is selected from R', halo, CN, C(O)NR'$_2$, halo($C_1$-$C_6$) alkyl, SO$_2$R', SO$_2$NR'$_2$, NR'SO$_2$R', NR'C(O)R', NR'C(O)OR', NR'C(O)NR'$_2$, OR' and NR'$_2$, wherein each R' is independently as defined above; and
$R^4$ is an indole group which is unsubstituted or substituted;
or a pharmaceutically acceptable salt thereof.

2. A compound according to claim 1 wherein the thienopyrimidine is of

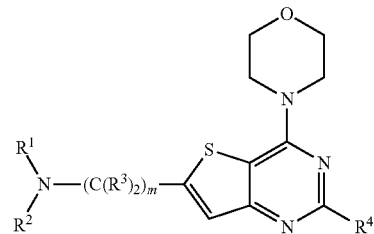

wherein $R^1$, $R^2$, $R^3$, $R^4$ and m are as defined in claim 1.

3. A compound according to claim 1 wherein the thienopyrimidine is of formula (Ib):

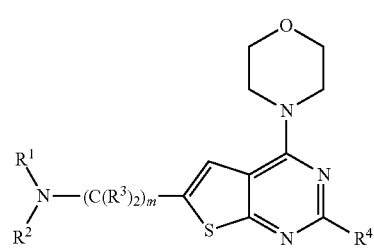

wherein $R^1$, $R^2$, $R^3$, $R^4$ and m are as defined in claim 1.

4. A compound according to claim 1 wherein $R^4$ is an indole group which is unsubstituted or substituted by a group selected from CN, halo, —C(O)NR$_2$, halo($C_1$-$C_6$)alkyl, —SO$_2$R, —SO$_2$NR$_2$, and a 5-membered heteroaryl group containing 1, 2, 3 or 4 heteroatoms selected from O, N and S, wherein R is H or $C_1$-$C_6$ alkyl.

5. A compound of claim 1 which is selected from:
6-(4-Azetidin-1-yl-piperidin-1-ylmethyl)-2-(6-fluoro-1H-indol-4-yl)-4-morpholin-4-yl-thieno[3,2-d]pyrimidine;

Cyclopropylmethyl-{1-[2-(5-fluoro-1H-indol-4-yl)-4-morpholin-4-yl-thieno[3,2-d]pyrimidin-6-ylmethyl]-piperidin-4-yl}-amine;
Cyclopropylmethyl-{1-[2-(6-fluoro-1H-indol-4-yl)-4-morpholin-4-yl-thieno[3,2-d]pyrimidin-6-ylmethyl]-piperidin-4-yl}-amine;
Cyclopropyl-{1-[2-(6-fluoro-1H-indol-4-yl)-4-morpholin-4-yl-thieno[3,2-d]pyrimidin-6-ylmethyl]-piperidin-4-yl}-amine;
6-[(S)-1-(Hexahydro-pyrrolo[1,2-c]pyrazin-2-yl)methyl]-2-(1H-indol-4-yl)-4-morpholin-4-yl-thieno[3,2-d]pyrimidine;
2-(5-Fluoro-1H-indol-4-yl)-6-[(S)-1-(hexahydro-pyrrolo[1,2-c]pyrazin-2-yl)methyl]-4-morpholin-4-yl-thieno[3,2-d]pyrimidine;
2-(6-Fluoro-1H-indol-4-yl)-6-[(S)-1-(hexahydro-pyrrolo[1,2-c]pyrazin-2-yl)methyl]-4-morpholin-4-yl-thieno[3,2-d]pyrimidine;
6-(Hexahydro-pyrrolo[3,4-c]pyrrol-2-ylmethyl)-2-(1H-indol-4-yl)-4-morpholin-4-yl-thieno[3,2-d]pyrimidine;
2-(5-Fluoro-1H-indol-4-yl)-6-(hexahydro-pyrrolo[3,4-c]pyrrol-2-ylmethyl)-4-morpholin-4-yl-thieno[3,2-d]pyrimidine;
2-(6-Fluoro-1H-indol-4-yl)-6-(hexahydro-pyrrolo[3,4-c]pyrrol-2-ylmethyl)-4-morpholin-4-yl-thieno[3,2-d]pyrimidine;
6-(2,7-Diaza-spiro[3.5]non-2-ylmethyl)-2-(1H-indol-4-yl)-4-morpholin-4-yl-thieno[3,2-d]pyrimidine;
6-(2,7-Diaza-spiro[3.5]non-2-ylmethyl)-2-(5-fluoro-1H-indol-4-yl)-4-morpholin-4-yl-thieno[3,2-d]pyrimidine;
6-(2,7-Diaza-spiro[3.5]non-2-ylmethyl)-2-(6-fluoro-1H-indol-4-yl)-4-morpholin-4-yl-thieno[3,2-d]pyrimidine;
6-(3,8-Diaza-bicyclo[3.2.1]oct-3-ylmethyl)-2-(6-fluoro-1H-indol-4-yl)-4-morpholin-4-yl-thieno[3,2-d]pyrimidine;
6-[(1S,5S)-1-(3,6-Diaza-bicyclo[3.1.1]hept-6-yl)methyl]-2-(6-fluoro-1H-indol-4-yl)-4-morpholin-4-yl-thieno[3,2-d]pyrimidine;
6-(2,7-Diaza-spiro[3.5]non-7-ylmethyl)-2-(6-fluoro-1H-indol-4-yl)-4-morpholin-4-yl-thieno[3,2-d]pyrimidine;
6-(2,8-Diaza-spiro[4.5]dec-8-ylmethyl)-2-(6-fluoro-1H-indol-4-yl)-4-morpholin-4-yl-thieno[3,2-d]pyrimidine;
6-(2,7-Diaza-spiro[4.4]non-2-ylmethyl)-2-(6-fluoro-1H-indol-4-yl)-4-morpholin-4-yl-thieno[3,2-d]pyrimidine;
2-(6-Fluoro-1H-indol-4-yl)-4-morpholin-4-yl-6-(octahydro-pyrrolo[3,2-c]pyridin-5-ylmethyl)-thieno[3,2-d]pyrimidine;
2-(6-Fluoro-1H-indol-4-yl)-4-morpholin-4-yl-6-[(3aS,7aR)-1-(octahydro-pyrrolo[3,2-c]pyridin-5-yl)methyl]-thieno[3,2-d]pyrimidine;
2-(6-Fluoro-1H-indol-4-yl)-4-morpholin-4-yl-6-[(3aR,7aS)-1-(octahydro-pyrrolo[3,2-c]pyridin-5-yl)methyl]-thieno[3,2-d]pyrimidine;
2-(6-Fluoro-1H-indol-4-yl)-6-[(R)-1-(hexahydro-pyrrolo[1,2-c]pyrazin-2-yl)methyl]-4-morpholin-4-yl-thieno[3,2-d]pyrimidine;
4-[2-(5-Fluoro-1H-indol-4-yl)-4-morpholin-4-yl-thieno[3,2-d]pyrimidin-6-ylmethyl]-1-oxa-4,9-diaza-spiro[5.5]undecane;
9-[2-(5-Fluoro-1H-indol-4-yl)-4-morpholin-4-yl-thieno[3,2-d]pyrimidin-6-ylmethyl]-1-oxa-4,9-diaza-spiro[5.5]undecane;
7-[2-(5-Fluoro-1H-indol-4-yl)-4-morpholin-4-yl-thieno[3,2-d]pyrimidin-6-ylmethyl]-2,7-diaza-spiro[3.5]nonan-1-one;
6-(4-Azetidin-1-yl-piperidin-1-ylmethyl)-2-(1H-indol-4-yl)-4-morpholin-4-yl-thieno[3,2-d]pyrimidine;
6-(4-Azetidin-1-yl-piperidin-1-ylmethyl)-2-(5-fluoro-1H-indol-4-yl)-4-morpholin-4-yl-thieno[3,2-d]pyrimidine;
6-(3,8-Diaza-bicyclo[3.2.1]oct-3-ylmethyl)-2-(1H-indol-4-yl)-4-morpholin-4-yl-thieno[3,2-d]pyrimidine;
6-(3,8-Diaza-bicyclo[3.2.1]oct-3-ylmethyl)-2-(5-fluoro-1H-indol-4-yl)-4-morpholin-4-yl-thieno[3,2-d]pyrimidine;
6-(3,8-Diaza-bicyclo[3.2.1]oct-8-ylmethyl)-2-(6-fluoro-1H-indol-4-yl)-4-morpholin-4-yl-thieno[3,2-d]pyrimidine;
6-(4-Cyclopropyl-piperazin-1-ylmethyl)-4-morpholin-4-yl-2-(2-trifluoromethyl-1H-indol-4-yl)-thieno[2,3-d]pyrimidine;
4-[6-(4-Cyclopropyl-piperazin-1-ylmethyl)-4-morpholin-4-yl-thieno[2,3-d]pyrimidin-2-yl]-1H-indole-6-sulfonic acid dimethylamide;
4-[6-(4-Cyclopropyl-piperazin-1-ylmethyl)-4-morpholin-4-yl-thieno[2,3-d]pyrimidin-2-yl]-1H-indole-6-carboxylic acid amide;
6-(4-Cyclopropyl-piperazin-1-ylmethyl)-4-morpholin-4-yl-2-(6-trifluoromethyl-1H-indol-4-yl)-thieno[2,3-d]pyrimidine;
6-(4-Cyclopropyl-piperazin-1-ylmethyl)-2-(6-fluoro-1H-indol-4-yl)-4-morpholin-4-yl-thieno[2,3-d]pyrimidine;
6-(4-Cyclopropyl-piperazin-1-ylmethyl)-2-(6-methanesulfonyl-1H-indol-4-yl)-4-morpholin-4-yl-thieno[2,3-d]pyrimidine;
6-(4-Cyclopropyl-piperazin-1-ylmethyl)-2-(5-fluoro-1H-indol-4-yl)-4-morpholin-4-yl-thieno[2,3-d]pyrimidine;
4-[6-(4-Cyclopropyl-piperazin-1-ylmethyl)-4-morpholin-4-yl-thieno[2,3-d]pyrimidin-2-yl]-1H-indole-2-carbonitrile;
4-[6-(4-Cyclopropyl-piperazin-1-ylmethyl)-4-morpholin-4-yl-thieno[2,3-d]pyrimidin-2-yl]-1H-indole-6-carbonitrile;
4-[6-(4-Cyclopropyl-piperazin-1-ylmethyl)-4-morpholin-4-yl-thieno[3,2-d]pyrimidine-2-yl]-1H-indole-6-carbonitrile;
4-[6-(4-Cyclopropyl-piperazin-1-ylmethyl)-4-morpholin-4-yl-thieno[3,2-d]pyrimidine-2-yl]-1H-indole-6-carboxylic acid amide;
6-(4-Cyclopropyl-piperazin-1-ylmethyl)-2-(6-fluoro-1H-indol-4-yl)-4-morpholin-4-yl-thieno[3,2-d]pyrimidine;
6-(4-Cyclopropyl-piperazin-1-ylmethyl)-4-morpholin-4-yl-2-(2-trifluoromethyl-1H-indol-4-yl)-thieno[3,2-d]pyrimidine;
6-(4-Cyclopropyl-piperazin-1-ylmethyl)-4-morpholin-4-yl-2-(6-trifluoromethyl-1H-indol-4-yl)-thieno[3,2-d]pyrimidine;
6-(4-Cyclopropyl-piperazin-1-ylmethyl)-2-(6-methyl-1H-indol-4-yl)-4-morpholin-4-yl-thieno[3,2-d]pyrimidine;
6-(4-Cyclopropyl-piperazin-1-ylmethyl)-2-(6-methanesulfonyl-1H-indol-4-yl)-4-morpholin-4-yl-thieno[3,2-d]pyrimidine;
6-(4-Cyclopropyl-piperazin-1-ylmethyl)-2-(5-fluoro-1H-indol-4-yl)-4-morpholin-4-yl-thieno[3,2-d]pyrimidine;
6-(1,8-Diaza-spiro[4.5]dec-8-ylmethyl)-2-(5-fluoro-1H-indol-4-yl)-4-morpholin-4-yl-thieno[3,2-d]pyrimidine;
2-(5-Fluoro-1H-indol-4-yl)-6-(7-methyl-2,7-diaza-spiro[3.5]non-2-ylmethyl)-4-morpholin-4-yl-thieno[3,2-d]pyrimidine;
1-{2-[2-(5-Fluoro-1H-indol-4-yl)-4-morpholin-4-yl-thieno[3,2-d]pyrimidin-6-ylmethyl]-2,7-diaza-spiro[3.5]non-7-yl}-ethanone;

(3R*,4S*)-4-Azetidin-1-yl-1-[2-(5-fluoro-1H-indol-4-yl)-4-morpholin-4-yl-thieno[3,2-d]pyrimidin-6-ylmethyl]-piperidine-3-carboxylic acid amide;
(3R*,4R*)-4-Azetidin-1-yl-1-[2-(5-fluoro-1H-indol-4-yl)-4-morpholin-4-yl-thieno[3,2-d]pyrimidin-6-ylmethyl]-piperidine-3-carboxylic acid amide;
(±)-6-((Cis)-4-Azetidin-1-yl-3-fluoro-piperidin-1-ylmethyl)-2-(5-fluoro-1H-indol-4-yl)-4-morpholin-4-yl-thieno[3,2-d]pyrimidine;
(±)-{(trans)-4-Azetidin-1-yl-1-[2-(5-fluoro-1H-indol-4-yl)-4-morpholin-4-yl-thieno[3,2-d]pyrimidin-6-ylmethyl]-piperidin-3-yl}-methanol;
(±)-{(Cis)-4-Azetidin-1-yl-1-[2-(5-fluoro-1H-indol-4-yl)-4-morpholin-4-yl-thieno[3,2-d]pyrimidin-6-ylmethyl]-piperidin-3-yl}-methanol;
2-(5-Fluoro-1H-indol-4-yl)-6-(7-methanesulfonyl-2,7-diaza-spiro[3.5]non-2-ylmethyl)-4-morpholin-4-yl-thieno[3,2-d]pyrimidine;
2-[2-(5-Fluoro-1H-indol-4-yl)-4-morpholin-4-yl-thieno[3,2-d]pyrimidin-6-ylmethyl]-2,7-diaza-spiro[3.5]nonane-7-carboxylic acid dimethylamide;
2-[2-(5-Fluoro-1H-indol-4-yl)-4-morpholin-4-yl-thieno[3,2-d]pyrimidin-6-ylmethyl]-2,7-diaza-spiro[3.5]nonane-7-carboxylic acid methyl ester;
(R)-8-[2-(5-Fluoro-1H-indol-4-yl)-4-morpholin-4-yl-thieno[3,2-d]pyrimidin-6-ylmethyl]-hexahydro-pyrazino[1,2-a]pyrazine-1,4-dione;
7-[2-(5-Fluoro-1H-indol-4-yl)-4-morpholin-4-yl-thieno[3,2-d]pyrimidin-6-ylmethyl]-3-oxa-7,9-diaza-bicyclo[3.3.1]nonane;
6-[4-(3,3-Difluoro-azetidin-1-yl)-piperidin-1-ylmethyl]-2-(5-fluoro-1H-indol-4-yl)-4-morpholin-4-yl-thieno[3,2-d]pyrimidine;
6-[4-(3,3-Difluoro-azetidin-1-yl)-piperidin-1-ylmethyl]-2-(1H-indol-4-yl)-4-morpholin-4-yl-thieno[3,2-d]pyrimidine;
6-(6,9-Diaza-spiro[4.5]dec-9-ylmethyl)-2-(5-fluoro-1H-indol-4-yl)-4-morpholin-4-yl-thieno[3,2-c]pyrimidine;
(R)-7-[2-(5-Fluoro-1H-indol-4-yl)-4-morpholin-4-yl-thieno[3,2-d]pyrimidin-6-ylmethyl]-hexahydro-oxazolo[3,4-a]pyrazin-3-one;
7-[2-(5-Fluoro-1H-indol-4-yl)-4-morpholin-4-yl-thieno[3,2-d]pyrimidin-6-ylmethyl]-5,6,7,8-tetrahydro-[1,2,4]triazolo[4,3-a]pyrazine;
6-(5,6-Dihydro-8H-imidazo[1,2-a]pyrazin-7-ylmethyl)-2-(6-fluoro-1H-indol-4-yl)-4-morpholin-4-yl-thieno[3,2-c]pyrimidinel;
6-[4-(3-Fluoro-azetidin-1-yl)-piperidin-1-ylmethyl]-2-(1H-indol-4-yl)-4-morpholin-4-yl-thieno[3,2-c]pyrimidine;
6-[4-(3-Fluoro-azetidin-1-yl)-piperidin-1-ylmethyl]-2-(5-fluoro-1H-indol-4-yl)-4-morpholin-4-yl-thieno[3,2-c]pyrimidine;
1-{1-[2-(1H-Indol-4-yl)-4-morpholin-4-yl-thieno[3,2-d]pyrimidin-6-ylmethyl]-piperidin-4-yl}-azetidin-2-one;
1-{1-[2-(5-Fluoro-1H-indol-4-yl)-4-morpholin-4-yl-thieno[3,2-d]pyrimidin-6-ylmethyl]-piperidin-4-yl}-azetidin-2-one;
(±)-8-[2-(5-Fluoro-1H-indol-4-yl)-4-morpholin-4-yl-thieno[3,2-d]pyrimidin-6-ylmethyl]-octahydro-pyrazino[2,1-c][1,4]oxazine;
(R)-8-[2-(5-Fluoro-1H-indol-4-yl)-4-morpholin-4-yl-thieno[3,2-d]pyrimidin-6-ylmethyl]-octahydro-pyrazino[2,1-c][1,4]oxazine;
(S)-8-[2-(5-Fluoro-1H-indol-4-yl)-4-morpholin-4-yl-thieno[3,2-d]pyrimidin-6-ylmethyl]-octahydro-pyrazino[2,1-c][1,4]oxazine;
(R)-8-[2-(5-Fluoro-1H-indol-4-yl)-4-morpholin-4-yl-thieno[3,2-d]pyrimidin-6-ylmethyl]-hexahydro-pyrazino[2,1-c][1,4]oxazin-4-one;
5-[2-(5-Fluoro-1H-indol-4-yl)-4-morpholin-4-yl-thieno[3,2-d]pyrimidin-6-ylmethyl]-hexahydro-pyrrolo[3,4-c]pyrrole-2-carboxylic acid dimethylamide;
5-[2-(5-Fluoro-1H-indol-4-yl)-4-morpholin-4-yl-thieno[3,2-d]pyrimidin-6-ylmethyl]-hexahydro-pyrrolo[3,4-c]pyrrole-2-carboxylic acid amide;
2-[2-(5-Fluoro-1H-indol-4-yl)-4-morpholin-4-yl-thieno[3,2-d]pyrimidin-6-ylmethyl]-2,7-diaza-spiro[3.5]nonane-7-carboxylic acid amide;
6-(4-Azetidin-1-yl-piperidin-1-ylmethyl)-2-(6-methanesulfonyl-1H-indol-4-yl)-4-morpholin-4-yl-thieno[3,2-d]pyrimidine;
(4aR*,8aR*)-6-[2-(5-Fluoro-1H-indol-4-yl)-4-morpholin-4-yl-thieno[3,2-d]pyrimidin-6-ylmethyl]-1-methyl-hexahydro-pyrido[3,4-b][1,4]oxazin-2-one;
4-{4-[2-(5-Fluoro-1H-indol-4-yl)-4-morpholin-4-yl-thieno[3,2-d]pyrimidin-6-ylmethyl]-piperazin-1-yl}-tetrahydro-pyran-4-carboxylic acid amide;
6-[(S)-1-(Hexahydro-pyrrolo[1,2-a]pyrazin-2-yl)methyl]-2-(6-methanesulfonyl-1H-indol-4-yl)-4-morpholin-4-yl-thieno[3,2-d]pyrimidine;
2-(5-Fluoro-1H-indol-4-yl)-4-morpholin-4-yl-6-[4-(tetrahydro-pyran-4-yl)-piperazin-1-ylmethyl]-thieno[3,2-d]pyrimidine;
2-(1H-Indol-4-yl)-4-morpholin-4-yl6-[4-(tetrahydro-pyran-4-yl)-piperazin-1-ylmethyl]-thieno[3,2-d]pyrimidine;
(±)-2-(5-Fluoro-1H-indol-4-yl)-6-[4-(2-methyl-tetrahydro-furan-3-yl)-piperazin-1-ylmethyl]-4-morpholin-4-yl-thieno[3,2-d]pyrimidine;
(±)-2-(5-Fluoro-1H-indol-4-yl)-4-morpholin-4-yl-6-[4-(tetrahydro-furan-3-yl)-piperazin-1-ylmethyl]-thieno[3,2-d]pyrimidine;
2-(5-Fluoro-1H-indol-4-yl)-6-(5-methanesulfonyl-hexahydro-pyrrolo[3,4-c]pyrrol-2-ylmethyl)-4-morpholin-4-yl-thieno[3,2-d]pyrimidine;
1-{5-[2-(5-Fluoro-1H-indol-4-yl)-4-morpholin-4-yl-thieno[3,2-d]pyrimidin-6-ylmethyl]-hexahydro-pyrrolo[3,4-c]pyrrol-2-yl}-ethanone;
{1-[2-(5-Fluoro-1H-indol-4-yl)-4-morpholin-4-yl-thieno[3,2-d]pyrimidin-6-ylmethyl]-piperidin-4-yl}-methyl-(tetrahydro-pyran-4-yl)-amine;
Cyclobutyl-{1-[2-(5-fluoro-1H-indol-4-yl)-4-morpholin-4-yl-thieno[3,2-d]pyrimidin-6-ylmethyl]-piperidin-4-yl}-methyl-amine;
(±)-{1-[2-(5-Fluoro-1H-indol-4-yl)-4-morpholin-4-yl-thieno[3,2-d]pyrimidin-6-ylmethyl]-piperidin-4-yl}-methyl-(tetrahydro-furan-3-yl)-amine;
1-{1-[2-(5-Fluoro-1H-indol-4-yl)-4-morpholin-4-yl-thieno[3,2-d]pyrimidin-6-ylmethyl]-piperidin-4-yl}-azetidin-3-ol;
2-(5-Fluoro-1H-indol-4-yl)-6-[4-(3-methoxy-azetidin-1-yl)-piperidin-1-ylmethyl]-4-morpholin-4-yl-thieno[3,2-d]pyrimidine; and
4-[2-(5-Fluoro-1H-indol-4-yl)-4-morpholin-4-yl-thieno[3,2-d]pyrimidin-6-ylmethyl]-1-(tetrahydro-pyran-4-yl)-piperazin-2-one;
and the pharmaceutically acceptable salts thereof.

6. A pharmaceutical composition which comprises a pharmaceutically acceptable carrier or diluent and, as an active ingredient, a compound as defined in claim 1.

7. A method of treating a disease or disorder arising from abnormal cell growth, function or behaviour associated with PI3 kinase, which method comprises administering to a patient in need thereof a compound as defined in claim 1, wherein the disease or disorder is inflammation.

8. A compound according to claim 1 wherein the compound is 2-fold or more selective for the p110δ (delta) isoform of PI3K over the p110α (alpha), p110β (beta), and p110γ (gamma) isoforms of PI3K.

9. A compound according to claim 1 wherein $R^3$ is H and m is 1.

10. A compound according to claim 1 wherein $R^a$ is H.

11. A compound according to claim 1 wherein formula IIa is selected from structures (i)-(iv):

(i)
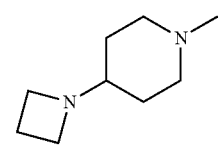

(ii)
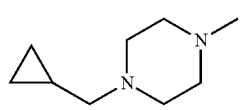

(iii)
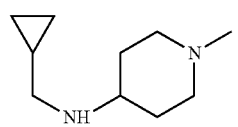

(iv)
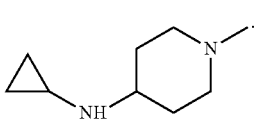

12. A compound according to claim 1 wherein the heteropolycyclic group is selected from structures (a)-(g):

(a)
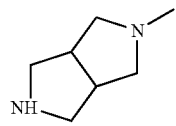

(b)
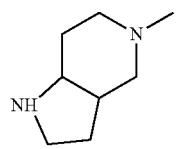

(c)
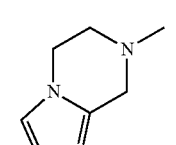

(d)
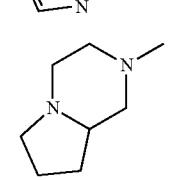

(e)
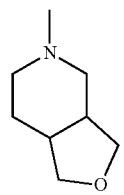

(f)
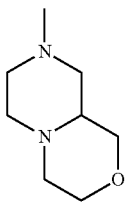

(g)
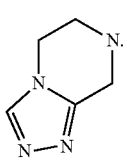

13. A compound according to claim 1 wherein the 4- to 7-membered saturated N-containing heterocyclic ring is selected from structures (a')-(f'):

(a')
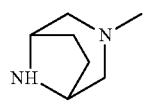

(b')
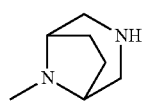

(c')
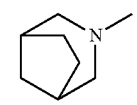

(d')
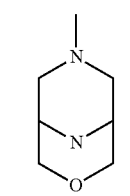

(e')
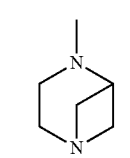

(f')
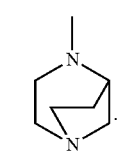

14. A compound according to claim 1 wherein the group of formula IIb is selected from structures (i')-(xii'):
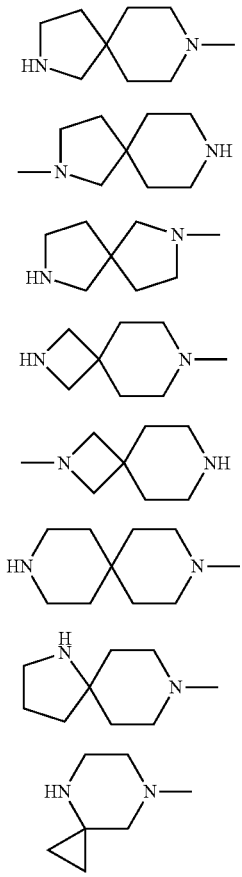
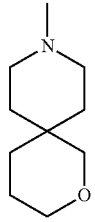
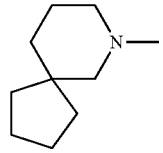
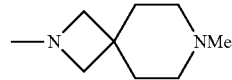
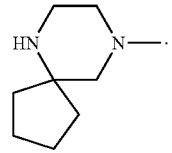
15. A compound according to claim 1 wherein the indole group is indol-4-yl.
16. A compound according to claim 15 wherein the indol-4-yl is unsubstituted or substituted with one or more fluorine.
* * * * *